US012778975B2

(12) United States Patent
Sommadossi et al.

(10) Patent No.: US 12,778,975 B2
(45) **Date of Patent: *Nov. 3, 2026**

(54) ADVANTAGEOUS ANTI-HCV COMBINATION THERAPY

(71) Applicant: Atea Pharmaceuticals, Inc., Boston, MA (US)

(72) Inventors: Jean-Pierre Sommadossi, Boston, MA (US); Adel Moussa, Burlington, MA (US); Keith M. Pietropaolo, Boxford, MA (US); Xiao-Jian Zhou, Arlington, MA (US)

(73) Assignee: Atea Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/350,774

(22) Filed: Oct. 6, 2025

(65) Prior Publication Data

US 2026/0091050 A1 Apr. 2, 2026

Related U.S. Application Data

(63) Continuation of application No. 19/215,054, filed on May 21, 2025, now Pat. No. 12,458,656, which is a continuation of application No. 18/540,608, filed on Dec. 14, 2023, which is a continuation of application No. PCT/US2022/034083, filed on Jun. 17, 2022.

(60) Provisional application No. 63/212,047, filed on Jun. 17, 2021.

(51) Int. Cl.

| | |
|---|---|
| ***A61K 31/7076*** | (2006.01) |
| ***A61K 31/5365*** | (2006.01) |
| ***A61P 31/16*** | (2006.01) |

(52) U.S. Cl.

CPC ...... *A61K 31/7076* (2013.01); *A61K 31/5365* (2013.01); *A61P 31/16* (2018.01)

(58) Field of Classification Search

None

See application file for complete search history.

(56) References Cited

U.S. PATENT DOCUMENTS

| | | | |
|---|---|---|---|
| 5,977,061 | A | 11/1999 | Holy et al. |
| 6,348,587 | B1 | 2/2002 | Schinazi et al. |
| 6,602,999 | B1 | 8/2003 | Kumar et al. |
| 6,660,721 | B2 | 12/2003 | Devos et al. |
| 6,777,395 | B2 | 8/2004 | Bhat et al. |
| 6,784,166 | B2 | 8/2004 | Devos et al. |
| 6,812,219 | B2 | 11/2004 | LaColla et al. |
| 6,908,924 | B2 | 6/2005 | Watanabe et al. |
| 6,911,424 | B2 | 6/2005 | Schinazi et al. |
| 6,914,054 | B2 | 7/2005 | Sommadossi et al. |

(Continued)

FOREIGN PATENT DOCUMENTS

| | | | |
|---|---|---|---|
| AU | 2012241173 | A1 | 11/2012 |
| CA | 3096916 | A1 | 11/2019 |

(Continued)

OTHER PUBLICATIONS

U.S. Appl. No. 19/350,713, Moussa, filed Oct. 6, 2025.

(Continued)

*Primary Examiner* — Patrick T Lewis

(74) *Attorney, Agent, or Firm* — Knowles Intellectual Property Strategies, LLC

(57) ABSTRACT

A synergistic pharmaceutical combination of Compound 1 or a pharmaceutically acceptable salt thereof (e.g., Compound 1-A) and Compound 2 or a pharmaceutically acceptable salt thereof, as well as its uses to treat hepatitis C or a condition related to hepatitis C, as well as methods for the manufacture of the pharmaceutical combination:

Compound 1

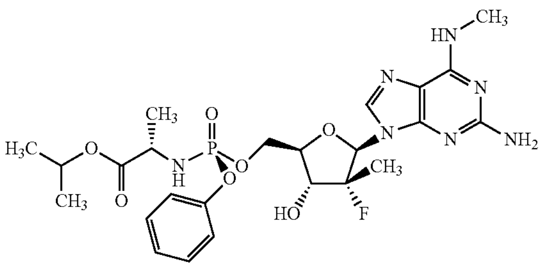

Compound 1-A

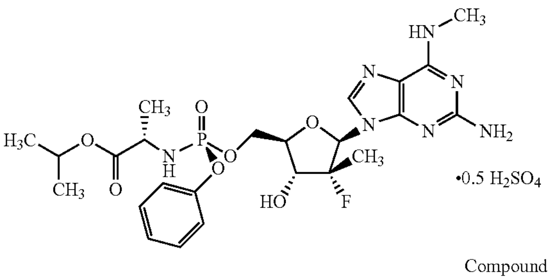

Compound 2

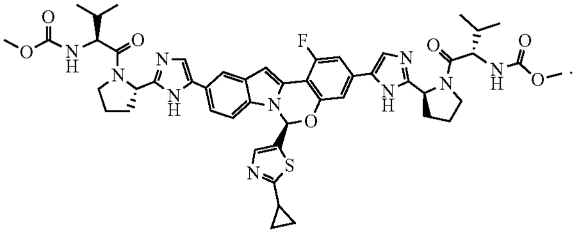

20 Claims, 41 Drawing Sheets

(56) References Cited

U.S. PATENT DOCUMENTS

| | | | |
|---|---|---|---|
| 6,949,522 B2 | 9/2005 | Otto et al. | |
| 7,094,770 B2 | 8/2006 | Watanabe et al. | |
| 7,105,493 B2 | 9/2006 | Sommadossi et al. | |
| 7,105,499 B2 | 9/2006 | Carroll et al. | |
| 7,125,855 B2 | 10/2006 | Bhat et al. | |
| 7,138,376 B2 | 11/2006 | Gosselin et al. | |
| 7,148,206 B2 | 12/2006 | Sommadossi et al. | |
| 7,157,441 B2 | 1/2007 | Sommadossi et al. | |
| 7,163,929 B2 | 1/2007 | Sommadossi et al. | |
| 7,169,766 B2 | 1/2007 | Sommadossi et al. | |
| 7,192,936 B2 | 3/2007 | LaColla et al. | |
| 7,202,224 B2 | 4/2007 | Eldrup et al. | |
| 7,211,570 B2 | 5/2007 | Schinazi et al. | |
| 7,268,119 B2 | 9/2007 | Cook et al. | |
| 7,285,658 B2 | 10/2007 | Cook et al. | |
| 7,307,065 B2 | 12/2007 | Schinazi et al. | |
| 7,323,449 B2 | 1/2008 | Olsen et al. | |
| 7,339,054 B2 | 3/2008 | Xu et al. | |
| 7,365,057 B2 | 4/2008 | LaColla et al. | |
| 7,384,924 B2 | 6/2008 | LaColla et al. | |
| 7,388,002 B2 | 6/2008 | Babu et al. | |
| 7,429,571 B2 | 9/2008 | Chand et al. | |
| 7,429,572 B2 | 9/2008 | Clark | |
| 7,456,155 B2 | 11/2008 | Sommadossi et al. | |
| 7,495,006 B2 | 2/2009 | Liotta et al. | |
| 7,514,410 B2 | 4/2009 | Babu et al. | |
| 7,534,767 B2 | 5/2009 | Butora et al. | |
| 7,547,704 B2 | 6/2009 | LaColla et al. | |
| 7,560,434 B2 | 7/2009 | Babu et al. | |
| 7,560,550 B2 | 7/2009 | Doring et al. | |
| 7,582,618 B2 | 9/2009 | Sommadossi et al. | |
| 7,601,820 B2 | 10/2009 | Wang et al. | |
| 7,608,597 B2 | 10/2009 | Sommadossi et al. | |
| 7,608,599 B2 | 10/2009 | Klumpp et al. | |
| 7,608,600 B2 | 10/2009 | Storer et al. | |
| 7,608,601 B2 | 10/2009 | Devos et al. | |
| 7,625,875 B2 | 12/2009 | Gosselin et al. | |
| 7,632,821 B2 | 12/2009 | Butora et al. | |
| 7,635,689 B2 | 12/2009 | LaColla et al. | |
| 7,638,502 B2 | 12/2009 | Schinazi et al. | |
| 7,652,001 B2 | 1/2010 | Hostetler et al. | |
| 7,662,798 B2 | 2/2010 | LaColla et al. | |
| 7,662,938 B2 | 2/2010 | Schinazi et al. | |
| 7,691,603 B2 | 4/2010 | DeFrees | |
| 7,713,941 B2 | 5/2010 | Cook et al. | |
| 7,718,790 B2 | 5/2010 | Stuyver et al. | |
| 7,749,983 B2 | 7/2010 | Hostetler et al. | |
| 7,772,208 B2 | 8/2010 | Schinazi et al. | |
| 7,824,851 B2 | 11/2010 | Sommadossi et al. | |
| 7,842,672 B2 | 11/2010 | Boojamra et al. | |
| RE42,015 E | 12/2010 | Watanabe et al. | |
| 7,879,815 B2 | 2/2011 | MacCoss et al. | |
| 7,902,202 B2 | 3/2011 | Sommadossi et al. | |
| 7,919,247 B2 | 4/2011 | Stuyver et al. | |
| 7,932,240 B2 | 4/2011 | Dousson et al. | |
| 7,951,789 B2 | 5/2011 | Sommadossi et al. | |
| 7,964,580 B2 | 6/2011 | Sofia et al. | |
| 7,973,013 B2 | 7/2011 | Cho et al. | |
| 7,994,139 B2 | 8/2011 | Babu et al. | |
| 8,008,264 B2 | 8/2011 | Butler et al. | |
| 8,012,941 B2 | 9/2011 | Cho et al. | |
| 8,012,942 B2 | 9/2011 | Butler et al. | |
| 8,071,567 B2 | 12/2011 | Devos et al. | |
| 8,071,568 B2 | 12/2011 | Narjes et al. | |
| 8,093,380 B2 | 1/2012 | Wang et al. | |
| 8,114,994 B2 | 2/2012 | Liotta et al. | |
| 8,114,997 B2 | 2/2012 | Otto et al. | |
| 8,119,607 B2 | 2/2012 | Francom et al. | |
| 8,133,870 B2 | 3/2012 | Babu et al. | |
| 8,148,349 B2 | 4/2012 | Meppen et al. | |
| 8,163,703 B2 | 4/2012 | Babu et al. | |
| 8,168,583 B2 | 5/2012 | Schinazi et al. | |
| 8,173,621 B2 | 5/2012 | Du et al. | |
| 8,193,372 B2 | 6/2012 | Dousson et al. | |
| 8,242,085 B2 | 8/2012 | Babu et al. | |
| 8,299,038 B2 | 10/2012 | Sommadossi et al. | |
| 8,318,682 B2 | 11/2012 | Butler et al. | |
| 8,324,179 B2 | 12/2012 | Chen et al. | |
| 8,334,270 B2 | 12/2012 | Sofia et al. | |
| 8,343,937 B2 | 1/2013 | Sommadossi et al. | |
| 8,362,068 B2 | 1/2013 | Dousson et al. | |
| 8,399,428 B2 | 3/2013 | Wagner | |
| 8,399,429 B2 | 3/2013 | Jonckers et al. | |
| 8,415,308 B2 | 4/2013 | Cho et al. | |
| 8,415,309 B2 | 4/2013 | Francom et al. | |
| 8,415,321 B2 | 4/2013 | Schinazi et al. | |
| 8,415,322 B2 | 4/2013 | Clark | |
| 8,431,588 B2 | 4/2013 | Jonckers et al. | |
| 8,440,813 B2 | 5/2013 | Babu et al. | |
| 8,455,451 B2 | 6/2013 | Cho et al. | |
| 8,470,834 B2 | 6/2013 | Kwong et al. | |
| 8,481,510 B2 | 7/2013 | Jonckers et al. | |
| 8,481,712 B2 | 7/2013 | Bhat et al. | |
| 8,481,713 B2 | 7/2013 | Wang et al. | |
| 8,492,539 B2 | 7/2013 | Chun et al. | |
| 8,501,699 B2 | 8/2013 | Francom et al. | |
| 8,507,460 B2 | 8/2013 | Surleraux et al. | |
| 8,541,434 B2 | 9/2013 | Kwong et al. | |
| 8,551,973 B2 | 10/2013 | Bao et al. | |
| 8,552,021 B2 | 10/2013 | Jonckers et al. | |
| 8,563,530 B2 | 10/2013 | Chang et al. | |
| 8,575,119 B2 | 11/2013 | Wang et al. | |
| 8,575,135 B2 | 11/2013 | Bacon et al. | |
| 8,580,765 B2 | 11/2013 | Sofia et al. | |
| 8,609,627 B2 | 12/2013 | Cho et al. | |
| 8,618,076 B2 | 12/2013 | Ross et al. | |
| 8,629,263 B2 | 1/2014 | Ross et al. | |
| 8,633,309 B2 | 1/2014 | Ross et al. | |
| 8,637,475 B1 | 1/2014 | Storer et al. | |
| 8,642,756 B2 | 2/2014 | Ross et al. | |
| 8,658,616 B2 | 2/2014 | McGuigan et al. | |
| 8,673,926 B2 | 3/2014 | Chu | |
| 8,674,085 B2 | 3/2014 | Sommadossi et al. | |
| 8,680,071 B2 | 3/2014 | Surleraux et al. | |
| 8,691,788 B2 | 4/2014 | Sommadossi et al. | |
| 8,697,694 B2 | 4/2014 | Arasappan et al. | |
| 8,715,638 B2 | 5/2014 | Kwong et al. | |
| 8,716,262 B2 | 5/2014 | Sofia et al. | |
| 8,716,263 B2 | 5/2014 | Chun et al. | |
| 8,735,345 B2 | 5/2014 | Porter et al. | |
| 8,735,372 B2 | 5/2014 | Du et al. | |
| 8,735,569 B2 | 5/2014 | Ross et al. | |
| 8,742,101 B2 | 6/2014 | Storer et al. | |
| 8,759,318 B2 | 6/2014 | Chamberlain et al. | |
| 8,759,372 B2 | 6/2014 | Roberts et al. | |
| 8,759,510 B2 | 6/2014 | Du et al. | |
| 8,765,710 B2 | 7/2014 | Sofia et al. | |
| 8,772,474 B2 | 7/2014 | Beigelman et al. | |
| 8,802,840 B2 | 8/2014 | Francom et al. | |
| 8,815,829 B2 | 8/2014 | Schinazi et al. | |
| 8,816,074 B2 | 8/2014 | Chu et al. | |
| 8,841,275 B2 | 9/2014 | Du et al. | |
| 8,846,638 B2 | 9/2014 | Or et al. | |
| 8,846,896 B2 | 9/2014 | Serebryany et al. | |
| 8,853,171 B2 | 10/2014 | Butler et al. | |
| 8,859,595 B2 | 10/2014 | Coats et al. | |
| 8,859,756 B2 | 10/2014 | Ross et al. | |
| 8,871,737 B2 | 10/2014 | Smith et al. | |
| 8,871,785 B2 | 10/2014 | Boojamra et al. | |
| 8,877,731 B2 | 11/2014 | Beigelman et al. | |
| 8,877,733 B2 | 11/2014 | Cho et al. | |
| 8,889,159 B2 | 11/2014 | Cleary et al. | |
| 8,889,701 B1 | 11/2014 | Ivachtchenko et al. | |
| 8,895,531 B2 | 11/2014 | Shi | |
| 8,895,723 B2 | 11/2014 | Serebryany et al. | |
| 8,906,880 B2 | 12/2014 | Du et al. | |
| 8,912,321 B2 | 12/2014 | Axt et al. | |
| 8,921,341 B2 | 12/2014 | Bacon et al. | |
| 8,921,384 B2 | 12/2014 | Chu | |
| 8,927,513 B2 | 1/2015 | Manoharan et al. | |
| 8,933,052 B2 | 1/2015 | Jonckers et al. | |
| 8,940,718 B2 | 1/2015 | Bacon et al. | |
| 8,946,244 B2 | 2/2015 | Chu et al. | |
| 8,951,985 B2 | 2/2015 | Surleraux et al. | |

(56) References Cited

U.S. PATENT DOCUMENTS

| | | | |
|---|---|---|---|
| 8,957,045 | B2 | 2/2015 | Sofia et al. |
| 8,957,046 | B2 | 2/2015 | Du et al. |
| 8,980,865 | B2 | 3/2015 | Wang et al. |
| 9,012,427 | B2 | 4/2015 | Blatt et al. |
| 9,012,428 | B2 | 4/2015 | Jonckers et al. |
| 9,045,520 | B2 | 6/2015 | Chun et al. |
| 9,061,041 | B2 | 6/2015 | Girijavallabhan et al. |
| 9,085,573 | B2 | 7/2015 | Du et al. |
| 9,085,599 | B2 | 7/2015 | Or et al. |
| 9,090,642 | B2 | 7/2015 | Cho et al. |
| 9,109,001 | B2 | 8/2015 | Parsy et al. |
| 9,139,604 | B2 | 9/2015 | Boojamra et al. |
| 9,156,872 | B2 | 10/2015 | Girijavallabhan et al. |
| 9,173,893 | B2 | 11/2015 | Cho et al. |
| 9,187,515 | B2 | 11/2015 | Mayes et al. |
| 9,192,621 | B2 | 11/2015 | Mayes et al. |
| 9,206,217 | B2 | 12/2015 | Ross et al. |
| 9,211,300 | B2 | 12/2015 | Mayes et al. |
| 9,243,025 | B2 | 1/2016 | Surleraux et al. |
| 9,249,174 | B2 | 2/2016 | Beigelman et al. |
| 9,284,342 | B2 | 3/2016 | Ross et al. |
| 9,339,541 | B2 | 5/2016 | Dousson et al. |
| 9,351,989 | B2 | 5/2016 | McGuigan et al. |
| 9,403,863 | B2 | 8/2016 | Surleraux et al. |
| 9,408,863 | B2 | 8/2016 | Verma et al. |
| 9,447,132 | B2 | 9/2016 | Deshpande et al. |
| 9,487,544 | B2 | 11/2016 | Cho et al. |
| 9,555,038 | B2 | 1/2017 | Yu et al. |
| 9,598,457 | B2 | 3/2017 | Smith et al. |
| 9,603,863 | B2 | 3/2017 | Blatt et al. |
| 9,603,864 | B2 | 3/2017 | Blatt et al. |
| 9,637,512 | B2 | 5/2017 | Chun et al. |
| 9,757,406 | B2 | 9/2017 | Gorman et al. |
| 9,758,544 | B2 | 9/2017 | Beigelman et al. |
| 9,815,864 | B2 | 11/2017 | Beigelman et al. |
| 9,822,137 | B2 | 11/2017 | Dehaen et al. |
| 9,828,410 | B2 | 11/2017 | Sommadossi et al. |
| 9,890,188 | B2 | 2/2018 | Wang et al. |
| 10,000,523 | B2 | 6/2018 | Sommadossi et al. |
| 10,005,810 | B2 | 6/2018 | McGuigan et al. |
| 10,005,811 | B2 | 6/2018 | Sommadossi et al. |
| 10,086,011 | B2 | 10/2018 | Gorman et al. |
| 10,202,401 | B2 | 2/2019 | Li et al. |
| 10,202,412 | B2 | 2/2019 | Sommadossi et al. |
| 10,239,911 | B2 | 3/2019 | Sommadossi et al. |
| 10,287,311 | B2 | 5/2019 | Clark |
| 10,457,690 | B2 | 10/2019 | Yin et al. |
| 10,519,186 | B2 | 12/2019 | Moussa et al. |
| 10,577,359 | B2 | 3/2020 | Chun et al. |
| 10,815,266 | B2 | 10/2020 | Sommadossi et al. |
| 10,870,672 | B2 | 12/2020 | Sommadossi et al. |
| 10,870,673 | B2 | 12/2020 | Sommadossi et al. |
| 10,874,687 | B1 | 12/2020 | Sommadossi et al. |
| 10,875,885 | B2 | 12/2020 | Sommadossi et al. |
| 10,894,804 | B2 | 1/2021 | Moussa et al. |
| 10,906,928 | B2 | 2/2021 | Moussa et al. |
| 10,946,033 | B2 | 3/2021 | Sommadossi et al. |
| 11,116,783 | B2 | 9/2021 | Gorman et al. |
| 11,642,361 | B2 | 5/2023 | Sofia et al. |
| 11,690,860 | B2 | 7/2023 | Sommadossi et al. |
| 11,707,479 | B2 | 7/2023 | Gorman et al. |
| 11,707,480 | B2 | 7/2023 | Sommadossi et al. |
| 11,738,038 | B2 | 8/2023 | Sommadossi et al. |
| 11,813,278 | B2 | 11/2023 | Sommadossi et al. |
| 11,975,016 | B2 | 5/2024 | Sommadossi et al. |
| 12,006,340 | B2 | 6/2024 | Moussa et al. |
| 12,084,473 | B2 | 9/2024 | Sommadossi et al. |
| 12,226,429 | B2 | 2/2025 | Sommadossi et al. |
| 12,458,656 | B2 | 11/2025 | Sommadossi et al. |
| 2002/0045599 | A1 | 4/2002 | Arimilli et al. |
| 2002/0058635 | A1 | 5/2002 | Averett |
| 2003/0087873 | A1 | 5/2003 | Stuyver et al. |
| 2004/0063658 | A1 | 4/2004 | Roberts et al. |
| 2004/0229839 | A1 | 11/2004 | Babu et al. |
| 2004/0259934 | A1 | 12/2004 | Olsen et al. |
| 2005/0009737 | A1 | 1/2005 | Clark |
| 2005/0038240 | A1 | 2/2005 | Connolly et al. |
| 2005/0203044 | A1 | 9/2005 | Zinnen |
| 2006/0122146 | A1 | 6/2006 | Chun et al. |
| 2006/0199783 | A1 | 9/2006 | Wang et al. |
| 2007/0265222 | A1 | 11/2007 | MacCoss et al. |
| 2008/0207554 | A1 | 8/2008 | Beigelman et al. |
| 2008/0286230 | A1 | 11/2008 | Sommadossi et al. |
| 2009/0156545 | A1 | 6/2009 | Hostetler et al. |
| 2009/0176732 | A1 | 7/2009 | Beigelman et al. |
| 2009/0181921 | A1 | 7/2009 | Blatt et al. |
| 2009/0318380 | A1 | 12/2009 | Sofia et al. |
| 2010/0137576 | A1 | 6/2010 | Stec et al. |
| 2010/0240604 | A1 | 9/2010 | Beigelman et al. |
| 2010/0249068 | A1 | 9/2010 | Beigelman et al. |
| 2010/0279969 | A1 | 11/2010 | Schinazi et al. |
| 2010/0286083 | A1 | 11/2010 | Bao et al. |
| 2010/0331397 | A1 | 12/2010 | Beigelman et al. |
| 2011/0015146 | A1 | 1/2011 | Sofia et al. |
| 2011/0091943 | A1 | 4/2011 | Gallou et al. |
| 2011/0223659 | A1 | 9/2011 | Scholl et al. |
| 2011/0257121 | A1 | 10/2011 | Chang et al. |
| 2012/0070411 | A1 | 3/2012 | Beigelman et al. |
| 2012/0135951 | A1 | 5/2012 | Schinazi et al. |
| 2012/0245335 | A1 | 9/2012 | Clark |
| 2013/0064794 | A1 | 3/2013 | Surleraux et al. |
| 2013/0225636 | A1 | 8/2013 | Roberts et al. |
| 2013/0244966 | A1 | 9/2013 | Milne et al. |
| 2013/0273005 | A1 | 10/2013 | Delaney et al. |
| 2013/0315868 | A1 | 11/2013 | Mayes et al. |
| 2014/0038916 | A1 | 2/2014 | Wang et al. |
| 2014/0066395 | A1 | 3/2014 | Cho et al. |
| 2014/0112886 | A1 | 4/2014 | Moussa et al. |
| 2014/0187511 | A1 | 7/2014 | Du et al. |
| 2014/0212382 | A1 | 7/2014 | Schinazi et al. |
| 2014/0235566 | A1 | 8/2014 | Amblard et al. |
| 2015/0011481 | A1 | 1/2015 | Vilchez et al. |
| 2015/0011497 | A1 | 1/2015 | Beigelman et al. |
| 2015/0057243 | A1 | 2/2015 | Zhou et al. |
| 2015/0105341 | A1 | 4/2015 | Beigelman et al. |
| 2015/0150897 | A1 | 6/2015 | Denning et al. |
| 2015/0175646 | A1 | 6/2015 | Casteel et al. |
| 2015/0183818 | A1 | 7/2015 | Tran et al. |
| 2015/0335648 | A1 | 11/2015 | Yu et al. |
| 2016/0002281 | A1 | 1/2016 | Mayes et al. |
| 2016/0220595 | A1 | 8/2016 | Liotta et al. |
| 2016/0257706 | A1 | 9/2016 | Sommadossi et al. |
| 2016/0271162 | A1 | 9/2016 | Moussa et al. |
| 2017/0022242 | A1 | 1/2017 | Herdewyn et al. |
| 2017/0029456 | A1 | 2/2017 | Dousson et al. |
| 2017/0042961 | A1 | 2/2017 | Delaney, IV et al. |
| 2017/0275322 | A1 | 9/2017 | Oinho et al. |
| 2018/0009836 | A1 | 1/2018 | Sommadossi et al. |
| 2018/0179223 | A1 | 6/2018 | Yin et al. |
| 2018/0215776 | A1 | 8/2018 | Moussa et al. |
| 2018/0228826 | A1 | 8/2018 | Harris et al. |
| 2019/0153017 | A1 | 5/2019 | Sommadossi et al. |
| 2019/0201433 | A1 | 7/2019 | Sommadossi et al. |
| 2019/0255085 | A1 | 8/2019 | Clarke et al. |
| 2020/0087339 | A1 | 3/2020 | Moussa et al. |
| 2023/0049294 | A1 | 2/2023 | Moussa et al. |
| 2023/0331751 | A1 | 10/2023 | Moussa et al. |
| 2023/0364121 | A1 | 11/2023 | Sommadossi et al. |
| 2023/0365611 | A1 | 11/2023 | Moussa |
| 2024/0148770 | A1 | 5/2024 | Sommadossi et al. |
| 2024/0226131 | A1 | 7/2024 | Sommadossi et al. |
| 2024/0261316 | A1 | 8/2024 | Sommadossi et al. |
| 2025/0082656 | A1 | 3/2025 | Moussa et al. |
| 2025/0109163 | A1 | 4/2025 | Moussa et al. |
| 2025/0243235 | A1 | 7/2025 | Sommadossi et al. |

FOREIGN PATENT DOCUMENTS

| | | | |
|---|---|---|---|
| CN | 103435672 | A | 12/2013 |
| CN | 103980332 | A | 8/2014 |
| CN | 105646629 | A | 6/2016 |
| CN | 106188192 | A | 12/2016 |
| CN | 109232612 | A | 1/2019 |
| EP | 547008 | A1 | 6/1993 |

(56) References Cited

FOREIGN PATENT DOCUMENTS

| | | | |
|---|---|---|---|
| EP | 398231 | B1 | 7/1997 |
| EP | 2945952 | B1 | 8/2019 |
| WO | WO-1998/16184 | A2 | 4/1998 |
| WO | WO-2001/009143 | A1 | 2/2001 |
| WO | WO-2001/90121 | A2 | 11/2001 |
| WO | WO-2001/92282 | A2 | 12/2001 |
| WO | WO-2002/32920 | A2 | 4/2002 |
| WO | WO-2003/033508 | A1 | 4/2003 |
| WO | WO-2003/039523 | A2 | 5/2003 |
| WO | WO-2003/062256 | A1 | 7/2003 |
| WO | WO-2003/093290 | A2 | 11/2003 |
| WO | WO-2004/002999 | A2 | 1/2004 |
| WO | WO-2004/003000 | A2 | 1/2004 |
| WO | WO-2004/014312 | A2 | 2/2004 |
| WO | WO-2004/052906 | A2 | 6/2004 |
| WO | WO-2004/074350 | A2 | 9/2004 |
| WO | WO-2004/091499 | A2 | 10/2004 |
| WO | WO-2004/106356 | A1 | 12/2004 |
| WO | WO-2005/000864 | A1 | 1/2005 |
| WO | WO-2005/003147 | A2 | 1/2005 |
| WO | WO-2005/020884 | A2 | 3/2005 |
| WO | WO-2005/021568 | A2 | 3/2005 |
| WO | WO-2005/084192 | A2 | 9/2005 |
| WO | WO-2005/090370 | A1 | 9/2005 |
| WO | WO-2006/012078 | A2 | 2/2006 |
| WO | WO-2006/063149 | A1 | 6/2006 |
| WO | WO-2006/063717 | A2 | 7/2006 |
| WO | WO-2006/094347 | A1 | 9/2006 |
| WO | WO-2006/102533 | A2 | 9/2006 |
| WO | WO-2006/121820 | A1 | 11/2006 |
| WO | WO-2006/130217 | A2 | 12/2006 |
| WO | WO-2007/022073 | A2 | 2/2007 |
| WO | WO-2007/112028 | A2 | 10/2007 |
| WO | WO-2007/130783 | A1 | 11/2007 |
| WO | WO-2008/012555 | A2 | 1/2008 |
| WO | WO-2008/048128 | A1 | 4/2008 |
| WO | WO-2008/062206 | A2 | 5/2008 |
| WO | WO-2008/095040 | A2 | 10/2008 |
| WO | WO-2009/001097 | A2 | 12/2008 |
| WO | WO-2009/003042 | A1 | 12/2008 |
| WO | WO-2009/067409 | A1 | 5/2009 |
| WO | WO-2009/086192 | A1 | 7/2009 |
| WO | WO-2009/086201 | A1 | 7/2009 |
| WO | WO-2009/129120 | A2 | 10/2009 |
| WO | WO-2010/081082 | A2 | 7/2010 |
| WO | WO-2010/091386 | A2 | 8/2010 |
| WO | WO-2010/108135 | A1 | 9/2010 |
| WO | WO-2010/145778 | A1 | 12/2010 |
| WO | WO-2011/005595 | A1 | 1/2011 |
| WO | WO-2011/005860 | A2 | 1/2011 |
| WO | WO-2012/041014 | A1 | 4/2012 |
| WO | WO-2012/041965 | A1 | 4/2012 |
| WO | WO-2012/048013 | A2 | 4/2012 |
| WO | WO-2012/092484 | A2 | 7/2012 |
| WO | WO-2012/125900 | A1 | 9/2012 |
| WO | WO-2012/154321 | A1 | 11/2012 |
| WO | WO-2012/158811 | A2 | 11/2012 |
| WO | WO-2013/009737 | A1 | 1/2013 |
| WO | WO-2013/019874 | A1 | 2/2013 |
| WO | WO-2013/025992 | A1 | 2/2013 |
| WO | WO-2013/039855 | A1 | 3/2013 |
| WO | WO-2013/039920 | A1 | 3/2013 |
| WO | WO-2013/040492 | A2 | 3/2013 |
| WO | WO-2013/044030 | A1 | 3/2013 |
| WO | WO-2013/059735 | A1 | 4/2013 |
| WO | WO-2013/090420 | A2 | 6/2013 |
| WO | WO-2013/096680 | A1 | 6/2013 |
| WO | WO-2013/142125 | A1 | 9/2013 |
| WO | WO-2013/142157 | A1 | 9/2013 |
| WO | WO-2013/142159 | A1 | 9/2013 |
| WO | WO-2013/151975 | A1 | 10/2013 |
| WO | WO-2013/177219 | A1 | 11/2013 |
| WO | WO-2013/187978 | A1 | 12/2013 |
| WO | WO-2014/008236 | A1 | 1/2014 |
| WO | WO-2014/047117 | A1 | 3/2014 |
| WO | WO-2014/052638 | A1 | 4/2014 |
| WO | WO-2014/063019 | A1 | 4/2014 |
| WO | WO-2014/076490 | A1 | 5/2014 |
| WO | WO-2014/082935 | A1 | 6/2014 |
| WO | WO-2014/100498 | A1 | 6/2014 |
| WO | WO-2014/100505 | A1 | 6/2014 |
| WO | WO-2014/110687 | A1 | 7/2014 |
| WO | WO-2014/110705 | A1 | 7/2014 |
| WO | WO-2014/120981 | A1 | 8/2014 |
| WO | WO-2014/124430 | A1 | 8/2014 |
| WO | WO-2014/137930 | A1 | 9/2014 |
| WO | WO-2014/169278 | A1 | 10/2014 |
| WO | WO-2014/169280 | A2 | 10/2014 |
| WO | WO-2014/209979 | A1 | 12/2014 |
| WO | WO-2015/038596 | A1 | 3/2015 |
| WO | WO-2015/053662 | A1 | 4/2015 |
| WO | WO-2015/081133 | A2 | 6/2015 |
| WO | WO-2015/095305 | A1 | 6/2015 |
| WO | WO-2015/158913 | A1 | 10/2015 |
| WO | WO-2016/041877 | A1 | 3/2016 |
| WO | WO-2016/100441 | A1 | 6/2016 |
| WO | WO-2016/100569 | A1 | 6/2016 |
| WO | WO-2016/144918 | A1 | 9/2016 |
| WO | WO-2016/145142 | A1 | 9/2016 |
| WO | WO-2016/196932 | A1 | 12/2016 |
| WO | WO-2017/023714 | A1 | 2/2017 |
| WO | WO-2018/013937 | A1 | 1/2018 |
| WO | WO-2018/048937 | A1 | 3/2018 |
| WO | WO-2019/200005 | A1 | 10/2019 |
| WO | WO-2020/117966 | A1 | 6/2020 |

OTHER PUBLICATIONS

Ahmad, T. et al., "Cardiac dysfunction associated with a nucleotide polymerase inhibitor for treatment of hepatitis C" Hepatology, 62, 409, 2015.

Asante-Appiah, Ernest, et al. "In vitro antiviral profile of ruzasvir, a potent and pangenotype inhibitor of hepatitis C virus NS5a." Antimicrobial Agents and Chemotherapy 62.11, 10-1128, 2018.

ATE1062 BEM-RZR Phase 2 study EASL2024 poster, May 23, 2024.

ATE1083 EASL Vo poster SAT-411 poster 1400×900mm, 2024.

ATE1087 EASL Vo SAT-412_poster 1400×900mm, May 22, 2024.

ATE1088 BEM in vitro resistance EASL poster, May 22, 2024.

Atea Pharmaceuticals Introduces New Strategic Clinical Development Program for AT-527 in COVID-19; Dec. 14, 2021.

Atea Pharmaceuticals Provides Update and Topline Results for Phase 2 MOONSONG Trial Evaluating AT-527 in the Outpatient Setting, Oct. 19, 2021.

Atea Pharmaceuticals Reports Nonclinical Bemnifosbuvir (AT-527) Toxicology Data at Society of Toxicology 61st Annual Meeting; Mar. 28, 2022.

Atea Pharmaceuticals to Present at the 2022 Jefferies Healthcare Conference; Jun. 1, 2022.

Atea Pharmaceuticals to Present at the 2023 Jefferies Healthcare Conference, Jun. 8, 2023.

Atea Pharmaceuticals to Present at the 2025 JPM Healthcare Conference Slide Deck, Jan. 2025.

Atea Pharmaceuticals Announces Positive Initial Data from Phase 2 Study for Hepatitis C Virus (HCV) and Significant Enrollment Milestone for Phase 3 SUNRISE-3 Trial for COVID-19, Jan. 8, 2024.

Atea Pharmaceuticals Presents Multiple New Datasets Supporting the Combination of Bemnifosbuvir and Ruzasvir for the Treatment of Hepatitis C Virus at AASLD's The Liver Meeting, Nov. 15, 2024.

Atea Pharmaceuticals Presents New Data Showcasing Potential Best-in-Class Combination Profile of Bemnifosbuvir and Ruzasvir for Treatment of Hepatitis C Virus at EASL Congress, May 22, 2024.

Atea Pharmaceuticals Presents Positive Initial Phase 2 Data for Bemnifosbuvir and Ruzasvir Combination for Treatment of Hepatitis C Virus at EASL Congress, Jun. 5, 2024.

Atea Pharmaceuticals to Present and Provide a Business Update at the 7th Annual Evercore HealthCONx Conference, Nov. 26, 2024.

(56) References Cited

OTHER PUBLICATIONS

Atea Pharmaceuticals to Present New Data Supporting the Combination of Bemnifosbuvir and Ruzasvir for the Treatment of Hepatitis C Virus at AASLD's The Liver Meeting, Oct. 30, 2024.
Atea Pharmaceuticals Phase 2 Open Label Study of Bemnifosbuvir + Ruzasvir, Dec. 4, 2024.
Atea Pharmaceuticals Corporate Presentation at the Jefferies Global Healthcare Conference, Jun. 5, 2024.
Belikov, V.G., Pharmaceutical Chemistry, Fourth Edition, revised textbook, 2007, Moscow, 30 "MEDpress-inform" pp. 27-29, 2007.
Berge, M.S. et al., "Pharmaceutical Salts" Journal of Pharmaceutical Sciences, 66, 1, 1977.
Berliba et al., "Safety, Pharmacokinetics, and Antiviral Activity of AT-527, a Novel Purine Nucleotide Prodrug, in Hepatitis C Virus-Infected Subjects with or without Cirrhosis" Antimicrobial Agents and Chemotherapy, vol. 63, Issue 12, Dec. 2019.
Bukrinskaya, A.G. Virology—M.: Medicine, p. 152, lines 12-15 from the top, 1986.
Chang, W. et al., "Discovery of PSI-353661, a Novel Purine Nucleotide Prodrug for the Treatment of HCV Infection" ACS Med Chem Lett., 2, 130, 2011.
Cretton-Scott, E. et al., "In vitro antiviral activity and pharmacology of idx184, a novel and potent inhibitor of HCV replication" (Abstract 588) J. Hepatol., 48, Supplement 2, S220, 2008.
Declaration of Alexander M. Klibanov, Ph.D. (PGR2023-00046—Exhibit No. 15) Filed Aug. 6, 2023.
Ershov, F.I. et al., Ministry of Health and Social Development of The Russian Federation Federal State Budgetary Institution "Scientific Center on Expertise of Medical Application Products" Guidelines on Preclinical Trials of Medicinal Products, Moscow, 2012.
Freeman et al., "2-amino-9(3-azido-2,3-dideoxy-β-D-erythro-pentofuranosyl)-6-Substituted-9H-Purines: Synthesis and Anti-HIV Activity" Bioorganic and Medicinal Chemistry, 3(4): 447-448, 1995.
Good et al., "AT-527, a Double Prodrug of a Guanosine Nucleotide Analog, Is a Potent Inhibitor of SARS-CoV-2 In Vitro and a Promising Oral Antiviral for Treatment of COVID19" Antimicrobial Agents and Chemotherapy, vol. 65, Issue 4, Apr. 2021.
Good et al., "Preclinical evaluation of AT-527, a novel guanosine nucleotide prodrug with potent, pan-genotypic activity against hepatitis C virus" PLOS ONE, https://doi.org/10.1371/journal.pone.0227104, Jan. 8, 2020.
Good, S. et al., "AT-337, AT-511, and its Salt Form, AT-527: Novel Potent and Selective Pan-genotypic Purine Nucleotide Prodrug Inhibitors of HCV Polymerase" presented at the AASLD 2017 Liver Meeting; Washington, D.C., Oct. 20, 2017-Oct. 24, 2017.
Herman, B. et al., "Substrate mimicry: HIV-1 reverse transcriptase recognizes 6-modified-30-azido-20,30-dideoxyguanosine-50-triphosphates as adenosine analogs" Nucleic Acids Research, 40, 381, 2012.
Hirayama, Noriaki "Handbook for Producing Organic Compound Crystals" pp. 17-23, 37-40, 45-51, and 57-65 and English partial translation, 2008.
Huang et al., "Impact of solid state properties on developability assessment of drug candidates" Advanced Drug Delivery Reviews, 56, 321, 2004.
ICAR 2023 BEM-RZR poster, Feb. 10, 2023.
International Search Report and Written Opinion of PCT/US22/34083, dated Sep. 21, 2022.
Krausslich et al., Antiviral Strategies, Springer-Verlag Berlin Heidelberg, pp. 1-24, Dec. 3, 2009.
Lawitz et al., "Safety and Efficacy of a fixed-dose combination regimen of grazoprevir, ruzasvir, and uprifosbuvir with or without ribavirin in participants with and without cirrhosis with chronic hepatitis C virus genotype 1, 2, or 3 infection (C-CREST-1 and C-CREST-2, part B): two randomised, phase 2, open-label trials" Lancet Gastroenterol Hepatol, 2017.
Lawitz et al., "Efficacy and safety of a two-drug direct-acting antiviral agent regimen" Journal of Viral Hepatitis, 2019.
Lawitz et al., "Efficacy and safety of ruzasvir 60 mg and uprifosbuvir 450 mg for 12 weeks in" Journal of Viral Hepatitis, 2019.
Luo, Shouqi et al., 4793: Lack of Reproductive and Developmental Toxicity for AT-527 (Bemnifosbuvir), an Oral Purine Nucleotide Prodrug for COVID-19 Infection; Mar. 27-31, 2022.
Luo, Shouqi et al., 4794: Characterization of the Toxicity Profile of AT-527 (Bemnifosbuvir), a Novel Guanosine Nucleotide Prodrug with Antiviral Activity for COVID-19 Infection; Mar. 27-31, 2022.
Mashkovsky, M.D., "Medicines, a guide for doctors" part. 1, Moscow, "Medicine" p. 8, 1993.
Mcguigan, C. et al. "Design, synthesis and evaluation of a novel double pro-drug: INX-08189. A new clinical candidate for hepatitis C virus" Bioorganic & Medicinal Chemistry Letters, 20, 4850, 2010.
Mcguigan, C. et al. "Dual pro-drugs of 2'-C-methyl guanosine monophosphate as potent and selective inhibitors of hepatitis C virus" Bioorganic & Medicinal Chemistry Letters, 21, 6007, 2011.
Murakami, E. et al., "Adenosine Deaminase-like Protein 1 (ADAL1): Characterization and Substrate Specificity in the Hydrolysis of N6- or O6-Substituted Purine or 2-Aminopurine Nucleoside Monophosphates" J Med Chem, 54, 5902, 2011.
Nguyen, Lien et al., International Journal of Biomedical Science: Chiral Drugs: An Overview, 20, 85-100, Jun. 2, 2006.
Petition for Post Grant Review of U.S. Pat. No. 11,642,361 (PGR2023-00046—Paper No. 1) Filed Aug. 7, 2023.
Poordad et al., "Daclatasvir with Sofosbuvir and Ribavirin for Hepatitis C Virus Infection with Advanced Cirrhosis or Post-Liver Transplantation Recurrence" Hepatology, 63, 1493, 2016.
Pradere, U. et al., "Synthesis of 5'-Methylene-Phosphonate Furanonucleoside Prodrugs: Application to D-2'-Deoxy-2'-α-fluoro-2'-β-C-methyl Nucleosides" Organic Letters, 14, 4426, 2012.
Reddy, P. et al., "2'-Deoxy-2'-α-fluoro-2'-β-C-methyl 3',5'-cyclic phosphate nucleotide prodrug analogs as inhibitors of HCV NS5B polymerase: Discovery of PSI-352938" Bioorganic & Medicinal Chemistry Letters, 20, 7376, 2010.
Serajuddin, A.T.M., "Salt formation to improve drug solubility" Advanced Drug Delivery Reviews, 59, 603, 2007.
Sofia, M.J. "Nucleotide Prodrugs for HCV Therapy" Antiviral Chemistry & Chemotherapy, 22, 23, 2011.
Stahl et al., "Handbook of Pharmaceutical Salts Properties, Selection, and Use" International Union of Pure and Applied Chemistry (IUPAC), Chapters 6 and 7, 2002.
Study Details, Efficacy and Safety of Grazoprevir (MK-5172) and Uprifosbuvir (MK-3682) With Elbasvir (MK-8742) or Ruzasvir (MK-8408) for Chronic Hepatitis C Genotype (GT)1 and GT2 Infection (MK-3682-011), ClinicalTrials.gov.
Study Details, Efficacy and Safety of Grazoprevir (MK-5172) and Uprifosbuvir (MK-3682) With Elbasvir (MK-8742) or Ruzasvir (MK-8408) for Chronic Hepatitis C Virus (HCV) Genotype (GT) 3, GT4, GT5, and GT6 Infection (MK- 3682-012), ClinicalTrials.gov.
Study Details, Efficacy and Safety of Uprifosbuvir (MK-3682) With Ruzasvir (MK-8408) in Adults With Chronic Hepatitis C Genotype 1, 2, 3, 4, 5 or 6 Infection (MK-3682-035), ClinicalTrials.gov, Jun. 26, 2019.
Tao, S., Zhou, L., Zhang, H., Zhou, S., Amiralaei, S., Shelton, J.R., Coats, S.J., Schinazi, R.F., "Comparison of Three 2'-C-Methyl Guanosine Prodrugs for Hepatitis C including a Novel $^{2}$-D-2'-C-Me-2,6-Diaminopurine Ribonucleoside Phosphoramidate (RS-1389): Interspecies Hepatocyte and Human Cardiomyocyte Metabolism Profiles" The Liver Meeting 2014, Boston, MA, USA. Nov. 6-11, 2014.
Tong, Ling, et al. "Discovery of ruzasvir (MK-8408): a potent, pan-genotype HCV NS5A inhibitor with optimized activity against common resistance-associated polymorphisms." Journal of Medicinal Chemistry 60.1, 290-306, 2017.
Wu, Jim Zhen et al., "Ribavirin, viramidine and adenosine-deaminase-catalysed drug activation: implication for nucleoside prodrugs design" Journal of Antimicrobial Chemotherapy, 52, 543-546, 2003.
Yoon et al., "Design, Synthesis, and Anti-RNA Virus of 6'-Fluorinated-Aristeromycin Analogues" Journal of Medicine Chemistry, vol. 62, p. 6346-6362, Jun. 7, 2019.

(56) References Cited

OTHER PUBLICATIONS

Zhang et al., "Synthesis and evaluation of 30-azido-20,30-dideoxypurine nucleosides as inhibitors of human immunodeficiency virus" Bioorganic and Medicinal Chemistry Letters, 20, 60, 2010.
Zhou, L. et al., "β-D-2'-C-Methyl-2,6-diaminopurine Ribonucleoside Phosphoramidates are Potent and Selective Inhibitors of Hepatitis C Virus (HCV) and Are Bioconverted Intracellularly to Bioactive 2,6-Diaminopurine and Guanosine 5'-Triphosphate Forms" J Med Chem, 58, 3445, 2015.
Zhou, X. et al., "A Phase 1a Study of AT-527, a Novel Pan-Genotypic Purine Nucleotide Prodrug Inhibitor of Hepatitis C Virus (HCV)" presented at The Liver Meeting, Washington, D.C., Oct. 23, 2017.
Zhou, X. et al., "AT-527, a pan-genotypic purine nucleotide prodrug, exhibits potent antiviral activity in subjects with chronic hepatitis C" presented at The International Liver Congress, Paris, France, Apr. 13, 2018.
Zhou, X. et al., "A Phase 1 Study to Evaluate the Interaction of HCV NS5B Inhibitor MK-3682 With HCV_NS3 4A Protease Inhibitor MK-5172 and HCV NS5A Inhibitor MK-8408 in Healthy Subjects" presented at The International Liver Congress, Vienna, Austria, Apr. 22-26, 2015.
Bastin, R. J. et al. "Salt selection and optimisation procedures for pharmaceutical new chemical entities." Organic Process Research & Development, 4.5, 2000.
U.S. Pat. No. 12,551,499, Feb. 17, 2026, Sommadossi et al., U.S. Appl. No. 18/368,959.
US-2026/0035404-A1, Feb. 5, 2026, Moussa, U.S. Appl. No. 19/350,713.
U.S. Appl. No. 19/541,274, Sommadossi et al., filed Feb. 16, 2026.

Compound 1-A

Compound 2

ADVANTAGEOUS ANTI-HCV COMBINATION THERAPY

CROSS REFERENCE TO RELATED APPLICATIONS

This application is a continuation of U.S. application Ser. No. 19/215,054, filed May 21, 2025, which is a continuation of U.S. application Ser. No. 18/540,608, filed Dec. 14, 2023, which is a continuation of International Patent Application No. PCT/US2022/034083, filed in the U.S. Receiving Office on Jun. 17, 2022, which claims the benefit of provisional U.S. Application No. 63/212,047, filed Jun. 17, 2021. The entirety of each of these applications is incorporated herein by reference for all purposes.

FIELD OF THE INVENTION

The present invention is a pharmaceutical combination of a specific NS5B polymerase inhibitor and a specific NS5A inhibitor for advantageous and synergistic HCV therapy.

BACKGROUND OF THE INVENTION

Hepatitis C (HCV) is an RNA single-stranded virus and member of the Hepacivirus genus. It is estimated that the majority of all cases of liver disease are caused by HCV. HCV infection can lead to cirrhosis and liver cancer, and if left to progress, liver failure that may require a liver transplant.

RNA polymerase is a key target for drug development against RNA single stranded viruses. The HCV non-structural protein NS5B RNA-dependent RNA polymerase is a key enzyme responsible for initiating and catalyzing viral RNA synthesis. There are two major subclasses of NS5B inhibitors: nucleoside analogs and non-nucleoside inhibitors (NNIs). Nucleoside analogs are anabolized to active triphosphates that act as alternative substrates for the polymerase. Non-nucleoside inhibitors (NNIs) bind to allosteric regions on the protein. Nucleoside or nucleotide inhibitors mimic natural polymerase substrates and act as chain terminators. They inhibit the initiation of RNA transcription and/or elongation of a nascent RNA chain.

In addition to targeting RNA polymerase, other RNA viral proteins may also be targeted for treatment. Examples of HCV proteins that are additional targets for therapeutic approaches are NS3/4A (a serine protease) and NS5A (a non-structural protein that is an essential component of HCV replicase and exerts a range of effects on cellular pathways).

In December 2013, the first nucleoside NS5B polymerase inhibitor sofosbuvir (Sovaldi®, Gilead Sciences) was approved. Sovaldi® is a uridine phosphoramidate prodrug that is taken up by hepatocytes and undergoes intracellular activation to afford the active metabolite, 2'-deoxy-2'-α-fluoro-β-C-methyluridine-5'-triphosphate.

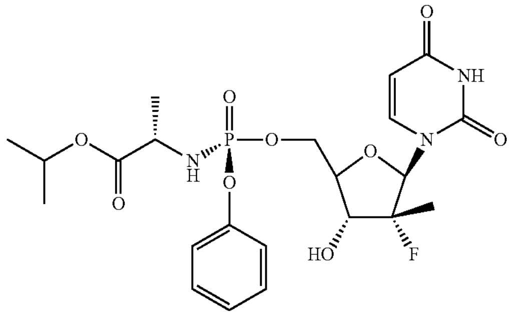

Sovaldi®

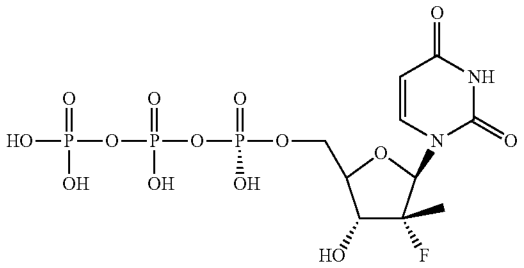

2′-Deoxy-2′-α-fluoro-β-C-methyluridine-5′-triphosphate

Sovaldi® is the first drug that demonstrated safety and efficacy to treat certain types of HCV infection without the need for co-administration of interferon. Sovaldi® is the third drug with breakthrough therapy designation to receive FDA approval.

A number of fixed-dose drug combinations have been approved for the treatment of HCV. In 2014, the U.S. FDA approved Harvoni® (Ledispasvir, a NS5A inhibitor, and sofosbuvir) to treat chronic hepatitis C virus Genotype 1 infection. Harvoni® is the first combination pill approved to treat chronic HCV Genotype 1 infection. It is also the first approved regimen that does not require administration with interferon or ribavirin. In addition, the FDA approved simeprevir (Olysio™) in combination with sofosbuvir (Sovaldi®) as a once-daily, all oral, interferon and ribavirin-free treatment for adults with Genotype 1 HCV infection.

The U.S. FDA also approved AbbVie's VIEKIRA Pak™ in 2014, a multi-pill pack containing dasabuvir (a non-nucleoside NS5B polymerase inhibitor), ombitasvir (a NS5A inhibitor), paritaprevir (a NS3/4A inhibitor), and ritonavir. The VIEKIRA Pak™ can be used with or without ribavirin to treat Genotype 1 HCV infected patients including patients with compensated cirrhosis. VIEKIRA Pak™ does not require interferon co-therapy.

In July 2015, the U.S. FDA approved Technivie™ and Daklinza™ for the treatment of HCV genotype 4 and HCV Genotype 3, respectively. Technivie™ (Ombitasvir/paritaprevir/ritonavir) was approved for use in combination with ribavirin for the treatment of HCV genotype 4 in patients without scarring and cirrhosis and is the first option for HCV-4 infected patients who do not require co-administration with interferon. Daklinza™ was approved for use with Sovaldi® to treat HCV genotype 3 infections. Daklinza™ is the first drug that demonstrated safety and efficacy in treating HCV Genotype 3 without the need for co-administration of interferon or ribavirin. In October 2015, the U.S. FDA warned that HCV treatments Viekira Pak and Technivie can cause serious liver injury primarily in patients with underlying advanced liver disease and required that additional information about safety be added to the label.

In August 2017, Mavyret® (glecaprevir/pibrentasvir) was approved by the U.S. FDA for the treatment of patients with all major genotypes of HCV (genotypes 1-6). The treatment was also approved for patients without cirrhosis or with mild cirrhosis, those on dialysis, and those with a genotype 1 infection who have been previously treated with a regimen containing an NS5A or an NS3/4A inhibitor. Mavyret® is taken as an 8-week course in non-cirrhotic patients who have not been previously treated. In 2019, the FDA approved an 8-week course in patients who have compensated cirrhosis and have not been previously treated.

Along with Mavyret®, Epclusa® is another therapeutic for HCV treatment. Epclusa was developed by Gilead and is a fixed-dose combination therapy containing sofosbuvir (an NS5B inhibitor) and velpatasvir (an NS5A inhibitor). Epclusa® was approved in 2016 for the treatment of adults with chronic HCV infection of all major genotypes of HCV (genotypes 1-6) and is prescribed for a 12-week course in patients without cirrhosis or with compensated cirrhosis. For patients with decompensated cirrhosis, Epclusa® is approved for use in combination with ribavirin.

Other approved therapies for HCV include interferon alpha-2b or pegylated interferon alpha-2b (Pegintron®), which can be administered with ribavirin (Rebetol®), NS3/4A telaprevir (Incivek®, Vertex and Johnson & Johnson), boceprevir (Victrelis™, Merck), simeprevir (Olysio™, Johnson & Johnson), paritaprevir (AbbVie), Ombitasvir (AbbVie), and the NNI Dasabuvir (ABT-333).

United States patents and WO applications that describe nucleoside polymerase inhibitors for the treatment of Flaviviridae, including HCV, include those filed by Idenix Pharmaceuticals (U.S. Pat. Nos. 6,812,219; 6,914,054; 7,105,493; 7,138,376; 7,148,206; 7,157,441; 7,163,929; 7,169,766; 7,192,936; 7,365,057; 7,384,924; 7,456,155; 7,547,704; 7,582,618; 7,608,597; 7,608,600; 7,625,875; 7,635,689; 7,662,798; 7,824,851; 7,902,202; 7,932,240; 7,951,789; 8,193,372; 8,299,038; 8,343,937; 8,362,068; 8,507,460; 8,637,475; 8,674,085; 8,680,071; 8,691,788, 8,742,101, 8,951,985; 9,109,001; 9,243,025; US2016/0002281; US2013/0064794; WO/2015/095305; WO/2015/081133; WO/2015/061683; WO/2013/177219; WO/2013/039920; WO/2014/137930; WO/2014/052638; WO/2012/154321); Merck (U.S. Pat. Nos. 6,777,395; 7,105,499; 7,125,855; 7,202,224; 7,323,449; 7,339,054; 7,534,767; 7,632,821; 7,879,815; 8,071,568; 8,148,349; 8,470,834; 8,481,712; 8,541,434; 8,697,694; 8,715,638, 9,061,041; 9,156,872 and WO/2013/009737); Emory University (U.S. Pat. Nos. 6,348,587; 6,911,424; 7,307,065; 7,495,006; 7,662,938; 7,772,208; 8,114,994; 8,168,583; 8,609,627; US 2014/0212382; and WO2014/1244430); Gilead Sciences/Pharmasset Inc. (U.S. Pat. Nos. 7,842,672; 7,973,013; 8,008,264; 8,012,941; 8,012,942; 8,318,682; 8,324,179; 8,415,308; 8,455,451; 8,563,530; 8,841,275; 8,853,171; 8,871,785; 8,877,733; 8,889,159; 8,906,880; 8,912,321; 8,957,045; 8,957,046; 9,045,520; 9,085,573; 9,090,642; and 9,139,604) and (U.S. Pat. Nos. 6,908,924; 6,949,522; 7,094,770; 7,211,570; 7,429,572; 7,601,820; 7,638,502; 7,718,790; 7,772,208; RE42,015; 7,919,247; 7,964,580; 8,093,380; 8,114,997; 8,173,621; 8,334,270; 8,415,322; 8,481,713; 8,492,539; 8,551,973; 8,580,765; 8,618,076; 8,629,263; 8,633,309; 8,642,756; 8,716,262; 8,716,263; 8,735,345; 8,735,372; 8,735,569; 8,759,510 and 8,765,710); Hoffman La-Roche (U.S. Pat. No. 6,660,721), Roche (U.S. Pat. Nos. 6,784,166; 7,608,599, 7,608,601 and 8,071,567); Alios BioPharma Inc. (8,895,723; 8,877,731; 8,871,737, 8,846,896, 8,772,474; 8,980,865; 9,012,427; US 2015/0105341; US 2015/0011497; US 2010/0249068; US2012/0070411; WO 2015/054465; WO 2014/209979; WO 2014/100505; WO 2014/100498; WO 2013/142159; WO 2013/142157; WO 2013/096680; WO 2013/088155; WO 2010/108135), Enanta Pharmaceuticals (U.S. Pat. Nos. 8,575,119; 8,846,638; 9,085,599; WO 2013/044030; WO 2012/125900), Biota (U.S. Pat. Nos. 7,268,119; 7,285,658; 7,713,941; 8,119,607; 8,415,309; 8,501,699 and 8,802,840), Biocryst Pharmaceuticals (U.S. Pat. Nos. 7,388,002; 7,429,571; 7,514,410; 7,560,434; 7,994,139; 8,133,870; 8,163,703; 8,242,085 and 8,440,813), Alla Chem, LLC (U.S. Pat. No. 8,889,701 and WO 2015/053662), Inhibitex (U.S. Pat. No. 8,759,318 and WO/2012/092484), Janssen Products (U.S. Pat. Nos. 8,399,429; 8,431,588, 8,481,510, 8,552,021, 8,933,052; 9,006,29 and 9,012,428) the University of Georgia Foundation (U.S. Pat. Nos. 6,348,587; 7,307,065; 7,662,938; 8,168,583; 8,673,926, 8,816,074; 8,921,384 and 8,946,244), RFS Pharma, LLC (U.S. Pat. Nos. 8,895,531; 8,859,595; 8,815,829; 8,609,627; 7,560,550; US 2014/0066395; US 2014/0235566; US 2010/0279969; WO/2010/091386 and WO 2012/158811) University College Cardiff Consultants Limited (WO/2014/076490, WO 2010/081082; WO/2008/062206), Achillion Pharmaceuticals, Inc. (WO/2014/169278 and WO 2014/169280), Cocrystal Pharma, Inc. (U.S. Pat. No. 9,173,893), Katholieke Universiteit Leuven (WO 2015/158913), Catabasis (WO 2013/090420) and the Regents of the University of Minnesota (WO 2006/004637).

Elbasvir is an HCV NS5A inhibitor approved by the FDA in 2016 as a component of a fixed-dose combination with grazoprevir, an NS3/4A protease inhibitor. The combination (Zepatier®) is approved for treatment of naïve and previously treated patients and a normal course is 12 weeks. However, in patients with an HCV genotype 1a carrying mutations at positions 28, 30, 31, and/or 93, Zepatier® must be administered for 16 weeks with ribavirin to be effective. Ribavirin carries several FDA boxed warnings, including the risk of hemolytic anemia and teratogenicity.

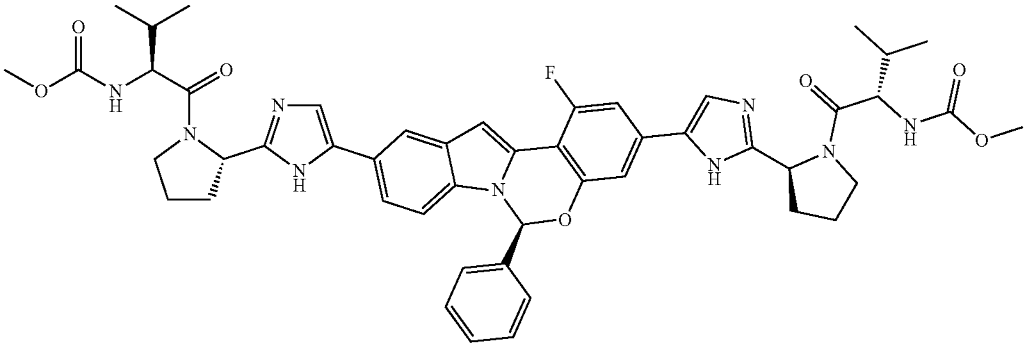

Elbasvir (MK-8742)

Ruzasvir (MK-8408) is an oral, pan genotypic NS5A inhibitor that has been clinically evaluated for the treatment of chronic HCV infection. Ruzasvir has a sub- to low-picomolar affinity for HCV NS5A, across a wide range of HCV genotypes and common clinical mutants, including HCV genotype 1 with Y93H, Q30R, L31V, and Y93C mutations. (Tong et al. "Discovery of Ruzasvir (MK-8408): A Potent, Pan-Genotype HCV NS5A Inhibitor with Optimized Activity against Common Resistance-Associated Polymorphisms" J. Med. Chem. 2017, 60, 290-306). WO 2014/110705 and U.S. Pat. No. 9,555,038 assigned to Merck and Company disclose ruzasvir, pharmaceutical compositions comprising ruzasvir and their methods of use.

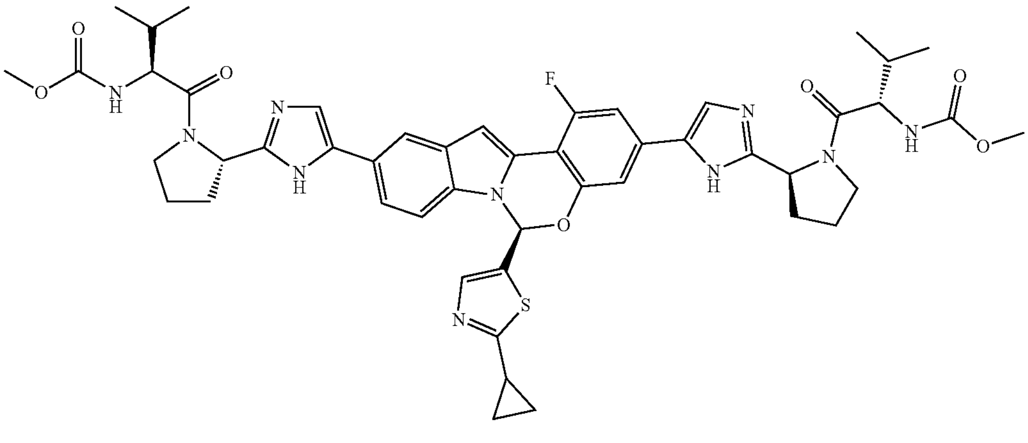

Ruzasvir (MK-8408)

In 2015, Merck, Sharp & Dohme sponsored clinical trials to determine the efficacy of grazoprevir and uprifosbuvir in combination with elbasvir or rusazvir against patients with a range of HCV genotypes. This three-drug regimen achieved sustained virological response after 12 weeks in 85-100% of patients infected with a range of HCV genotypes. (See, for example, NCT02332707, NCT02332720, Lawitz, E. "Safety and efficacy of a fixed-dose combination regimen of grazoprevir, ruzasvir and uprifosbuvir with or without ribavirin in participants with and without cirrhosis with chronic hepatitis C virus genotype 1, 2, or 3 infection (C-CREST-1 and C-CREST-2, part B): two randomized, phase 2, open-label trials" 2017, *Lancet Gastroenterol Hepatol*, doi:10.1016/S2468-1253(17)30163-2). Grazoprevir, one component of the three-drug regimen, is a NS3/4A protease inhibitor. This class of therapeutics can cause drug-drug interactions and elevated hepatic transaminase levels.

In 2016, Merck initiated Phase II open-label clinical trials of ruzasvir and the NS5B inhibitor uprifosbuvir, in a two-drug regimen without the NS3/4A inhibitor. At the studied dose of 60 mg ruzasvir and 450 mg uprifosbuvir per day, the combination was well tolerated but suboptimal efficacy was observed, and the clinical trial was terminated (C-BREEZE 1; NCT02759315). The same combination but in higher doses (180 mg ruzasvir, 450 mg uprifozbuvir), achieved sustained virological responses of over 90% in participants infected with HCV GT1, GT2, GT4, GT5, and GT6. However, the response in participants infected with GT3 was only 73.8%. Furthermore, over 30% of trial participants experienced a drug-related adverse event (C-BREEZE 2; NCT02956629; Lawitz, E. "Efficacy and Safety of Two-Drug Direct-Acting Antiviral Agent Regimen Ruzasvir 180 mg and Uprifosbuvir 450 mg for 12 Weeks in Adults with Chronic Hepatitis C Virus Genotype 1, 2, 3, 4, 5, or 6" 2019, *J Viral Hepat.* 26, 9, 1127-1138). The second, higher dose trial was also terminated.

Atea Pharmaceuticals, Inc. has discovered advantageous nucleotide phosphoramidates of the structure β-D-2'-deoxy-2'-α-fluoro-2'-β-C-substituted-2-modified-$N^6$-(mono- and di-methyl) purine nucleosides for the treatment of HCV. (U.S. Pat. Nos. 9,828,410; 10,000,523; 10,005,811; 10,239,911; 10,519,186; 10,815,266; 10,870,672; 10,870,673;

10,875,885; 10,894,804; and 10,906,928 and US Applications US 2021-0015841; US 2020-0179415). In particular, isopropyl ((S)-(((2R,3R,4R,5R)-5-(2-amino-6-(methylamino)-9H-purin-9-yl)-4-fluoro-3-hydroxy-4-methyltetrahydrofuran-2-yl) methoxy) (phenoxy)phosphoryl)-L-alaninate hemisulfate (AT-527, bemnifosbuvir) has surprising benefits such as high bioavailability, target organ selectivity, and high potency against all genotypes of HCV including GT3 (WO2018/144640).

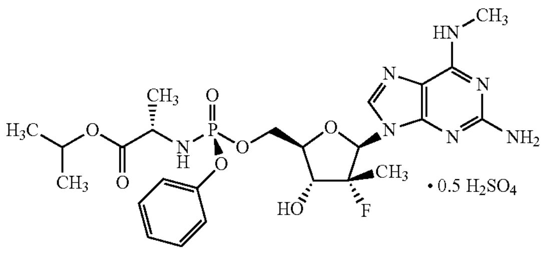

Bemnifosbuvir (AT-527)

In the multidose arm of a Phase I trial, bemnifosbuvir reduced viral load by 4.5 log 10 IU/mL in non-cirrhotic participants and 4.6 log 10 IU/mL in cirrhotic participants. In the cirrhotic patient group, it was equally effective against a range of genotypes, including the hard to treat GT3 (GT1b: 4.0, 4.0, 4.5; GT2: 5.0; GT3: 4.8, 5.2) (NCT03219957; Berliba, E. et al. "Safety, Pharmacokinetics, and Antiviral Activity of AT-527, a Novel Purine Nucleotide Prodrug, in Hepatitis C Virus-Infected Subjects with or without Cirrhosis" 2019, *Antimicrob Agents Chemother,* 63 (12): e01201-19).

In a combination trial of bemnifosbuvir and a first-generation HCV NS5A inhibitor daclatasvir, all ten subjects reached HCV RNA below the lower limit of quantification. 90% of subjects experienced sustained undetectable viral load 12 weeks after treatment (SVR12). The one subject who did not experience SVR12 had a series of resistance-associated variants (NS5A: R30Q, NS5B: L159F/A218S/C316N) (NCT04019717; Mungur, O. et al. "A combination of AT-527, a potent pan-genotypic guanosine nucleotide prodrug and daclatasvir was well-tolerated and effective in HCV-infected subjects", 2020, poster THU438 at The International Liver Congress meeting). However, this trial was terminated.

There remains a strong medical need to develop anti-HCV therapies that are safe, effective and well-tolerated. The need is accentuated by potential drug resistance. The HCV RNA polymerase exhibits a high rate of replication that contributes to the production of potentially resistant single and double point mutations throughout the genome and the maintenance of viral quasispecies. Resistance mutations have been identified both in vitro and in vivo upon treatment with nearly all monotherapies.

It is therefore an object of the present invention to provide compounds, pharmaceutical compositions, methods, and dosage forms to treat and/or prevent infections of HCV.

SUMMARY OF THE INVENTION

The present invention provides the highly synergistic combination of Compound 1, which is a potent pan-genotypic NS5B polymerase inhibitor, or a pharmaceutically acceptable salt thereof (e.g., AT-527, bemnifosbuvir), and Compound 2, which is an NS5A inhibitor, or a pharmaceutically acceptable salt thereof (ruzasvir, MK-8408), for treatment of a hepatitis C infection in a host, typically a human.

Compound 1 is isopropyl((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate:

Compound 1

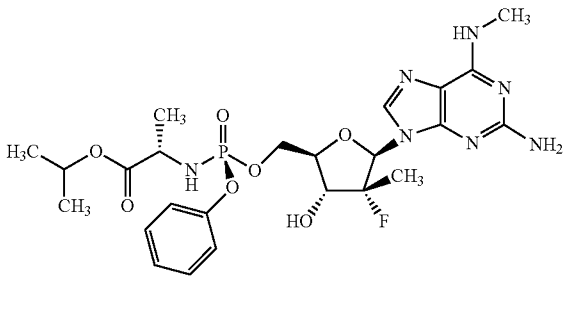

Compound 1 was previously described in U.S. Pat. Nos. 9,828,410; 10,000,523; 10,005,811; 10,239,911; 10,815,266; 10,80,672; 10,870,673; 10,875,885; and PCT Applications WO 2016/21276 and WO 2019/200005 assigned to Atea Pharmaceuticals.

The hemisulfate salt of Compound 1 is shown below as Compound 1-A:

Compound 1-A

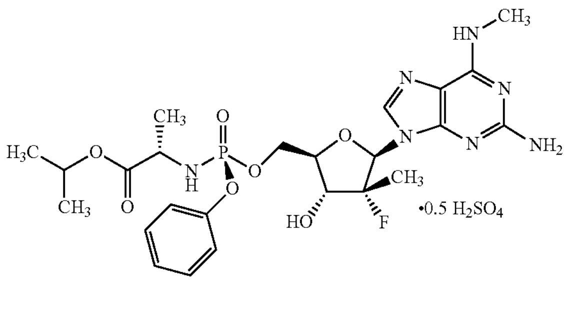

Compound 1-A is disclosed in U.S. Pat. Nos. 10,519,186; 10,906,928; 10,894,804; and PCT Applications WO 2018/144640 and WO 2019/200005 assigned to Atea Pharmaceuticals.

Compound 2 is ruzasvir (dimethyl N,N'-([(6S)-6-(2-Cyclopropyl-1,3-thiazol-5-yl)-1-fluoro-6H-indolo[1,2-c][1,3]benzoxazine-3,10-diyl]bis{1H-imidazole-5,2-diyl-(2S)-pyrrolidine-2,1-diyl[(2S)-3-methyl-1-oxobutane-1,2-diyl]}) dicarbamate):

Compound 2

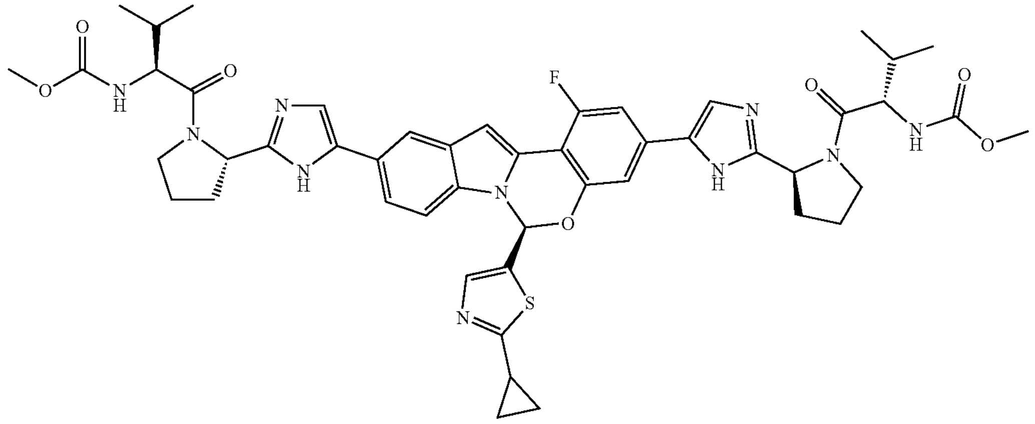

In one embodiment, Compound 2 is an amorphous solid. In yet another embodiment, Compound 2 is a crystalline solid. In one embodiment, Compound 2 is administered as the pharmaceutically acceptable salt thereof. Compound 2 is disclosed in WO 2014/110705 and U.S. Pat. No. 9,555,038.

Previous clinical trials of ruzasvir in combination with the NS5B inhibitor uprifosbuvir were terminated due to lack of efficacy. With this background, it was discovered that the combination of Compound 1 (e.g., AT-527) and ruzasvir are highly synergistic when tested at multiple doses (see Example 30 and FIG. 34). At each combination dose, the expected additive antiviral protection was subtracted from the experimentally observed antiviral activity resulting in a positive value for synergy, a zero value for additive or a negative value for antagonistic. Synergy volumes of −50 to 50 $\mu M^2\%$ are considered additive, 50 to 100 $\mu M^2\%$ indicate slight synergy and volumes greater than 100 $\mu M^2\%$ are considered highly synergistic. The combination of Compound 1 and Compound 2 was evaluated at a range of doses and demonstrates high synergy. A plot of synergy versus dose of each compound is shown in FIG. 34. At 40 nM Compound 1 and 0.008 nM Compound 2, the synergy volume is 255 $\mu M^2\%$, more than five times the cutoff for synergistic effects and in the category of highly synergistic.

This synergistic combination of two anti-HCV agents acting together with distinct mechanisms can be provided systemically, for example, orally, as two or more separate dosage forms or a combined dosage form. If administered separately, the medications should be provided in a manner that the host receives the benefit of both active agents acting in a concerted biological manner, for example, in a manner that achieves an overlapping pharmacokinetic, plasma and/or AUC exposure. In addition to effectively treating the virus, the combination drug therapy is especially advantageous in limiting the emergence of drug resistance.

In one nonlimiting embodiment, Compound 1 is provided as a hemisulfate salt.

In one embodiment, this fixed-dose combination is intended to achieve a sustained viral response in about or less than 12 weeks, for example about or less than 10 weeks, 8 weeks or 6 weeks or less. In addition to effectively treating the virus, the combination drug therapy is helpful in limiting the emergence of drug resistance.

The weight of active compound in the dosage form described herein is with respect to either the free form or the salt form of the compound unless otherwise specifically indicated. For example, 600 mg of Compound 1-A is the equivalent of 550 mg of Compound 1.

In a typical embodiment, Compound 1 is administered in a dosage of between about 300 and 1000 mg (with or without regard to the weight of the salt), more typically between 400 or 500 and 600 or 800 mg, or between 500 and 750 mg. In certain embodiments, Compound 1 is administered in a dosage of between about 500 and about 1,500 mg. In one example 550 mg of Compound 1 is administered as a dosage of about 600 mg of Compound 1-A. In an alternative embodiment, 1,100 mg of Compound 1 is administered as a dosage of about 1,200 mg Compound 1-A.

In a typical embodiment, Compound 2 or its pharmaceutically acceptable salt is administered in a dosage of about between 20 and 500 mg, more typically between 40 and 250 mg, for example, including but not limited to at least 60, 70, 75, 100, 125, 150, 180, 200, 225, 250, 270, 300, 350 or 400 mg in the dosage form. In certain embodiments, Compound 2 is administered in a dosage form that includes about at least 90, 180, 270 or 360 mg.

In certain embodiments, the combination includes 550 mg of Compound 1-A and about at least 90, 180, 270 or 360 mg of Compound 2 or its pharmaceutically acceptable salt (for example 180 mg). In certain embodiments, this combination is provided once, twice or three times a day.

The combined therapeutic can be administered once, twice or three times or more a day, as recommended by the healthcare practitioner. In certain embodiments, the combined therapeutic is provided once a day. In other embodiments, the combined therapeutic is provided twice a day. In yet another embodiment, the combined therapeutic is provided three times a day.

In certain embodiments, Compound 1-A is provided in a solid dosage of 600 mg per day and Compound 2 is provided in the combined or a separate dosage form at 180 mg/day, which together can be given 1, 2, or 3 times a day.

In various aspects, Compound 1 or its pharmaceutically acceptable salt and Compound 2 or its pharmaceutically acceptable salt are formulated together in a single dosage form or provided in several dosage forms (e.g., two or more dosages, each of which has both actives or wherein one dosage has one active agent and the other dosage has the other active agent). In an alternative embodiment, Compound 1 or its pharmaceutically acceptable salt and Compound 2 or its pharmaceutically acceptable salt, are provided in separate dosage forms but in a manner that they can act in concert, for example, synergistically, in the host. For example, the separate dosage forms can be administered such that there is an overlapping AUC, or other pharmacokinetic parameter that indicates that the actives are working together against the virus.

In one aspect of the present invention, Compound 1 and Compound 2 are provided in separate pills and are administered at approximately the same time, or simultaneously, over the course of a day.

The combination of Compound 1 (or a pharmaceutically acceptable salt thereof, for example Compound 1-A) and Compound 2 (or a pharmaceutically acceptable salt thereof) can also be used to treat related conditions such as anti-HCV antibody positive and antigen positive conditions, viral-based chronic liver inflammation, liver cancer resulting from advanced hepatitis C (hepatocellular carcinoma (HCC)), cirrhosis, chronic or acute hepatitis C, fulminant hepatitis C, chronic persistent hepatitis C and anti-HCV-based fatigue.

In certain embodiments, Compound 1 or a pharmaceutically acceptable salt thereof, for example Compound 1-A, and Compound 2 or a pharmaceutically acceptable salt thereof are administered for up to 24 weeks, up to 12 weeks, for up to 10 weeks, for up to 8 weeks, for up to 6 weeks, or for up to 4 weeks. In alternative embodiments, Compound 1 or a pharmaceutically acceptable salt thereof, for example Compound 1-A, and Compound 2 or a pharmaceutically acceptable salt thereof are administered for at least 4 weeks, for at least 6 weeks, for at least 8 weeks, for at least 10 weeks, for at least 12 weeks, or for at least 24 weeks. In certain embodiments, Compound 1 or a pharmaceutically acceptable salt thereof and Compound 2 or a pharmaceutically acceptable salt thereof are administered at least once a day or every other day. In alternative embodiments, Compound 1 or a pharmaceutically acceptable salt thereof and Compound 2 or a pharmaceutically acceptable salt thereof are administered twice a day. In alternative embodiments, Compound 1 or a pharmaceutically acceptable salt thereof and Compound 2 or a pharmaceutically acceptable salt thereof are administered three times a day or more.

In certain embodiments, the patient is non-cirrhotic. In certain embodiments, the patient is cirrhotic. In a further embodiment, the cirrhotic host has compensated cirrhosis. In an alternative embodiment, the cirrhotic host has decompensated cirrhosis. In one embodiment, the host has Child-Pugh A cirrhosis. In an alternative embodiment, the host has Child-Pugh B or Child-Pugh C cirrhosis.

The above combinations can also be used to treat the range of HCV genotypes. At least six distinct genotypes of HCV, each of which have multiple subtypes, have been identified globally. Genotypes 1-3 are prevalent worldwide and Genotypes 4, 5, and 6 are more limited geographically. Genotype 4 is common in the Middle East and Africa. Genotype 5 is mostly found in South Africa. Genotype 6 predominately exists in Southeast Asia. Although the most common genotype in the United States is Genotype 1, defining the genotype and subtype can assist in treatment type and duration. For example, different genotypes respond differently to different medications. Optimal treatment times vary depending on the genotype infection. Within genotypes, subtypes, such as Genotype 1a and Genotype 1b, may respond differently to treatment as well. Infection with one type of genotype does not preclude a later infection with a different genotype.

In one embodiment, a combination of Compound 1 or a pharmaceutically acceptable salt thereof, for example Compound 1-A, and Compound 2 or a pharmaceutically acceptable salt thereof are used to treat HCV Genotype 1, HCV Genotype 2, HCV Genotype 3, HCV Genotype 4, HCV Genotype 5, or HCV Genotype 6. In one embodiment, Compound 1 or a pharmaceutically acceptable salt thereof and Compound 2 or a pharmaceutically acceptable salt thereof are used to treat HCV Genotype 1a. In one embodiment, Compound 1 or a pharmaceutically acceptable salt thereof and Compound 2 or a pharmaceutically acceptable salt thereof are used to treat HCV Genotype 1b. In one embodiment, Compound 1 or a pharmaceutically acceptable salt thereof and Compound 2 or a pharmaceutically acceptable salt thereof are used to treat HCV Genotype 2a. In one embodiment, Compound 1 or a pharmaceutically acceptable salt thereof and Compound 2 or a pharmaceutically acceptable salt thereof are used to treat HCV Genotype 2b. In one embodiment, Compound 1 or a pharmaceutically acceptable salt thereof and Compound 2 or a pharmaceutically acceptable salt thereof are used to treat HCV Genotype 3a. In one embodiment, Compound 1 or a pharmaceutically acceptable salt thereof and Compound 2 or a pharmaceutically acceptable salt thereof are used to treat HCV Genotype 3b. In one embodiment, Compound 1 or a pharmaceutically acceptable salt thereof and Compound 2 or a pharmaceutically acceptable salt thereof are used to treat HCV Genotype 4a. In one embodiment, Compound 1 or a pharmaceutically acceptable salt thereof and Compound 2 or a pharmaceutically acceptable salt thereof are used to treat HCV Genotype 4d. In one embodiment, Compound 1 or a pharmaceutically acceptable salt thereof and Compound 2 or a pharmaceutically acceptable salt thereof are used to treat HCV Genotype 5a. In one embodiment, Compound 1 or a pharmaceutically acceptable salt thereof and Compound 2 or a pharmaceutically acceptable salt thereof are used to treat HCV Genotype 6a. In one embodiment, Compound 1 or a pharmaceutically acceptable salt thereof and Compound 2 or a pharmaceutically acceptable salt thereof are used to treat HCV Genotype 6b, 6c, 6d, 6e, 6f, 6g, 6h, 6i, 6j, 6k, 6l, 6m, 6n, 6o, 6p, 6q, 6r, 6s, 6t, or 6u.

The invention also includes the specific combination and dosage forms wherein Compound 1-A may be in the form of an amorphous or crystalline salt and, independently, Compound 2 may be crystalline or amorphous.

The present invention thus includes at least the following embodiments:

(a) An effective anti-HCV combination of Compound 1 or a pharmaceutically acceptable salt thereof and Compound 2 or a pharmaceutically acceptable salt thereof;
(b) An effective solid dosage form of a combination of Compound 1 or a pharmaceutically acceptable salt thereof and Compound 2 or a pharmaceutically acceptable salt thereof;
(c) Embodiment (a) or (b) wherein Compound 1 is Compound 1-A;
(d) Embodiments (a)-(c), wherein a third anti-HCV effective agent is used in the combination;
(e) Embodiment (d) wherein the third anti-HCV effective agent acts through a different mechanism than Compound 1, Compound 1-A, or Compound 2;
(f) A pharmaceutical composition comprising the combination of any one of embodiments (a)-(e) in a pharmaceutically acceptable excipient.
(g) Embodiment (f) wherein the combination is in the form of a combined pharmaceutical composition form;
(h) Embodiment (f) wherein the combination is in the form of separate pharmaceutical dosage forms for each active agent, for use in a concerted fashion;
(i) The pharmaceutical dosage forms of (f)-(h) which are suitable for oral delivery;

(j) The dosage form of (i) that is in the form of a pill, tablet, or gel;

(k) The pharmaceutical dosage forms of (f)-(h) which are suitable for parental delivery;

(l) The pharmaceutical dosage forms of (f)-(h) which are suitable for intravenous delivery;

(m) Use of an effective combination of any one of embodiments (a)-(l) in the manufacture of a medicament for treatment of a hepatitis C virus infection in a patient in need thereof, (n) A method for manufacturing a medicament intended for the therapeutic use for treating a hepatitis C virus infection in a patient in need thereof, characterized in that an effective combination of any one of embodiments (a)-(l) is used in the manufacture;

(o) A method for treating a hepatitis C virus infection comprising administering to a patient in need thereof an effective combination of any one of embodiments (a)-(l);

(p) A method for curing a hepatitis C virus infection comprising administering to a patient in need thereof an effective combination of any one of embodiments (a)-(l);

(q) A method for prophylactically treating a patient at risk of a hepatitis C virus infection comprising administering to the patient in need thereof an effective combination of any one of embodiments (a)-(l);

(r) A method for treating conditions related to a hepatitis C viral infection selected from viral-based chronic liver inflammation, liver cancer resulting from advanced hepatitis C (hepatocellular carcinoma (HCC)), cirrhosis, chronic or acute hepatitis C, fulminant hepatitis C, chronic persistent hepatitis C and anti-HCV-based fatigue comprising administering to the patient in a patient in need thereof an effective combination of any one of embodiments (a)-(l);

(s) Any of embodiments (m)-(r) wherein the patient is cirrhotic.

(t) Any of embodiments (m)-(r) wherein the patient is non-cirrhotic.

(u) Any of embodiments (m)-(t) wherein the HCV infection is genotype 1.

(v) Any of embodiments (m)-(t) wherein the HCV infection is genotype 2.

(w) Any of embodiments (m)-(t) wherein the HCV infection is genotype 3.

(x) Any of embodiments (m)-(t) wherein the HCV infection is genotype 4.

(y) Any of embodiments (m)-(t) wherein the HCV infection is genotype 5.

(z) Any of embodiments (m)-(t) wherein the HCV infection is genotype 6.

(aa) The combination of (a)-(l) for use to treat HCV or an HCV-related condition.

In the present invention, Compound 1-A can be provided in the synergistic combination therapy as a crystalline form, or alternatively, a crystalline form can be used in a spray dry manufacturing procedure. FIGS. 1-15 depict the characterization of the physical form of Compound 1-A by XRPD, DSC, and TGA. Compound 1-A can be isolated in a crystalline form which may facilitate synthesis and processing.

The pharmacokinetics of Compound 1-A are important to the success of the combination therapy. FIG. 16 depicts the advantageous biodistribution properties of Compound 1-A. The compound concentrates in the liver, the target organ for HCV infection, over the heart. Because the liver concentration is high, it is advantageous for liver combination therapy.

Likewise, FIGS. 17, 18, and 21-23 depict the pharmacokinetic properties of Compound 1-A and major metabolites. Although Compound 1-A is metabolized within 8 hours, active metabolites are present for up to 24 hours. During the 24 hour period in which the metabolites are present, a suppression of HCV viral RNA is observed. At doses of 300 mg, the plasma concentrations of Compound 1-A metabolites are higher than the $EC_{95}$ of HCV GT1b. These pharmacokinetics and pharmacodynamics assist with successful combination therapy.

FIGS. 19 and 20 demonstrate the pan genotypic potency of Compound 1-A. Pan-genotypic activity in this combination therapy can prevent the development of resistant HCV mutants.

FIGS. 25-31 depict Compound 1 metabolite and HCV viral RNA levels in cirrhotic hosts who were administered Compound 1. FIG. 27 highlights that in the hosts, Compound 1 is equally effective in cirrhotic patients as in non-cirrhotic patients. The combination of Compound 1, or a pharmaceutically acceptable salt thereof, and Compound 2, or a pharmaceutically acceptable salt thereof may be used to treat HCV in both cirrhotic and non-cirrhotic patients. The pharmaceutical composition comprising Compound 1 or a pharmaceutically acceptable salt thereof and Compound 2 or a pharmaceutically acceptable salt thereof may be formulated as an oral dosage form. FIG. 32 depicts an example process by which tablets for oral dosing may be prepared. Compound 1 or a pharmaceutically acceptable salt thereof and Compound 2 or a pharmaceutically acceptable salt thereof, are combined together, sieved, blended and tableted to provide the combination as an oral dosage form.

Figure 5A:
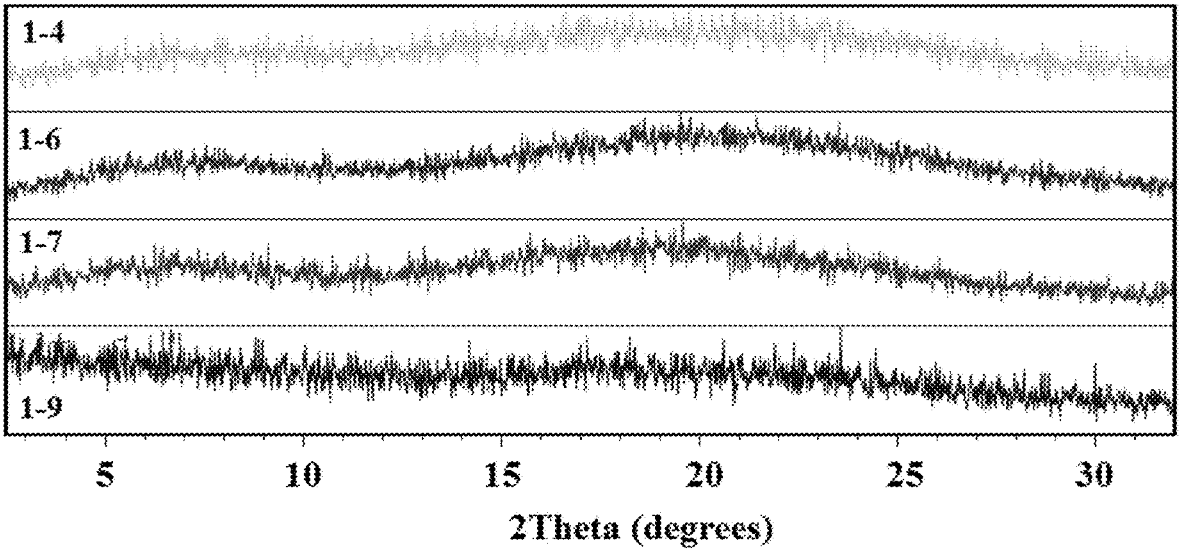

FIG. 5A is an overlay of XRPD diffractograms of samples 1-4, 1-6, 1-7, and 1-9 after storing at 25° C. and 60% relative humidity for 14 days as described in Example 4. The x-axis is 2Theta measured in degrees and the y-axis is intensity measured in counts.

Figure 5B:
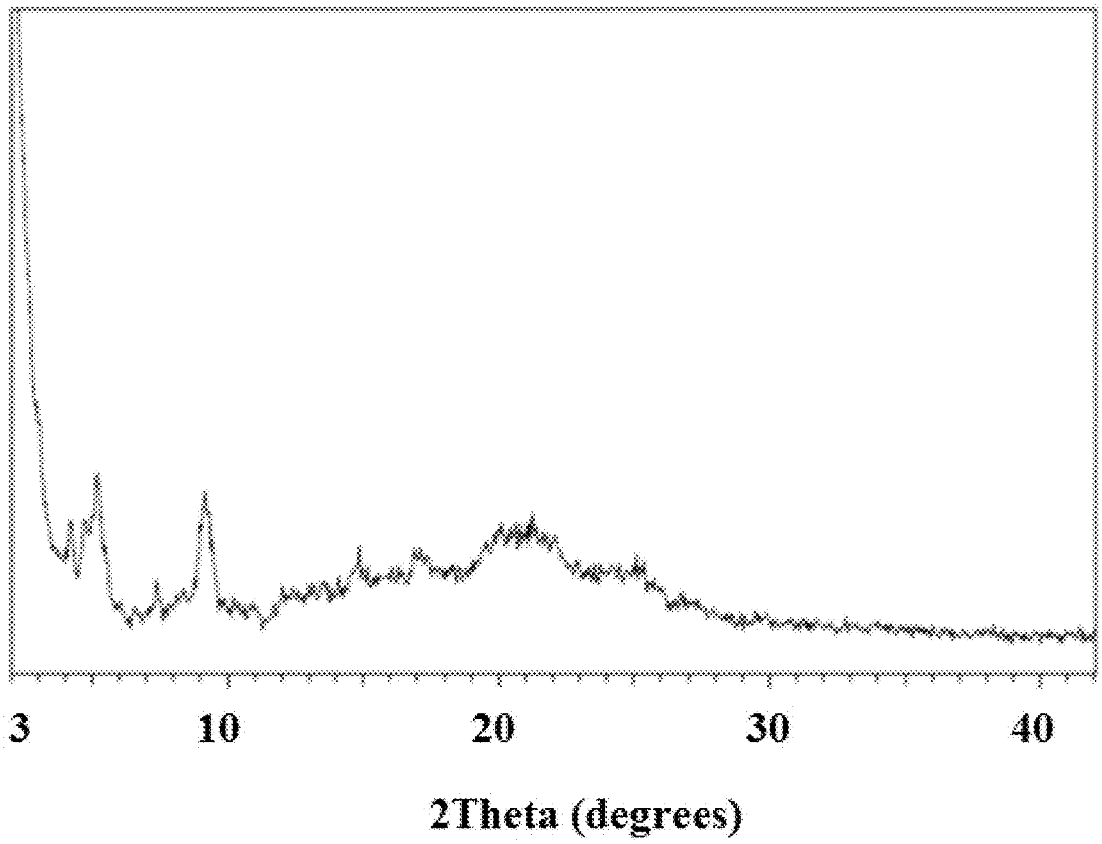

FIG. 5B is the XRPD pattern of amorphous Compound 1-A (sample 1-3) as described in Example 5. The x-axis is 2Theta measured in degrees and the y-axis is intensity measured in counts.

Figure 6A:
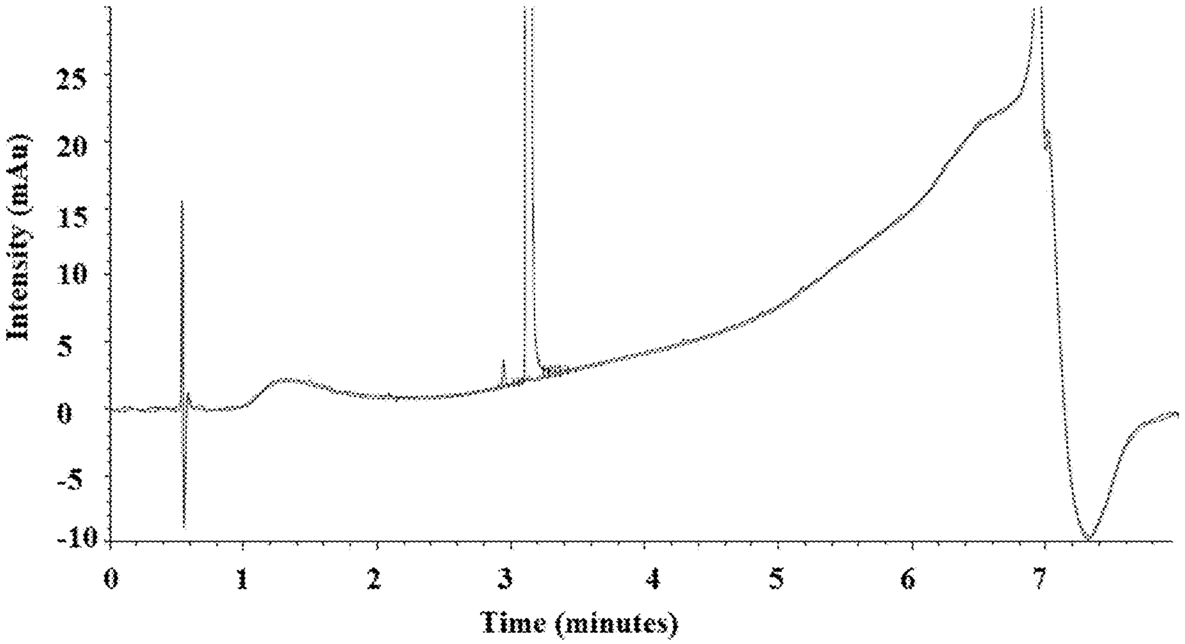

FIG. 6A is the HPLC chromatograph of amorphous Compound 1-A (sample 1-3) to determine purity as described in Example 5. The purity of the sample was 99.6%. The x-axis is time measured in minutes and the y-axis is intensity measured in counts.

Figure 6B:
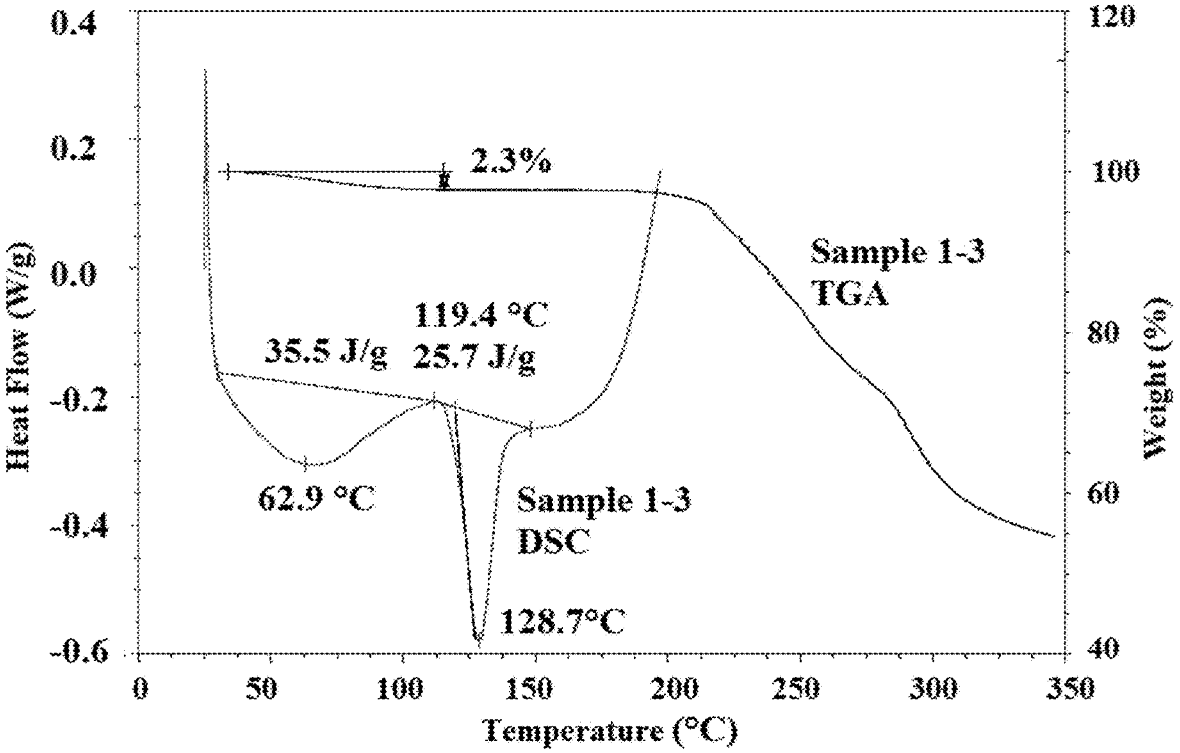

FIG. 6B is a DSC and TGA graph for amorphous Compound 1-A (sample 1-3) prior to any stability studies for characterization purposes as described in Example 5. The x-axis is temperature measured in ° C., the left y-axis heat flow measured in (W/g), and the right y-axis is weight measured in percent.

Figure 7A:
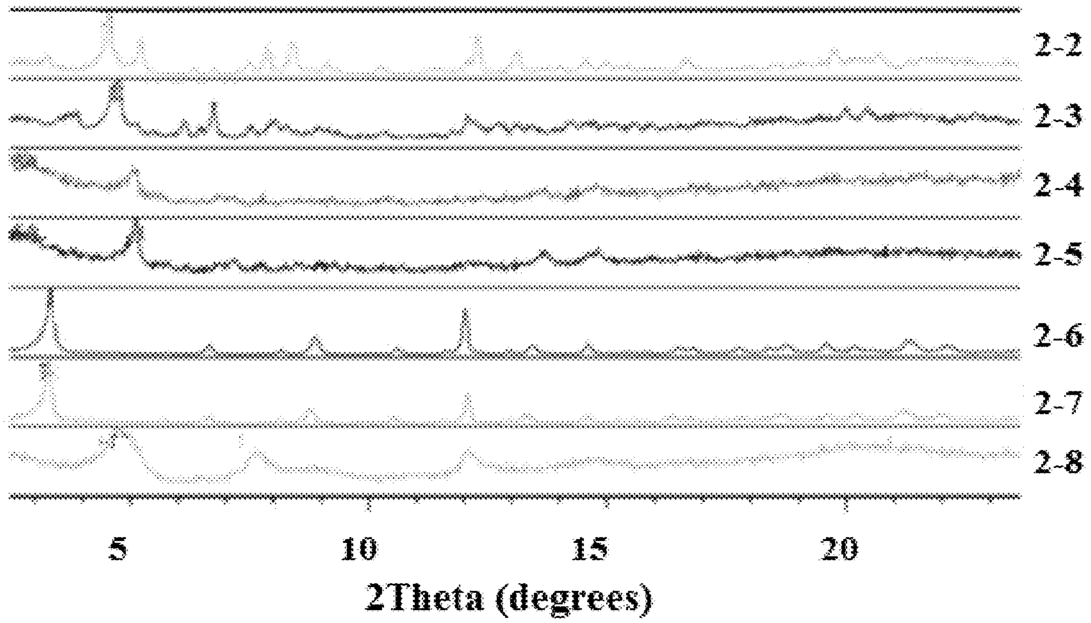

FIG. 7A is an overlay of XRPD diffractograms of crystalline samples (samples 2-2, 2-6, and 2-7) and poorly crystalline samples (samples 2-3, 2-4, 2-5, and 2-8) identified from the crystallizations of Compound 1-A (Example 6). The x-axis is 2Theta measured in degrees and the y-axis intensity measured in counts.

Figure 7B:
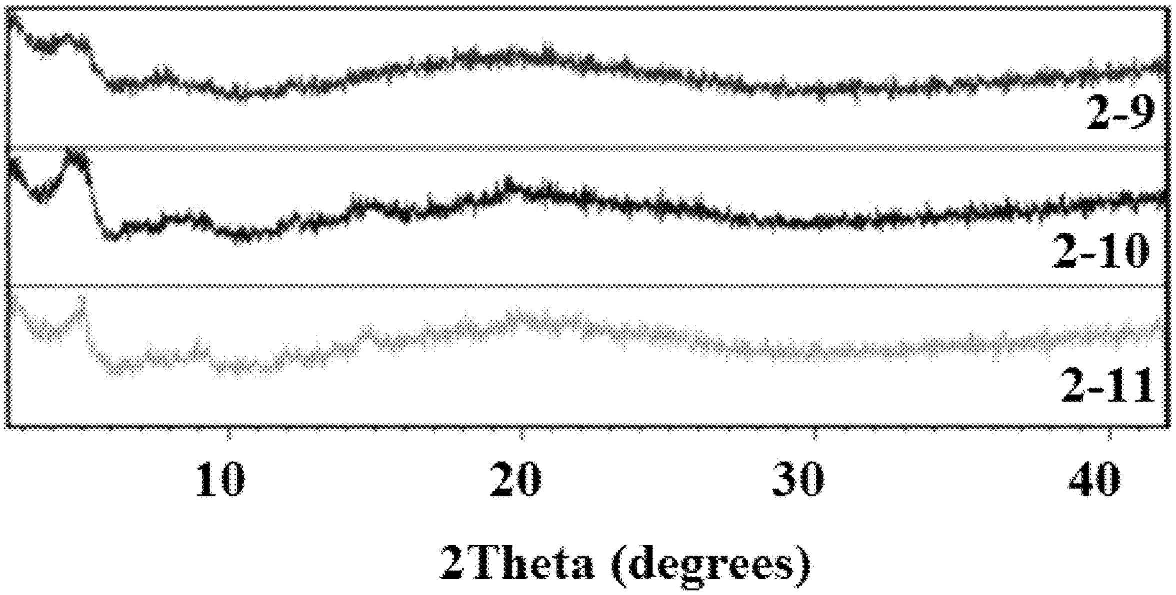

FIG. 7B is an overlay of XRPD diffractograms of amorphous samples (samples 2-9, 2-10, and 2-11) identified from the crystallizations of Compound 1-A (Example 6). The x-axis is 2Theta measured in degrees and the y-axis intensity measured in counts.

Figure 8A:
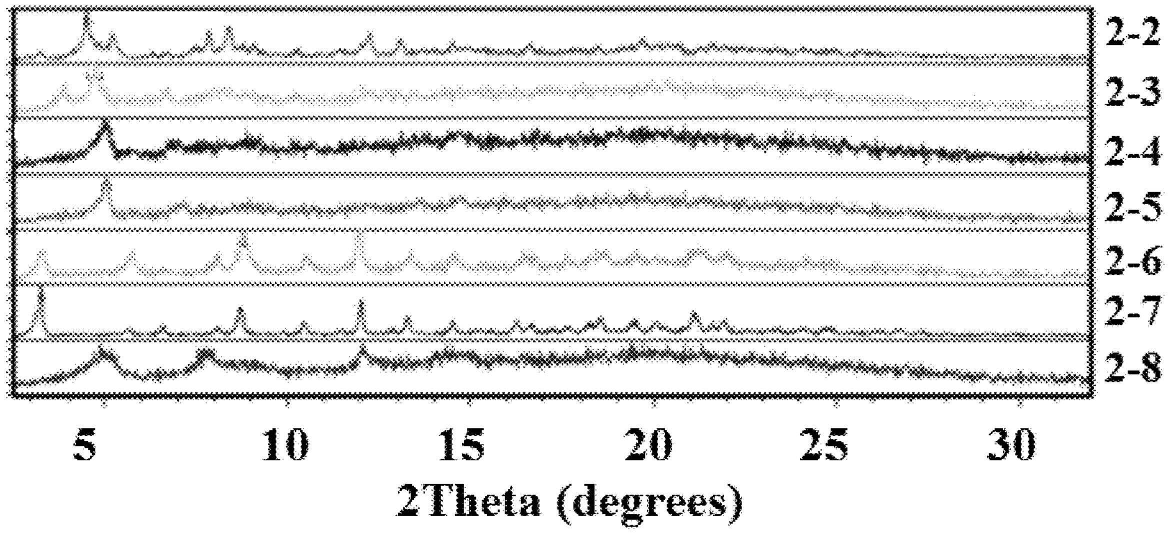

FIG. 8A is an overlay of XRPD diffractograms of samples (samples 2-2, 2-3, 2-4, 2-5, 2-6, 2-7 and 2-8) after 6 days storage at 25° C. and 60% relative humidity (Example 6). The x-axis is 2Theta measured in degrees and the y-axis intensity measured in counts.

Figure 8B:
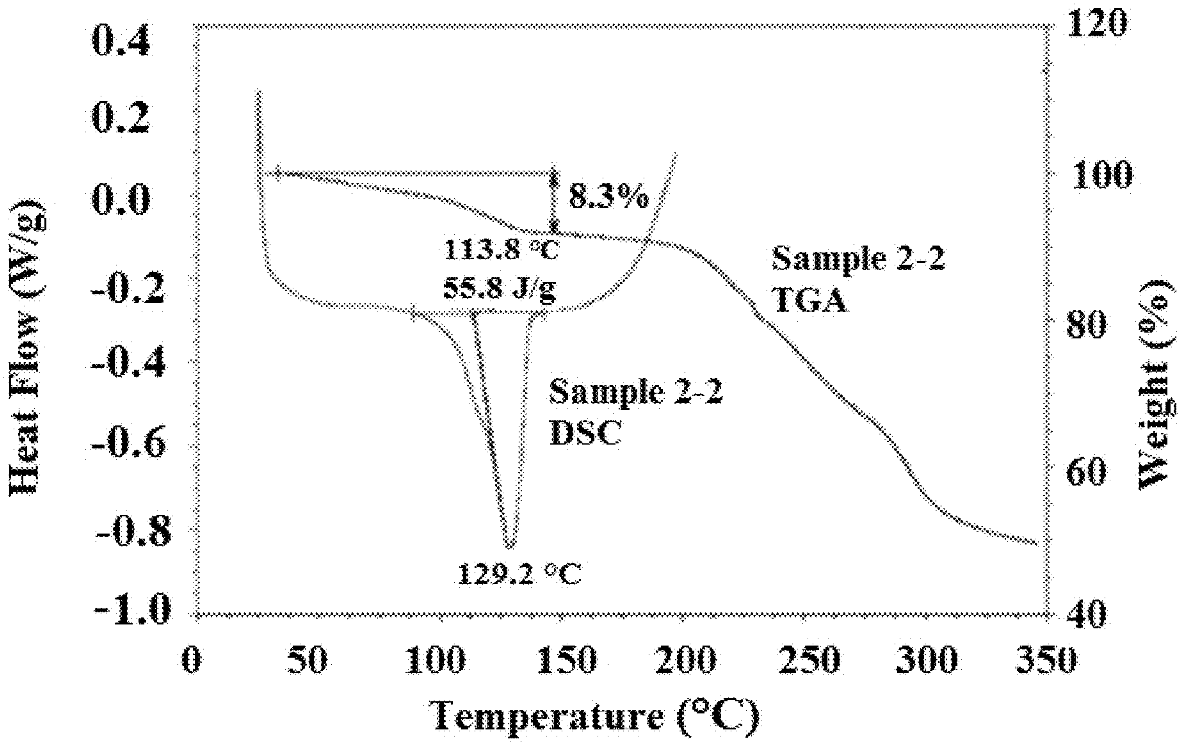

FIG. 8B is a DSC and TGA graph for sample 2-2 (Example 6). The x-axis is temperature measured in ° C., the left y-axis heat flow measured in (W/g), and the right y-axis is weight measured in percent. Experimental procedures for DSC and TGA collection are given in Example 2.

Figure 9A:
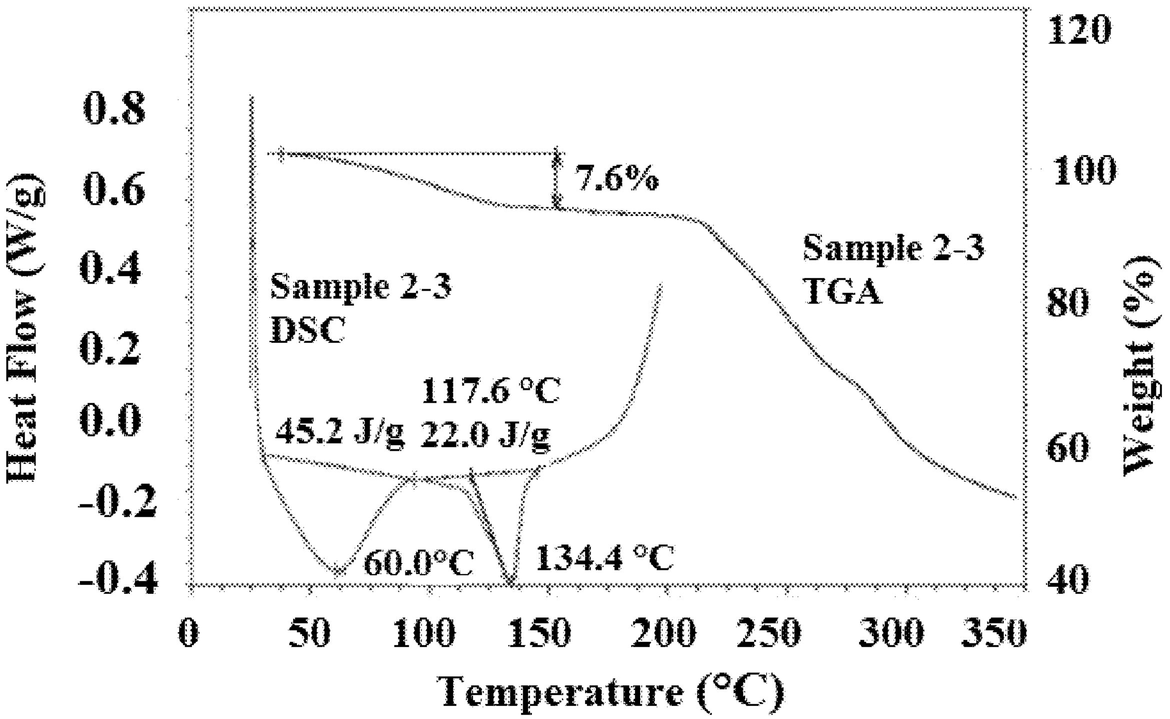

FIG. 9A is a DSC and TGA graph for sample 2-3 (Example 6). The x-axis is temperature measured in ° C., the left y-axis heat flow measured in (W/g), and the right y-axis is weight measured in percent. Experimental procedures for DSC and TGA collection are given in Example 2.

Figure 9B:
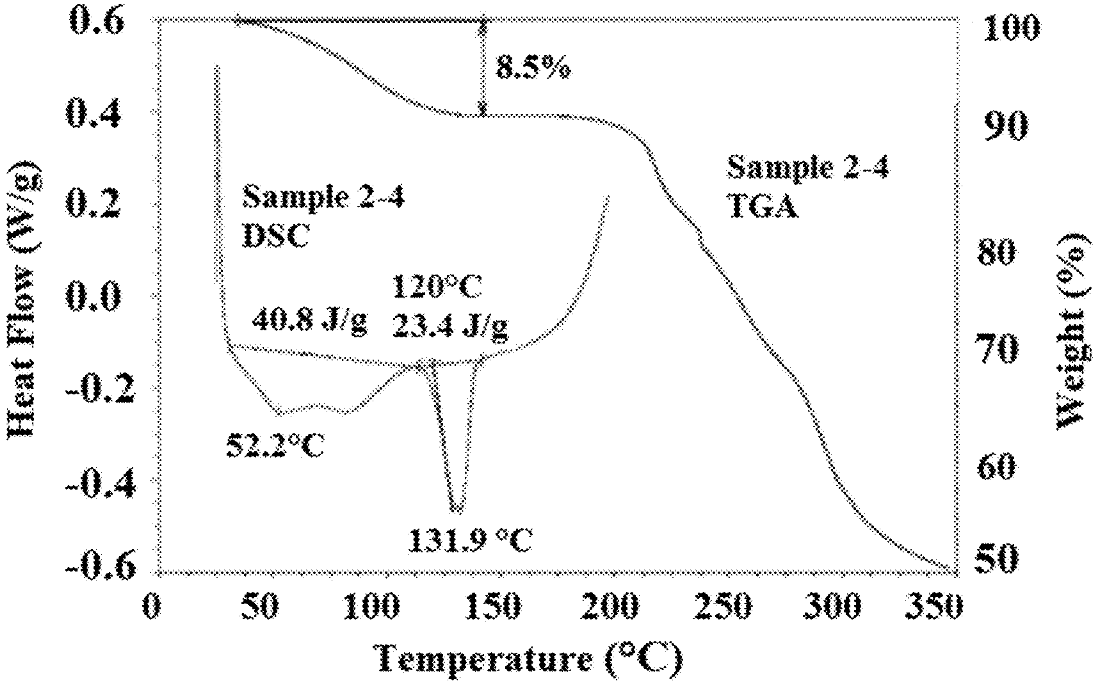

FIG. 9B is a DSC and TGA graph for sample 2-4 (Example 6). The x-axis is temperature measured in ° C., the left y-axis heat flow measured in (W/g), and the right y-axis is weight measured in percent. Experimental procedures for DSC and TGA collection are given in Example 2.

Figure 10A:
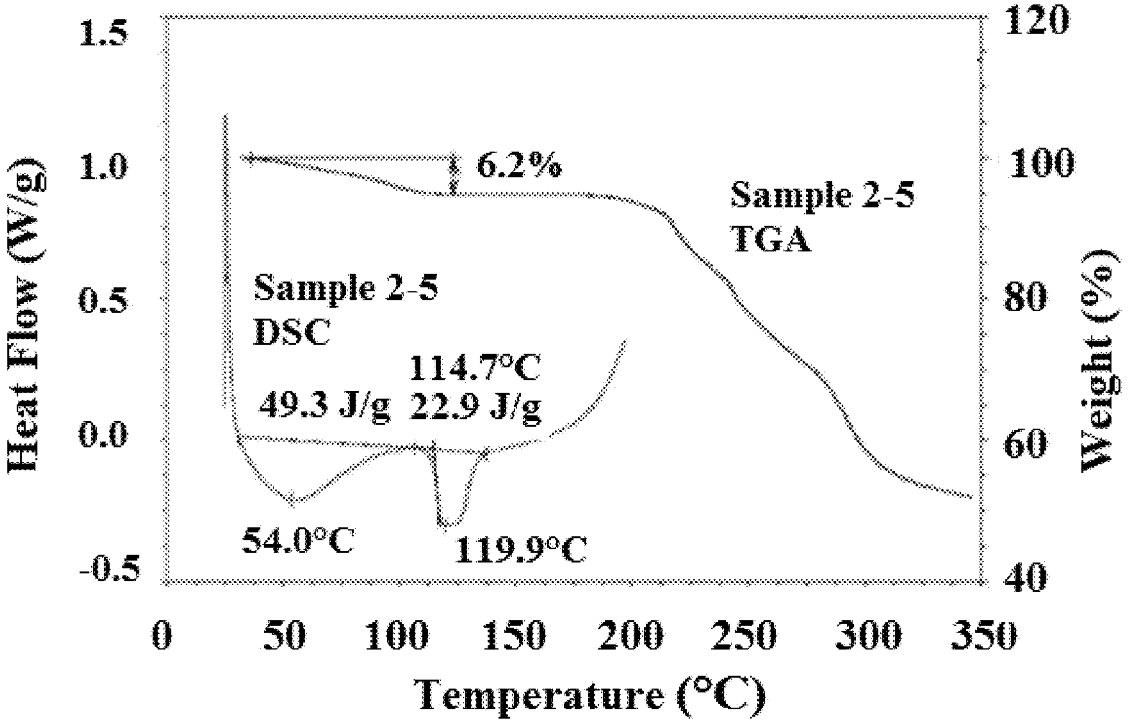

FIG. 10A is a DSC and TGA graph for sample 2-5 (Example 6). The x-axis is temperature measured in ° C., the left y-axis heat flow measured in (W/g), and the right y-axis is weight measured in percent. Experimental procedures for DSC and TGA collection are given in Example 2.

Figure 10B:
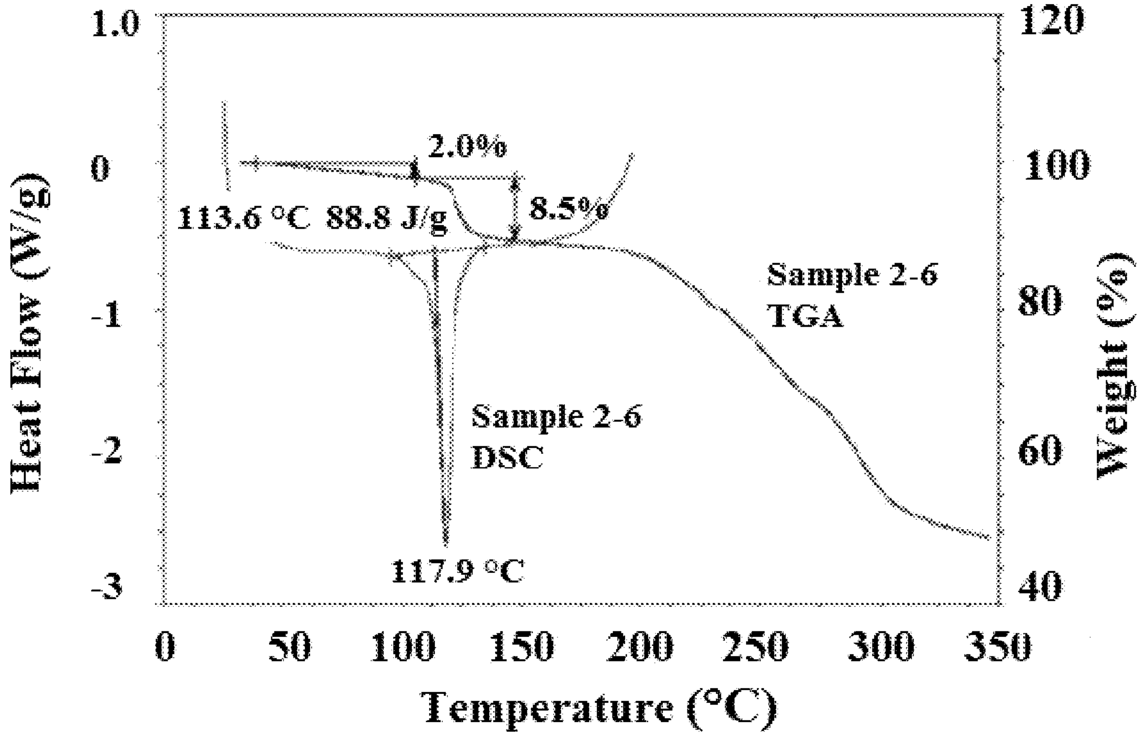

FIG. 10B is a DSC and TGA graph for sample 2-6 (Example 6). The x-axis is temperature measured in ° C., the left y-axis heat flow measured in (W/g), and the right y-axis is weight measured in percent. Experimental procedures for DSC and TGA collection are given in Example 2.

Figure 11A:
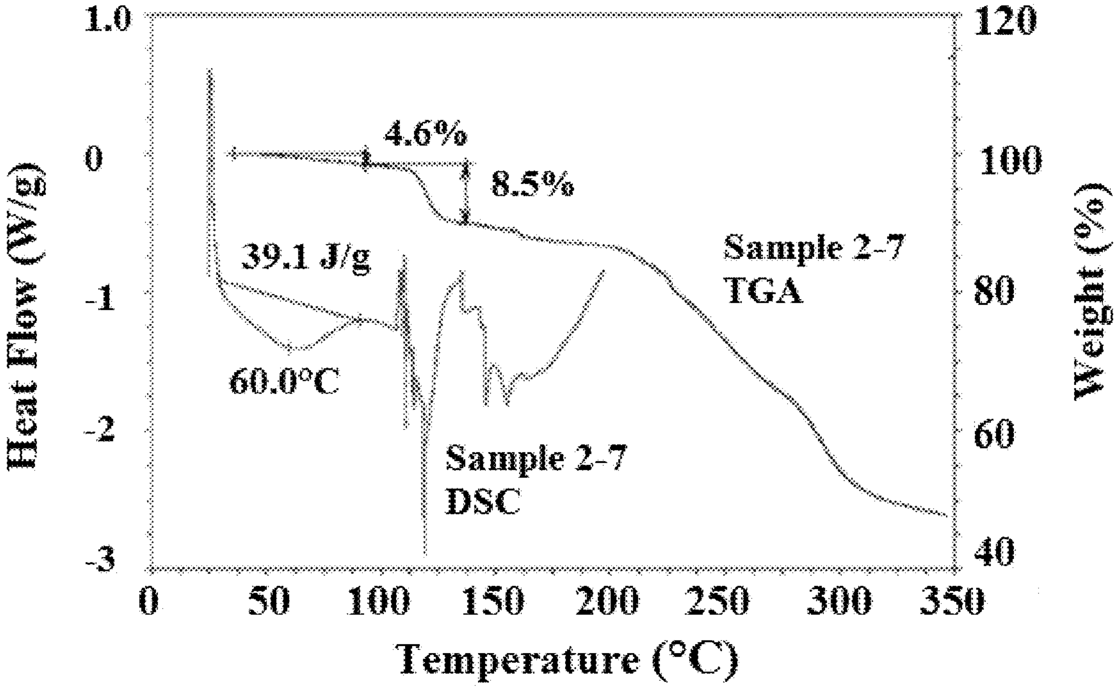

FIG. 11A is a DSC and TGA graph for sample 2-7 (Example 6). The x-axis is temperature measured in ° C., the left y-axis heat flow measured in (W/g), and the right y-axis is weight measured in percent. Experimental procedures for DSC and TGA collection are given in Example 2.

Figure 11B:
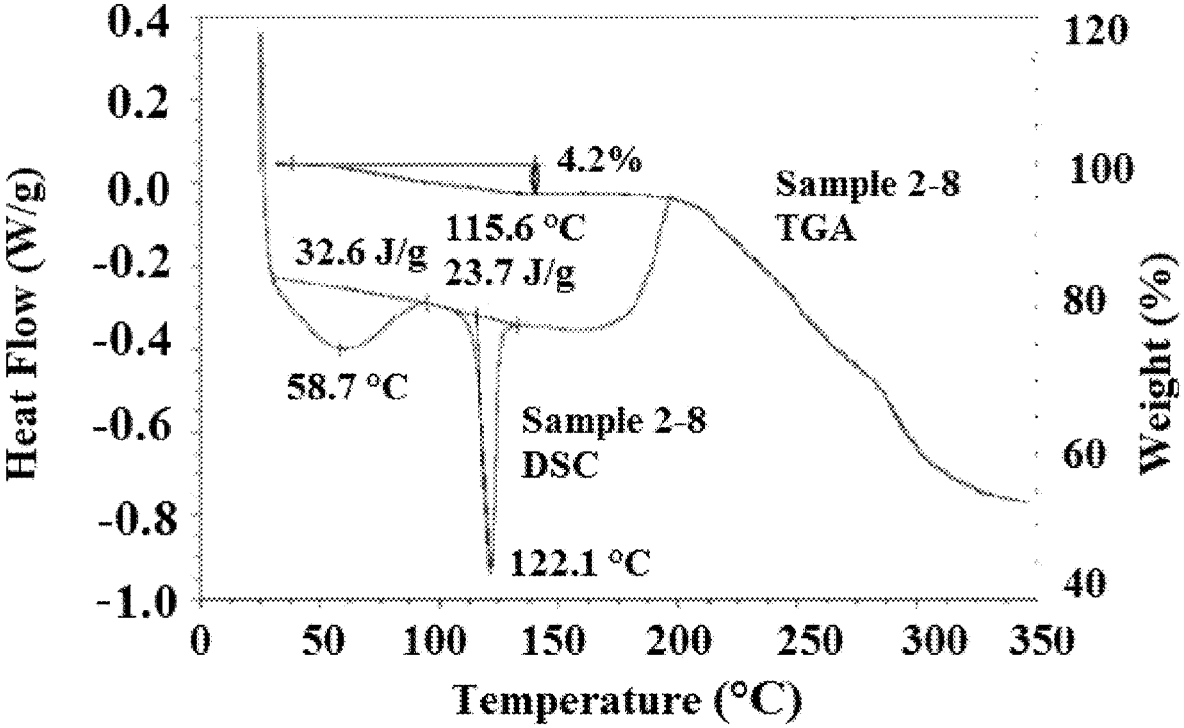

FIG. 11B is a DSC and TGA graph for sample 2-8 (Example 6). The x-axis is temperature measured in ° C., the left y-axis heat flow measured in (W/g), and the right y-axis is weight measured in percent. Experimental procedures for DSC and TGA collection are given in Example 2.

Figure 12A:
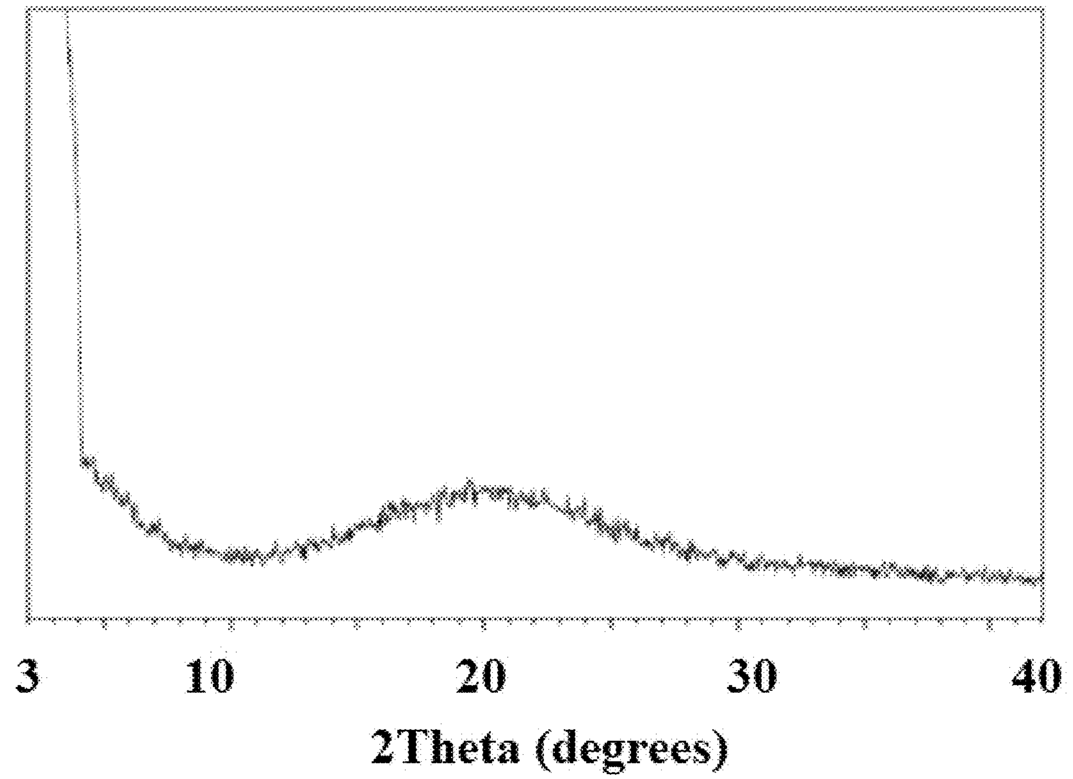

FIG. 12A is the XRPD pattern of amorphous Compound 1-B (sample 3-12) as discussed in Example 7. The x-axis is 2Theta measured in degrees and the y-axis is intensity measured in counts. No crystallization of a malonate salt was observed regardless of the solvent used.

Figure 12B:
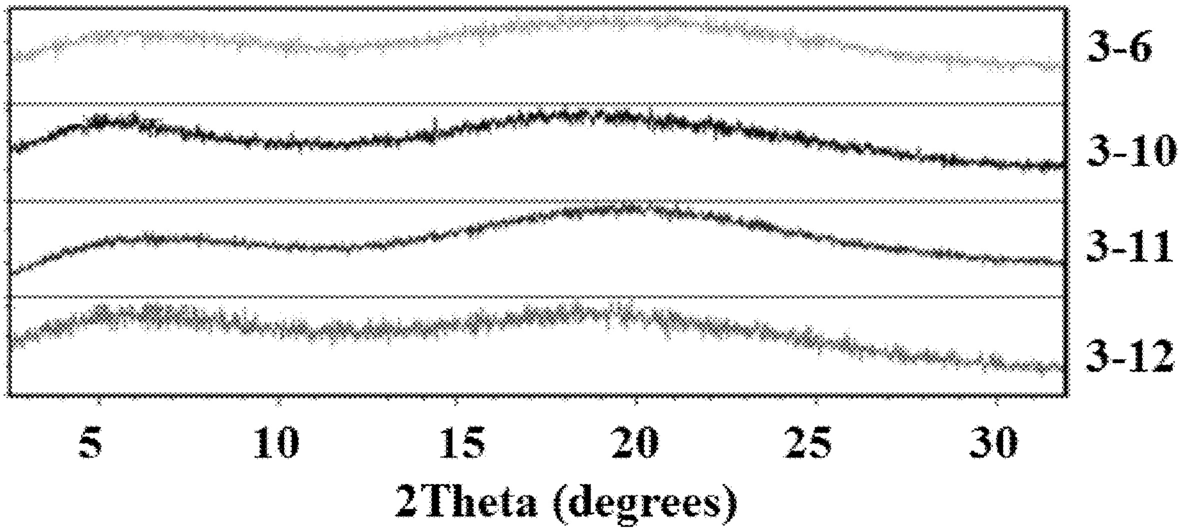

FIG. 12B is an overlay of XRPD diffractograms of amorphous samples (samples 3-6, 3-10, 3-11, and 3-12) identified from the attempted crystallization of compound 1 with malonate salt (Example 7). The x-axis is 2Theta measured in degrees and the y-axis is intensity measured in counts.

Figure 13A:
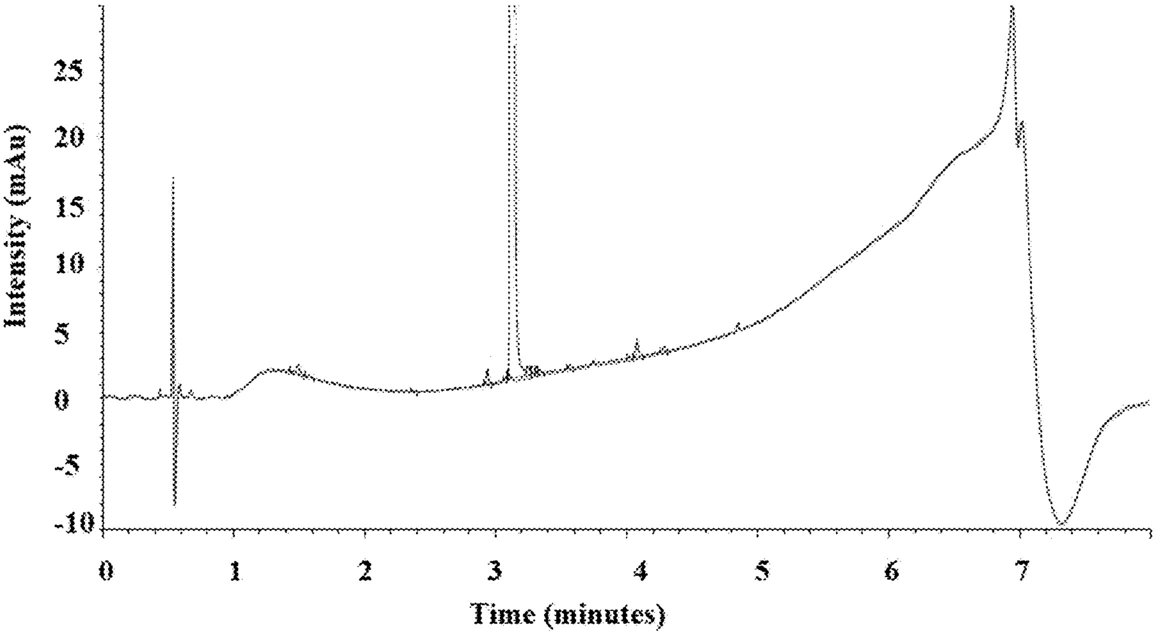

FIG. 13A is the HPLC chromatogram of sample 3-12 from the attempted crystallizations of Compound 1 with malonate salt as described in Example 7. The sample was 99.2% pure. The x-axis is time measured in minutes and the y-axis is intensity measured in mAu.

Figure 13B:
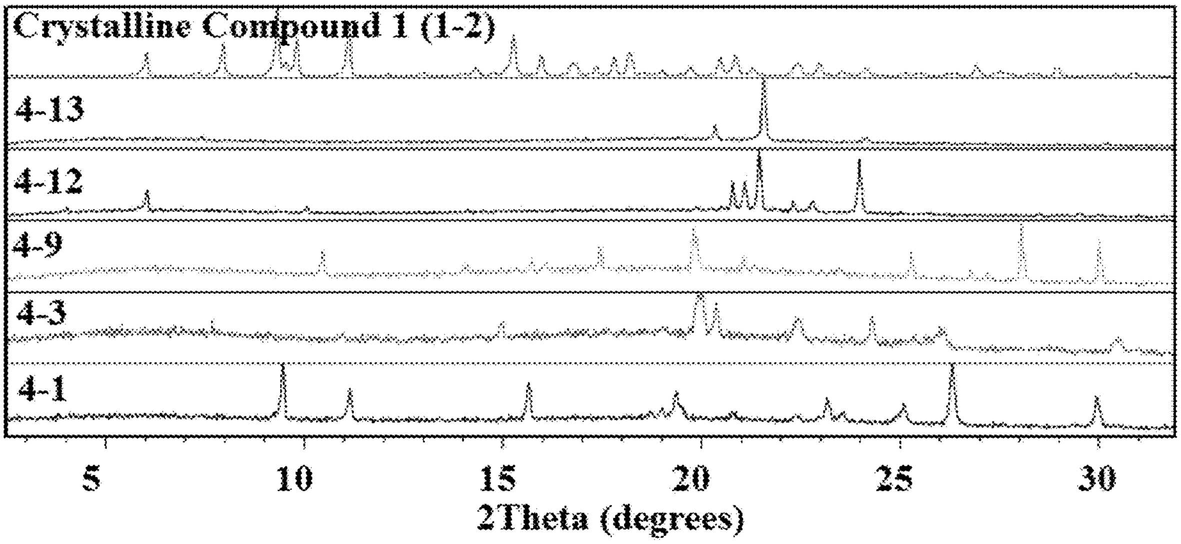

FIG. 13B is an overlay of XRPD diffractograms of solid samples obtained from the crystallization using LAG (samples 4-13, 4-12, 4-9, 4-3, and 4-1) compared to Compound 1 (sample 1-2) as described in Example 8. All the XRDP match the patterns of the crystalline acid counter ion with no additional peaks. The x-axis is 2Theta measured in degrees and the y-axis is intensity measured in counts.

Figure 14A:
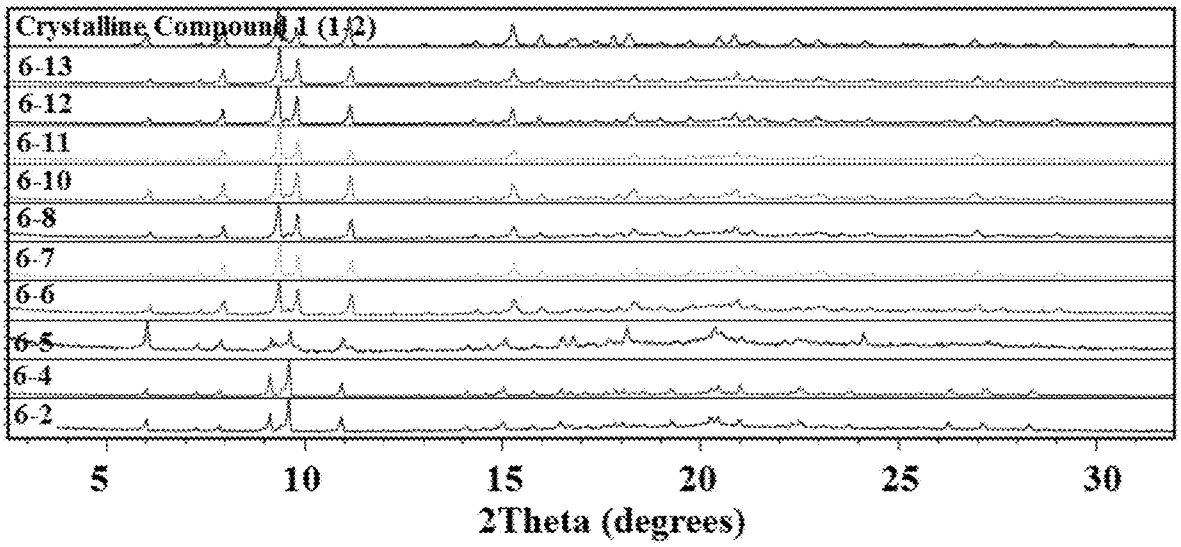

FIG. 14A is an overlay of XRPD diffractograms of samples obtained from utilizing ethyl acetate as a crystallization solvent (samples 6-13, 6-12, 6-11, 6-10, 6-8, 6-7, 6-6, 6-5, 6-4, and 6-2) compared to crystalline Compound 1 (sample 1-2) as described in Example 10. The XRPD patterns were generally found to match the Compound 1 pattern with the exception of samples 6-2, 6-4, and 6-5 that exhibit slight differences. The x-axis is 2Theta measured in degrees and the y-axis is intensity measured in counts.

Figure 14B:
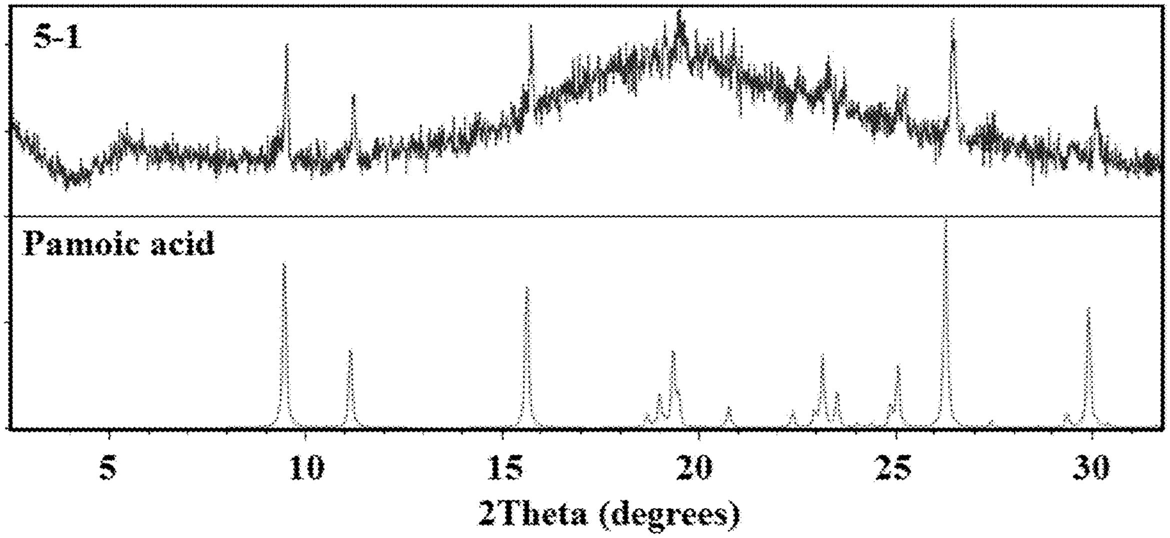

FIG. 14B is an overlay of XRPD diffractogram of sample 5-1 following a second dissolution in MEK and the addition of the antisolvent cyclohexane and pamioc acid as described in Example 9. Sample 5-1, crystallized in pamioc acid, was a solid following maturation, but the XRPD pattern matched the pattern of pamioc acid.

Figure 15A:
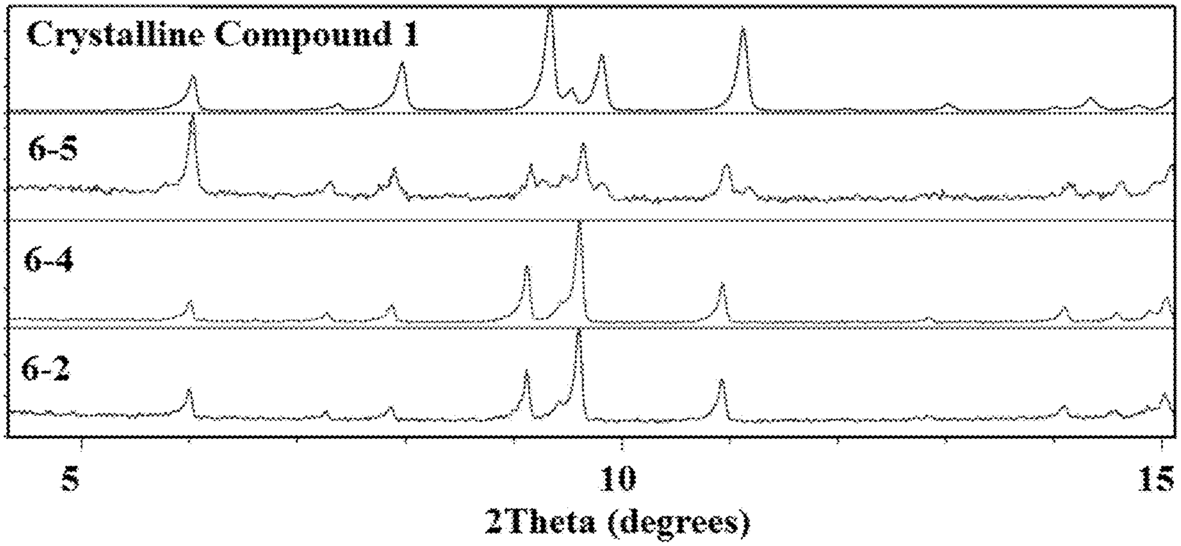

FIG. 15A is an overlay of XRPD diffractograms of samples obtained from utilizing ethyl acetate as a crystallization solvent (samples 6-5, 6-4, and 6-2) compared to crystalline Compound 1 (sample 1-2) as described in Example 10. The XRPD patterns were generally found to match the Compound 1 pattern with the exception of samples 6-2, 6-4, and 6-5 that exhibit slight differences. The x-axis is 2Theta measured in degrees and the y-axis is intensity measured in counts and labeled with the acid used in crystallization.

Figure 15B:
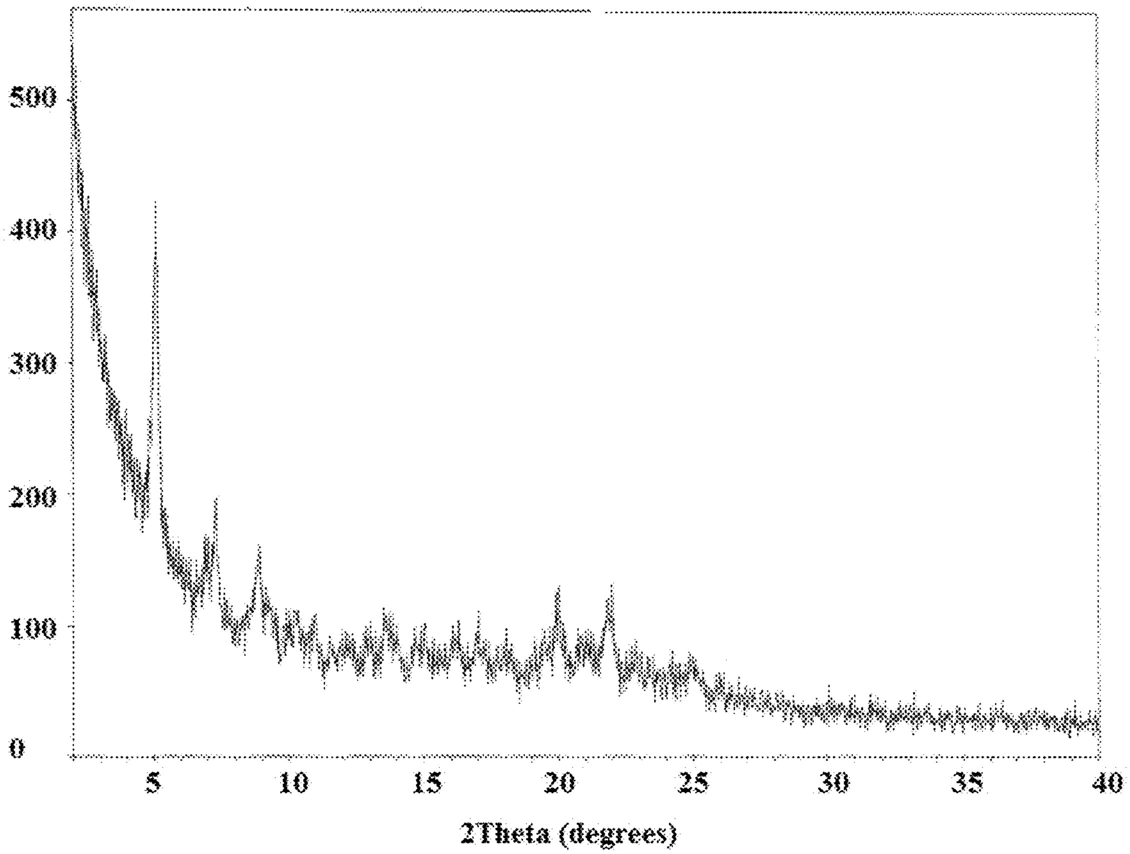

FIG. 15B is the XRPD pattern for Compound 1-A as described in Example 14. The x-axis is 2Theta measured in degrees and the y-axis is intensity measured in counts.

Figure 16A:
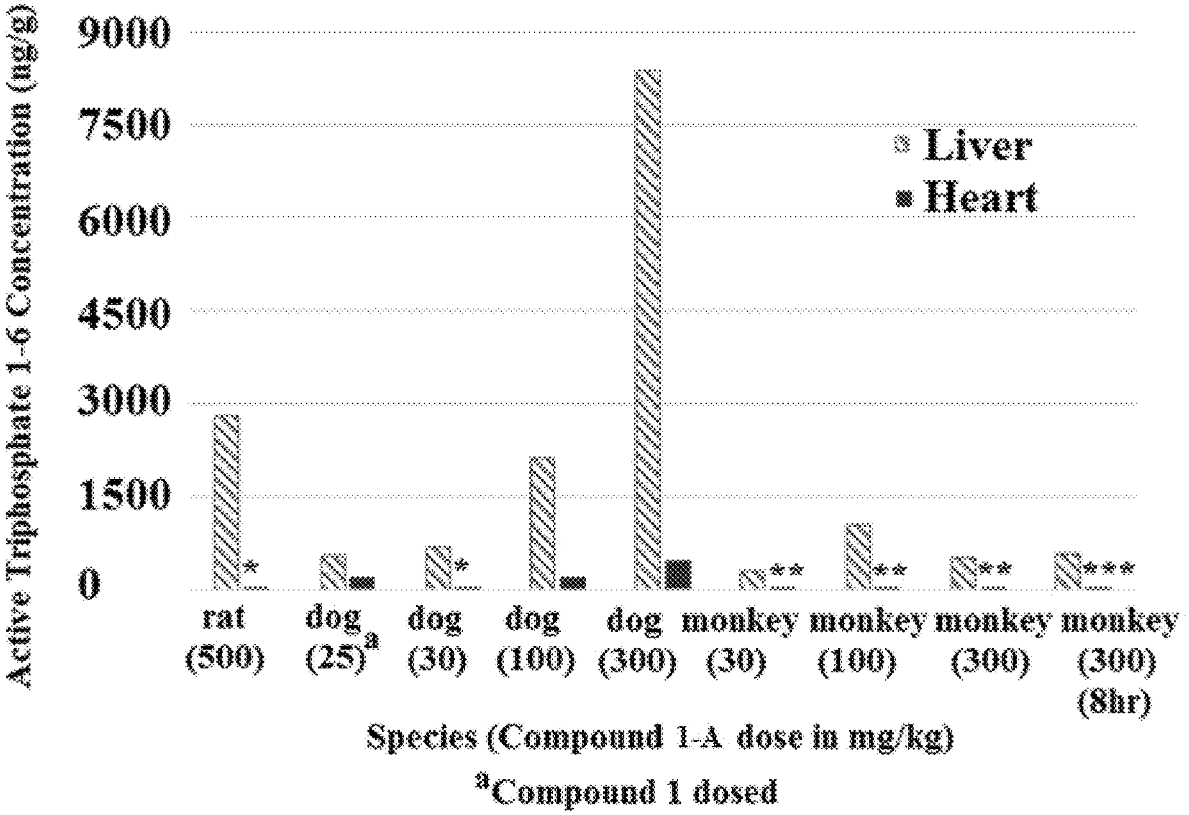

FIG. 16A is a graph of the active TP (metabolite 1-6) concentration levels in the livers and hearts of rats, dogs, and monkeys (Example 18). The x-axis is the dosage measured in mg/kg for each species and the y-axis is the active TP concentration measured in ng/g.

Figure 16B:
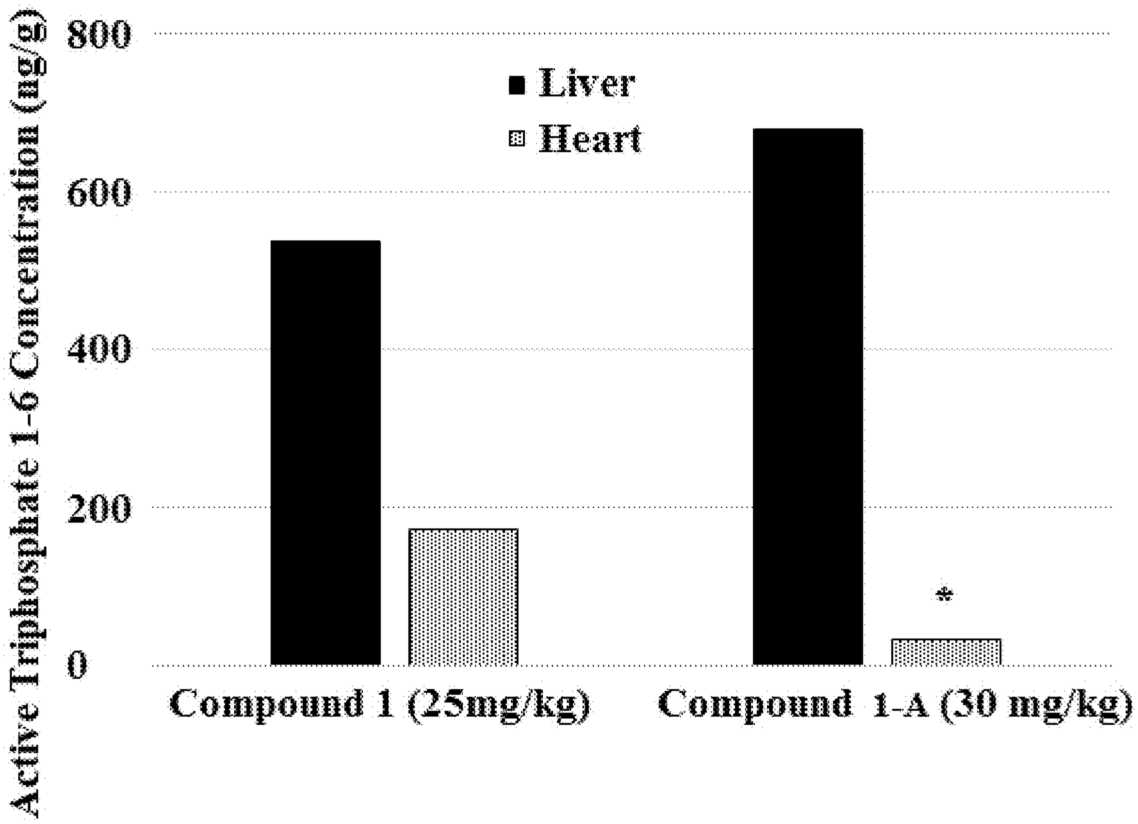

FIG. 16B is a graph of the active TP (metabolite 1-6) concentration levels in the liver and heart of dogs (n=2) measured 4 hours after a single oral dose of Compound 1 or Compound 1-A (Example 19). The x-axis is the dosage of each compound measured in mg/kg and the y-axis is the active TP concentration measured in ng/g.

Figure 17:
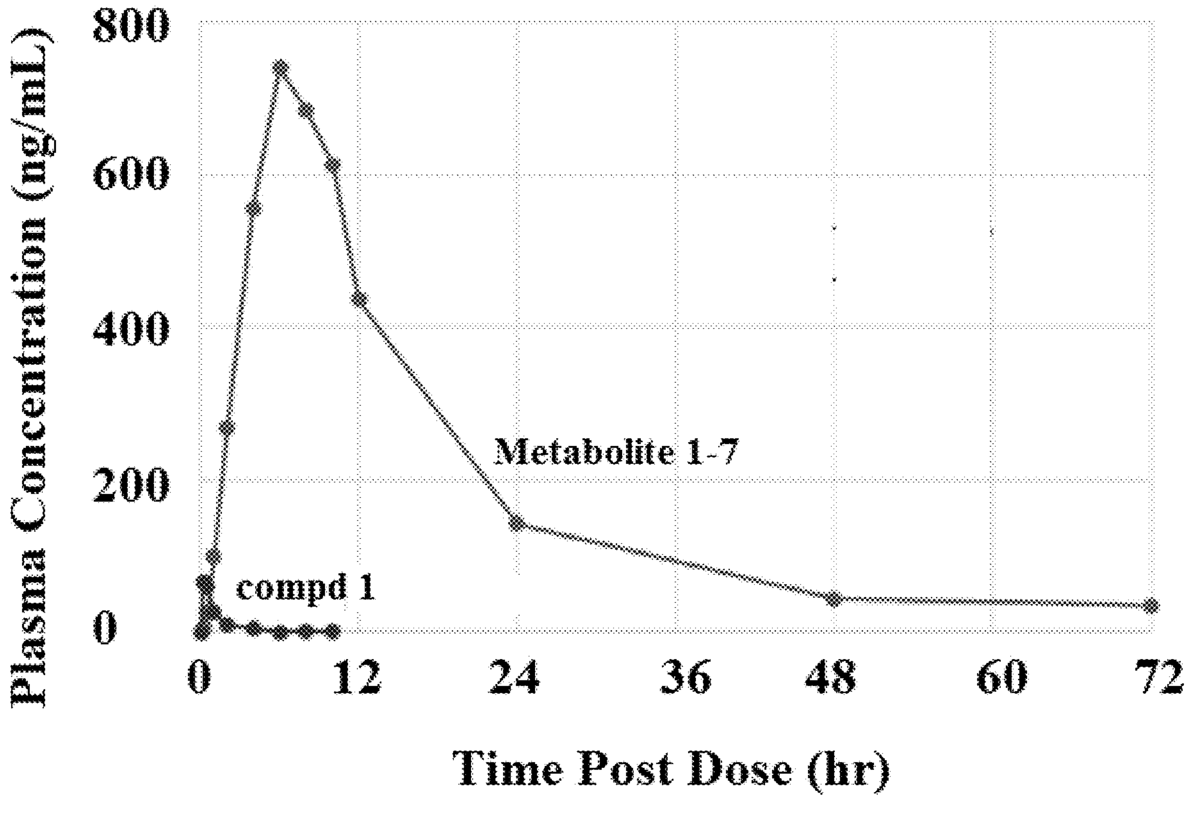

FIG. 17 is the plasma profile of Compound 1 and metabolite 1-7 in rats given a single 500 mg/kg oral dose of Compound 1-A (Example 20) measured up to 72 hours post-dose. The x-axis is time measured in hours and the y-axis is plasma concentration measured in ng/mL.

Figure 18:
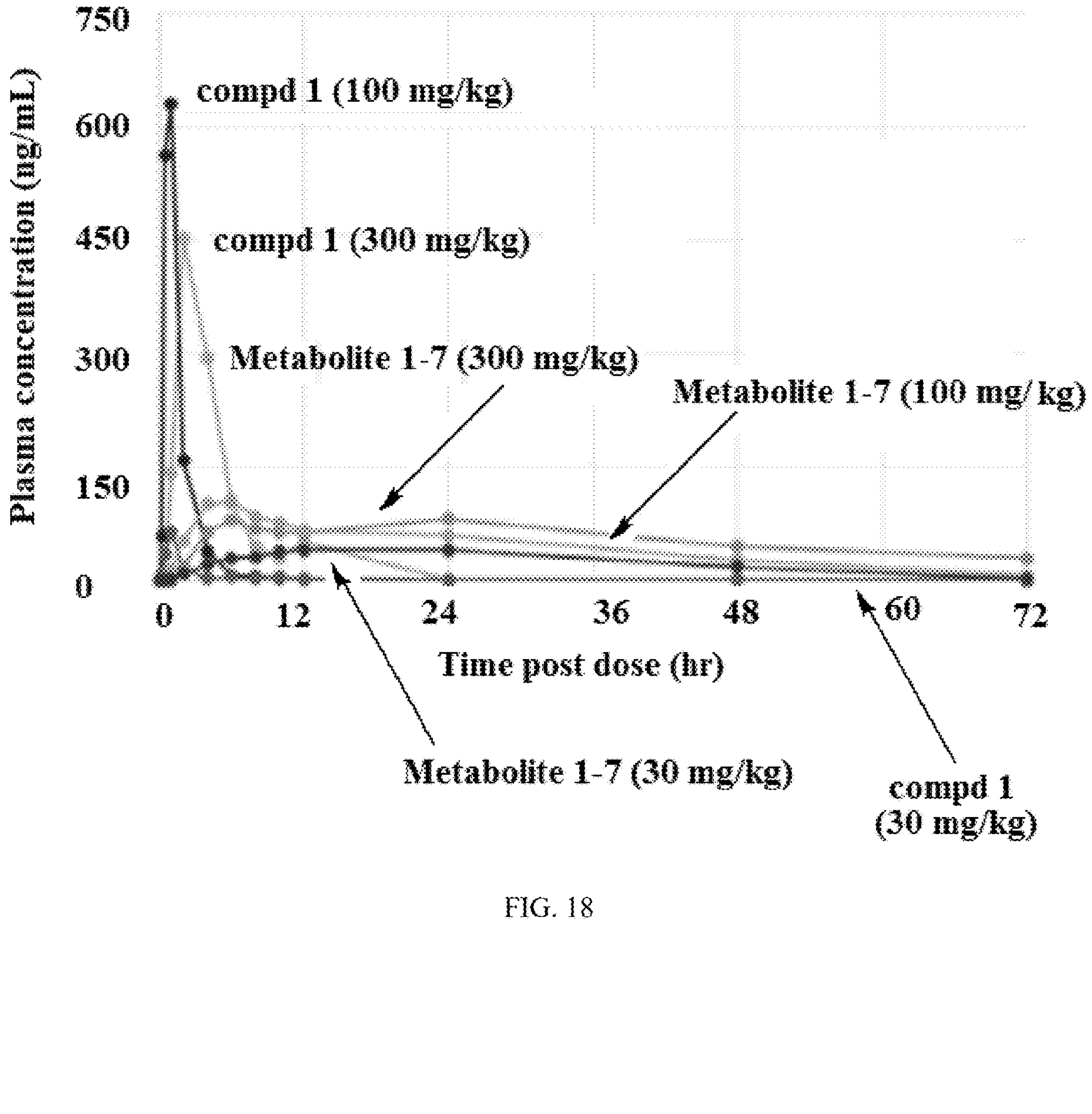

FIG. 18 is the plasma profile of Compound 1 and metabolite 1-7 in monkeys given single oral doses of 30 mg, 100 mg, or 300 mg of Compound 1-A (Example 20) measured up to 72 hours post-dose. The x-axis is time measured in hours and the y-axis is plasma concentration measured in ng/mL.

Figure 19:
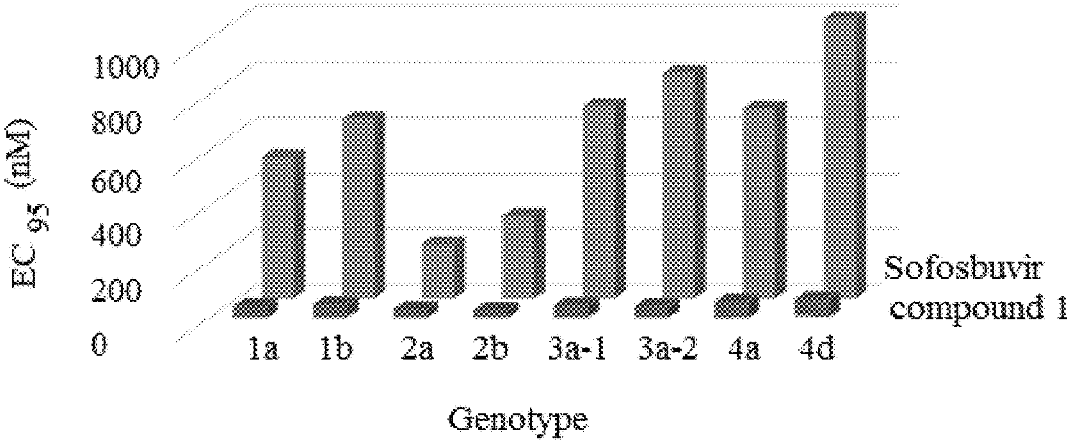

FIG. 19 is a graph of $EC_{95}$ values measured in nM of sofosbuvir and Compound 1 against HCV clinical isolates. $EC_{95}$ values for Compound 1 are 7-33 times lower than sofosbuvir (Example 22). The x-axis is labeled with the genotype and the y-axis is $EC_{95}$ measured in nM.

Figure 20:
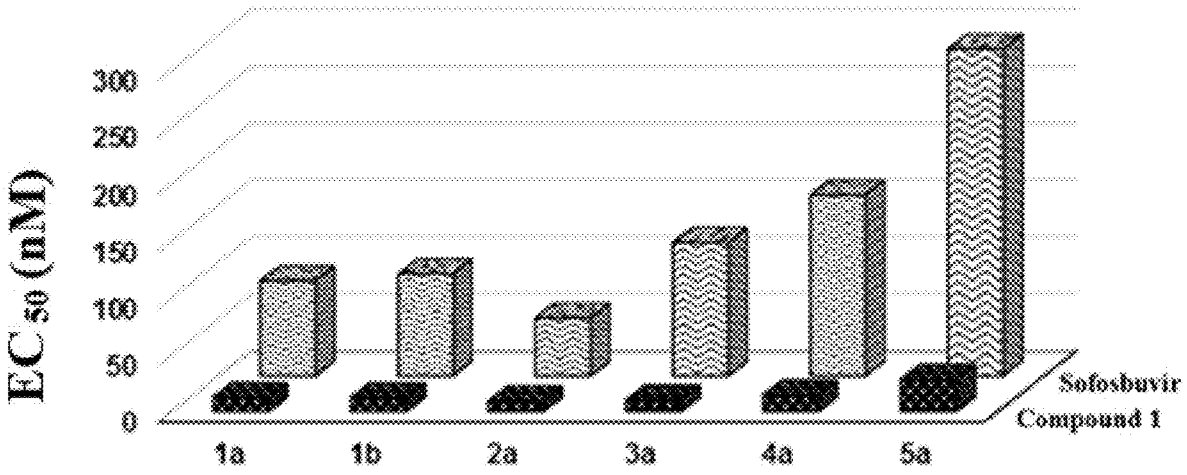

FIG. 20 is a graph of $EC_{50}$ values measured in nM of sofosbuvir and Compound 1 against laboratory strains of HCV Genotypes 1a, 1b, 2a, 3a, 4a, and 5a. Compound 1 is approximately 6-11 times more potent than sofosbuvir in Genotypes 1-5 (Example 22). The x-axis is labeled with the genotype and the y-axis is $EC_{50}$ measured in nM.

Figure 21:
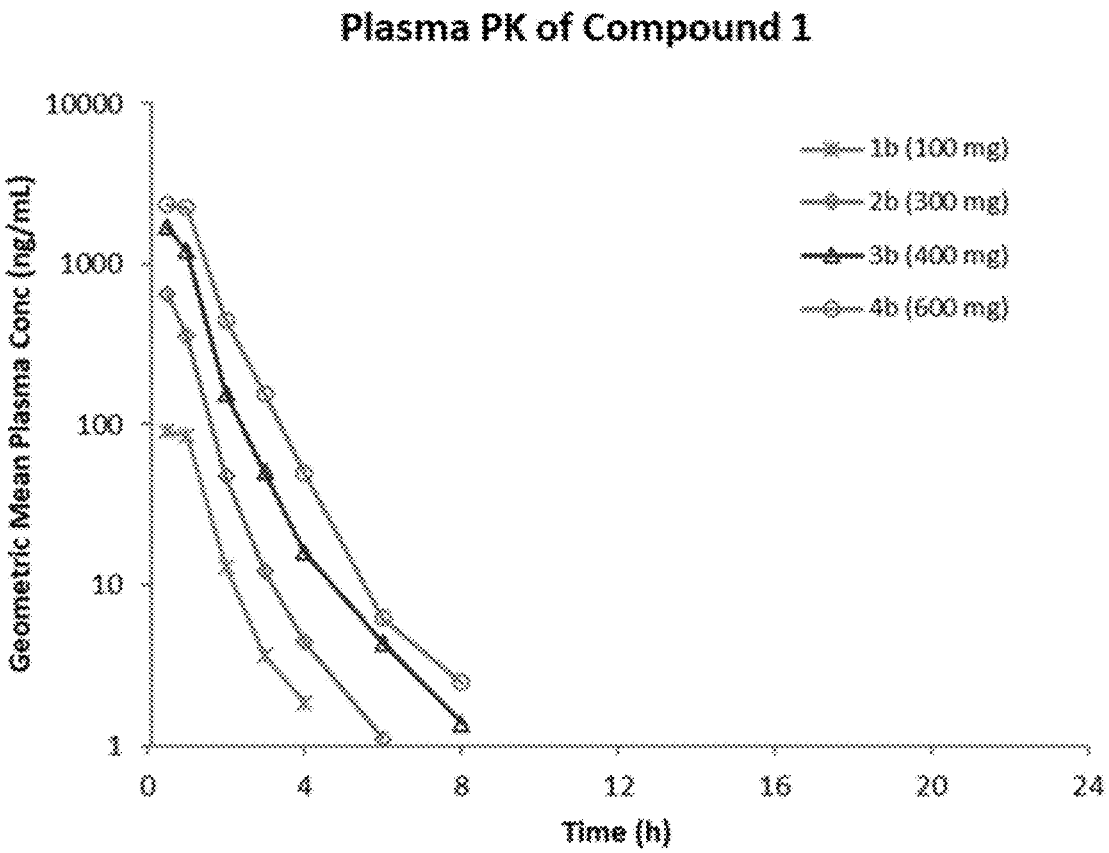

FIG. 21 is a graph of the mean plasma concentration-time profile of Compound 1 following the administration of a single oral dose of Compound 1-A in all cohorts of Part B of the study as described in Example 24. Compound 1 was quickly absorbed and rapidly metabolized within approximately 8 hours in all cohorts from Part B. The x-axis is the time measured in hours and the y-axis is the geometric mean plasma concentration measured in ng/mL.

Figure 22:
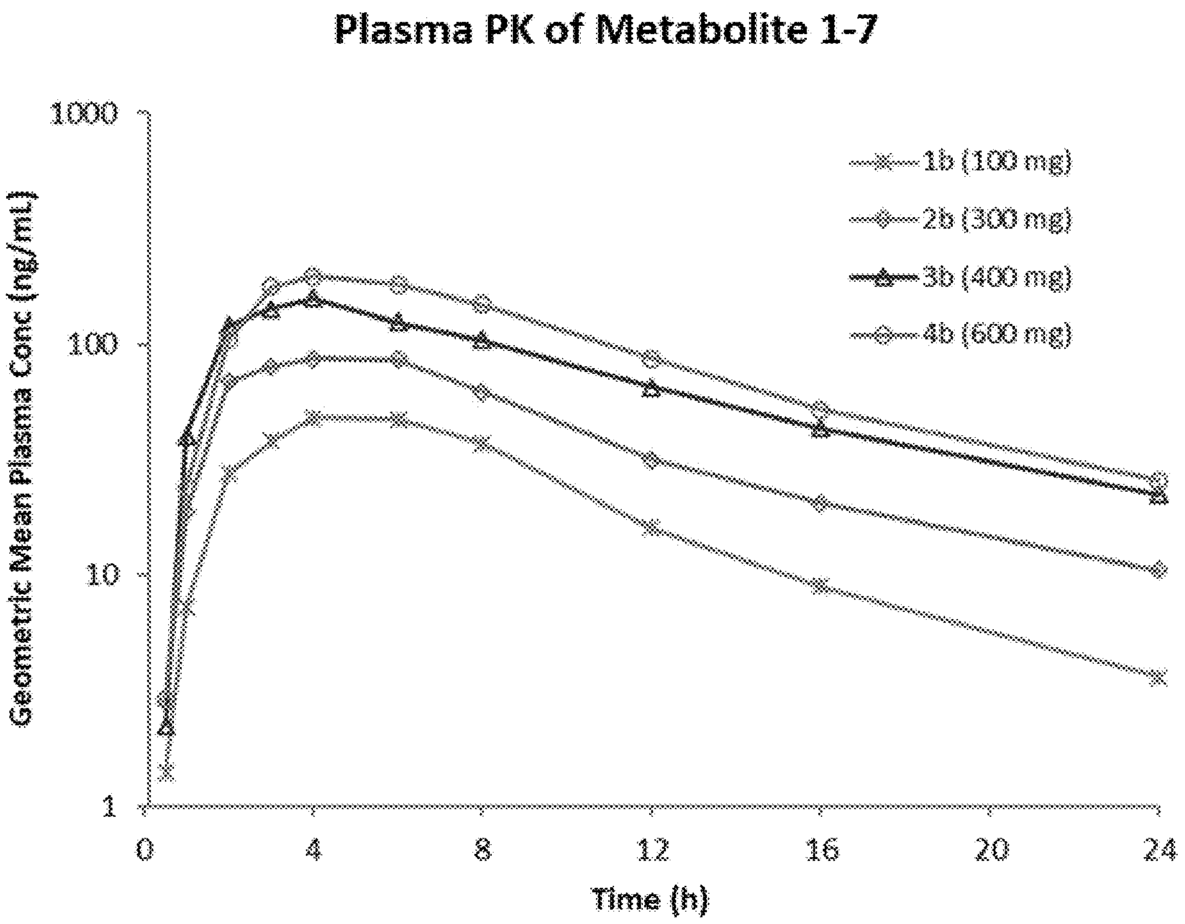

FIG. 22 is a graph of the mean plasma concentration-time profile of metabolite 1-7 following the administration of a single oral dose of Compound 1-A in all cohorts of Part B of the study as described in Example 24. Metabolite 1-7 exhibited sustained plasma concentration in all cohorts from Part B. The x-axis is the time measured in hours and the y-axis is the geometric mean plasma concentration measured in ng/mL.

Figure 23A:
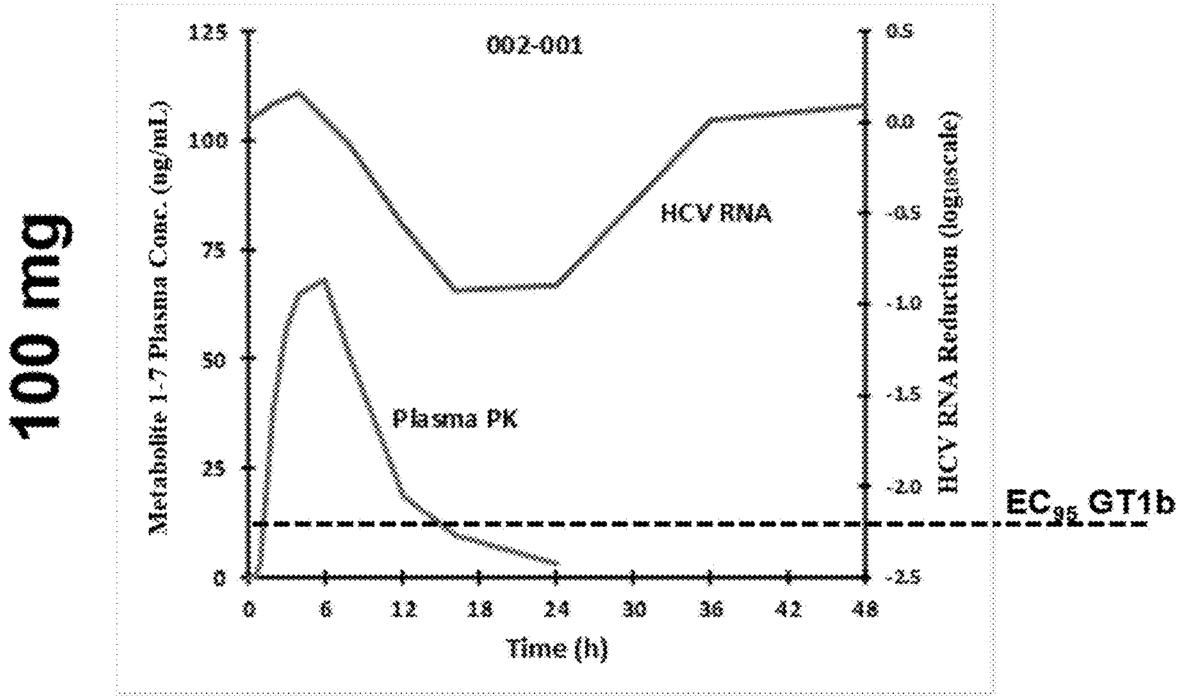

FIG. 23A is an individual pharmacokinetic/pharmacodynamic analysis of a subject enrolled in the 1b cohort as described in Example 24. The graph shows plasma metabolite 1-7 exposure and HCV RNA reduction levels. The dashed line represents the minimum concentration of metabolite 1-7 required to sustain a viral response greater than the $EC_{95}$ value against GT1b. The x-axis is time measured in hours. The left y-axis is metabolite 1-7 plasma concentration measured in ng/mL and the right y-axis is the HCV RNA reduction measured in $log_{10}$ IU/mL.

Figure 23B:
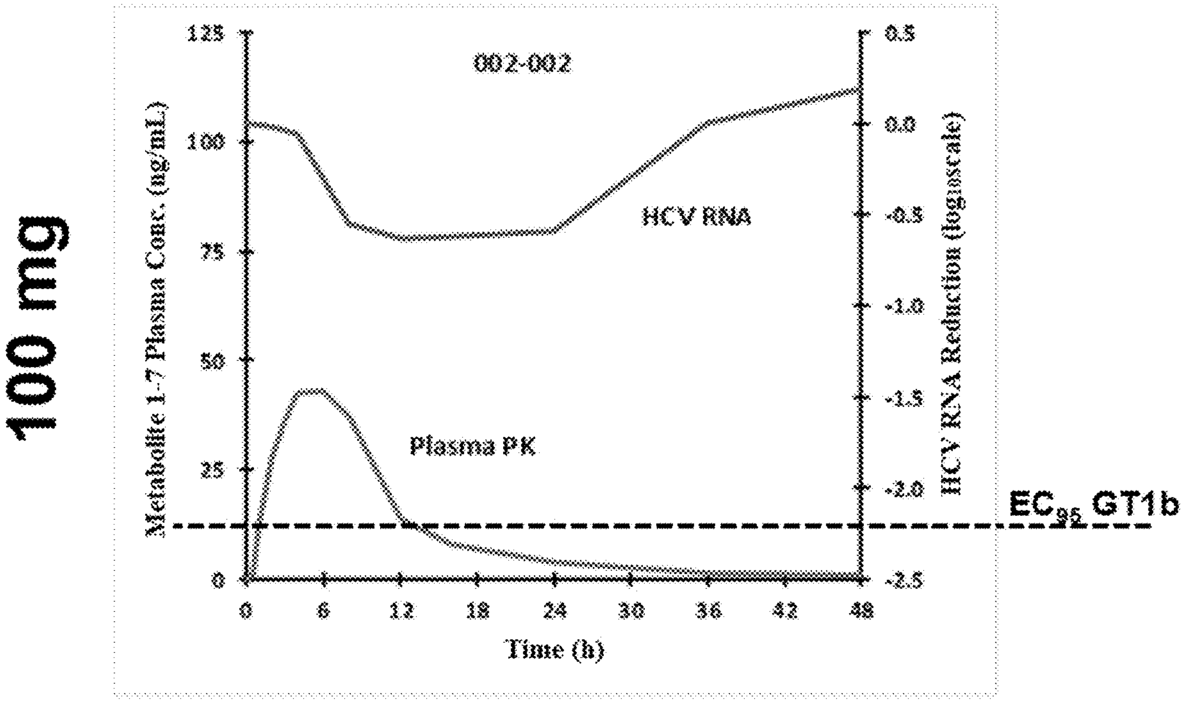

FIG. 23B is an individual pharmacokinetic/pharmacodynamic analysis of a subject enrolled in the 1b cohort as described in Example 24. The graph shows plasma metabolite 1-7 exposure and HCV RNA reduction levels. The dashed line represents the minimum concentration of metabolite 1-7 required to sustain a viral response greater than the $EC_{95}$ value against GT1b. The x-axis is time measured in hours. The left y-axis is metabolite 1-7 plasma concentration measured in ng/mL and the right y-axis is the HCV RNA reduction measured in $log_{10}$ IU/mL.

Figure 23C:
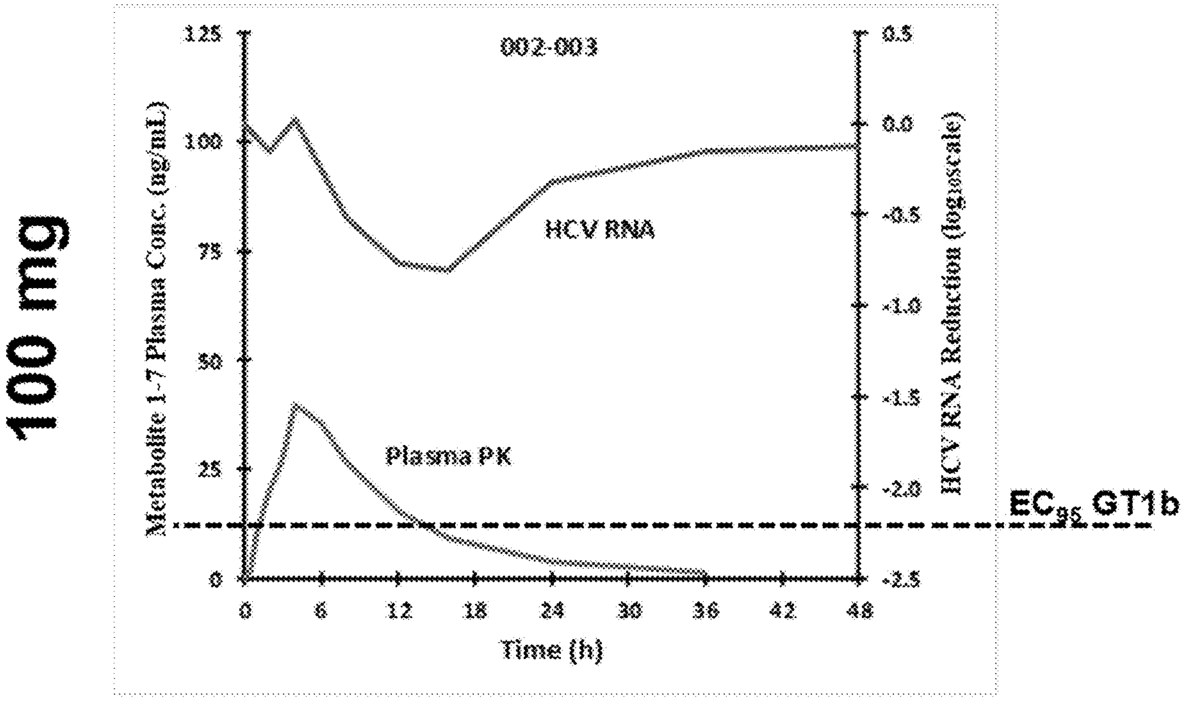

FIG. 23C is an individual pharmacokinetic/pharmacodynamic analysis of a subject enrolled in the 1b cohort as described in Example 24. The graph shows plasma metabolite 1-7 exposure and HCV RNA reduction levels. The dashed line represents the minimum concentration of metabolite 1-7 required to sustain a viral response greater than the $EC_{95}$ value against GT1b. The x-axis is time measured in hours. The left y-axis is metabolite 1-7 plasma concentration measured in ng/mL and the right y-axis is the HCV RNA reduction measured in $log_{10}$ IU/mL.

Figure 23D:
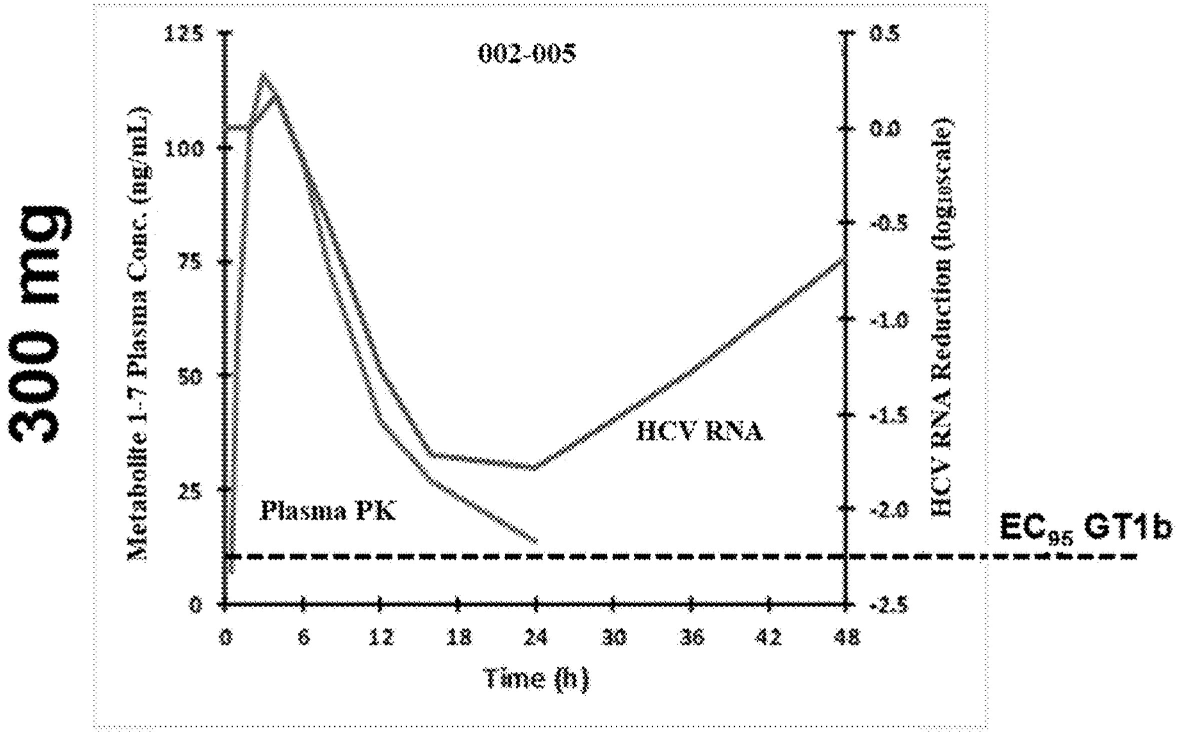

FIG. 23D is an individual pharmacokinetic/pharmacodynamic analysis of a subject enrolled in the 3b cohort as described in Example 24. Each graph shows plasma metabolite 1-7 exposure and HCV RNA reduction levels. The dashed line represents the minimum concentration of metabolite 1-7 required to sustain a viral response greater than the $EC_{95}$ value against GT1b. The x-axis is time measured in hours. The left y-axis is metabolite 1-7 plasma concentration measured in ng/mL and the right y-axis is the HCV RNA reduction measured in $log_{10}$ IU/mL.

Figure 23E:
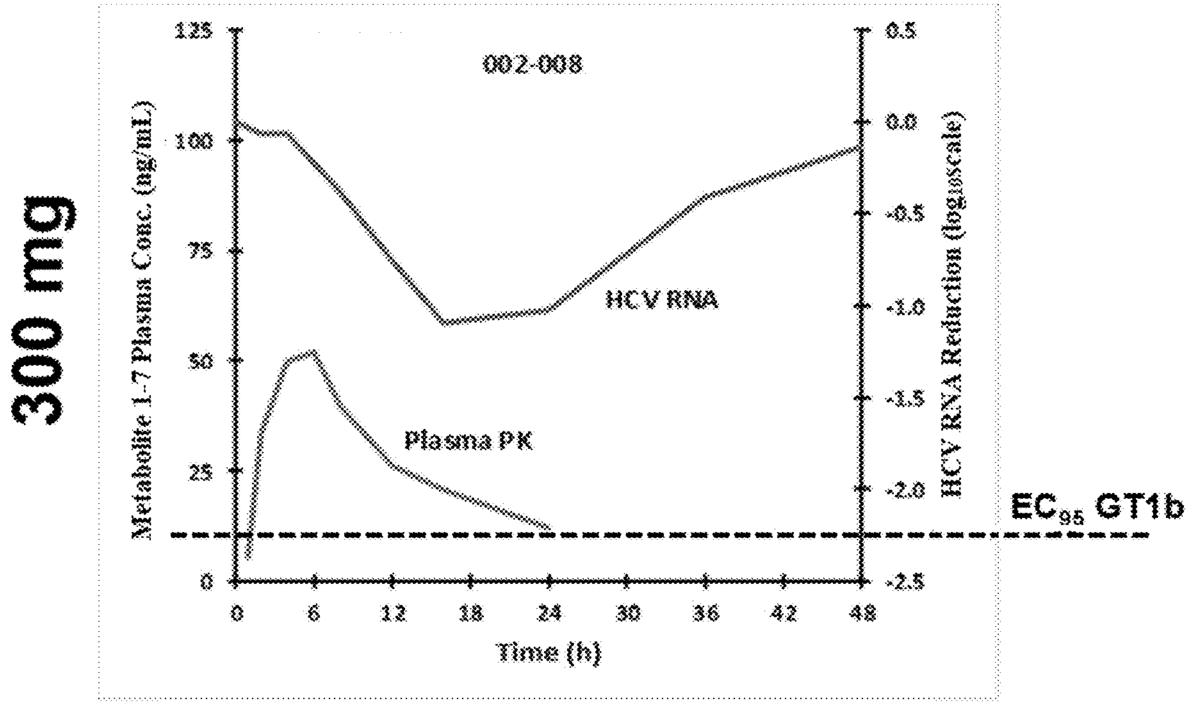

FIG. 23E is an individual pharmacokinetic/pharmacodynamic analysis of a subject enrolled in the 3b cohort as described in Example 24. Each graph shows plasma metabolite 1-7 exposure and HCV RNA reduction levels. The dashed line represents the minimum concentration of metabolite 1-7 required to sustain a viral response greater than the $EC_{95}$ value against GT1b. The x-axis is time measured in hours. The left y-axis is metabolite 1-7 plasma concentration measured in ng/mL and the right y-axis is the HCV RNA reduction measured in $log_{10}$ IU/mL.

Figure 23F:
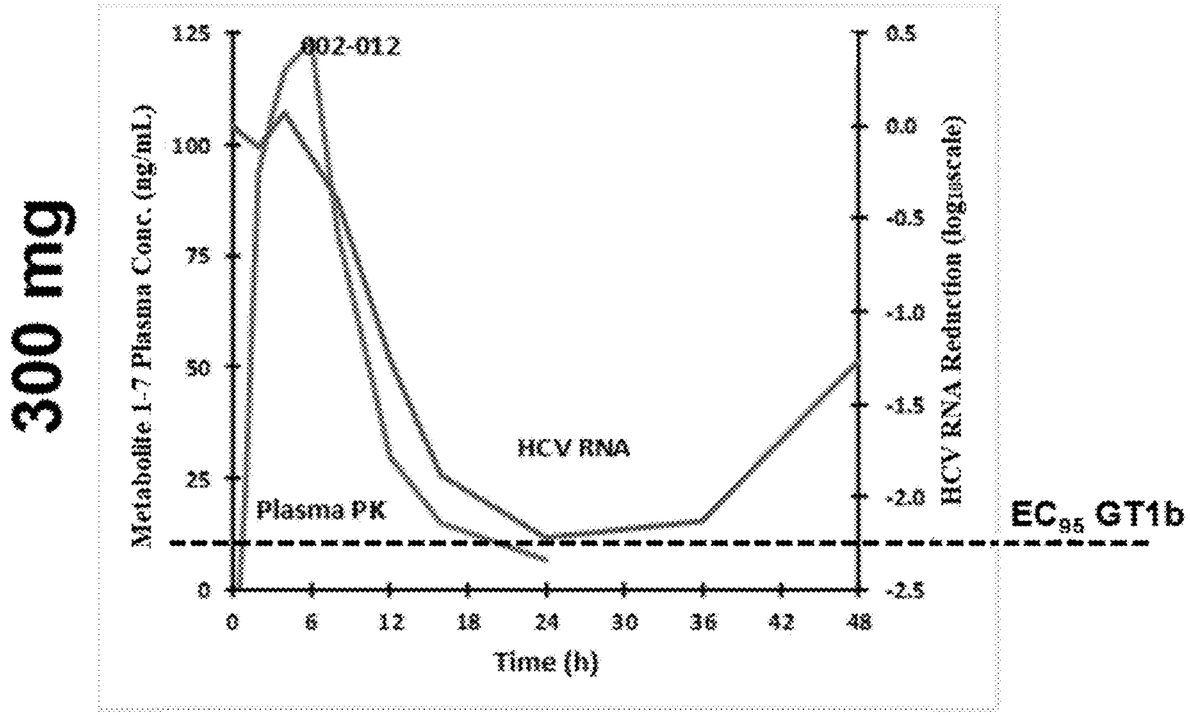

FIG. 23F is an individual pharmacokinetic/pharmacodynamic analysis of a subject enrolled in the 3b cohort as described in Example 24. Each graph shows plasma metabolite 1-7 exposure and HCV RNA reduction levels. The dashed line represents the minimum concentration of metabolite 1-7 required to sustain a viral response greater than the $EC_{95}$ value against GT1b. The x-axis is time measured in hours. The left y-axis is metabolite 1-7 plasma concentration measured in ng/mL and the right y-axis is the HCV RNA reduction measured in $log_{10}$ IU/mL.

Figure 24:
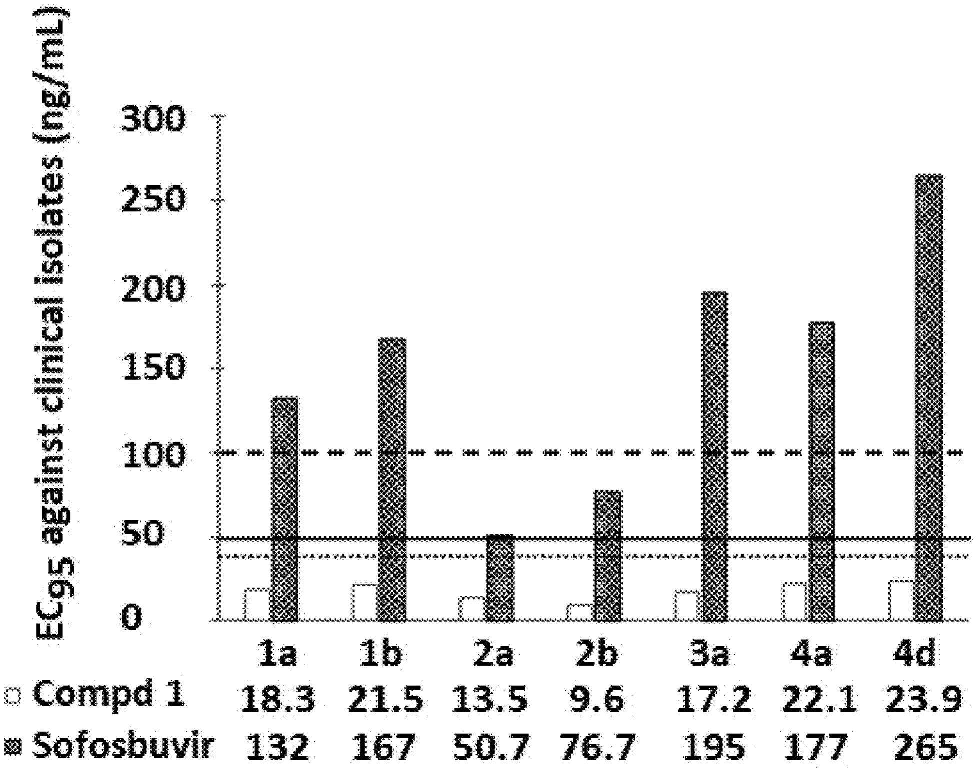

FIG. 24 is a graph of the $EC_{95}$ values of Compound 1 and sofosbuvir against clinical isolates of GT1, GT2, GT3, and GT4 HCV-infected patients. The dashed horizontal line (- - - - -) represents the steady-state trough concentration ($C_{24,ss}$) of sofosbuvir nucleoside following a dose of 400 mg QD of sofosbuvir. The full horizontal line (-) represents the steady-state trough concentration ($C_{24,ss}$) of metabolite 1-7 following 600 mg of Compound 1-A (equivalent to 550 mg of Compound 1). The dotted horizontal line (---------) represents the steady-state trough concentration ($C_{24,ss}$) of metabolite 1-7 following 450 mg of Compound 1-A (equivalent to 400 mg of Compound 1). As discussed in Example 25, the predicted steady-state trough plasma level ($C_{24,ss}$) of metabolite 1-7 following 600 mg and 450 mg of Compound 1-A exceeds the in vitro $EC_{95}$ of Compound 1 against all tested clinical isolates. The steady state trough plasma level ($C_{24,ss}$) of sofosbuvir only exceeds the $EC_{95}$ at GT2 clinical isolates. The x-axis is labeled with the clinical isolates and the table under the x-axis lists the $EC_{95}$ values for Compound 1 and sofosbuvir. The y-axis is the $EC_{95}$ against the clinical isolates measured in ng/mL. $EC_{95}$ is expressed as nucleoside equivalent. Sofosbuvir and Compound 1-A were administered daily (QD).

Figure 25:
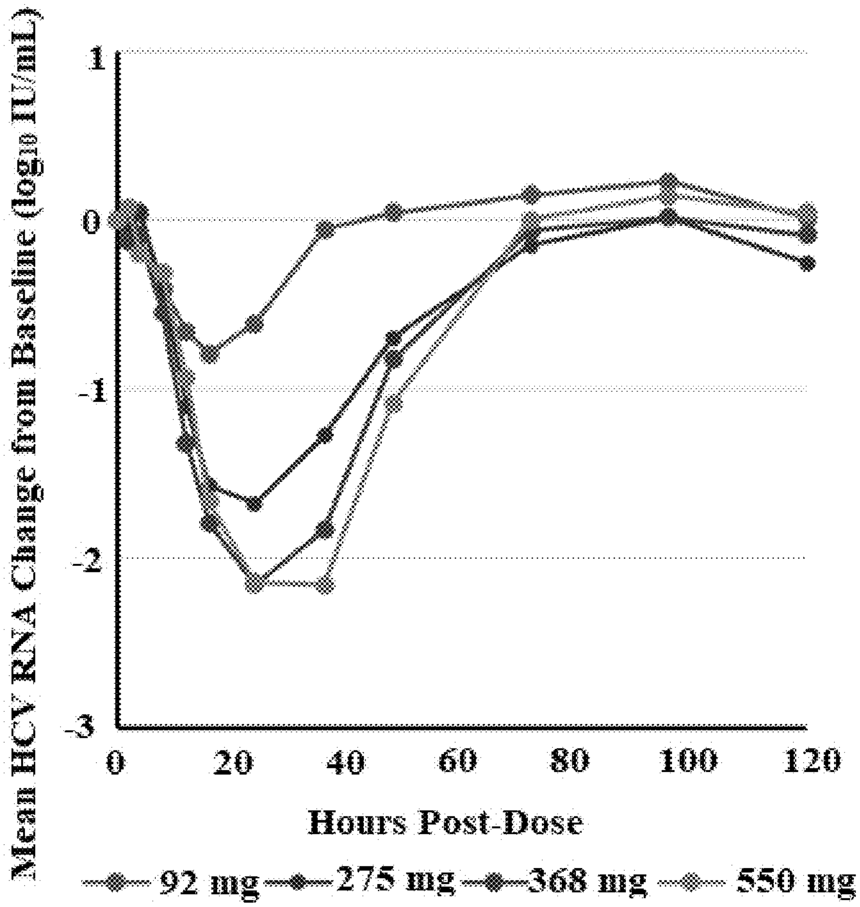

FIG. 25 is a graph demonstrating the mean HCV RNA change from baseline in subjects with non-cirrhotic GT1b HCV infection after a single dose of the Compound 1-A equivalent of 92 mg, 275 mg, 368 mg, or 550 mg of Compound 1 as described in Examples 26 and 27. The x-axis is hours measured post dose and the y-axis is mean HCV RNA change from baseline measured in $log_{10}$ IU/mL.

Figure 26:
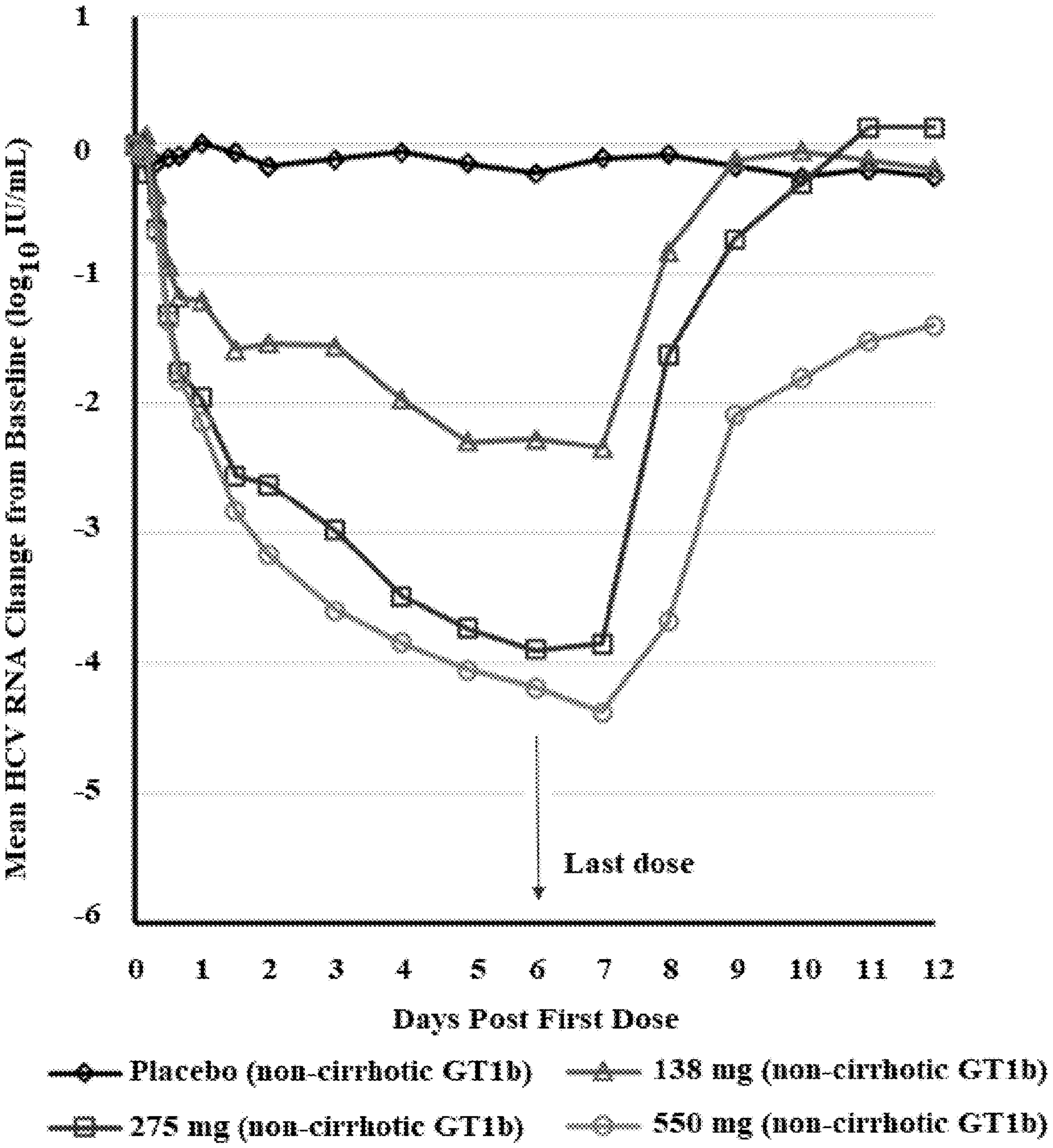

FIG. 26 is a graph demonstrating the mean HCV RNA change from baseline in subjects with non-cirrhotic GT1b HCV infection following 7 days QD of dosing with Compound 1-A as described in Examples 26 and 27. The x-axis is days measured post first-dose and the y-axis is mean HCV RNA change from baseline measured in $log_{10}$ IU/mL.

Figure 27:
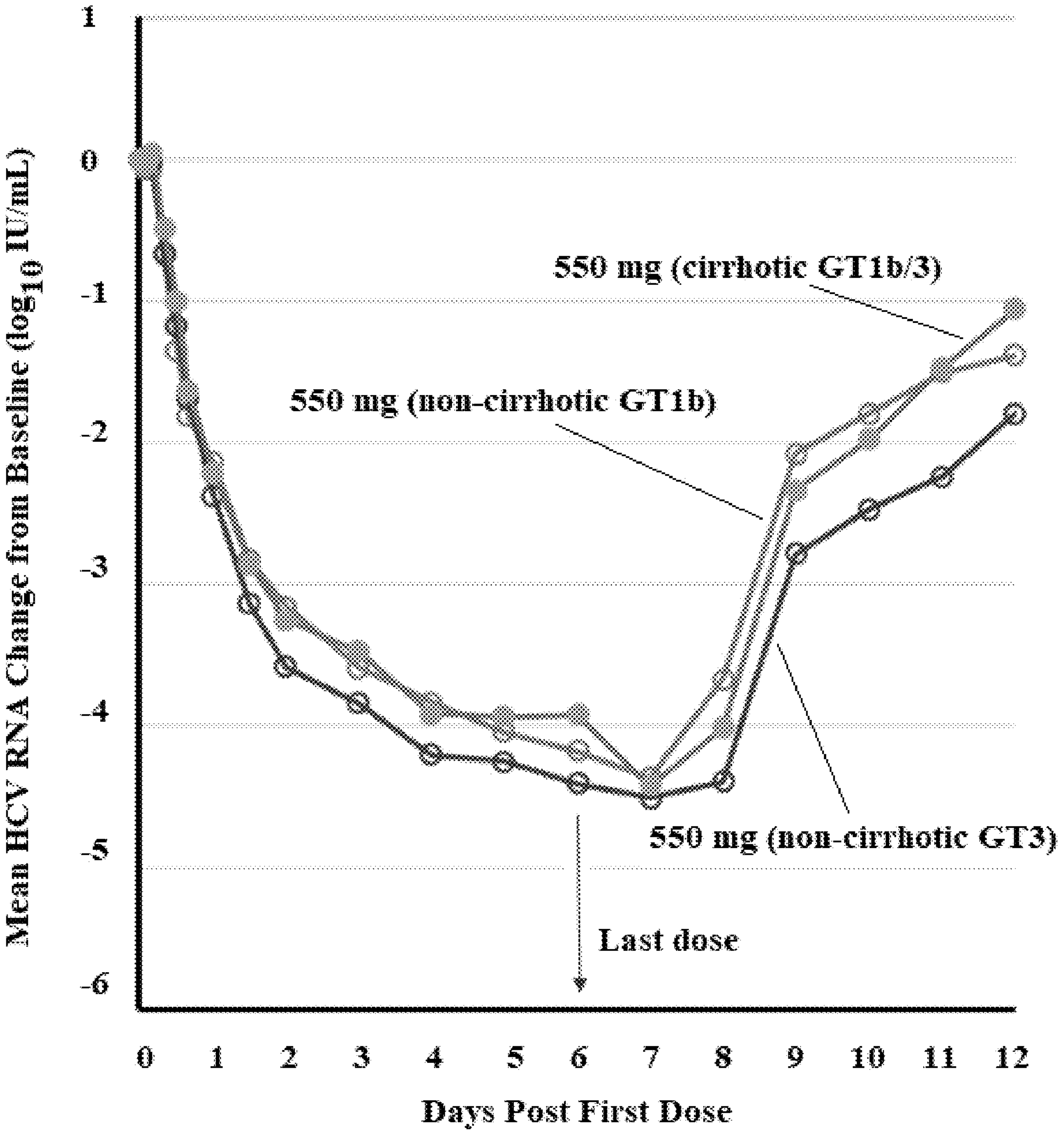

FIG. 27 is graph comparing the mean HCV RNA change from baseline in subjects with non-cirrhotic GT1 HCV infection, subjects with non-cirrhotic GT3 HCV infection, and subjects with cirrhotic GT1 or GT3 HCV infection following doses of 600 mg/day QD of Compound 1-A (equivalent to 550 mg of Compound 1) as described in Examples 26 and 27. As shown in the graph, subjects with cirrhosis of the liver exhibited mean HCV RNA change that were similar to subjects with non-cirrhosis of the liver. The x-axis is days measured post first-dose and the y-axis is mean HCV RNA change from baseline measured in $log_{10}$ IU/mL.

Figure 28A:
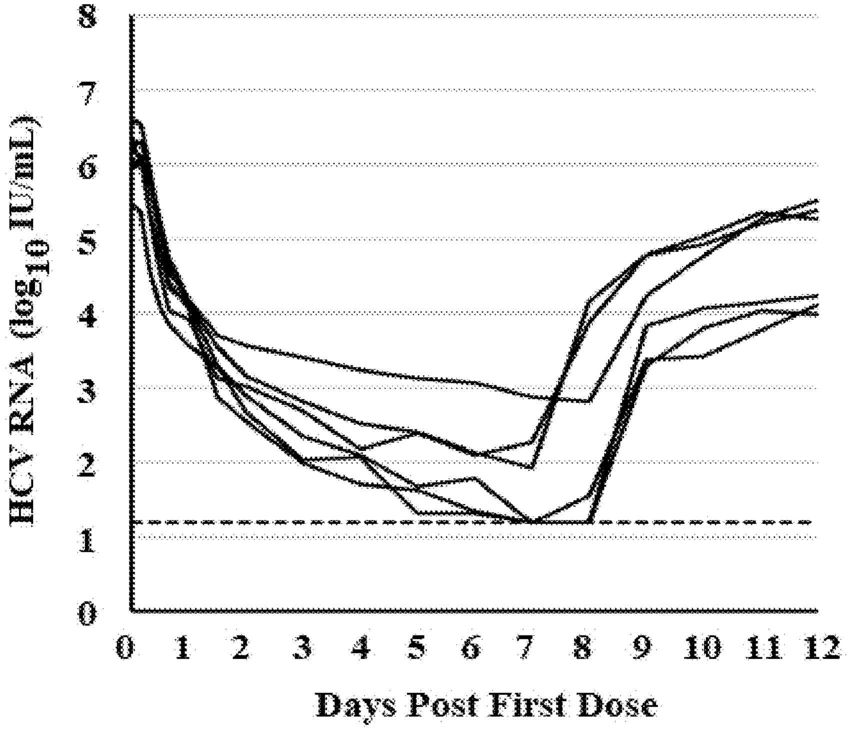

FIG. 28A is a graph of the individual HCV RNA change from baseline in subjects with non-cirrhotic GT1b HCV infection following doses of 600 mg/day QD of Compound 1-A (equivalent to 550 mg of Compound 1) as described in Examples 26 and 27. The dashed horizontal line (----) is the limit of quantification (LOQ=15 IU/mL) and 50% of subjects achieved HCV RNA <LOQ. The x-axis is days measured post first-dose and the y-axis is HCV RNA change from baseline measured in $log_{10}$ IU/mL.

Figure 28B:
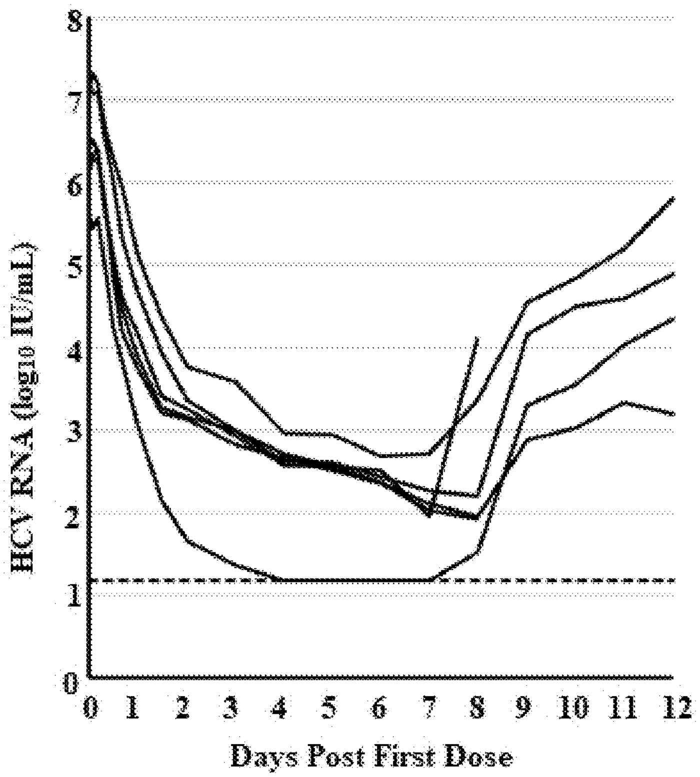

FIG. 28B is a graph of the individual HCV RNA change from baseline in subjects with non-cirrhotic GT3 HCV infection following doses of 600 mg/day QD of Compound 1-A (equivalent to 550 mg of Compound 1) as described in Examples 26 and 27. The dashed horizontal line (----) is the limit of quantification (LOQ=15 IU/mL). The x-axis is days measured post first-dose and the y-axis is HCV RNA change from baseline measured in $log_{10}$ IU/mL.

Figure 28C:
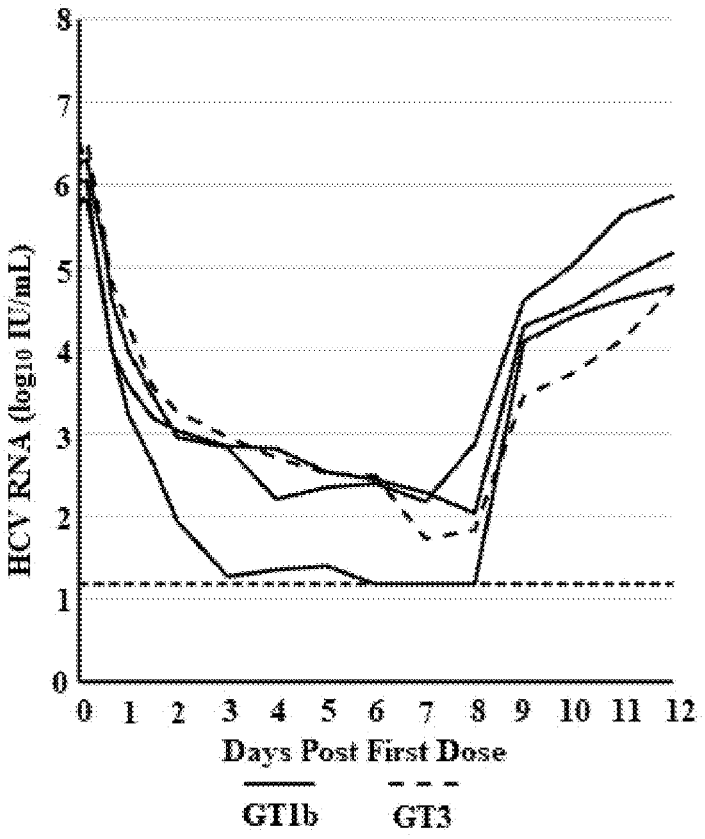

FIG. 28C is a graph of the individual HCV RNA change from baseline in subjects with cirrhotic GT1 or GT3 HCV infection following doses of 600 mg/day QD of Compound 1-A (equivalent to 550 mg of Compound 1) as described in Examples 26 and 27. The dashed horizontal line (----) is the limit of quantification (LOQ=15 IU/mL). The x-axis is days measured post first-dose and the y-axis is HCV RNA change from baseline measured in $log_{10}$ IU/mL.

Figure 29:
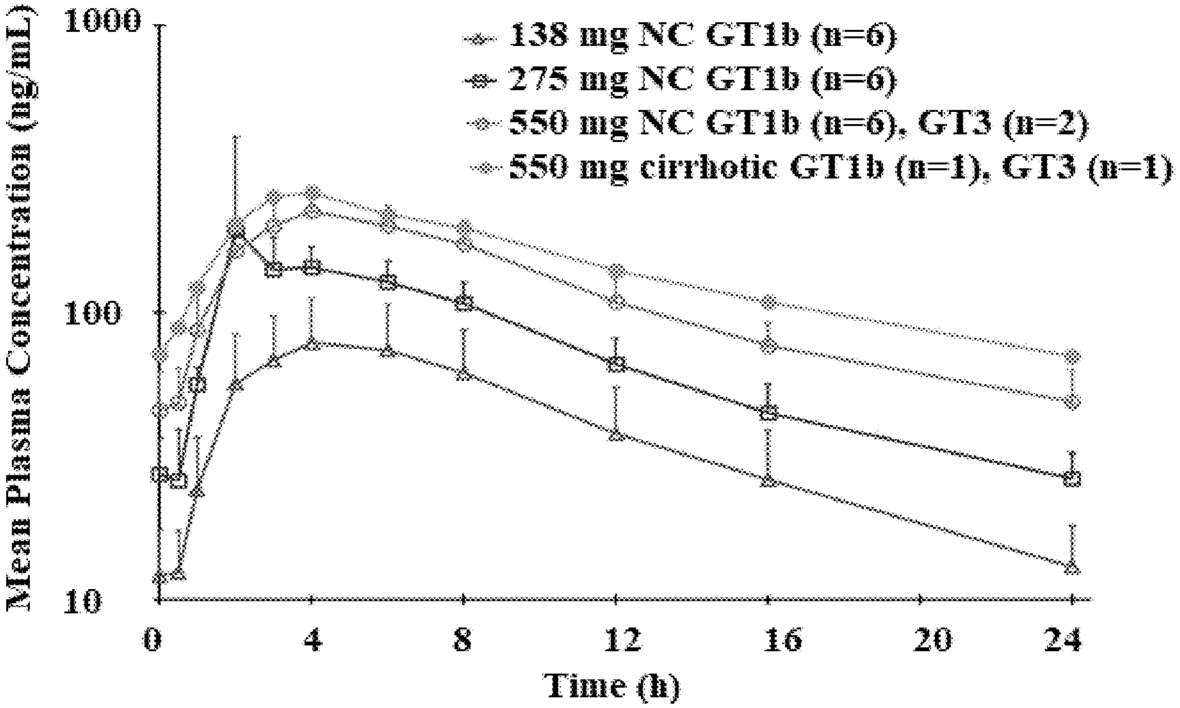

FIG. 29 is the mean plasma concentration-time profile of metabolite 1-7 in GT1/GT3 HCV-infected cirrhotic and non-cirrhotic subjects. The GT1-infected non-cirrhotic subjects were given the Compound 1-A equivalent of either 138 mg/d, 275 mg/d, or 550 mg/d QD of Compound 1, the GT3-infected non-cirrhotic subjects were given 600 mg/d QD of Compound 1-A (550 mg/d of Compound 1), and the GT1/GT3-infected cirrhotic subjects were given 600 mg of Compound 1-A QD (550 mg/d of Compound 1) as described in Examples 26 and 27. The x-axis is time measured in hours and the y-axis is mean plasma concentration measured in ng/mL.

Figure 30A:
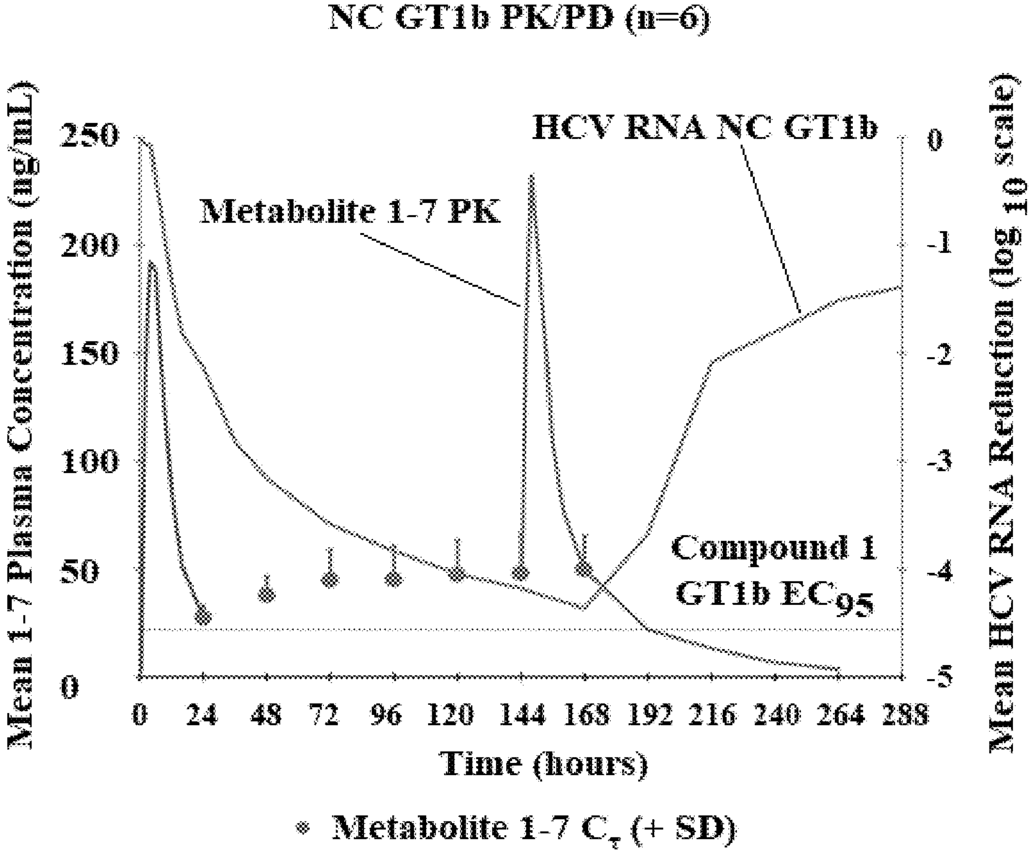

FIG. 30A is a graph plotting the mean metabolite 1-7 plasma concentration (left y-axis) and the mean HCV RNA reduction following 600 mg/day QD of Compound 1-A (equivalent to 550 mg of Compound 1) (right y-axis) against time for subjects with non-cirrhotic GT1b HCV infection as described in Examples 26 and 27. The $EC_{95}$ of Compound 1 in GT1b is shown as a horizontal dashed line (-----). The dots represent the steady state plasma trough levels ($C_\tau$) of metabolite 1-7 and as shown in the figure, ($C_\tau$) is consistently above the $EC_{95}$ at all time points studied. The left y-axis is mean metabolite 1-7 plasma concentration measured in ng/mL, the right y-axis is HCV RNA reduction following 550 mg of Compound 1 QD measured in log 10 IU/mL, and the x-axis is time measured in hours.

Figure 30B:
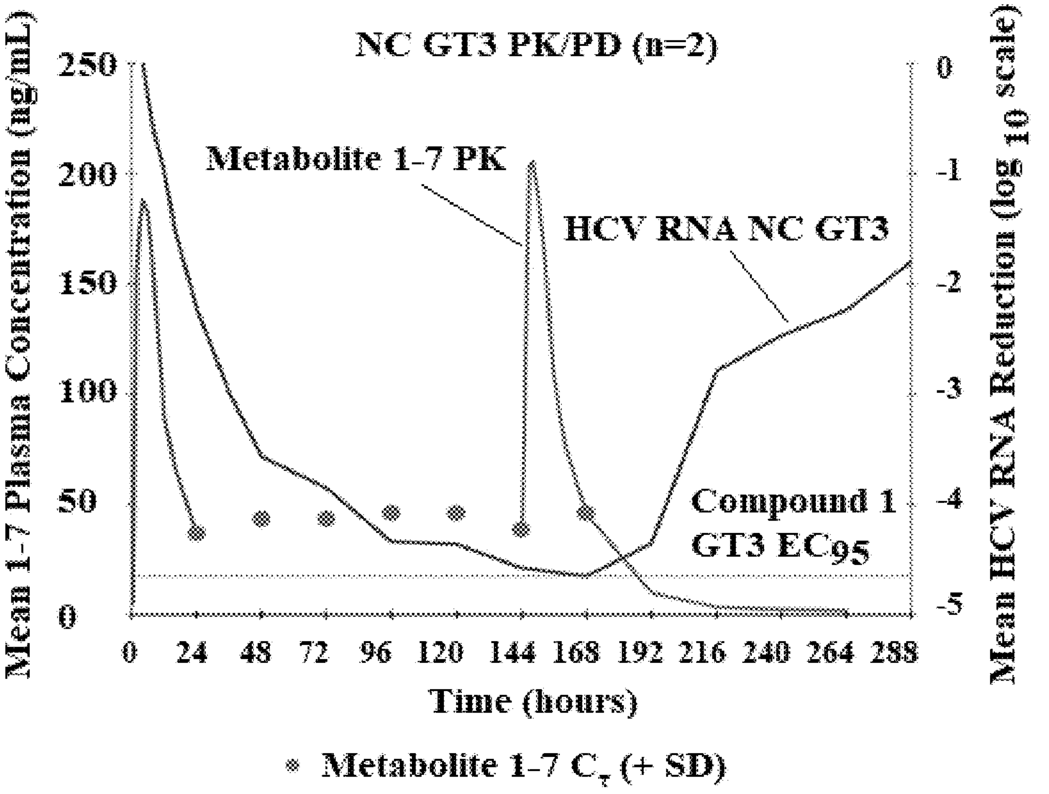

FIG. 30B is a graph plotting the mean metabolite 1-7 plasma concentration (left y-axis) and the mean HCV RNA reduction following 600 mg/day QD of Compound 1-A (equivalent to 550 mg of Compound 1) (right y-axis) against time for subjects with non-cirrhotic GT3 HCV infection as described in Examples 26 and 27. The $EC_{95}$ of Compound 1 in GT3 is shown as a horizontal dashed line (-----). The dots represent the steady state plasma trough levels ($C_\tau$) of metabolite 1-7 and as shown in the figure, ($C_\tau$) is consistently above the $EC_{95}$ at all time points studied. The left y-axis is mean metabolite 1-7 plasma concentration measured in ng/mL, the right y-axis is HCV RNA reduction following 550 mg of Compound 1 QD measured in log 10 IU/mL, and the x-axis is time measured in hours.

Figure 30C:
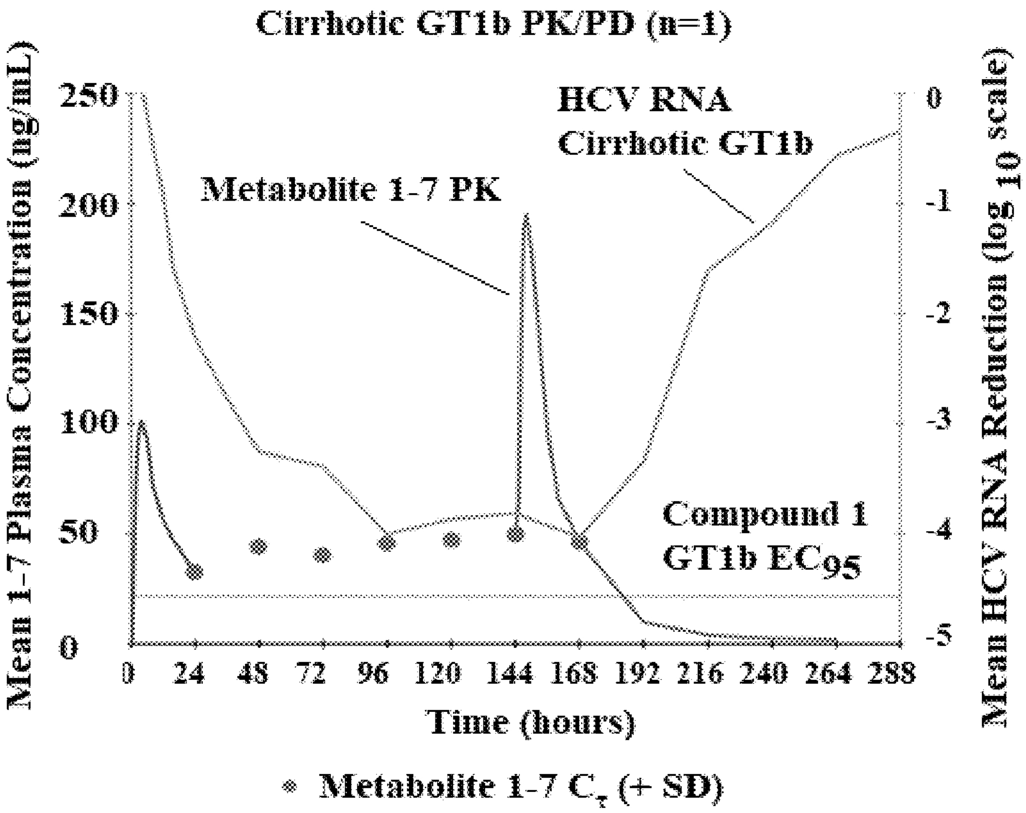

FIG. 30C is a graph plotting the mean metabolite 1-7 plasma concentration (left y-axis) and the mean HCV RNA reduction following 600 mg/day QD of Compound 1-A (equivalent to 550 mg of Compound 1) (right y-axis) against time for subjects with cirrhotic GT 1b HCV infection as described in Examples 26 and 27. The $EC_{95}$ of Compound 1 in GT1b is shown as a horizontal dashed line (-----). The dots represent the steady state plasma trough levels ($C_\tau$) of metabolite 1-7 and as shown in the figure, ($C_\tau$) is consistently above the $EC_{95}$ at all time points studied. The left y-axis is mean metabolite 1-7 plasma concentration measured in ng/mL, the right y-axis is HCV RNA reduction following 550 mg of Compound 1 QD measured in log 10 IU/mL, and the x-axis is time measured in hours.

Figure 30D:
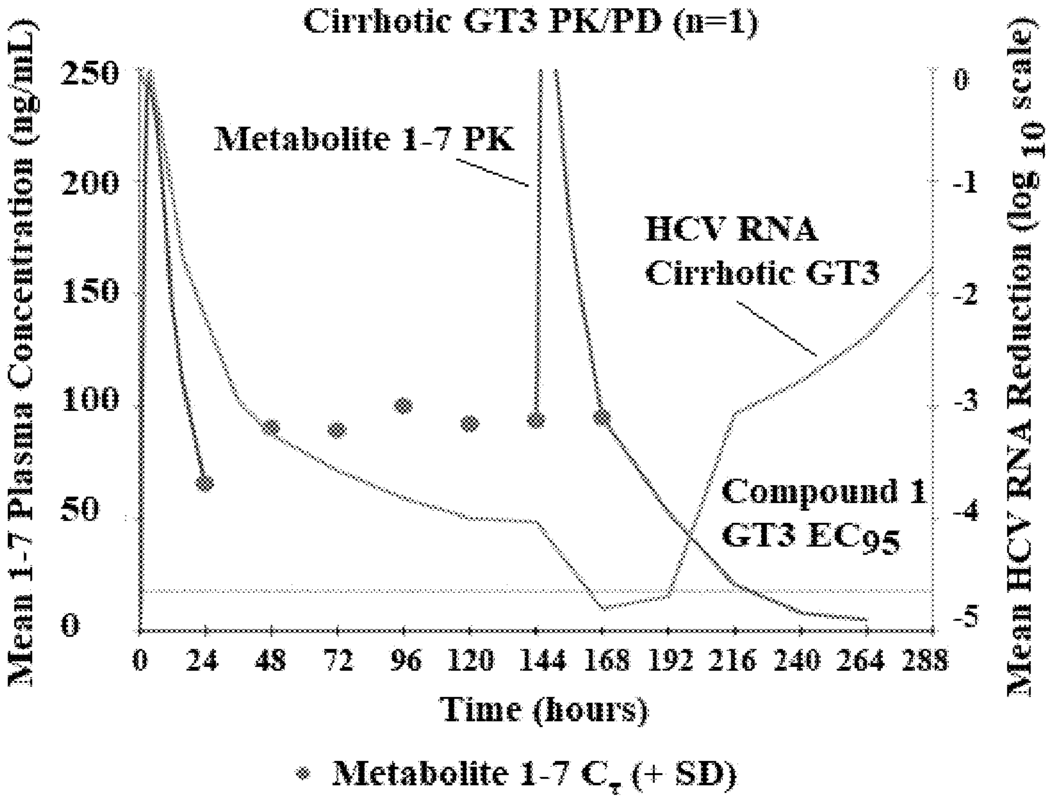

FIG. 30D is a graph plotting the mean metabolite 1-7 plasma concentration (left y-axis) and the mean HCV RNA reduction following 600 mg/day QD of Compound 1-A (equivalent to 550 mg of Compound 1) QD (right y-axis) against time for subjects with cirrhotic GT3 HCV infection as described in Examples 26 and 27. The $EC_{95}$ of Compound 1 in GT1b is shown as a horizontal dashed line (-----). The dots represent the steady state plasma trough levels ($C_\tau$) of metabolite 1-7 and as shown in the figure, ($C_\tau$) is consistently above the $EC_{95}$ at all time points studied. The left y-axis is mean metabolite 1-7 plasma concentration measured in ng/mL, the right y-axis is HCV RNA reduction following 550 mg of Compound 1 QD measured in log 10 IU/mL, and the x-axis is time measured in hours.

Figure 31:
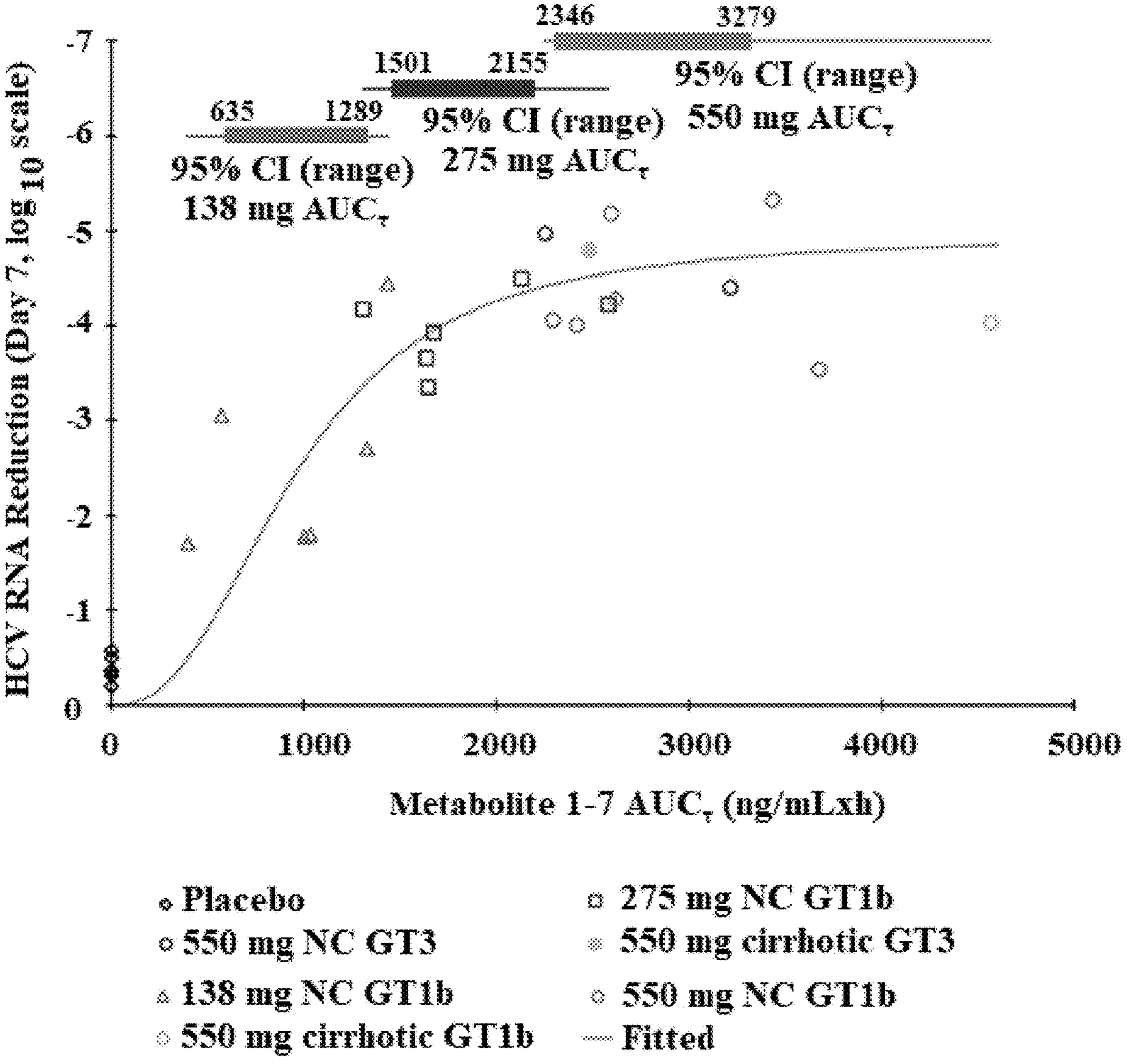

FIG. 31 is an Emax model where the HCV RNA reduction as measured on day 7 for subjects with non-cirrhotic GT1b HCV infection, non-cirrhotic GT3 HCV infection, cirrhotic GT1b HCV, and cirrhotic GT3 HCV infection is plotted against the AUC of metabolite 1-7 following QD dosing of Compound 1-A. As described in Examples 26 and 27, subjects with non-cirrhotic GT1b HCV were administered multiple ascending doses of the Compound 1-A equivalent of 138 mg/d, 275 mg/d, or 550 mg/d of Compound 1 QD for 7 days. Subjects with non-cirrhotic GT3 and those with cirrhotic GT1/GT3 infections were given 600 mg of Compound 1-A (equivalent to 550 mg/d of Compound 1) QD for 7 days. The 95% CI interval ranges for non-cirrhotic GT1b HCV administered 138 mg/d, 275 mg/d, or 550 mg/d are shown. The model predicts that metabolite 1-7 exposure of greater than or equal to 2000 ng/mL×h will result in a maximum viral load reduction of at least 4 log after 7 days of dosing. All subjects were able to achieve a metabolite 1-7 exposure greater than 2000 ng/mL×h following doses of 550 mg of Compound 1 regardless of whether the subject exhibited cirrhosis or non-cirrhosis of the liver. The x-axis is the AUC of metabolite 1-7 measured in ng/mL×h and the y-axis is the HCV RNA reduction on day 7 measured on a $log_{10}$ scale.

Figure 32:
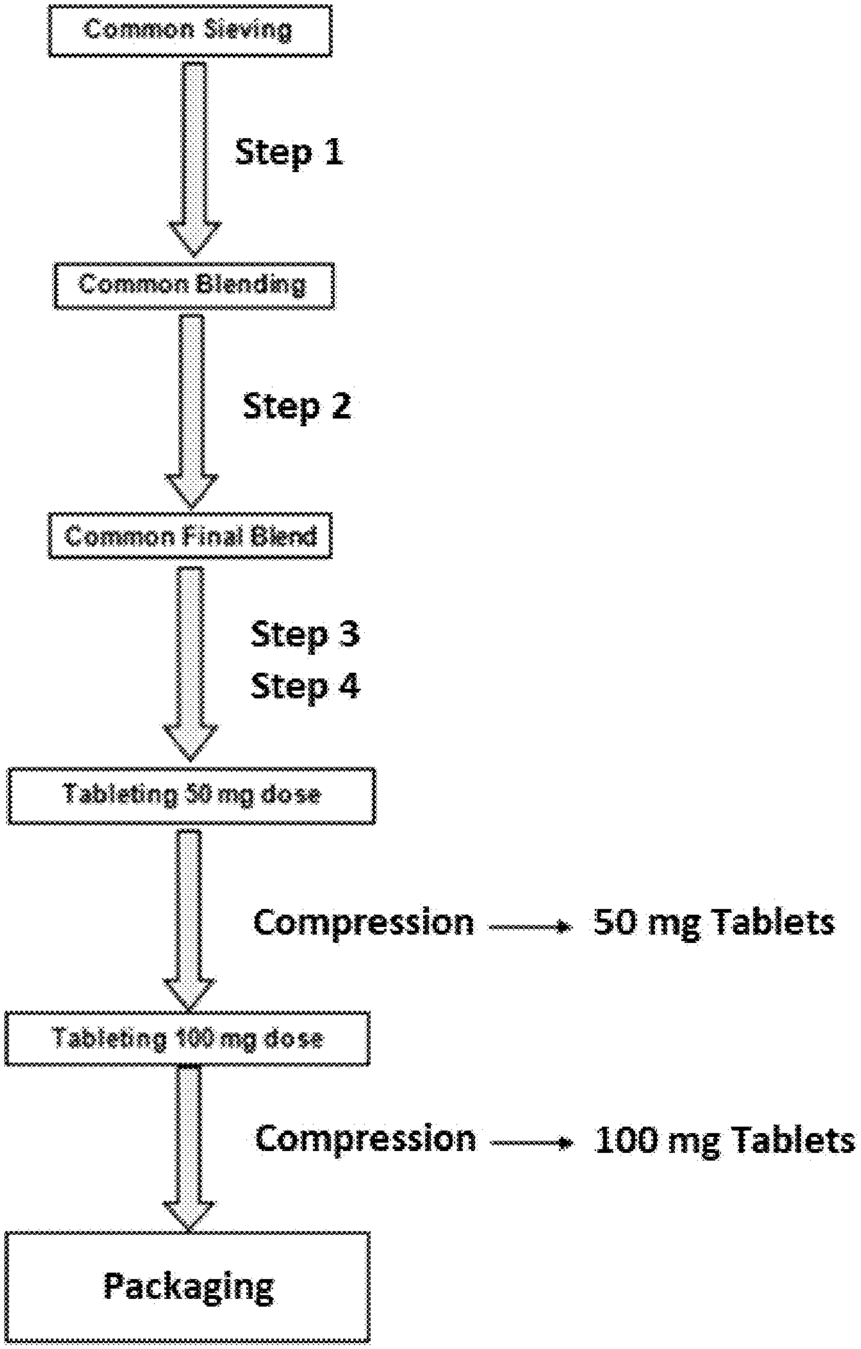

FIG. 32 is a flow diagram showing the manufacturing process of 50 mg and 100 mg tablets of Compound 1-A as described in Example 28. In step 1, microcrystalline cellulose, Compound 1-A, lactose monohydrate, and croscarmellose sodium are filtered through a 60 μM screen. In step 2, the contents from step 1 are loaded into a V-blender and mixed for 5 minutes at 25 rpm. In step 3, magnesium stearate is filtered through a 60 μM screen. In step 4, magnesium stearate is loaded into the V-blender containing the contents from step 2 (microcrystalline cellulose, Compound 1-A, lactose monohydrate, and croscarmellose sodium) and mixed for 2 minutes at 25 rpm. The common blend is then divided for the production of 50 mg tablets and 100 mg tablets. To produce 50 mg tablets, the blend from step 4 is compressed with 6 mm round standard concave tooling. To produce 100 mg tablets, the blend from step 4 is compressed with 8 mm round standard concave tooling. The tablets are then packaged into HDPE bottles induction-sealed with PP caps with desiccant.

Figure 33:
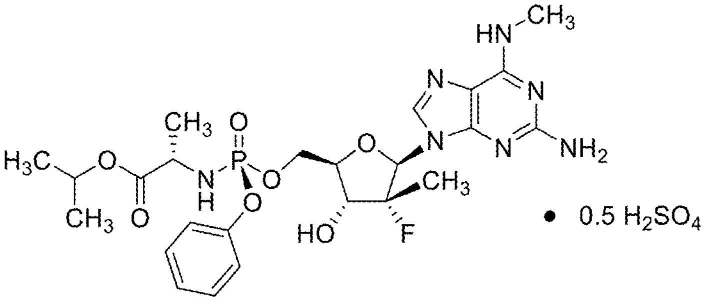
Figure 33:
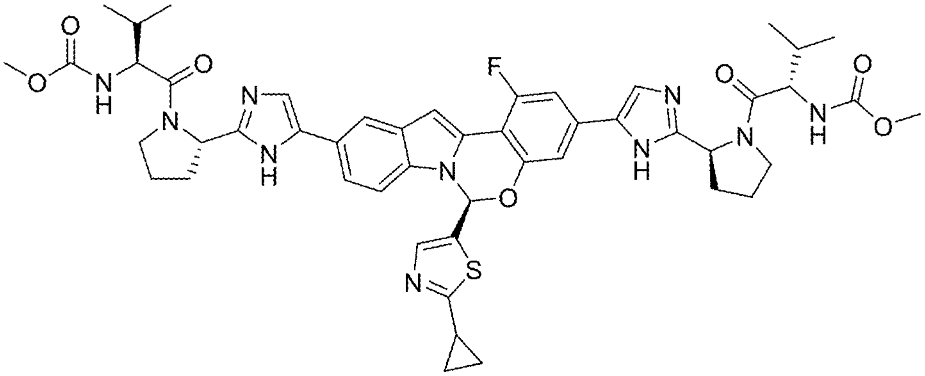

FIG. 33 is the NS5B polymerase inhibitor Compound 1-A and the NS5A inhibitor Compound 2.

Figure 34:
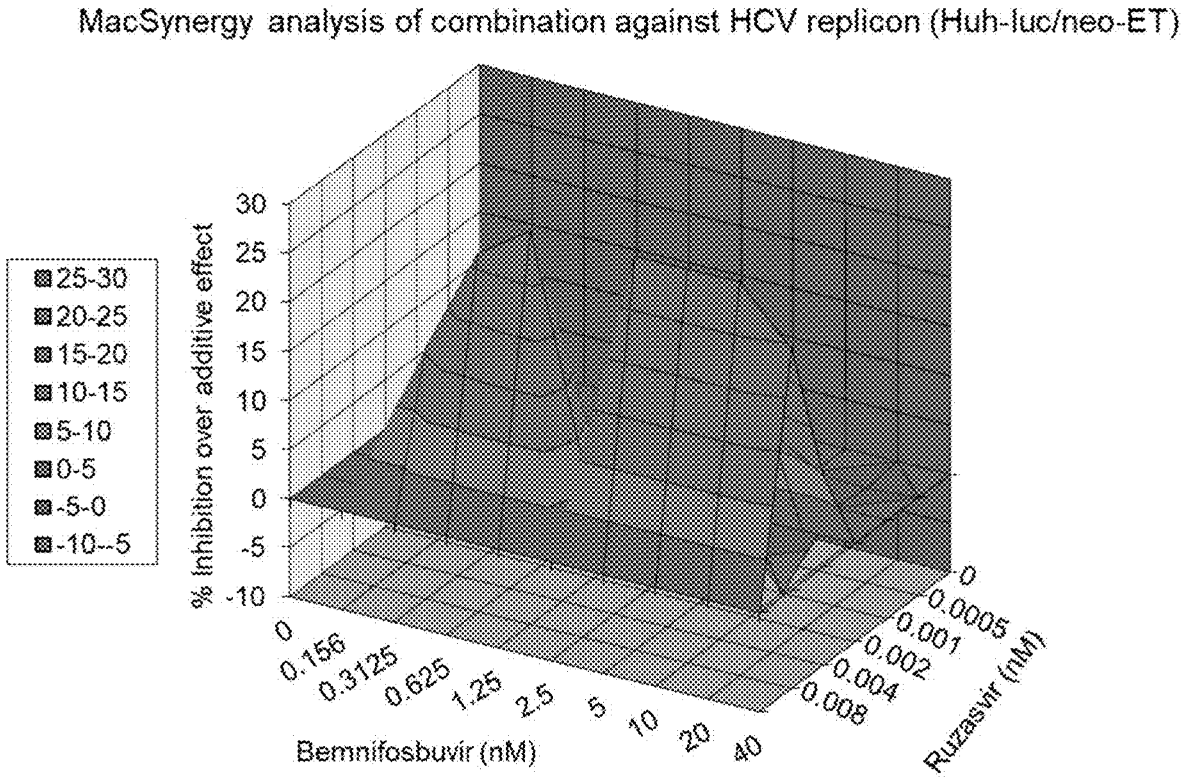

FIG. 34 is the three-dimensional combination surface plot showing at which concentrations the combination of Compound 1 and Compound 2 are synergistic, additive, or antagonistic. As described in Example 30, effects of the drug combination are calculated based on the activity of the two compounds when tested alone. The expected additive antiviral protection is subtracted from the experimentally determined antiviral activity at each combination concentration resulting in a positive value (synergy, or potentiation), a negative value (antagonism), or zero (additivity). The results of the combination assays are presented three dimensionally at each combination concentration, yielding a surface of activity extending above (synergy) or below (antagonism) the plane of additivity. The combination of Compound 1 and Compound 2 is synergistic over a wide range of concentrations of both Compound 1 and Compound 2. From about 0.156 to about 1 and 2.5 to 40 or more nM of Compound 1, synergy is observed. From about 0.001 nM to about 0.008 nM Compound 2 is the range of Compound 2 in which the most synergy is observed.

DETAILED DESCRIPTION OF THE INVENTION

The present invention provides a highly active synergistic combination of a specific NS5B polymerase inhibitor and a specific NS5A inhibitor for the advantageous treatment of a hepatitis C infection in a host, typically a human.

The anti-HCV compounds used in this combination therapy are: 1) the NS5B inhibitor isopropyl((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate (Compound 1), or a pharmaceutically acceptable salt thereof; and 2) the NS5A inhibitor Ruzasvir (dimethyl N,N'-([(6S)-6-(2-cyclopropyl-1,3-thiazol-5-yl)-1-fluoro-6H-indolo[1,2-c][1,3]benzoxazine-3,10-diyl]bis{1H-imidazole-5,2-diyl-(2S)-pyrrolidine-2,1-diyl[(2S)-3-methyl-1-oxobutane-1,2-diyl]})dicarbamate) (Compound 2) or a pharmaceutically acceptable salt thereof. In a typical embodiment, Compound 1 is administered as the hemi-sulfate salt derivative (Compound 1-A).

Compound 1

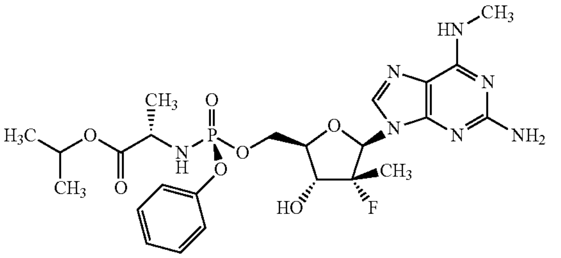

Compound 1-A

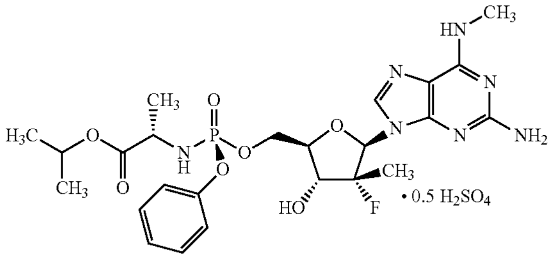

Compound 2

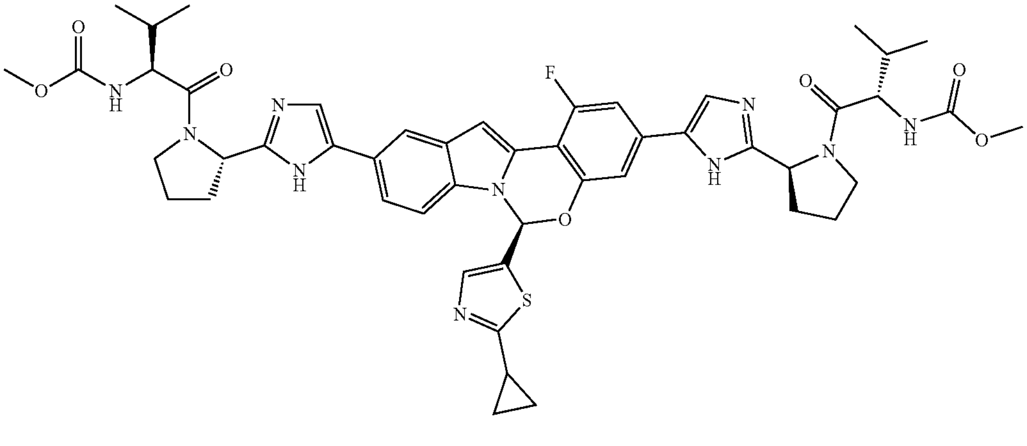

In one embodiment, the combination of drugs are administered in a fixed-dose dosage form, such as a pill or tablet. In an alternative embodiment, the two compounds are administered in a manner that the host in need thereof receives the benefit of the both compounds in a concerted fashion, as measured by standard pharmacokinetics.

Compound 1 and Compound 1-A

Compound 1 (isopropyl((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy) phosphoryl)-L-alaninate) was previously described in U.S. Pat. Nos. 9,828,410; 10,000,523; 10,005,811; and, 10,239,911 and PCT Applications WO 2016/21276 and WO 2019/200005 assigned to Atea Pharmaceuticals. The synthesis of Compound 1 is described in Example 1 below.

Compound 1-A was previously disclosed in US 2018-0215776 and PCT Applications WO 2018/144640 and WO 2019/200005 assigned to Atea Pharmaceuticals. The synthesis of Compound 1-A (the hemi-sulfate salt of isopropyl ((S)-(((2R,3R,4R,5R)-5-(2-amino-6-(methylamino)-9H-purin-9-yl)-4-fluoro-3-hydroxy-4-methyltetrahydrofuran-2-yl) methoxy)(phenoxy)phosphoryl)-L-alaninate) is described in Example 4 below. In one embodiment Compound 1-A is provided in a pharmaceutically acceptable composition or solid dosage form thereof. In another embodiment, Compound 1-A is an amorphous solid. In one embodiment, Compound 1-A is a crystalline solid. FIGS. 1-15 depict the characterization of the physical form of Compound 1-A by XRPD, DSC, and TGA.

As described above, Compound 1-A has completed a Phase 1b/2a clinical trial for patients infected with HCV. The multiple part study evaluated the effect of single and multiple doses of Compound 1-A in healthy subjects, non-cirrhotic HCV-infected patients, and cirrhotic HCV-infected patients. Compound 1-A induced significant antiviral reduction when administered to all HCV-infected cohorts tested. Compound 1-A was administered once daily (QD) over the course of seven days, and potent antiviral activity was observed. In non-cirrhotic HCV-infected patients who were given 600 mg QD of Compound 1-A (equivalent to 550 mg of Compound 1), the mean maximum HCV RNA reduction was 4.4 $\log_{10}$ IU/mL in HCV GT1-infected patients and 4.6 $\log_{10}$ IU/mL in HCV GT3-infected patients. The effect of Compound 1-A on antiviral reduction also extended to the difficult-to-treat cirrhotic patients. In a cohort of HCV GT1 or HCV GT3-infected patients with CPA cirrhosis, the mean maximum HCV RNA reduction was 4.4 $\log_{10}$ IU/mL when administered QD for seven days (Zhou, X. et al. "AT-527, a pan-genotypic purine nucleotide prodrug, exhibits potent antiviral activity in subjects with chronic hepatitis C" presented at The International Liver Congress 2018; Apr. 13, 2018; Paris, France). FIGS. 25-31 depict Compound 1 metabolite and HCV viral RNA levels in cirrhotic patients who were administered Compound 1. FIG. 27 highlights that Compound 1 is equally effective in cirrhotic patients as it is in non-cirrhotic patients.

Unless otherwise specified, Compound 1 or a pharmaceutically acceptable salt thereof, for example, Compound 1-A, is provided in the β-D-configuration. In an alternative embodiment, Compound 1 or a pharmaceutically acceptable salt thereof, for example Compound 1-A, can be provided in a β-L-configuration. The phosphoramidate of Compound 1 or a pharmaceutically acceptable salt thereof, for example Compound 1-A, can be provided as an R or S chiral phosphorus derivative or a mixture thereof, including a racemic or a diastereomeric mixture. All of the combinations of these stereo configurations are alternative embodiments in the invention described herein.

These alternative configurations include, but are not limited to:

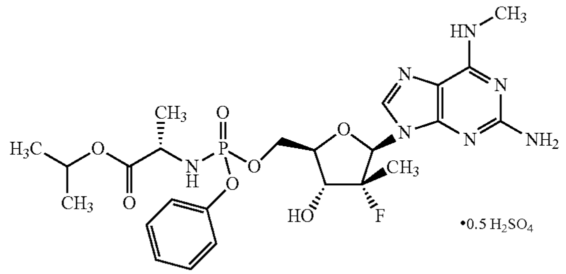

•0.5 $H_2SO_4$

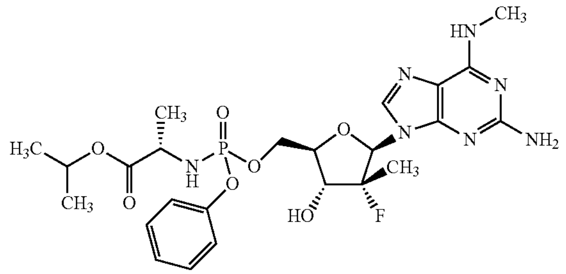

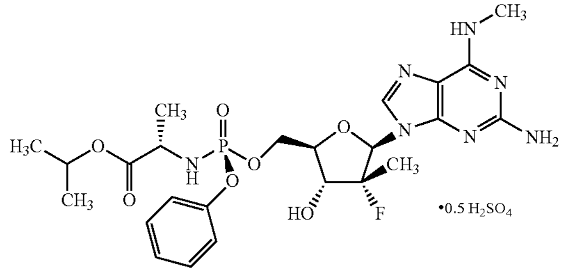

•0.5 $H_2SO_4$

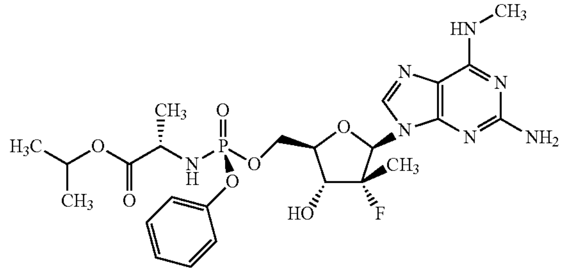

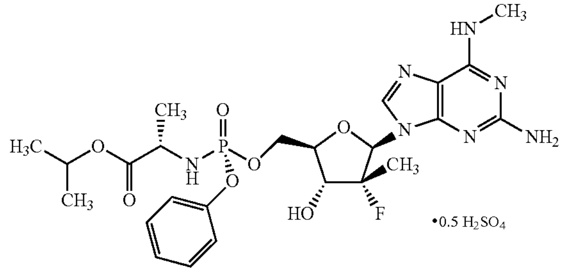

•0.5 $H_2SO_4$

-continued

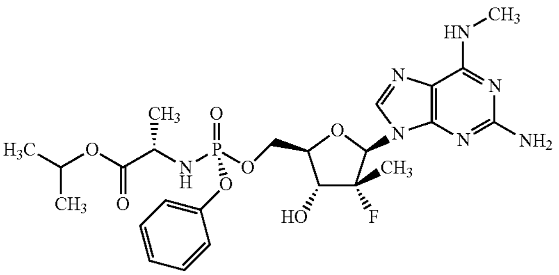

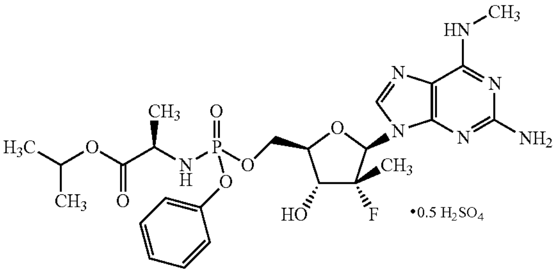

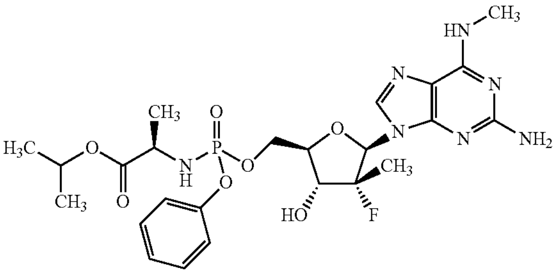

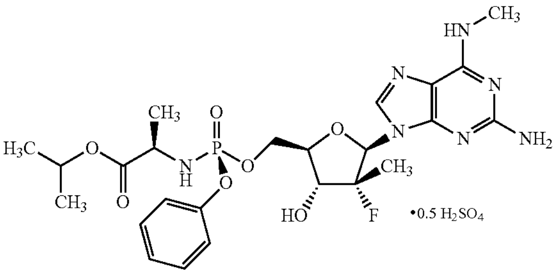

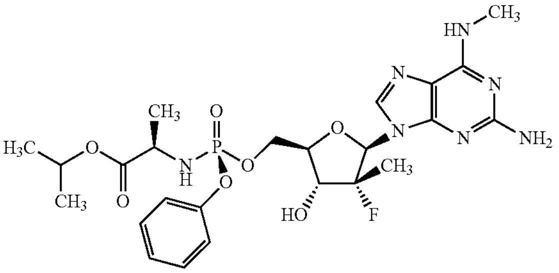

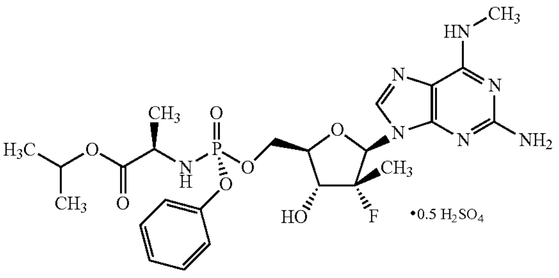

-continued

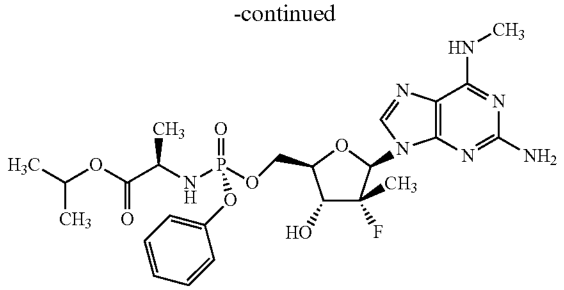

An additional alternative configuration includes

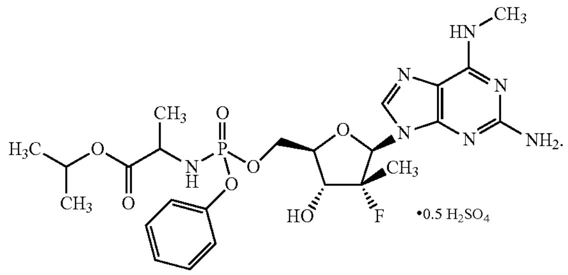

In one embodiment, any of the above stereoisomers or a pharmaceutically acceptable salt thereof is used as Compound 1, or a pharmaceutically acceptable salt thereof, in any aspect of the present invention herein. In another embodiment any one of the above stereoisomers or a pharmaceutically acceptable salt thereof is used as Compound 1-A in any aspect of the present invention herein.

In an alternative embodiment, Compound 1-A is provided as the hemisulfate salt of a phosphoramidate other than the specific phosphoramidate described in the compound illustration. In another alternative embodiment, Compound 1 or a pharmaceutically acceptable salt thereof is provided as a phosphoramidate other than the specific phosphoramidate described in the compound illustration. A wide range of phosphoramidates are known to those skilled in the art which can be selected as desired to provide an active compound as described herein. For example, the phosphoramidate of Compound 1 or a pharmaceutically acceptable salt thereof includes a compound or pharmaceutically acceptable salt thereof of Formula A:

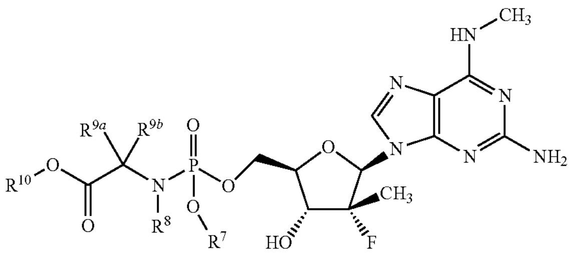

wherein:

$R^7$ is hydrogen, $C_{1-6}$alkyl (including methyl, ethyl, propyl, and isopropyl), $C_{3-7}$cycloalkyl, or aryl (including phenyl and napthyl);

$R^8$ is hydrogen or $C_{1-6}$alkyl (including methyl, ethyl, propyl, and isopropyl);

$R^{9a}$ and $R^{9b}$ are independently selected from hydrogen, $C_{1-6}$alkyl (including methyl, ethyl, propyl, and isopropyl), or $C_{3-7}$cycloalkyl; and $R^{10}$ is hydrogen, $C_{1-6}$alkyl (including methyl, ethyl, propyl, and isopropyl), $C_{1-6}$haloalkyl, or $C_{3-7}$cycloalkyl.

In alternative non-limiting embodiments, the present invention includes Compound 1 as an oxalate salt (Compound 1-B), an HCl salt (Compound 1-C), or a sulfate salt (Compound 1-D).

Compound 1-B

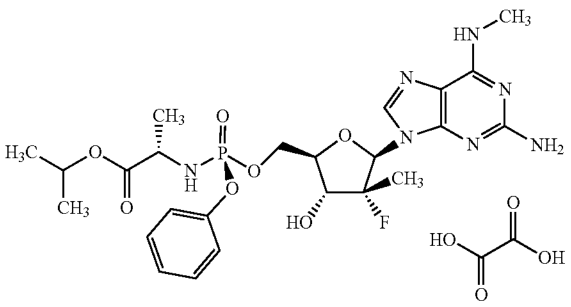

Compound 1-C

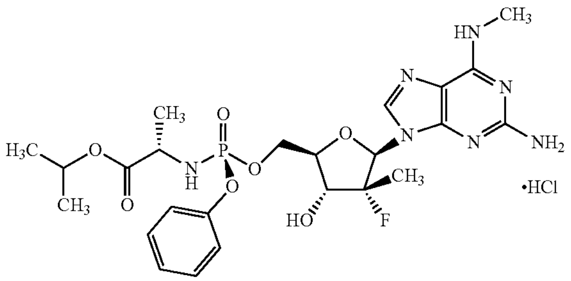

Compound 1-D

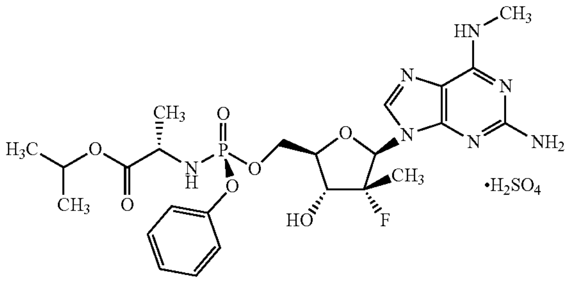

The metabolism of Compound 1 and Compound 1-A involves the production of a 5'-monophosphate and the subsequent anabolism of the $N^6$-methyl-2,6-diaminopurine base (1-3) to generate ((2R,3R,4R,5R)-5-(2-amino-6-oxo-1,6-dihydro-9H-purin-9-yl)-4-fluoro-3-hydroxy-4-methyltetrahydrofuran-2-yl)methyl dihydrogen phosphate (1-4) as the 5'-monophosphate. The monophosphate is then further anabolized to the active triphosphate species: the 5'-triphosphate (1-6). The 5'-triphosphate can be further metabolized to generate 2-amino-9-((2R,3R,4R,5R)-3-fluoro-4-hydroxy-5-(hydroxymethyl)-3-methyltetrahydrofuran-2-yl)-1,9-dihydro-6H-purin-6-one (1-7). FIGS. 17-24 depict the pharmacokinetic properties of Compound 1-A and major metabolites. Although Compound 1-A is metabolized within 8 hours, active metabolites are present for up to 24 hours. During the 24 hour period in which the metabolites are present, a suppression of HCV viral RNA is observed. At doses of 300 mg, the plasma concentrations of Compound 1-A metabolites are higher than the $EC_{95}$ of HCV GT1b. FIG. 16 depicts the advantageous biodistribution properties of Compound 1-A. The compound concentrates in the liver, the target organ for HCV infection, over the heart. Because the liver concentration is high, a lower dose may be used. The effect is not species specific and was observed in three different preclinical species. FIG. 24 shows a comparison of the EC95 for Compound 1 and sofosbuvir against various HCV genotypes. Sofosbuvir has variable EC95s based on the genotype, the EC95 for Compound 1 has little variation based on genotype.

Alternatively, 5'-monophosphate 1-2 can be metabolized to generate the purine base 1-8. The metabolic pathway for isopropyl((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate is illustrated in Scheme 1:

Scheme 1

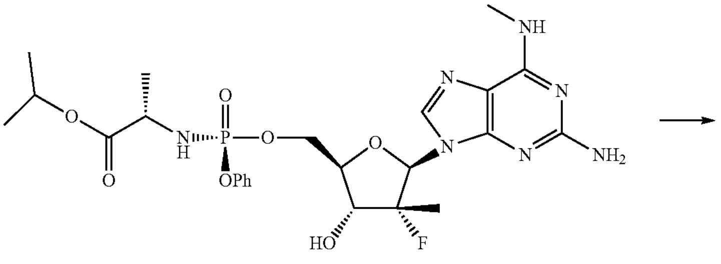

Compound 1

-continued

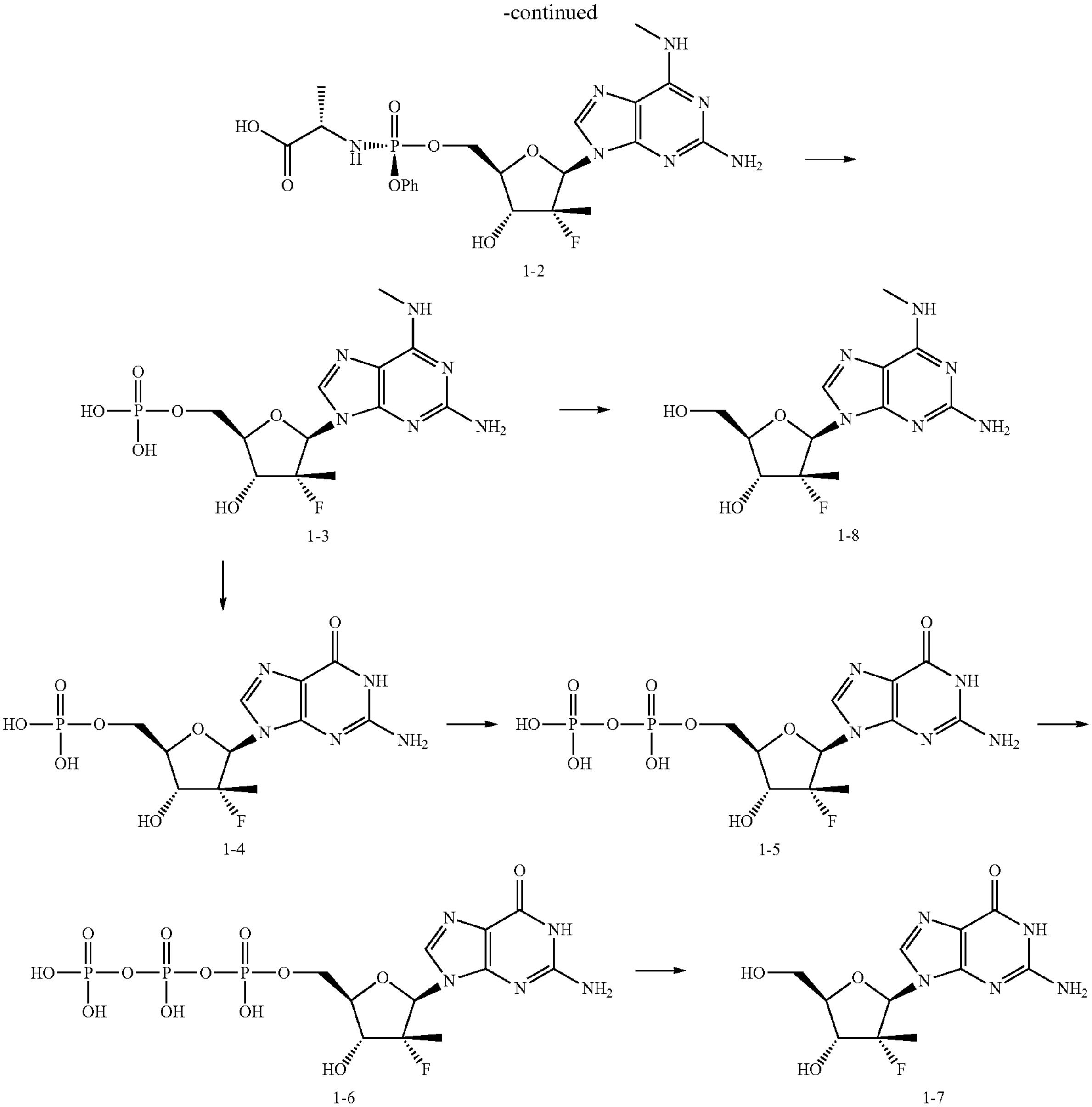

1-2

1-3

1-8

1-4

1-5

1-6

1-7

Atea Pharmaceuticals, Inc. has disclosed β-D-2'-deoxy-2'-α-fluoro-2'-β-C-substituted-2-modified-N$^6$-(mono- and di-methyl) purine nucleotides for the treatment of HCV in U.S. Pat. Nos. 9,828,410; 10,000,523; 10,005,811; 10,239,911, 10,815,266; 10,870,672; 10,870,673; 10,870,885; 10,519,186; 10,906,928; 10,894,804; and, PCT Application Nos. WO 2016/144918; WO 2018/048937; WO 2018/013937; and, WO 2018/144640. Atea has also disclosed β-D-2'-deoxy-2'-substituted-4'-substituted-2-N$^6$-substituted-6-aminopurine nucleotides for the treatment of paramyxovirus and orthomyxovirus infections in U.S. Pat. No. 10,202,412 and PCT Application No. WO 2018/009623.

Compound 2

Compound 2 is disclosed in WO 2014/110705 and U.S. Pat. No. 9,555,038 assigned to Merck and Company. In one embodiment, Compound 2 is administered as the pharmaceutically acceptable salt thereof. In one embodiment a solid form of Compound 2 is used. In one embodiment the solid form of Compound 2 is a crystalline solid.

The synthesis of ruzasvir (dimethyl N,N'-([(6S)-6-(2-Cyclopropyl-1,3-thiazol-5-yl)-1-fluoro-6H-indolo[1,2-c][1,3]benzoxazine-3,10-diyl]bis{1H-imidazole-5,2-diyl-(2S)-pyrrolidine-2,1-diyl[(2S)-3-methyl-1-oxobutane-1,2-diyl]}) dicarbamate, Compound 2) is known in the art. Non-limiting examples of synthetic methods that can be used to synthesize Compound 2 include those shown in Example 29 and reported in WO 2016/196932 assigned to Merck.

Definitions

The term "D-configuration" as used in the context of the present invention refers to the principle configuration which mimics the natural configuration of sugar moieties as opposed to the unnatural occurring nucleosides or "L" configuration. The term "0" or "3 anomer" is used with reference to nucleoside analogs in which the nucleoside base is configured (disposed) above the plane of the furanose moiety in the nucleoside analog.

The terms "coadminister" and "coadministration" or combination therapy are used to describe the administration of Compound 1 or a pharmaceutically acceptable salt thereof according to the present invention in combination with Compound 2 or a pharmaceutically acceptable salt thereof. In certain embodiments, Compound 1 or a pharmaceutically acceptable salt thereof, for example Compound 1-A, and Compound 2 or a pharmaceutically acceptable salt thereof are administered with at least one other active agent, for example where appropriate at least one additional anti-HCV agent. The timing of the coadministration is best determined by the medical specialist treating the patient. It is sometimes preferred that the agents be administered at the same time or at least in a manner that allows for an overlapping pharmacologic effect of the two drugs in the treated patient. Alternatively, the drugs selected for combination therapy may be administered at different times to the patient. Of course, when more than one viral or other infection or other condition is present, the present compounds may be combined with other agents to treat that other infection or condition as required.

The term "host", as used herein, refers to a unicellular or multicellular organism in which a HCV virus can replicate, including cell lines and animals, and typically a human. The term host specifically refers to infected cells, cells transfected with all or part of a HCV genome, and animals, in particular, primates (including chimpanzees) and humans which bear the HCV genome or a part thereof capable of treatment with the combination described herein. In most animal applications of the present invention, the host is a human patient which includes, but is not limited to a dosage regime with overlapping pharmacokinetics. Veterinary applications, in certain indications, however, are clearly anticipated by the present invention (such as chimpanzees). The host can be for example, bovine, equine, avian, canine, feline, etc., which is capable of hosting the virus.

A "pharmaceutically acceptable salt" is a derivative of the disclosed compound in which the parent compound is modified to an inorganic and organic, acid or base addition salt thereof without undue toxicity. The salts of the present compounds can be synthesized from the parent compound with a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds may optionally be provided in the form of a solvate.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional salts and the quaternary ammonium salts of the parent compound formed, for example, from inorganic or organic acids that are not unduly toxic. For example, conventional acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like, or using a different acid that produces the same counterion. Lists of additional suitable salts may be found, e.g., in Remington's Pharmaceutical Sciences, 17th ed., Mack Publishing Company, Easton, Pa., p. 1418 (1985).

The compound can be delivered in any molar ratio that delivers the desired result. For example, the compound can be provided with less than a molar equivalent of a counter ion, such as in the form of a hemi-sulfate salt. Alternatively, the compound can be provided with more than molar equivalent of counter ion, such as in the form of a di-sulfate salt. Non-limiting examples of molar ratios of the compound to the counter ion include 1:0.25, 1:0.5, 1:1, and 1:2.

Isotopic Substitution

The present invention includes combinations of Compound 1 or a pharmaceutically acceptable salt thereof, for example Compound 1-A, and Compound 2 or a pharmaceutically acceptable salt thereof wherein one or both of the compounds has desired isotopic substitutions of atoms at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2H$) and tritium ($^3H$) may be used anywhere in described structures. Alternatively or in addition, isotopes of carbon, e.g., $^{13}C$ and $^{14}C$, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect). Achillion Pharmaceuticals, Inc. (WO/2014/169278 and WO/2014/169280) describes deuteration of nucleotides to improve their pharmacokinetic or pharmacodynamic, including at the 5-position of the molecule.

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break-down can reduce the rate of or eliminate the metabolism at that bond. At any position of the compound that a hydrogen atom may be present, the hydrogen atom can be any isotope of hydrogen, including protium ($^1H$), deuterium ($^2H$) and tritium ($^3H$). Thus, reference herein to a compound encompasses all potential isotopic forms unless the context clearly dictates otherwise.

The term "isotopically-labeled" analog refers to an analog that is a "deuterated analog", a "$^{13}C$-labeled analog," or a "deuterated/$^{13}C$-labeled analog." The term "deuterated analog" means a compound described herein, whereby a H-isotope, i.e., hydrogen/protium ($^1H$), is substituted by a H-isotope, i.e., deuterium ($^2H$). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location. Unless indicated to the contrary, the deuteration is at least 80% at the selected location. Deuteration of the nucleoside can occur at any replaceable hydrogen that provides the desired results.

Methods of Treatment

Treatment, as used herein, refers to the administration of the combination of the present invention in an effective amount to a host, for example a human that is or may become infected with an HCV virus. In one embodiment the method of treatment comprises administration of an effective amount of Compound 1 or a pharmaceutically acceptable salt thereof and Compound 2 or a pharmaceutically acceptable salt thereof, to a host, for example a human that is or may become infected with a HCV virus. In another embodiment the method of treatment comprises administration of Compound 1-A and Compound 2 to a host, for example a human that is or may become infected with a HCV virus.

The term "prophylactic" or preventative, when used, refers to the administration of a combination of the present invention to prevent or reduce the likelihood of an occurrence of the viral disorder. The present invention includes in an alternative embodiment, treatment and prophylactic or preventative therapies. In one embodiment, the combination is administered to a host who has been exposed to and thus is at risk of infection by a hepatitis C virus infection.

The invention includes a method of treatment of a hepatitis C virus, by administering an effective amount of the synergistic combination of Compound 1 (such as 1-A) and Compound 2 including drug resistant and multidrug resistant forms of HCV and related disease states, conditions, or complications of an HCV infection, including cirrhosis and related hepatotoxicities, as well as other conditions that are secondary to an HCV infection, such as weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, jaundice, and hepatocellular cancer, among others. The method comprises administering to a host in need thereof, typically a human, an effective amount of the combination described herein, optionally in combination with at least one additional bioactive agent, for example, an additional anti-HCV agent, further optionally in combination with a pharmaceutically acceptable carrier additive and/or excipient. In another embodiment the method comprises administering to a patient at risk of an HCV infection, an effective amount of a combination of the present invention. In another embodiment the combination as described above is used with a pharmaceutically acceptable carrier, additive, or excipient, optionally in combination with a third anti-HCV agent. In another embodiment, the combination of the present invention can be administered to a patient after a hepatitis-related liver transplantation to protect the new organ.

The combination therapy and dosage forms can also be used to treat conditions related to or occurring as a result of an HCV viral exposure. For example, the active compound can be used to treat HCV antibody-positive and HCV antigen-positive conditions, viral-based chronic liver inflammation, liver cancer resulting from advanced hepatitis C (e.g., hepatocellular carcinoma), cirrhosis, acute hepatitis C, fulminant hepatitis C, chronic persistent hepatitis C, and anti-HCV-based fatigue. The combination can also be used prophylactically to prevent or restrict the progression of clinical illness in individuals who are anti-HCV antibody- or antigen-positive or who have been exposed to hepatitis C.

Pharmaceutical Compositions and Dosage Forms

Administration of Compound 1 or pharmaceutically acceptable salt thereof and Compound 2 or a pharmaceutically acceptable salt thereof may be carried out using any desired form, including but not limited to oral, topical, parenteral, intramuscular, intravenous, sub-cutaneous, transdermal (which may include a penetration enhancement agent), buccal, and suppository administration, among other routes of administration. In one embodiment, the active compound or combination of compounds are provided in solid dosage forms which are well known in the art and described further below. Enteric coated oral tablets may also be used to enhance bioavailability of the compounds for an oral route of administration. The most effective dosage form will depend upon the bioavailability/pharmacokinetic of the particular agents chosen as well as the severity of disease in the patient. Oral dosage forms are particularly preferred, because of ease of administration and prospective favorable patient compliance.

In certain embodiments, pharmaceutical compositions according to the present invention comprise an anti-HCV virus effective amount of each separately or a combined form of Compound 1 or a pharmaceutically acceptable salt thereof and Compound 2 or a pharmaceutically acceptable salt thereof as described herein, optionally in combination with a pharmaceutically acceptable carrier, additive, or excipient, further optionally in combination or alternation with at least one other active compound.

In one embodiment, the combination includes a solid dosage form of Compound 1 or a pharmaceutically acceptable salt thereof, for example, Compound 1-A, and Compound 2 or a pharmaceutically acceptable salt thereof in a pharmaceutically acceptable carrier. This pharmaceutical composition may contain both Compound 1 or a pharmaceutically acceptable salt thereof and Compound 2 or a pharmaceutically acceptable salt thereof or alternatively the compounds may be in separate dosage forms that are administered in a manner that the host receives the benefit of both compounds in a concerted fashion as measured by standard pharmacokinetics.

One of ordinary skill in the art will recognize that a therapeutically effective amount will vary with the infection or condition to be treated, its severity, the treatment regimen to be employed, the pharmacokinetic of the agent used, as well as the patient or subject (animal or human) to be treated, and such therapeutic amount can be determined by the attending physician or specialist.

Compound 1 or a pharmaceutically acceptable salt thereof, for example Compound 1-A, and Compound 2 or a pharmaceutically acceptable salt thereof can be formulated as one or more mixtures with one or more pharmaceutically acceptable carriers. In general, it is preferable to administer the one or more pharmaceutical composition in orally-administrable form, and in particular, one or more solid dosage forms such as a pill or tablet. Certain formulations may be administered via a parenteral, intravenous, intramuscular, topical, transdermal, buccal, subcutaneous, suppository, or other route, including intranasal spray. Intravenous and intramuscular formulations are often administered in sterile saline. One of ordinary skill in the art may modify the formulations to render them more soluble in water or another vehicle, for example, this can be easily accomplished by minor modifications (salt formulation, esterification, etc.) that are well within the ordinary skill in the art. It is also well within the routineers' skill to modify the route of administration and dosage regimen of Compound 1 or a pharmaceutically acceptable salt thereof, for example Compound 1-A, and Compound 2 or a pharmaceutically acceptable salt thereof in order to manage the pharmacokinetic of the present compounds for maximum beneficial effect in patients.

In certain pharmaceutical dosage forms, the prodrug form of the compounds, including acylated (acetylated or other), and ether (alkyl and related) derivatives, phosphate esters, thiophosphoramidates, phosphoramidates, and various salt forms of the present compounds, may be used to achieve the desired effect. One of ordinary skill in the art will recognize how to readily modify the present compounds to prodrug forms to facilitate delivery of active compounds to a targeted site within the host organism or patient. The person of ordinary skill in the art also will take advantage of favorable pharmacokinetic parameters of the prodrug forms, where applicable, in delivering the present compounds to a targeted site within the host organism or patient to maximize the intended effect of the compound.

Amounts mentioned in this disclosure typically refer to the free form (i.e., non-salt, hydrate or solvate form). The typically values described herein represent free-form equivalents, i.e., quantities as if the free form would be administered. If salts are administered the amounts need to be calculated in function of the molecular weight ratio between the salt and the free form.

The amount of Compound 1 or a pharmaceutically acceptable salt thereof, for example Compound 1-A, and Compound 2 or a pharmaceutically acceptable salt thereof included within the therapeutically active formulation according to the present invention is an effective amount to achieve the desired outcome according to the present invention, for example, for treating the HCV infection, reducing the likelihood of a HCV infection or the inhibition, reduction, and/or abolition of HCV or its secondary effects, including disease states, conditions, and/or complications which occur secondary to HCV. In general, a therapeutically effective amount of the present compounds in a pharmaceutical dosage form may range, for example, from about 0.001 mg/kg to about 100 mg/kg per day or more. Compound 1 or Compound 1-A may for example be administered in amounts ranging from about 0.1 mg/kg to about 15 mg/kg per day of the patient, depending upon the pharmacokinetics of the agent in the patient.

In certain embodiments, 600 mg of Compound 1-A, which is 550 mg of Compound 1 is provided in a dosage form.

In certain embodiments, the pharmaceutical composition is in a dosage form that contains from about 1 mg to about 2000 mg, from about 10 mg to about 1000 mg, from about 100 mg to about 800 mg, from about 200 mg to about 600 mg, from about 300 mg to about 500 mg, or from about 400 mg to about 450 mg of Compound 1 or an equivalent amount of Compound 1-A in a unit dosage form in addition to from about 1 mg to about 2000 mg, from about 10 mg to about 1000 mg, from about 100 mg to about 800 mg of Compound 2 or an equivalent amount of a pharmaceutically acceptable salt of Compound 2.

In alternative embodiments, the pharmaceutical composition is in a dosage form that contains from about 500 mg to about 600 mg, from about 550 mg to about 750 mg, from about 600 mg to about 800 mg, or from about 1,000 mg to about 1,300 mg of Compound 1 or an equivalent amount of Compound 1-A in a unit dosage form in addition to from about 100 mg to about 800 mg, from about 150 mg to about 200 mg, from about 250 to about 300 mg, or from about 350 to about 400 mg of Compound 2 or an equivalent amount of a pharmaceutically acceptable salt of Compound 2.

In certain embodiments, the pharmaceutical composition is in a dosage form, for example in a solid dosage form, that contains up to about 10, about 50, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, or about 1000 mg or more of Compound 1 or an equivalent amount of Compound 1-A in a unit dosage form.

In certain embodiments, the pharmaceutical composition is in a dosage form, for example in a solid dosage form, that contains up to about 10, about 50, about 60, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, or about 1000 mg or more of Compound 2 or an equivalent amount of a pharmaceutically acceptable salt of Compound 2.

In alternative embodiments, the pharmaceutical composition is in a dosage form, for example in a solid dosage form, that contains up to about 90, about 180, about 270, or about 360 mg of Compound 2 or an equivalent amount of a pharmaceutically acceptable salt of Compound 2.

In one embodiment, a solid dosage form containing up to about 800 mg, up to about 700 mg, up to about 600 mg, up to about 550 mg, up to about 500 mg, up to about 400 mg, up to about 300 mg, up to about 200 mg, or up to about 100 mg of Compound 1 or an equivalent amount of Compound 1-A and up to about 360 mg, up to about 270 mg, up to about 180 mg, up to about 145 mg, up to about 130 mg, up to about 125 mg, up to about 110 mg, up to about 100 mg, up to about 90 mg, up to about 75 mg, up to about 70 mg, up to about 65 mg, up to about 60 mg, up to about 55 mg, up to about 50 mg, up to about 45 mg, up to about 40 mg, up to about 35 mg, up to about 30 mg, up to about 25 mg, up to about 20 mg, up to about 15 mg, up to about 10 mg, or up to about 5 mg of Compound 2 or an equivalent amount of a pharmaceutically acceptable salt of Compound 2 is administered once a day to a host in need thereof for the treatment of HCV.

In one embodiment, a solid dosage form containing at least about 100 mg, at least about 200 mg, at least about 300 mg, at least about 400 mg, at least about 500 mg, at least about 550 mg, at least about 600 mg, at least about 700 mg, at least about 750 mg, or at least about 1,100 mg of Compound 1 or an equivalent amount of Compound 1-A and at least about 5 mg, at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 90 mg, at least about 100 mg, at least about 110 mg, at least about 125 mg, at least about 130 mg, at least about 145 mg, at least about 180 mg, at least about 270 mg, at least about 360 mg, at least about 400 mg or at least about 500 mg of Compound 2 or an equivalent amount of a pharmaceutically acceptable salt of Compound 2 is administered once a day to a host in need thereof for the treatment of HCV.

In an alternative embodiment, a solid dosage form containing up to about 1,100, up to about 750 mg, or up to about 550 mg of Compound 1 or an equivalent amount of Compound 1-A and up to about 360 mg, up to about 270 mg, up to about 180 mg, up to about 90 mg of Compound 2 or an equivalent amount of a pharmaceutically acceptable salt of Compound 2 is administered once a day to a host in need thereof for the treatment of HCV.

In an alternative embodiment, a solid dosage form containing at least about 500 mg, at least about 550 mg, at least about 750 mg, or at least about 1,100 mg of Compound 1 or an equivalent amount of Compound 1-A and at least about 90 mg, at least about 180 mg, at least about 270 mg, at least about 360 mg of Compound 2 or an equivalent amount of a pharmaceutically acceptable salt of Compound 2 is administered twice a day to a host in need thereof for the treatment of HCV.

In one embodiment, the combination of compounds as described herein are administered as a single tablet that contains up to about 600 mg of Compound 1-A and up to about 90, 180, 270 or 360 mg of Compound 2 or an equivalent amount of a pharmaceutically acceptable salt of Compound 2.

In an alternative embodiment, the combination of compounds as described herein are administered as a single tablet that contains up to about 600 mg of Compound 1-A and up to about 180 mg of Compound 2 or an equivalent amount of a pharmaceutically acceptable salt of Compound 2.

In an alternative embodiment, the combination of compounds as described herein are administered as a single tablet that contains up to about 600 mg of Compound 1-A and up to about 270 mg of Compound 2 or an equivalent amount of a pharmaceutically acceptable salt of Compound 2.

In an alternative embodiment, the combination of compounds as described herein are administered as a single tablet that contains up to about 600 mg of Compound 1-A and up to about 360 mg of Compound 2 or an equivalent amount of a pharmaceutically acceptable salt of Compound 2.

In an alternative embodiment, the combination of compounds as described herein are administered as a single tablet that contains up to about 750 mg of Compound 1-A and up to about 180 mg of Compound 2 or an equivalent amount of a pharmaceutically acceptable salt of Compound 2.

In an alternative embodiment, the combination of compounds as described herein are administered as a single tablet that contains up to about 750 mg of Compound 1-A and up to about 270 mg of Compound 2 or an equivalent amount of a pharmaceutically acceptable salt of Compound 2.

In an alternative embodiment, the combination of compounds as described herein are administered as a single tablet that contains up to about 750 mg of Compound 1-A and up to about 360 mg of Compound 2 or an equivalent amount of a pharmaceutically acceptable salt of Compound 2.

In an alternative embodiment, the combination of compounds as described herein are administered as a single tablet that contains up to about 1,200 mg of Compound 1-A and up to about 180 mg of Compound 2 or an equivalent amount of a pharmaceutically acceptable salt of Compound 2.

In an alternative embodiment, the combination of compounds as described herein are administered as a single tablet that contains up to about 1,200 mg of Compound 1-A and up to about 270 mg of Compound 2 or an equivalent amount of a pharmaceutically acceptable salt of Compound 2.

In an alternative embodiment, the combination of compounds as described herein are administered as a single tablet that contains up to about 1,200 mg of Compound 1-A and up to about 360 mg of Compound 2 or an equivalent amount of a pharmaceutically acceptable salt of Compound 2.

Alternatively, the solid dosage form of Compound 1-A or an equivalent amount of Compound 1 may be dosed in combination with a separate solid dosage form containing Compound 2 or an equivalent amount of a pharmaceutically acceptable salt of Compound 2. This combination may be administered once, twice, three, or up to four times a day according to the direction of the healthcare provider. In one embodiment Compound 1-A or Compound 1 is administered in a separate schedule than Compound 2. For example, Compound 1 or an equivalent amount of Compound 1-A may be administered twice a day while Compound 2 is only administered once a day, or vice versa: Compound 2 may be administered multiple times a day while Compound 1 or an equivalent amount of Compound 1-A is only administered once a day.

In one embodiment, a solid dosage form containing up to about 800 mg, up to about 700 mg, up to about 600 mg, up to about 500 mg, up to about 400 mg, up to about 300 mg, up to about 200 mg, or up to about 100 mg of Compound 1 or an equivalent amount of Compound 1-A is administered once a day and a separate solid dosage form containing up to about 145 mg, up to about 130 mg, up to about 125 mg, up to about 110 mg, up to about 100 mg, up to about 90 mg, up to about 75 mg, up to about 70 mg, up to about 65 mg, up to about 60 mg, up to about 55 mg, up to about 50 mg, up to about 45 mg, up to about 40 mg, up to about 35 mg, up to about 30 mg, up to about 25 mg, up to about 20 mg, up to about 15 mg, up to about 10 mg, or up to about 5 mg of Compound 2 or an equivalent amount of a pharmaceutically acceptable salt of Compound 2 is administered once a day to a host in need thereof for the treatment of HCV.

In one embodiment, a solid dosage form containing at least about 100 mg, at least about 200 mg, at least about 300 mg, at least about 400 mg, at least about 500 mg, at least about 600 mg, at least about 700 mg, or at least about 800 mg of Compound 1 or an equivalent amount of Compound 1-A is administered once a day and a separate solid dosage form containing at least about 5 mg, at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 90 mg, at least about 100 mg, at least about 110 mg, at least about 125 mg, at least about 130 mg, or at least about 145 mg of Compound 2 or an equivalent amount of a pharmaceutically acceptable salt of Compound 2 is administered once a day to a host in need thereof for the treatment of HCV.

In certain embodiments, the combination of compounds as described herein are administered to a host in need thereof as (either as separate dosages of the two active agents or a combined dosage of the two active compounds):

(1) a single dosage form;
(2) two dosage forms;
(3) three or more dosage forms;
(4) a kit comprising two dosage forms;
(5) a kit comprising three or more dosage forms;

wherein the dosage form in each of embodiments (1)-(5) comprises:

(a) from about 500 or 550 mg to about 1100 mg of Compound 1-A and an effective amount of Compound 2;
(b) from about 100 mg to about 800 mg of Compound 1-A and an effective amount of Compound 2;
(c) from about 550 to about 650 mg of Compound 1-A and an effective amount of Compound 2;
(d) from about 500 to about 750 mg of Compound 1-A and an effective amount of Compound 2;
(e) from about 1,000 to about 1,300 mg of Compound 1-A and an effective amount of Compound 2;
(f) at least about 600 mg of Compound 1-A and an effective amount of Compound 2;
(g) at least about 750 mg of Compound 1-A and an effective amount of Compound 2;
(h) at least about 1,100 mg of Compound 1-A and an effective amount of Compound 2;
(i) Any one of embodiments (a)-(h), wherein there is from about 60 mg to about 500 mg of Compound 2;
(j) Any one of embodiments (a)-(h), wherein there is from about 90 mg to about 360 mg of Compound 2;
(k) Any one of embodiments (a)-(h), wherein there is from about 250 mg to about 300 mg of Compound 2;
(l) Any one of embodiments (a)-(h), wherein there is from about 350 mg to about 400 mg of Compound 2;
(m) Any one of embodiments (a)-(h), wherein there is at least about 90 mg of Compound 2;
(n) Any one of embodiments (a)-(h), wherein there is at least about 180 mg of Compound 2;
(o) Any one of embodiments (a)-(h), wherein there is at least about 270 mg of Compound 2;
(p) Any one of embodiments (a)-(h), wherein there is at least about 360 mg of Compound 2;
(q) Any one of embodiments (1)-(5) and (a)-(h), wherein the dosage form is administered once per day;
(r) Any one of embodiments (1)-(5) and (a)-(h), wherein the dosage form is administered twice per day;
(s) Any one of embodiments (1)-(5) and (a)-(h), wherein the dosage form is administered three times or more per day;
(t) Any one of embodiments (1)-(5) and (a)-(s), wherein the dosage form is orally administered;
(u) Any one of embodiments (1)-(5) and (a)-(t), wherein the host is a human;

In alternative embodiments, an amount of Compound 1 may be provided to a host in need thereof which results in plasma concentrations of from about 0.15 nM to about 1 nM of Compound 1. In one embodiment, an amount of Compound 1 may be provided to a host in need thereof which results in plasma concentrations of from about 0.25 to about 40 nM of Compound 1. In one embodiment, an amount of Compound 1 may be provided to a host in need thereof which results in plasma concentrations of from about 40 to about 200 nM of Compound 1. In one embodiment, an amount of Compound 1 may be provided to a host in need thereof which results in plasma concentrations of from about 0.001 nM to about 0.008 nM of Compound 2.

The compounds of the present combination are often administered orally, but may be administered parenterally, topically, or in suppository form, as well as intranasally, as a nasal spray or as otherwise described herein. More generally, these compounds can be administered in one or more tablets, capsules, injections, intravenous formulations, suspensions, liquids, emulsions, implants, particles, spheres, creams, ointments, suppositories, inhalable forms, transdermal forms, buccal, sublingual, topical, gel, mucosal, and the like.

In certain embodiments, the combination is administered at least once a day for up to 24 weeks. In certain embodiments, the combination is administered at least once a day for up to 12 weeks. In certain embodiments, the combination is administered at least once a day for up to 10 weeks. In certain embodiments, the combination is administered at least once a day for up to 8 weeks. In certain embodiments, the combination is administered at least once a day for up to 6 weeks. In certain embodiments, the combination is administered at least once a day for up to 4 weeks. In certain embodiments, the combination is administered at least once a day for at least 4 weeks. In certain embodiments, the combination is administered at least once a day for at least 6 weeks. In certain embodiments, the combination is administered at least once a day for at least 8 weeks. In certain embodiments, the combination is administered at least once a day for at least 10 weeks. In certain embodiments, the combination is administered at least once a day for at least 12 weeks. In certain embodiments, the combination is administered at least once a day for at least 24 weeks. In certain embodiments, the combination is administered at least every other day for up to 24 weeks, 12 weeks, up to 10 weeks, up to 8 weeks, up to 6 weeks, or up to 4 weeks. In certain embodiments, the combination is administered at least every other day for at least 4 weeks, at least 6 weeks, at least 8 weeks, at least 10 weeks, at least 12 weeks, or at least 24 weeks.

For purposes of the present invention, a prophylactically or preventive effective amount of the compositions according to the present invention falls within the same concentration range as set forth above for therapeutically effective amount and is usually the same as a therapeutically effective amount.

To prepare the pharmaceutical compositions according to the present invention, a therapeutically effective amount of Compound 1 or a pharmaceutically acceptable salt thereof, for example Compound 1-A, and Compound 2 or pharmaceutically acceptable salts thereof may be intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs, and solutions, suitable carriers and additives including water, glycols, oils, alcohols, flavoring agents, preservatives, coloring agents, and the like may be used. For solid oral preparations such as powders, tablets, capsules, and for solid preparations such as suppositories, suitable carriers and additives including starches, sugar carriers, such as dextrose, manifold, lactose, and related carriers, diluents, granulating agents, lubricants, binders, disintegrating agents, and the like may be used. If desired, the tablets or capsules may be enteric-coated or sustained release by standard techniques. The use of these dosage forms may significantly enhance the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents, and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In typical embodiments according to the present invention, the pharmaceutical composition is used to treat, prevent, or delay a HCV infection or a secondary disease state, condition or complication of HCV.

Solid Dosage Forms

An aspect of the invention is a fixed dosage form of the active compounds (separately or combined) or their pharmaceutically acceptable salts thereof, optionally in a combined fixed-dosage form.

Either or both Compounds can be provided in a crystalline or non-crystalline form. In certain embodiments, they are provided in separate or the same oral dosage form, for example, a gelcap, solid form, spray-dry dispersion, tablet, capsule or other form of pill.

In one embodiment, the fixed dose combination includes a spray dried solid dispersion of at least one of the Compounds or both Compounds, either in a pharmaceutically acceptable salt and the composition is suitable for oral delivery. In one aspect of this embodiment, the fixed dose combination includes Compound 1 or a pharmaceutically acceptable salt thereof and Compound 2 or a pharmaceutically acceptable salt thereof, wherein at least one the Compounds is in a spray dried solid dispersion.

In another embodiment, the fixed dose combination is a granulo layered solid dispersion of at least one of the Compounds or its pharmaceutically acceptable salt and the composition is suitable for oral delivery. An exemplary process for preparing solid dosage forms for oral delivery can be found in FIG. 32. In one aspect of this embodiment, the fixed dose combination is a granulo layered solid dispersion that includes Compound 1 or a pharmaceutically acceptable salt thereof and Compound 2 or a pharmaceutically acceptable salt thereof. In certain embodiments, a spray dried dispersion or granulo layered solid dispersion component is prepared using crystalline Compound 1-A. In an alternative embodiment, Compound 1 or a pharmaceutically acceptable salt, for example, Compound 1-A, or Compound 2 or a pharmaceutically acceptable can be delivered as an amorphous compound.

In other embodiments, the solid dispersion also contains at least one excipient selected from copovidone, poloxamer and HPMC-AS. In one embodiment the poloxamer is Poloxamer 407 or a mixture of poloxamers that may include Poloxamer 407. In one embodiment HPMC-AS is HPMC-AS-L.

In other embodiments, a fixed dose composition prepared from Compound 1 or a pharmaceutically acceptable salt thereof and Compound 2 or a pharmaceutically acceptable salt thereof, also comprises one or more of the following excipients: a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl stearate; isopropyl myristate; tyloxapol; poly(ethylene glycol)5000-phosphatidylethanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, silicified microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g., poly(1,3-dioxan-2one)), polyanhydride (e.g., poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g., poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly (ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), or hydroxypropylmethyl cellulose acetate succinate (HPMCAS).

In other embodiments, a fixed dose composition prepared from Compound 1 or a pharmaceutically acceptable salt thereof and Compound 2 or a pharmaceutically acceptable salt thereof, also comprises one or more of the following surfactants: polyoxyethylene glycol, polyoxypropylene glycol, decyl glucoside, lauryl glucoside, octyl glucoside, polyoxyethylene glycol octylphenol, Triton X-100, glycerol alkyl ester, glyceryl laurate, cocamide MEA, cocamide DEA, dodecyldimethylamine oxide, and poloxamers. Examples of poloxamers include, poloxamers 188, 237, 338 and 407. These poloxamers are available under the trade name Pluronic® (available from BASF, Mount Olive, N.J.) and correspond to Pluronic® F-68, F-87, F-108 and F-127, respectively. Poloxamer 188 (corresponding to Pluronic® F-68) is a block copolymer with an average molecular mass of about 7,000 to about 10,000 Da, or about 8,000 to about 9,000 Da, or about 8,400 Da. Poloxamer 237 (corresponding to Pluronic® F-87) is a block copolymer with an average molecular mass of about 6,000 to about 9,000 Da, or about 6,500 to about 8,000 Da, or about 7,700 Da. Poloxamer 338 (corresponding to Pluronic® F-108) is a block copolymer with an average molecular mass of about 12,000 to about 18,000 Da, or about 13,000 to about 15,000 Da, or about 14,600 Da. Poloxamer 407 (corresponding to Pluronic® F-127) is a polyoxyethylene-polyoxypropylene triblock copolymer in a ratio of between about E101 P56 E101 to about E106 P70 E106, or about E101 P56E101, or about E106 P70 E106, with an average molecular mass of about 10,000 to about 15,000 Da, or about 12,000 to about 14,000 Da, or about 12,000 to about 13,000 Da, or about 12,600 Da.

In yet other embodiments, a fixed dose composition prepared from Compound 1 or a pharmaceutically acceptable salt thereof and Compound 2 or a pharmaceutically acceptable salt thereof, also comprises one or more of the following surfactants: polyvinyl acetate, cholic acid sodium salt, dioctyl sulfosuccinate sodium, hexadecyltrimethyl ammonium bromide, saponin, sugar esters, Triton X series, sorbitan trioleate, sorbitan mono-oleate, polyoxyethylene (20) sorbitan monolaurate, polyoxyethylene (20) sorbitan monooleate, oleyl polyoxyethylene (2) ether, stearyl polyoxyethylene (2) ether, lauryl polyoxyethylene (4) ether, block copolymers of oxyethylene and oxypropylene, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, cetylpyridinium chloride, benzalkonium chloride, olive oil, glyceryl monolaurate, corn oil, cotton seed oil, and sunflower seed oil.

In alternative embodiments, a fixed dose composition prepared from Compound 1 or a pharmaceutically acceptable salt thereof and Compound 2 or a pharmaceutically acceptable salt thereof, is prepared by a process that includes solvent or dry granulation optionally followed by compression or compaction, spray drying, nano-suspension processing, hot melt extrusion, extrusion/spheronization, molding, spheronization, layering (e.g., spray layering suspension or solution), or the like. Examples of such techniques include direct compression, using appropriate punches and dies, for example wherein the punches and dies are fitted to a suitable tableting press; wet granulation using suitable granulating equipment such as a high shear granulator to form wetted particles to be dried into granules; granulation followed by compression using appropriate punches and dies, wherein the punches and dies are fitted to a suitable tableting press; extrusion of a wet mass to form a cylindrical extrudate to be cut into desire lengths or break into lengths under gravity and attrition; extrusion/spheronization where the extrudate is rounded into spherical particles and densified by spheronization; spray layering of a suspension or solution onto an inert core using a technique such as a convention pan or Wurster column; injection or compression molding using suitable molds fitted to a compression unit; and the like.

Exemplary disintegrants include alginic acid, carboxymethylcellulose calcium, carboxymethylcellulose sodium, cross-linked sodium carboxymethylcellulose (sodium croscarmellose), powdered cellulose, chitosan, croscarmellose sodium, crospovidone, guar gum, low substituted hydroxypropyl cellulose, methyl cellulose, microcrystalline cellulose, sodium alginate, sodium starch glycolate, partially pregelatinized starch, pregelatinized starch, starch, sodium carboxymethyl starch, and the like, or a combination thereof.

Exemplary lubricants include calcium stearate, magnesium stearate, glyceryl behenate, glyceryl palmitostearate, hydrogenated castor oil, light mineral oil, sodium lauryl sulfate, magnesium lauryl sulfate, sodium stearyl fumarate, stearic acid, zinc stearate, silicon dioxide, colloidal silicon dioxide, dimethyldichlorosilane treated with silica, talc, or a combination thereof.

The dosage form cores described herein may be coated to result in coated tablets. The dosage from cores can be coated with a functional or non-functional coating, or a combination of functional and non-functional coatings. "Functional coating" includes tablet coatings that modify the release properties of the total composition, for example, a sustained-release or delayed-release coating. "Non-functional coating" includes a coating that is not a functional coating, for example, a cosmetic coating. A non-functional coating can have some impact on the release of the active agent due to the initial dissolution, hydration, perforation of the coating, etc., but would not be considered to be a significant deviation from the non-coated composition. A non-functional coating can also mask the taste of the uncoated composition including the active pharmaceutical ingredient. A coating may comprise a light blocking material, a light absorbing material, or a light blocking material and a light absorbing material.

Exemplary polymethacrylates include copolymers of acrylic and methacrylic acid esters, such as a. an aminomethacrylate copolymer USP/NF such as a poly(butyl methacrylate, (2-dimethyl aminoethyl)methacrylate, methyl methacrylate) 1:2:1 (e.g., EUDRAGIT E 100, EUDRAGIT EPO, and EUDRAGIT E 12.5; CAS No. 24938-16-7); b. a poly(methacrylic acid, ethyl acrylate) 1:1 (e.g., EUDRAGIT L30 D-55, EUDRAGIT L100-55, EASTACRYL 30D, KOLLICOAT MAE 30D AND 30DP; CAS No. 25212-88-8); c. a poly(methacrylic acid, methyl methacrylate) 1:1 (e.g., EUDRAGIT L 100, EUDRAGIT L 12.5 and 12.5 P; also known as methacrylic acid copolymer, type A NF; CAS No. 25806-15-1); d. a poly(methacrylic acid, methyl methacrylate) 1:2 (e.g., EUDRAGIT S 100, EUDRAGIT S 12.5 and 12.5P; CAS No. 25086-15-1); e. a poly(methyl acrylate, methyl methacrylate, methacrylic acid) 7:3:1 (e.g., Eudragit FS 30 D; CAS No. 26936-24-3); f. a poly(ethyl acrylate, methylmethacrylate, trimethylammonioethyl methacrylate chloride) 1:2:0.2 or 1:2:0.1 (e.g., EUDRAGITS RL 100, RL PO, RL 30 D, RL 12.5, RS 100, RS PO, RS 30 D, or RS 12.5; CAS No. 33434-24-1); g. a poly(ethyl acrylate, methyl methacrylate) 2:1 (e.g., EUDRAGIT NE 30 D, Eudragit NE 40D, Eudragit NM 30D; CAS No. 9010-88-2); and the like, or a combination thereof.

Suitable alkylcelluloses include, for example, methylcellulose, ethylcellulose, and the like, or a combination thereof. Exemplary water based ethylcellulose coatings include AQUACOAT, a 30% dispersion further containing sodium lauryl sulfate and cetyl alcohol, available from FMC, Philadelphia, PA; SURELEASE a 25% dispersion further containing a stabilizer or other coating component (e.g., ammonium oleate, dibutyl sebacate, colloidal anhydrous silica, medium chain triglycerides, etc.) available from Colorcon, West Point, PA; ethyl cellulose available from Aqualon or Dow Chemical Co (Ethocel), Midland, MI. Those skilled in the art will appreciate that other cellulosic polymers, including other alkyl cellulosic polymers, can be substituted for part or all of the ethylcellulose.

Other suitable materials that can be used to prepare a functional coating include hydroxypropyl methylcellulose acetate succinate (HPMCAS); cellulose acetate phthalate (CAP); a polyvinylacetate phthalate; neutral or synthetic waxes, fatty alcohols (such as lauryl, myristyl, stearyl, cetyl or specifically cetostearyl alcohol), fatty acids, including fatty acid esters, fatty acid glycerides (mono-, di-, and tri-glycerides), hydrogenated fats, hydrocarbons, normal waxes, stearic acid, stearyl alcohol, hydrophobic and hydrophilic materials having hydrocarbon backbones, or a combination thereof. Suitable waxes include beeswax, glycowax, castor wax, carnauba wax, microcrystalline wax, candelilla, and wax-like substances, e.g., material normally solid at room temperature and having a melting point of from about 30° C. to about 100° C., or a combination thereof.

In other embodiments, a functional coating may include digestible, long chain (e.g., C8-C50, specifically $C_{12}$-$C_{40}$), substituted or unsubstituted hydrocarbons, such as fatty acids, fatty alcohols, glyceryl esters of fatty acids, mineral and vegetable oils, waxes, or a combination thereof. Hydrocarbons having a melting point of between about 25° C. and about 90° C. may be used. Specifically, long chain hydrocarbon materials, fatty (aliphatic) alcohols can be used.

The coatings can optionally contain additional pharmaceutically acceptable excipients such as a plasticizer, a stabilizer, a water-soluble component (e.g., pore formers), an anti-tacking agent (e.g., talc), a surfactant, and the like, or a combination thereof.

A functional coating may include a release-modifying agent, which affects the release properties of the functional coating. The release-modifying agent can, for example, function as a pore-former or a matrix disrupter. The release-modifying agent can be organic or inorganic, and include materials that can be dissolved, extracted or leached from the coating in the environment of use. The release-modifying agent can comprise one or more hydrophilic polymers including cellulose ethers and other cellulosics, such as hydroxypropyl methylcellulose, hydroxypropylcellulose, hydroxyethylcellulose, methyl cellulose, cellulose acetate phthalate, or hydroxypropyl methylcellulose acetate phthalate; povidone; polyvinyl alcohol; an acrylic polymer, such as gastric soluble Eudragit FS 30D, pH sensitive Eudragit L30D 55, L 100, S 100, or L 100-55; or a combination thereof. Other exemplary release-modifying agents include a povidone; a saccharide (e.g., lactose, and the like); a metal stearate; an inorganic salt (e.g., dibasic calcium phosphate, sodium chloride, and the like); a polyethylene glycol (e.g., polyethylene glycol (PEG) 1450, and the like); a sugar alcohol (e.g., sorbitol, mannitol, and the like); an alkali alkyl sulfate (e.g., sodium lauryl sulfate); a polyoxyethylene sorbitan fatty acid ester (e.g., polysorbate); or a combination thereof. Exemplary matrix disrupters include water insoluble organic or inorganic material. Organic polymers including but not limited to cellulose, cellulose ethers such as ethylcellulose, cellulose esters such as cellulose acetate, cellulose acetate butyrate and cellulose acetate propionate; and starch can function as matrix disrupters. Examples or inorganic disrupters include many calcium salts such as mono-, di- and tri calcium phosphate; silica and, talc.

The coating may optionally contain a plasticizer to improve the physical properties of the coating. For example, because ethylcellulose has a relatively high glass transition temperature and does not form flexible films under normal coating conditions, it may be advantageous to add plasticizer to the ethylcellulose before using the same as a coating material. Generally, the amount of plasticizer included in a coating solution is based on the concentration of the polymer, e.g., can be from about 1% to about 200% depending on the polymer but is most often from about 1 wt % to about 100 wt % of the polymer. Concentrations of the plasticizer, however, can be determined by routine experimentation.

Examples of plasticizers for ethylcellulose and other celluloses include plasticizers such as dibutyl sebacate, diethyl phthalate, triethyl citrate, tributyl citrate, triacetin, or a combination thereof, although it is possible that other water-insoluble plasticizers (such as acetylated monoglycerides, phthalate esters, castor oil, etc.) can be used.

Examples of plasticizers for acrylic polymers include citric acid esters such as triethyl citrate NF, tributyl citrate, dibutyl phthalate, 1,2-propylene glycol, polyethylene glycols, propylene glycol, diethyl phthalate, castor oil, triacetin, or a combination thereof, although it is possible that other plasticizers (such as acetylated monoglycerides, phthalate esters, castor oil, etc.) can be used.

Suitable methods can be used to apply the coating material to the surface of the dosage form cores. Processes such as simple or complex coacervation, interfacial polymerization, liquid drying, thermal and ionic gelation, spray drying, spray chilling, fluidized bed coating, pan coating, or electrostatic deposition may be used.

In certain embodiments, an optional intermediate coating is used between the dosage form core and an exterior coating. Such an intermediate coating can be used to protect the active agent or other component of the core subunit from the material used in the exterior coating or to provide other properties. Exemplary intermediate coatings typically include water-soluble film forming polymers. Such intermediate coatings may include film forming polymers such as hydroxyethyl cellulose, hydroxypropyl cellulose, gelatin, hydroxypropyl methylcellulose, polyethylene glycol, polyethylene oxide, and the like, or a combination thereof; and a plasticizer. Plasticizers can be used to reduce brittleness and increase tensile strength and elasticity. Exemplary plasticizers include polyethylene glycol propylene glycol and glycerin.

Combination and Alternation Therapy

Drug resistance sometimes occurs by mutation of a gene that encodes for an enzyme used in viral replication. The efficacy of a combination therapy against an HCV infection, can be prolonged, augmented, or restored by adding an additional compound to the combination therapy. This further combined therapy may be administered together or in alternation with another, and perhaps even two or three other, antiviral compounds that induce a different mutation or act through a different pathway, from that of the principle combination. Alternatively, the pharmacokinetic, bio-distribution, half-life, or other parameter of the combination can be altered by such combination therapy (which may include alternation therapy if considered concerted).

This invention already provides an advantageous combination therapy for the treatment of HCV, or a disorder associated with an HCV infection, by administering a selected NS5B inhibitor with an NS5A inhibitor. Additional therapeutic effects may be achieved by adding a third, fourth, or even fifth active agent either co-formulated or provided separately.

Since Compound 1 and Compound 1-A are NS5B polymerase inhibitors and Compound 2 is an NS5A inhibitor it may be useful to administer Compound 1 and Compound 2 to a host in combination with, for example a (1) Protease inhibitor, such as an NS3/4A protease inhibitor;
(2) Another NS5A inhibitor;
(3) Another NS5B polymerase inhibitor;
(4) NS5B non-substrate inhibitor;
(5) Interferon alfa-2a, which may be pegylated or otherwise modified, and/or ribavirin;
(6) Non-substrate-based inhibitor;
(7) Helicase inhibitor;
(8) Antisense oligodeoxynucleotide (S-ODN);
(9) Aptamer;

(10) Nuclease-resistant ribozyme;
(11) iRNA, including microRNA and SiRNA;
(12) Antibody, partial antibody or domain antibody to the virus, or
(13) Viral antigen or partial antigen that induces a host antibody response.

Non limiting examples of additional anti-HCV agents that can be administered in further combination or alternation with the combination of the present invention, include (i) protease inhibitors such as telaprevir (Incivek®), boceprevir (Victrelis™), simeprevir (Olysio™), paritaprevir (ABT-450), glecaprevir (ABT-493), ritonavir (Norvir), ACH-2684, AZD-7295, BMS-791325, danoprevir, Filibuvir, GS-9256, GS-9451, MK-5172, Setrobuvir, Sovaprevir, Tegobuvir, VX-135, VX-222, ALS-220, and voxilaprevir.
(ii) NS5A inhibitor such as ACH-2928, ACH-3102, IDX-719, daclatasvir, ledispasvir, velpatasvir (Epclusa), elbasvir (MK-8742), grazoprevir (MK-5172), and Ombitasvir (ABT-267);
(iii) NS5B inhibitors such as AZD-7295, Clemizole, dasabuvir (Exviera), ITX-5061, PPI-461, PPI-688, sofosbuvir (Sovaldi®), MK-3682, and mericitabine;
(iv) NS5B inhibitors such as ABT-333, and MBX-700;
(v) Antibody such as GS-6624;
(vi) Combination drugs such as Harvoni (ledipasvir/sofosbuvir); Viekira Pak (ombitasvir/paritaprevir/ritonavir/dasabuvir); Viekirax (ombitasvir/paritaprevir/ritonavir); G/P (paritaprevir and glecaprevir); Technivie™ (ombitasvir/paritaprevir/ritonavir), Epclusa (sofosbuvir/velpatasvir), Zepatier (elbasvir and grazoprevir), Mavyret (glecaprevir and pibrentasvir), and Vosevi (Sofosbuvir, velpatasvir, and voxilaprevir).

If the combination is administered to treat advanced hepatitis C virus leading to liver cancer or cirrhosis, in one embodiment, the compound can be administered in combination or alternation with another drug that is typically used to treat hepatocellular carcinoma (HCC), for example, as described by Andrew Zhu in "New Agents on the Horizon in Hepatocellular Carcinoma" Therapeutic Advances in Medical Oncology, V 5(1), January 2013, 41-50. Examples of suitable compounds for combination therapy where the host has or is at risk of HCC include anti-angiogenic agents, sunitinib, brivanib, linifanib, ramucirumab, bevacizumab, cediranib, pazopanib, TSU-68, lenvatinib, antibodies against EGFR, mTor inhibitors, MEK inhibitors, and histone decetylace inhibitors, capecitabine, cisplatin, carboplatin, doxorubicin, 5-fluorouracil, gemcitabine, irinotecan, oxaliplatin, topotecan, and other topoisomerases.

General Methods $^1H$, $^{19}F$ and $^{31}P$ NMR spectra were recorded on a 400 MHz Fourier transform Brucker spectrometer. Spectra were obtained DMSO-$d_6$ unless stated otherwise. The spin multiplicities are indicated by the symbols s (singlet), d (doublet), t (triplet), m (multiplet) and, br (broad). Coupling constants (J) are reported in Hz. The reactions were generally carried out under a dry nitrogen atmosphere using Sigma-Aldrich anhydrous solvents. All common chemicals were purchased from commercial sources.

The following abbreviations are used in the Examples:

BID: Twice a day
DCM: Dichloromethane
EtOAc: Ethyl acetate
EtOH: Ethanol
GT: Genotype
HPLC: High pressure liquid chromatography
LD: Loading dose
NaOH: Sodium hydroxide
$Na_2SO_4$: Sodium sulphate (anhydrous)
MeOH: Methanol
$Na_2SO_4$: Sodium sulfate
$NH_4Cl$: Ammonium chloride
PE: Petroleum ether
Silica gel (230 to 400 mesh, Sorbent)
t-BuMgCl: t-Butyl magnesium chloride
THF: Tetrahydrofuran (THF), anhydrous
TP: Triphosphate Example 1. Synthesis of Compound 1 and Compound 1-A Part A: Synthesis of (2R,3R,4R,5R)-5-(2-amino-6-(methylamino)-9H-purin-9-yl)-4-fluoro-2-(hydroxymethyl)-4-methyltetrahydrofuran-3-ol (1-7)

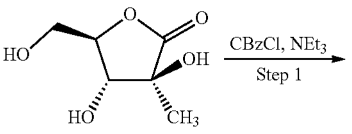

1-1

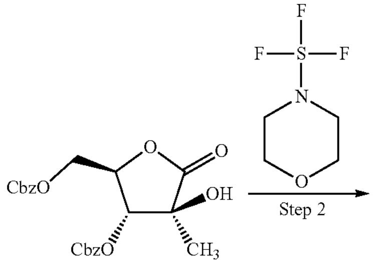

1-2

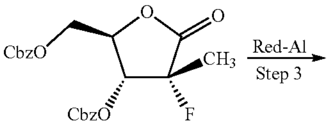

1-3

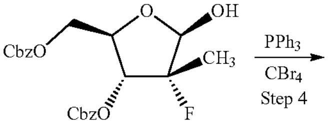

1-4

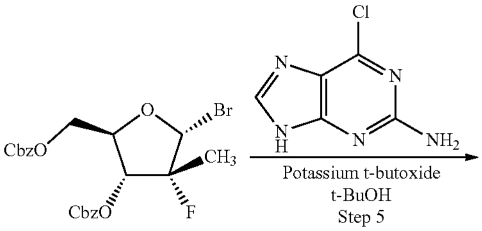

1-5

-continued

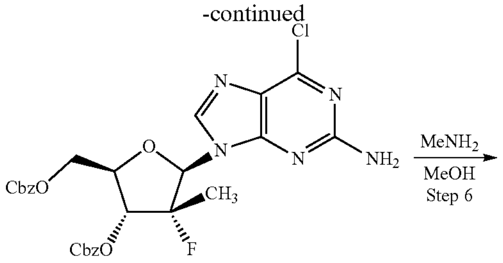

1-6

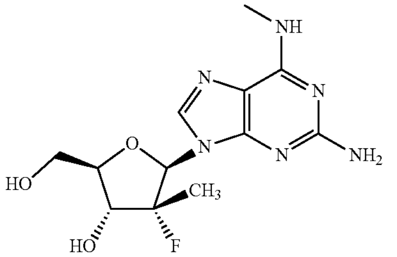

Compound 1-7

In Step 1, Compound 1-1 is dissolved in DCM and the reaction is cooled to 10° C. before benzyl chloroformate is added followed by $NEt_3$. The reaction is allowed to warm to room temperature and stir for 12-14 hours. Following appropriate work-up and purification conditions, Compound 1-2 is isolated. In Step 2, Compound 1-2 is dissolved in acetonitrile and cooled to −15 to 5° C. before Morpho DAST is added. The reaction is allowed to stir for 6 hours. Following appropriate work-up and purification conditions, Compound 1-3 is isolated. In Step 3, Compound 1-3 is dissolved in toluene and the reaction is cooled to 0-10° C. before Red Al is added. Following appropriate work-up and purification conditions, Compound 1-4 is isolated as the diastereomer with (R)-stereochemistry at the hydroxyl position. In Step 4, Compound 1-4 is dissolved in acetonitrile and cooled to −15 to 5° C. before $CBr_4$ and $PPh_3$ are added. Following appropriate work-up and purification conditions, Compound 1-5 is isolated. In Step 5, Compound 1-5 is dissolved is acetonitrile and t-BuOH, t-BuOK, and 6-chloro-9H-purin-2-amine are added. The reaction is heated to 40-50° C. Following appropriate work-up and purification conditions, Compound 1-6 is isolated. In Step 6, Compound 1-6 is dissolved in MeOH and $MeNH_2$ is added. The reaction is heated to 20-30 C. Following appropriate work-up and purification conditions, Compound 1-7 is isolated.

Part B: Synthesis of dihydroquinine salt of isopropyl (hydroxy(phenoxy)phosphoryl)-L-alaninate (1-12)

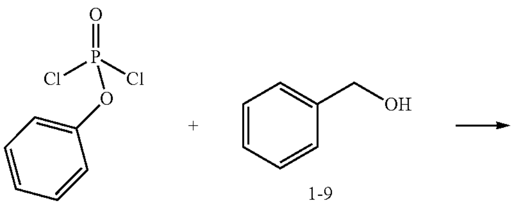

1-8 1-9

-continued

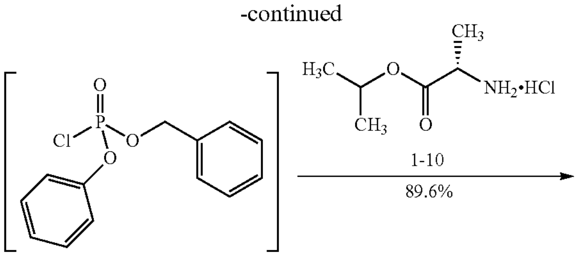

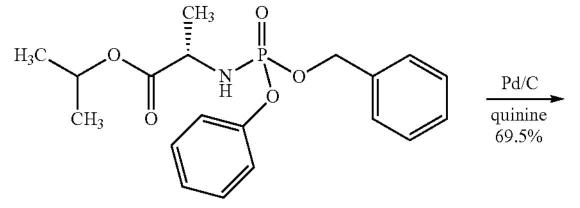

1-11

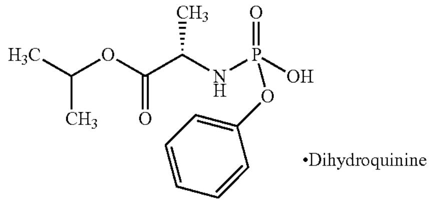

1-12

Phenyl dichlorophosphate (1-8, 150 g, 1.0 eq.) was added into 1300 mL of isopropyl acetate. The solution was cooled to −10° C.±5° C. and then a solution of benzyl alcohol (1-9, 80.6 g, 1.05 eq.) and $Et_3N$ (86.3 g, 1.2 eq.) was added. The mixture was stirred for 3 hours at −10±5° C. The end point of reaction was monitored by TLC.

L-Alanine isopropyl ester hydrochloride (1-10, 125 g, 1.05 eq.) and $Et_3N$ (152 g, 2.1 eq.) were added at −10° C.±5° C. The reaction mixture was stirred at −10±5° C. for 2 hours. The end point of reaction was monitored by TLC.

The reaction mixture was filtered, and the filter cake was washed with 20 mL of isopropyl acetate. The filtrate was washed with 1N HCl, water, and aqueous sodium bicarbonate. The separated organic layer was dried with anhydrous $Na_2SO_4$ and then concentrated to dryness under vacuum at 40° C.-50° C. to give 240 g of crude product 1-11 as a diastereomeric mixture (approximately, 1:1). (Pale yellow oil; yield: 89.6% mol/mol; HPLC purity: 83.4% by area; HPLC assay: 86.2% w/w). The product contained around 6%-7% residual benzyl alcohol. The crude 1-4 was used directly in the next step.

Compound 1-11 (135 g, 1.0 eq., 86.2% assay) and quinine (100 g, 1.0 eq.) were added into 650 mL of i-PrOH. After 5% Pd/C (19.2 g, 60% water by KF) was added, hydrogenation was performed at 20° C.-25° C. for 8 hours using a hydrogen bag in a closed system. After completion of reaction, the mixture was filtered through a Buchner funnel. The filtrate was concentrated under vacuum to remove the solvent.

To the above residue, 300 mL of TBME was added. The mixture was concentrated to remove the solvent under vacuum at 40° C.-45° C., and then this step was repeated with another 300 mL of MTBE. To the above, 600 mL of MTBE was added, and the mixture was stirred at 40° C.-45° C. for 1 hour and then stirred at 0° C.-5° C. for additional 1 hour. The mixture was filtered, and the filter cake was washed with 100 mL of MTBE. The cake was dried at 45° C. for 16 hours without vacuum to give 152 g of the dihydroquinine salt of isopropyl (hydroxy(phenoxy)phosphoryl)-L-alaninate (1-12, white solid; yield: 69.5% mol/mol; HPLC Purity: 97.91%).

Part C: Synthesis of Compound 1

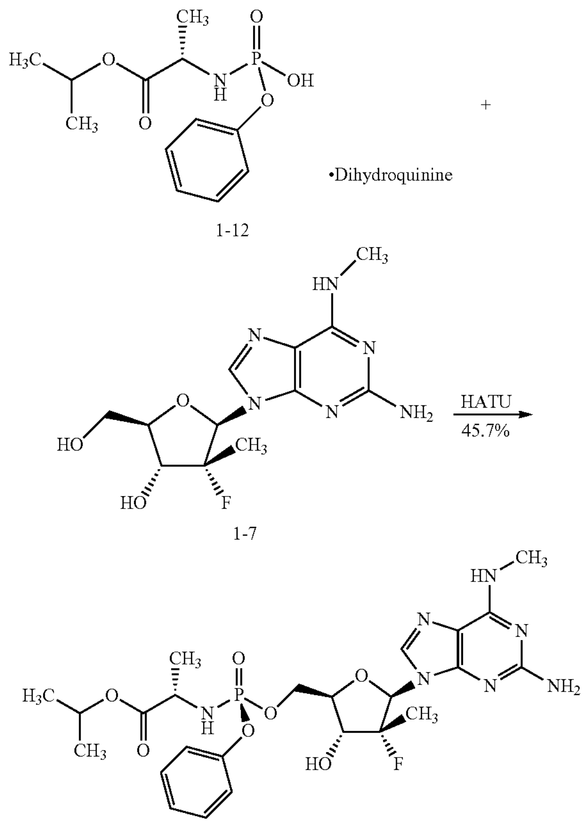

1-12

1-7

Compound 1

The dihydroquinine salt of isopropyl (hydroxy(phenoxy)phosphoryl)-L-alaninate (1-12, 5.9 g, 1.5 eq.), Compound 1-7 (2.0 g, 1.0 eq), DIPEA (0.83 g, 1.0 eq), and HATU (3.65 g, 1.5 eq) were added into 100 mL of dichloromethane. The mixture was heated to 40° C. and stirred for 18 hours. The reaction was monitored by TLC and HPLC.

After the reaction was completed, the reaction mixture was cooled to room temperature, washed with 1N hydrochloric acid (100 mL×2), water (100 mL×2), and 5% aqueous sodium bicarbonate 15 mL×1). The separated organic phase was dried with 2 g of anhydrous sodium sulfate, filtered, and concentrated at 40° C.-45° C. under vacuum to give a yellow oil.

Isopropyl acetate (10 mL of) was added. After stirring, the mixture was concentrated under vacuum. Then, 25 mL of isopropyl acetate was added. The mixture was heated to 45° C. to afford a clear solution. After stirring at room temperature for 2 hours, the solid precipitate was filtered and dried without vacuum at 45° C. for 15 hours to give 2.0 g of crude Compound 1 (yield: 53.8% mol/mol; HPLC purity: 93.1% by area (containing 3.7% of the compound with the opposite Rp-configuration).

The mixture of crude Compound 1 (2.0 g) and 15 mL of isopropyl acetate was heated to 80° C.-85° C. to afford a solution. The solution was cooled to 20° C.-25° C. and stirred for 1 hour. The precipitated solid was filtered, washed with isopropyl acetate (1 mL), and dried without vacuum at 50° C. for 16 hours to give 1.7 g of Compound 1 (yield: 45.7% mol/mol; HPLC purity: 98.99%). $^{1}H$ NMR, $^{19}F$ NMR, and $^{31}P$ NMR spectra confirmed the structure of Compound 1.

Example 2. Characterization of Amorphous and Crystalline Compound 1

Figure 1A:
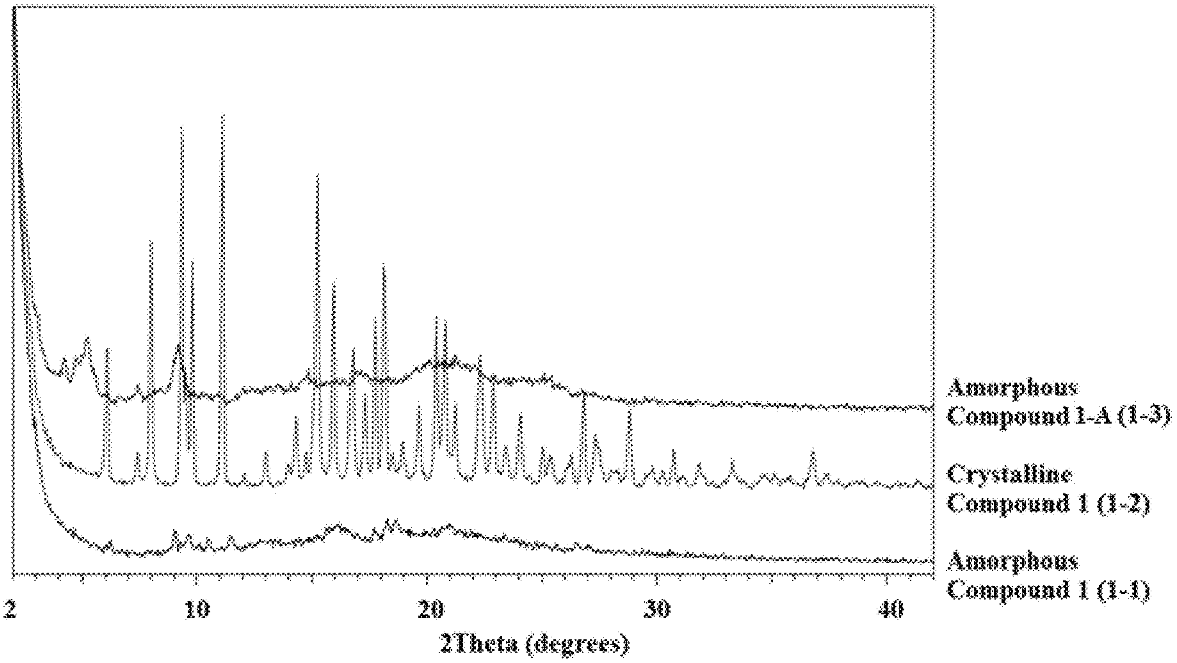
FIG. 1A is an overlay of XRPD diffractograms of samples 1-1 (amorphous Compound 1), 1-2 (crystalline Compound 1), and 1-3 (amorphous Compound 1-A) prior to stability studies for characterization purposes as described in Example 2 and Example 5. The x-axis is 2Theta measured in degrees and the y-axis is intensity measured in counts.
Figure 1B:
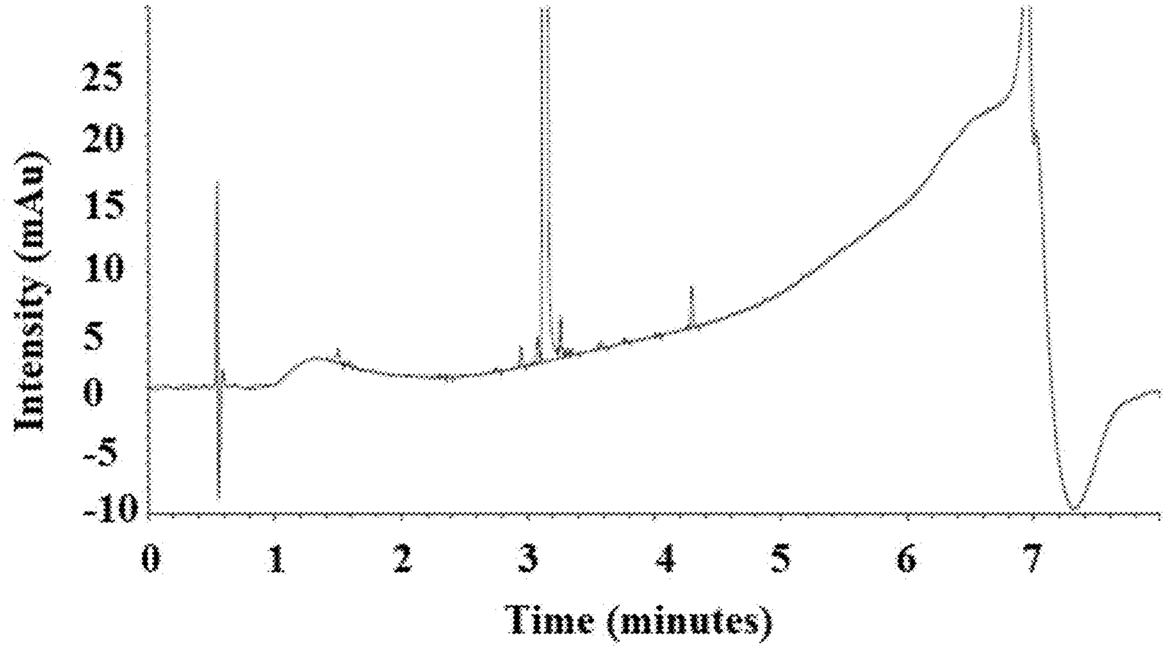
FIG. 1B is the HPLC chromatograph of amorphous Compound 1 (sample 1-1) to determine purity as described in Example 2. The purity of the sample was 98.7%. The x-axis is time measured in minutes and the y-axis is intensity measured in counts.
Figure 2A:
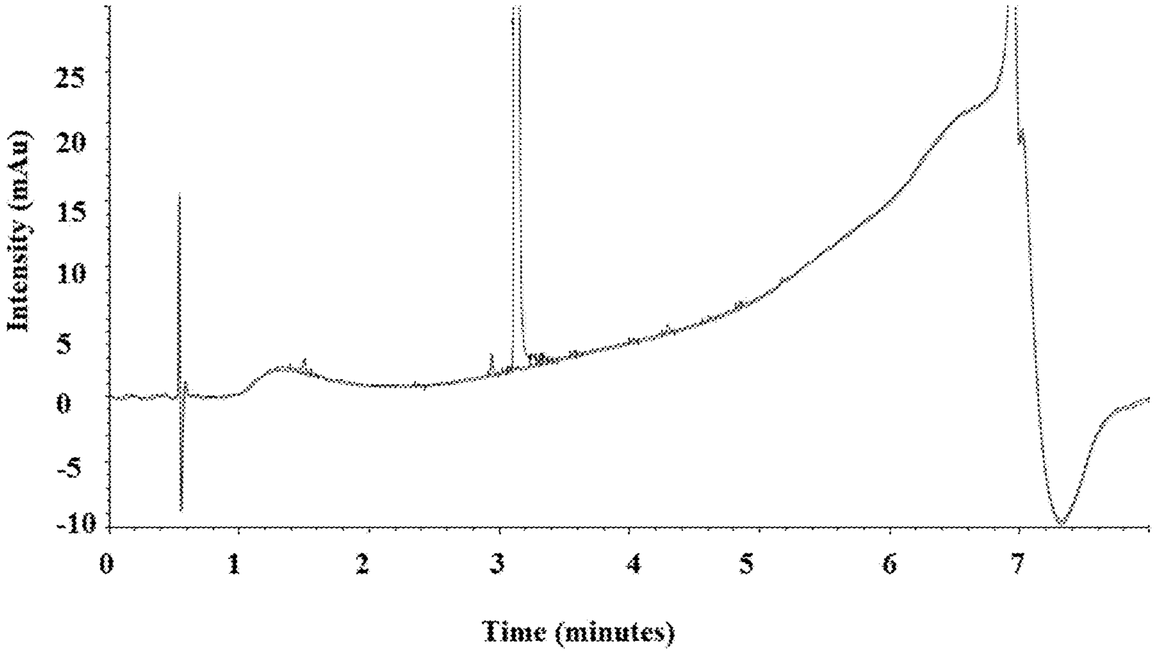
FIG. 2A is the HPLC chromatograph of crystalline Compound 1 (sample 1-2) to determine purity as described in Example 2. The purity of the sample was 99.11%. The x-axis is time measured in minutes and the y-axis is intensity measured in counts.
Figure 2B:
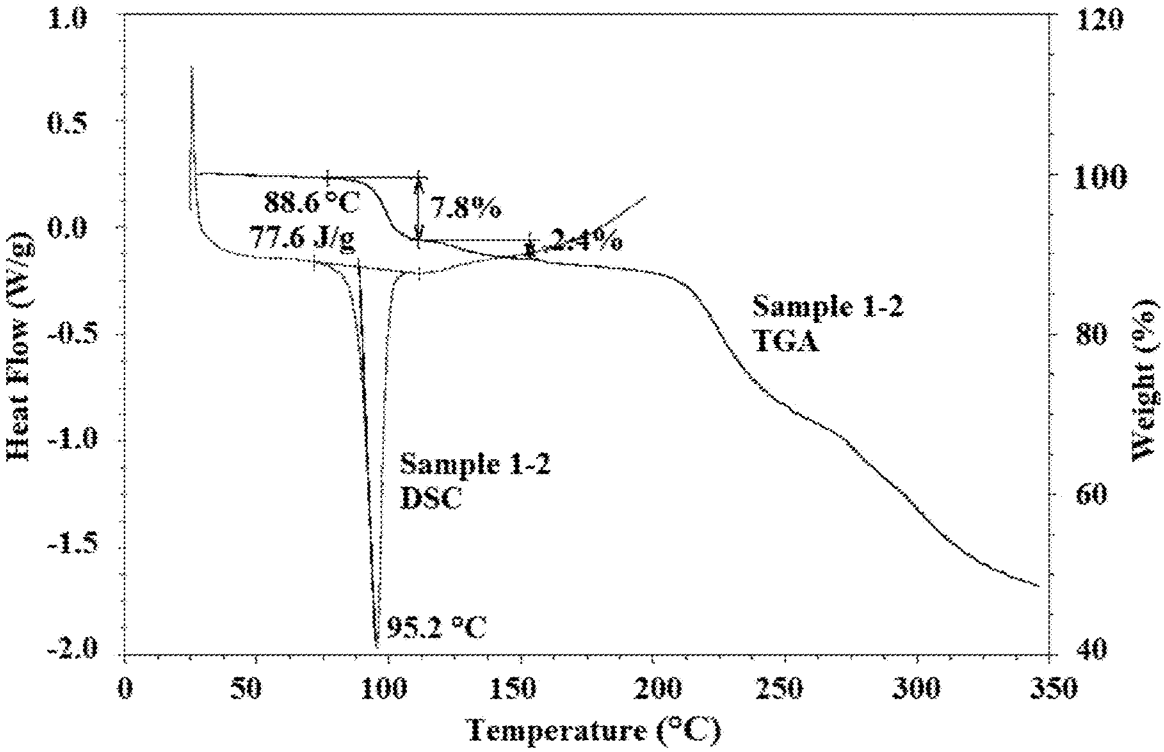
FIG. 2B is a DSC and TGA graph of crystalline Compound 1 (sample 1-2) prior to any stability studies for characterization purposes as described in Example 2. The x-axis is temperature measured in ° C., the left y-axis heat flow measured in (W/g), and the right y-axis is weight measured in percent.

Amorphous Compound 1 and crystalline Compound 1 were initially analyzed by XRPD, $^{1}H$ NMR, and HPLC. The XRPD patterns for both compounds are shown in FIG. 1A and the HPLC traces to determine purity are shown in FIGS. 1B and 2A, respectively. Table 1 is a list of peaks from the XRPD of crystalline Compound 1 and Table 2 is a list of relative retention times (RTT) from the HPLC traces. Amorphous Compound 1 was 98.61% pure and crystalline Compound 1 was 99.11% pure. Both compounds were a white solid. FIG. 2B is the TGA and DSC graphs of crystalline Compound 1. For crystalline Compound 1, an endotherm was observed at 88.6° C. and there was a 7.8% mass loss from 80-110° C.

Figure 3:
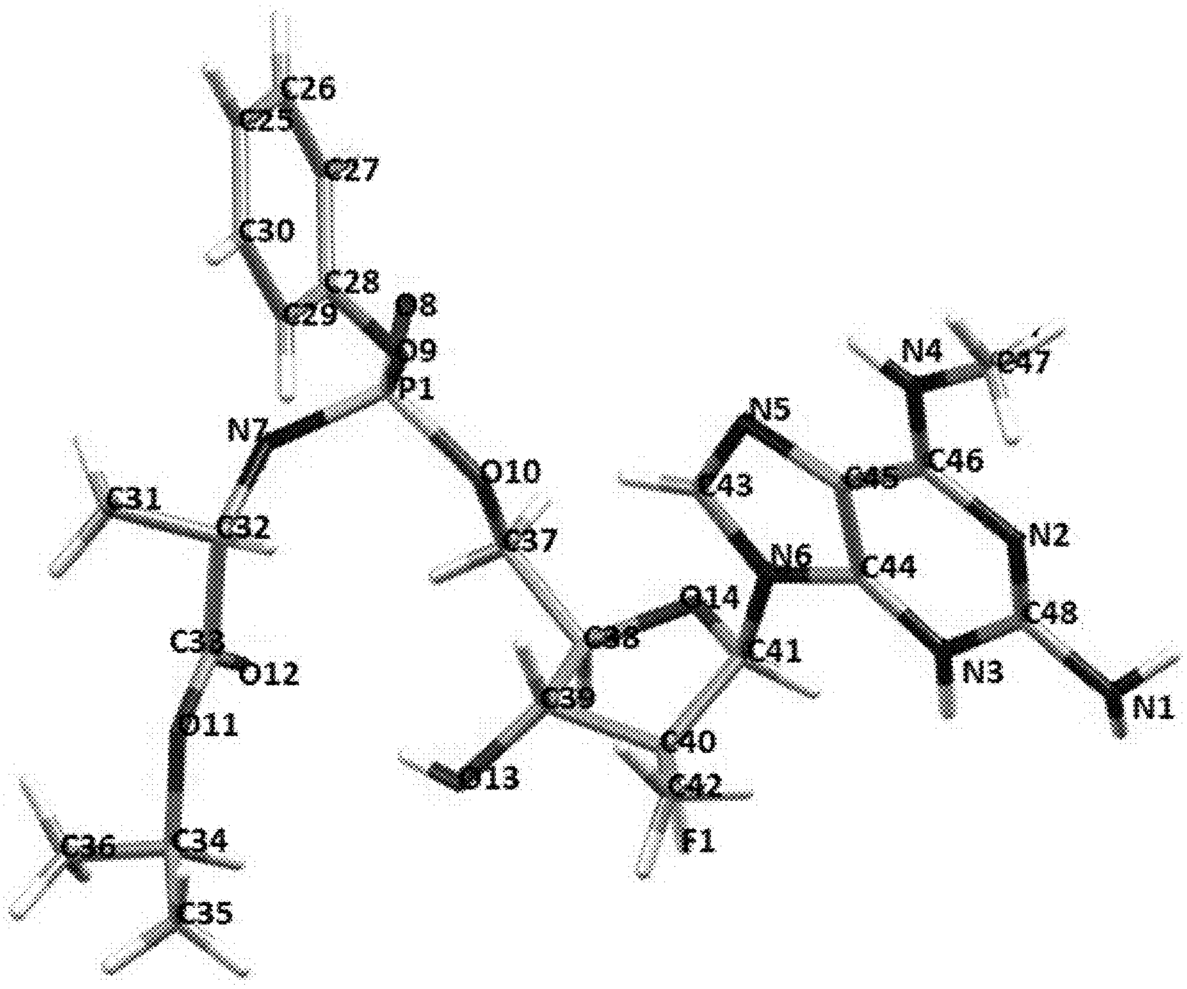
FIG. 3 is an X-ray crystallography image of Compound 1 showing the absolute stereochemistry as described in Example 2.

A sample of Compound 1 was recrystallized from EtOAc/hexane and drawn with ORTEP. The absolute structure of Compound 1 was confirmed by the recrystallization of a single crystal. FIG. 3 is the ORTEP drawing of Compound 1. Crystal data and measurement data are shown in Table 3. The absolute stereochemistry of Compound 1 based on the X-ray crystallography is shown below:

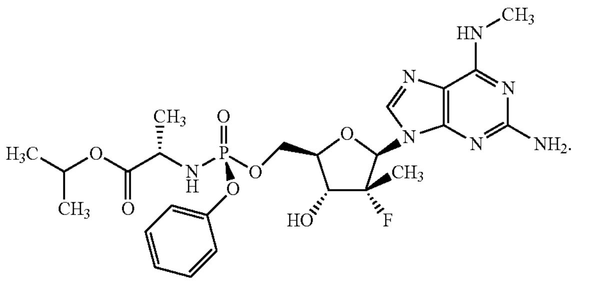 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

DSC data were collected on a TA Instruments Q2000 equipped with a 50 position auto-sampler. The calibration for thermal capacity was carried out using sapphire and the calibration for energy and temperature was carried out using certified indium. Typically approximately 3 mg of each sample, in a pin-holed aluminum pan, was heated at 10° C./min from 25° C. to 200° C. A purge of dry nitrogen at 50 ml/min was maintained over the sample. The instrument control software was Advantage for Q Series v2.8.0.394 and Thermal Advantage v5.5.3 and the data were analyzed using Universal Analysis v4.5A.

TGA data were collected on a TA Instruments Q500 TGA, equipped with a 16 position auto-sampler. The instrument was temperature calibrated using certified Alumel and Nickel. Typically, 5-10 mg of each sample was loaded onto a pre-tared aluminum DSC pan and heated at 10° C./min from ambient temperature to 350° C. A nitrogen purge at 60 ml/min was maintained over the sample. The instrument control software was Advantage for Q Series v2.5.0.256 and Thermal Advantage v5.5.3 and the data were analyzed using Universal Analysis v4.5.

Amorphous Compound 1 (1-1):

$^1$H NMR (400 MHz, DMSO-$d_6$) δ ppm 1.01-1.15 (m, 9H), 1.21 (d, J=7.20 Hz, 3H), 2.75-3.08 (m, 3H), 3.71-3.87 (m, 1H), 4.02-4.13 (m, 1H), 4.22-4.53 (m, 3H), 4.81 (s, 1H), 5.69-5.86 (m, 1H), 6.04 (br d, J=19.33 Hz, 4H), 7.12-7.27 (m, 3H), 7.27-7.44 (m, 3H), 7.81 (s, 1H)

Crystalline Compound 1 (1-2):

$^1$H NMR (400 MHz, DMSO-$d_6$) δ ppm 0.97-1.16 (m, 16H), 1.21 (d, J=7.07 Hz, 3H), 2.87 (br s, 3H), 3.08 (s, 2H), 3.79 (br d, J=7.07 Hz, 1H), 4.08 (br d, J=7.58 Hz, 1H), 4.17-4.55 (m, 3H), 4.81 (quin, J=6.25 Hz, 1H), 5.78 (br s, 1H), 5.91-6.15 (m, 4H), 7.10-7.26 (m, 3H), 7.26-7.44 (m, 3H), 7.81 (s, 1H)

TABLE 1

Peak list for crystalline Compound 1

| Angle/°2θ | d spacing/Å | Intensity/Counts | Intensity/% |
|---|---|---|---|
| 6.03 | 14.64 | 1005 | 39.0 |
| 7.36 | 12.00 | 315 | 12.2 |
| 7.94 | 11.13 | 1724 | 66.9 |
| 9.34 | 9.47 | 2500 | 97.0 |
| 9.51 | 9.29 | 860 | 33.4 |
| 9.77 | 9.05 | 1591 | 61.8 |
| 11.08 | 7.98 | 2576 | 100.0 |
| 12.02 | 7.36 | 171 | 6.6 |
| 12.95 | 6.83 | 319 | 12.4 |
| 13.98 | 6.33 | 241 | 9.4 |
| 14.30 | 6.19 | 550 | 21.4 |
| 14.69 | 6.03 | 328 | 12.7 |
| 15.20 | 5.82 | 2176 | 84.5 |
| 15.94 | 5.56 | 1446 | 56.1 |
| 16.75 | 5.29 | 1009 | 39.2 |
| 17.29 | 5.13 | 700 | 27.2 |
| 17.72 | 5.00 | 1213 | 47.1 |
| 18.11 | 4.89 | 1565 | 60.8 |
| 18.46 | 4.80 | 302 | 11.7 |
| 18.89 | 4.69 | 385 | 14.9 |
| 19.63 | 4.52 | 636 | 24.7 |
| 20.37 | 4.36 | 1214 | 47.1 |
| 20.74 | 4.28 | 1198 | 46.5 |
| 21.24 | 4.18 | 640 | 24.8 |
| 22.31 | 3.98 | 961 | 37.3 |
| 22.88 | 3.88 | 806 | 31.3 |
| 23.43 | 3.79 | 355 | 13.8 |
| 24.08 | 3.69 | 573 | 22.2 |
| 24.49 | 3.63 | 159 | 6.2 |
| 25.00 | 3.56 | 351 | 13.6 |
| 25.36 | 3.51 | 293 | 11.4 |
| 26.09 | 3.41 | 235 | 9.1 |
| 26.26 | 3.39 | 301 | 11.7 |
| 26.83 | 3.32 | 696 | 27.0 |
| 27.35 | 3.26 | 436 | 16.9 |
| 27.46 | 3.25 | 363 | 14.1 |
| 28.07 | 3.18 | 200 | 7.8 |
| 28.30 | 3.15 | 195 | 7.6 |
| 28.82 | 3.10 | 599 | 23.3 |
| 29.85 | 2.99 | 217 | 8.4 |
| 30.26 | 2.95 | 186 | 7.2 |
| 30.75 | 2.91 | 333 | 12.9 |
| 31.12 | 2.87 | 149 | 5.8 |
| 31.85 | 2.81 | 238 | 9.2 |
| 33.28 | 2.69 | 261 | 10.1 |
| 34.77 | 2.58 | 171 | 6.6 |
| 35.18 | 2.55 | 175 | 6.8 |
| 36.83 | 2.44 | 327 | 12.7 |
| 37.41 | 2.40 | 172 | 6.7 |

TABLE 2

Relative Retention Times from HPLC chromatographs of Amorphous Compound 1 and Crystalline Compound 1

| RRT | Area % |
|---|---|
| Amorphous Compound 1 | |
| 0.48 | 0.15 |
| 0.51 | 0.04 |
| 0.48 | 0.15 |
| 0.51 | 0.04 |
| 0.94 | 0.13 |
| 0.98 | 0.21 |
| 1.00 | 98.61 |
| 1.04 | 0.29 |
| 1.37 | 0.31 |
| Crystalline Compound 1 | |
| 0.48 | 0.17 |
| 0.48 | 0.17 |
| 0.94 | 0.12 |
| 1.00 | 99.11 |
| 1.04 | 0.22 |
| 1.37 | 0.07 |

TABLE 3

Crystal and Data Measurement of Compound 1

| | | |
|---|---|---|
| Bond Precision | C—C = 0.0297 A, Wavelength = 1.54184 | |
| Cell | a = 10.1884(3) b = 28.6482(9) c = 12.9497(5) alpha = 90 beta = 113.184(4) gamma = 90 | |
| Temperature | 150 K | |
| | Calculated | Reported |
| Volume | 3474.5(2) | 3474.5(2) |
| Space Group | P21 | P 1 21 1 |
| Hall Group | P 2yb | P 2yb |
| Moiety Formula | C24 H34 F N7 O7 P | 2(C24 H34 F N7 O7 P) |
| Sum Formula | C24 H34 F N7 O7 P | C48 H68 F2 N14 O14 P2 |
| Mr | 582.55 | 1165.10 |
| Dx, g $cm^{-1}$ | 1.114 | 1.114 |
| Z | 4 | 2 |
| Mu ($mm^{-1}$) | 1.139 | 1.139 |
| F000 | 1228.0 | 1228.0 |
| F000' | 1233.21 | |
| h, k, $l_{max}$ | 12, 34, 15 | 12, 34, 15 |
| $N_{ref}$ | 12742 [6510] | 8259 |
| $T_{min}$, $T_{max}$ | 0.790, 0.815 | 0.808, 1.000 |
| $T_{min'}$ | 0.716 | |
| Correction Method | # Reported T Limits: $T_{min}$ = 0.808 $T_{max}$ = 1.00 | |
| AbsCorr | MULTI-SCAN | |
| Data completeness | 1.27/0.65 | |
| Theta (max) | 68.244 | |
| R (reflections) | 0.2091 (7995) | |
| wR2 (reflections) | 0.5338 (8259) | |
| S | 2.875 | |
| Npar | 716 | |

Figure 4A:
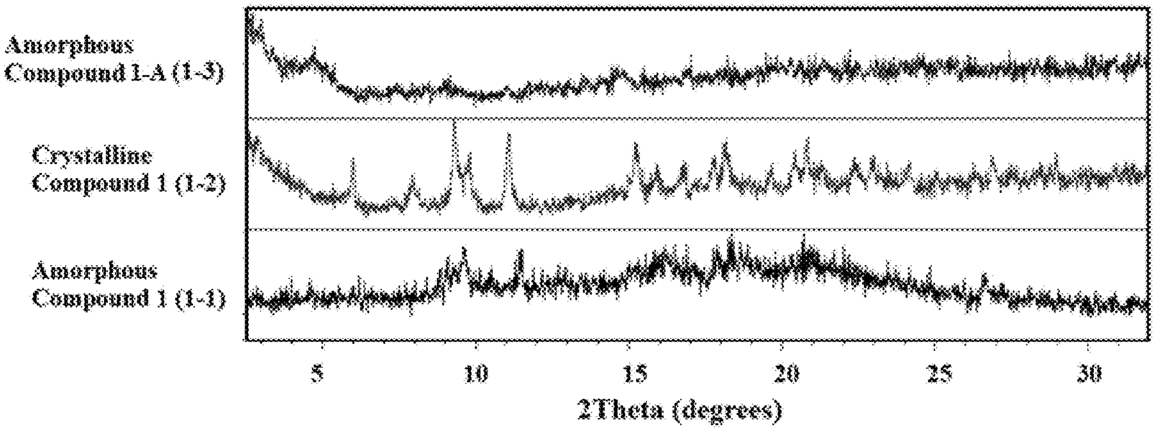
FIG. 4A is an overlay of XRPD diffractograms of samples 1-1 (amorphous Compound 1), 1-2 (crystalline Compound 1), and 1-3 (amorphous Compound 1-A) after storing at 25° C. and 60% relative humidity for 14 days as described in Example 2 and Example 5. The x-axis is 2Theta measured in degrees and the y-axis is intensity measured in counts.
Figure 4B:
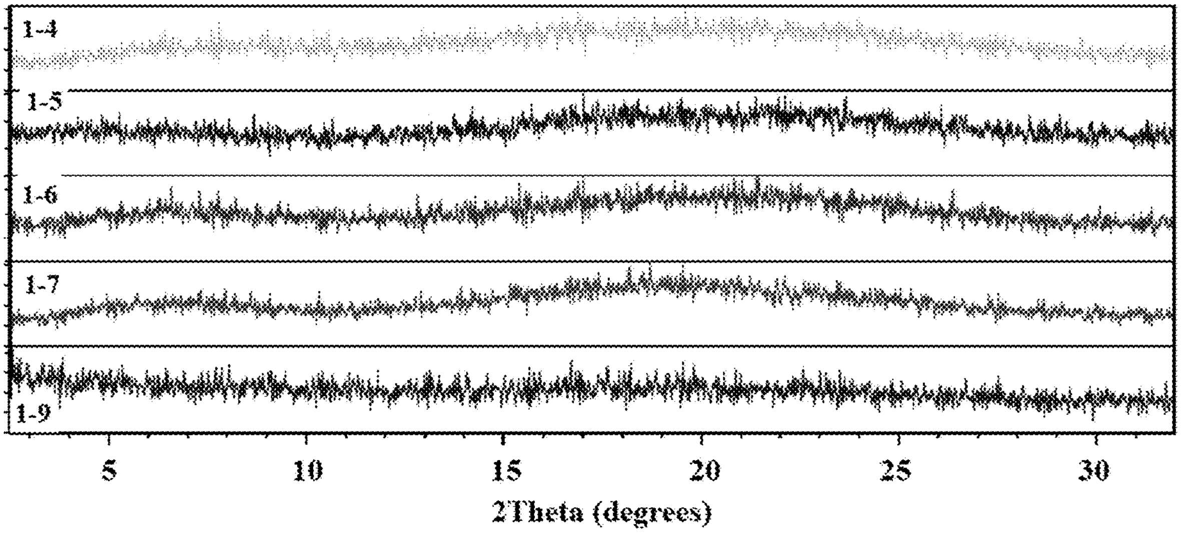
FIG. 4B is an overlay of XRPD diffractograms of samples 1-4, 1-5, 1-6, 1-7, and 1-9 after storing at 25° C. and 60% relative humidity for 7 days as described in Example 4. The x-axis is 2Theta measured in degrees and the y-axis is intensity measured in counts.

This initial characterization was followed by storage at 25° C./60% relative humidity (RH) for 14 days with analysis by HPLC and XRPD after 7 and 14 days. FIG. 4A is the XRPD after 14 days at 25° C./60% (RH). Amorphous Compound 1 (sample 1-1) remained poorly crystalline, whereas crystalline Compound 1 (sample 1-2) retained its crystallinity, but both compounds were stable after 14 days at 25° C./60% (RH).

Example 3. Formation of Oxalate Salt Compound 1-B

Initially, the oxalate salt of Compound 1, Compound 1-B, was formed by mixing the oxalic salt with solvent (5 vol, 100 μL) and allowing any solution to evaporate at room temperature. Any suspension was matured (room temperature—50° C.) for 3 hours and crystallinity was accessed.

Compound 1-B

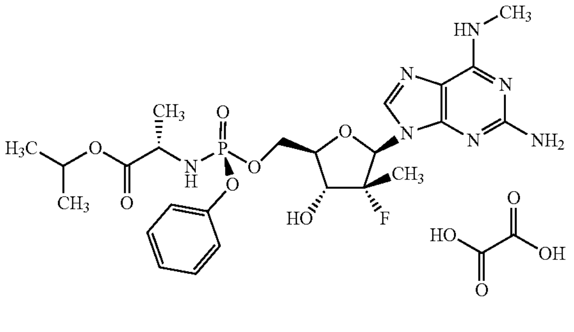

Table 4 shows the different solvents used in the production of Compound 1-B. All solvents except for two (cyclohexane and n-heptane) afforded crystalline products. Despite the high crystallinity and solubility of Compound 1-B, oxalate salts are not acceptable for clinical development due to the potential formation of kidney stones and other salts of compound 1 were explored.

TABLE 4

Formation of Oxalate Compound 1-B

| Solvent | Observation post acid addition at room temperature | Observation after maturation/evaporation |
|---|---|---|
| EtOH | Solution | OXA - Form 1 |
| IPA | Solution | OXA - Form 1 |
| Acetone | Solution | OXA - Form 1 |
| MEK | Solution | OXA - Form 1 |
| EtOAc | Suspension | OXA - Form 1 |
| iPrOAc | Suspension | OXA - Form 1 |
| THF | Solution | OXA - Form 1 |
| Toluene | Solution | OXA - Form 1 |
| MeCN | Solution | OXA - Form 1 |
| IPA:10% water | Solution | OXA - Form 1 |
| TBME | Suspension | OXA - Form 1 |
| Cyclohexane | Suspension | Amorphous |
| n-Heptane | Suspension | Amorphous |

Example 4. Salt Compounds of Amorphous Compound 1

Since the oxalate salt Compound 1-B (Example 3) could not be carried forward in clinical trials due to its potential to form kidney stones, amorphous salts of Compound 1 were formed with the counter ions listed in Table 5. Compound 1 was dissolved in t-butanol (20 vol, 6 ml) and the solution was treated with the acid counter-ions (1 equivalent for each sample except sample 1-9 which had 0.5 equivalent of sulfate). The samples were then frozen with the solvent removed by lyophilization. The residual solid in samples 1-4, 1-5, 1-6, 1-7, 1-8, and 1-9 was initially analyzed by XRPD and HPLC.

TABLE 5

Amorphous salt formation details

| Sample ID | Sample details | Stock solution details | Observation | NMR |
|---|---|---|---|---|
| 1-4 | HCl (1:1) | THF 1M | White solid | 3 fewer protons ~0.3 eq t-BuOH |
| 1-5 | Sulfuric (1:1) | THF 1M | White solid | 3 fewer protons ~0.3 eq t-BuOH |
| 1-6 | Fumaric (1:1) | MeOH:THF (1:1) 0.5M | Glassy solid | 1.05 eq fumaric acid 0.84 eq t-BuOH |
| 1-7 | Benzoic (1:1) | THF 1M | White solid | 1.0 eq benzoic acid 0.34 eq t-BuOH |
| 1-8 | Succinic (1:1) | MeOH 1M | Sticky white solid | ~1.1 eq succinic acid 0.37 eq t-BuOH |
| 1-9 | Sulfuric (0.5:1 acid:API) | THF 1M | White solid | 3 fewer protons ~0.3 eq t-BuOH |

$^1$HNMR spectrum were taken for all samples.

Sample 1-4, HCl (1:1) Salt:

$^1$H NMR (400 MHz, DMSO-$d_6$) δ ppm 0.93-1.39 (m, 16H), 2.97 (br s, 2H), 3.70-3.88 (m, 1H), 4.10 (br s, 1H), 4.18-4.49 (m, 3H), 4.70-4.88 (m, 1H), 5.71-5.94 (m, 1H), 6.07 (br d, J=19.07 Hz, 2H), 7.14-7.27 (m, 3H), 7.29-7.44 (m, 2H), 7.83-8.19 (m, 1H)

Sample 1-5, Sulfuric (1:1) Salt:

$^1$H NMR (400 MHz, DMSO-$d_6$) δ ppm 0.97-1.38 (m, 15H), 2.96 (br s, 2H), 4.06-4.18 (m, 1H), 4.19-4.49 (m, 3H), 4.66-4.91 (m, 1H), 5.70-5.95 (m, 1H), 5.96-6.16 (m, 2H), 7.10-7.27 (m, 3H), 7.30-7.43 (m, 2H), 7.88-8.19 (m, 1H)

Sample 1-6, Fumaric (1:1) Salt:

$^1$H NMR (400 MHz, DMSO-$d_6$) δ ppm 0.95-1.31 (m, 21H), 2.87 (br s, 3H), 3.79 (br d, J=7.20 Hz, 1H), 4.01-4.13 (m, 1H), 4.16-4.23 (m, 1H), 4.16-4.24 (m, 1H), 4.20 (s, 1H), 4.18-4.23 (m, 1H), 4.24-4.52 (m, 1H), 4.24-4.52 (m, 1H), 4.24-4.49 (m, 1H), 4.72-4.88 (m, 1H), 5.68-5.86 (m, 1H), 6.04 (br d, J=19.33 Hz, 4H), 6.63 (s, 1H), 6.61-6.66 (m, 1H), 7.12-7.27 (m, 3H), 7.27-7.45 (m, 3H), 7.81 (s, 1H), 13.16 (br s, 2H)

Sample 1-7, Benzoic (1:1) Salt:

$^1$H NMR (400 MHz, DMSO-$d_6$) δ ppm 0.96-1.30 (m, 15H), 2.87 (br s, 3H), 3.79 (br d, J=7.07 Hz, 1H), 4.07 (br s, 1H), 4.20 (s, 1H), 4.25-4.52 (m, 3H), 4.81 (s, 1H), 5.71-5.85 (m, 1H), 6.04 (br d, J=19.33 Hz, 4H), 7.08-7.27 (m, 3H), 7.27-7.43 (m, 3H), 7.45-7.57 (m, 2H), 7.63 (s, 1H), 7.81 (s, 1H), 7.95 (dd, J=8.27, 1.33 Hz, 2H), 12.98 (br s, 1H)

Sample 1-8, Succinic (1:1) Salt:

$^1$H NMR (400 MHz, DMSO-$d_6$) δ ppm 0.98-1.28 (m, 15H), 2.42 (s, 5H), 2.87 (br s, 3H), 3.57-3.62 (m, 1H), 3.70-3.86 (m, 1H), 4.02-4.14 (m, 1H), 4.20 (s, 1H), 4.24-4.51 (m, 3H), 4.70-4.88 (m, 1H), 5.69-5.86 (m, 1H), 6.04 (br d, J=19.33 Hz, 4H), 7.12-7.27 (m, 3H), 7.27-7.44 (m, 3H), 7.81 (s, 1H), 11.95-12.58 (m, 2H)

Sample 1-9, Sulfuric (0.5:1) Salt:

$^1$H NMR (400 MHz, DMSO-$d_6$) δ ppm 1.02-1.31 (m, 15H), 2.94 (br s, 3H), 3.79 (br d, J=7.20 Hz, 2H), 4.09 (br s, 1H), 4.22-4.48 (m, 3H), 4.72-4.90 (m, 1H), 5.71-5.92 (m, 1H), 6.07 (br d, J=19.07 Hz, 2H), 7.12-7.28 (m, 3H), 7.31-7.44 (m, 2H), 7.75-8.19 (m, 1H).

The samples were then subjected to storage at 25° C./60% relative humidity (RH) for 14 days with analysis by HPLC and XRPD after 7 (FIG. 4B) and 14 days (FIG. 5A). All prepared salts remained amorphous and the observations are shown in Table 6. The mono sulfate (sample 1-5) and succinate salts (sample 1-8) were found to be physically unstable and deliquesced or became a gum during the course of the study. Both the fumarate (sample 1-6) and benzoate salts (sample 1-7) were found to be glassy solids. The HCl salt (sample 1-4) was found to retain its physical appearance. Surprisingly, the hemi-sulfate salt (sample 1-9) also retained its physical appearance as a white solid in contrast to mono-sulfate compound (sample 1-5), which was a sticky gum. Results are shown in Table 6. The mono HCl salt (sample 1-4) and the hemi-sulfate salt (sample 1-9) were found to be physically and chemically stable after 2 weeks storage at 25° C./60% relative humidity (RH). Although both salts were stable over the two weeks, the hemi-sulfate salt was superior to the HCl salt because the HCl salt was hygroscopic, rendering it less useful compared to the hemi-sulfate salt for long-term storage or use.

TABLE 6

Stability of samples after 7 and 14 days at 25° C./60% RH

| Sample | Time exposed to 25° C./60% RH (days) | | | | | |
|---|---|---|---|---|---|---|
| | 0 | | 7 | | 14 | |
| ID | HPLC | Observation | HPLC | Observation | HPLC | Observation |
| 1-1 | 98.6 | White solid | 98.7 | White solid | 98.5 | White solid |
| 1-2 | 99.1 | White solid | 99.2 | White solid | 99.0 | White solid |
| 1-3 | 99.7 | White solid | 99.6 | White solid | 99.4 | White solid |
| 1-4 | 98.7 | White solid | 98.8 | White solid | 98.6 | White solid |
| 1-5 | 98.4 | White solid | 55.7 | Sticky white solid | — | Sticky gum |
| 1-6 | 98.7 | Glassy solid | 98.6 | Clear glassy solid | 98.4 | White glassy solid |
| 1-7 | 98.8 | White solid | 98.8 | Clear glassy solid | 98.7 | Clear glassy solid |
| 1-8 | 98.7 | Sticky white solid | — | Deliquesced/ sticky oil | — | Deliquesced |
| 1-9 | 98.7 | White solid | 98.1 | White solid | 96.4 | White solid |

Example 5. Characterization of Amorphous Compound 1-A

Amorphous Compound 1-A was initially analyzed by XRPD, $^{1}$H NMR, DSC, TGA, and HPLC. The XRPD pattern for amorphous Compound 1-A overlaid with amorphous Compound 1 and crystalline Compound 1 is shown in FIG. 1A and the XRPD pattern of amorphous Compound 1-A alone is shown in FIG. 5B. Table 7 is a peak list from the XRPD pattern shown in FIG. 5B. The HPLC trace to determine purity is shown in FIG. 6A. Table 8 is a list of relative retention times (RTT) from the HPLC trace shown in FIG. 6A. Amorphous Compound 1-A was 99.68% pure. FIG. 6B is a TGA and DSC graph of amorphous Compound 1-A. Experimental details for the TGA and DSC experiments are given in Example 2.

TABLE 7

Peak list for Amorphous Compound 1-A

| Angle/°2θ | d spacing/Å | Intensity/Counts | Intensity/% |
|---|---|---|---|
| 4.20 | 21.03 | 486 | 81.8 |
| 4.67 | 18.91 | 482 | 81.0 |
| 5.16 | 17.10 | 595 | 100.0 |
| 9.13 | 9.68 | 547 | 92.0 |

TABLE 8

HPLC chromatogram of Amorphous Compound 1-A

| Amorphous Compound 1-A | |
|---|---|
| RRT | Area % |
| 0.48 | 0.02 |
| 0.48 | 0.02 |
| 0.67 | 0.01 |
| 0.94 | 0.13 |
| 1.00 | 99.68 |
| 1.04 | 0.06 |

Amorphous Compound 1-A:

$^{1}$H NMR (400 MHz, DMSO-$d_6$) δ ppm 0.93-1.29 (m, 13H), 2.94 (br s, 3H), 3.79 (td, J=10.04, 7.07 Hz, 2H), 4.05-4.19 (m, 1H), 4.19-4.50 (m, 3H), 4.81 (quin, J=6.25 Hz, 1H), 5.71-5.94 (m, 1H), 5.97-6.16 (m, 2H), 7.14-7.28 (m, 3H), 7.31-7.44 (m, 2H), 7.82-8.09 (m, 1H)

Example 6. Crystallization of Amorphous Compound 1-A

Since the hemi-sulfate salt was found to remain as a solid after the 14-day stability study as shown in Table 6, preliminary tests studying crystallization conditions using 11 different solvents was conducted. Amorphous Compound 1-A was suspended in 5 volumes of solvent at 25° C. (sample 2-1, 2-2, 2-3, 2-4, 2-5, 2-6, 2-7, 2-8, 2-9, 2-10, and 2-11). To those samples that were not free flowing (2-1, 2-2, 2-3, 2-4, 2-5, 2-6, 2-7, 2-8, and 2-10), an additional 5 volumes of solvent was added. The samples were then matured at 25-50° C. (1° C./min between temperatures and 4 hour at each temperature) for 6 days except for sample 2-1, which was observed to be a clear solution after 1 day and was allowed to evaporate under ambient conditions. The results are shown in Table 9. Crystalline patterns resulted from crystallization with isobutanol (sample 2-1), acetone (sample 2-2), EtOAc (sample 2-6), and iPrOAc (sample 2-7). Two poorly crystalline samples were also identified from crystallization with MEK (sample 2-4) and MIBK (sample 2-5). The XRPD patterns are shown in FIG. 7A.

TABLE 9

| Crystallization Conditions of Compound 1-A | | | | | |
|---|---|---|---|---|---|
| Sample ID | Solvent | Observation after 5 volumes | Observation after 10 volumes | Observation after 1 day maturation | XRPD |
| 2-1 | IPA | Solid - not free flowing | Free flowing suspension | Solution, evaporated at RT yielding a gum | Gum |
| 2-2 | Isobutanol | Solid - not free flowing | Free flowing suspension | Suspension | Crystalline - Pattern 2 |
| 2-3 | Acetone | Solid - not free flowing | Free flowing suspension | Suspension | Crystalline - Pattern 3 |
| 2-4 | MEK | Solid - not free flowing | Free flowing suspension | Suspension | Poorly crystalline - Pattern 4 |
| 2-5 | MIBK | Solid - not free flowing | Free flowing suspension | Suspension | Poorly crystalline - Pattern 4 |
| 2-6 | EtOAc | Solid - not free flowing | Free flowing suspension | Suspension | Crystalline - Pattern 1 |
| 2-7 | iPrOAc | Solid - not free flowing | Free flowing suspension | Suspension | Crystalline - Pattern 1 |
| 2-8 | THF | Solid - not free flowing | Free flowing suspension | Suspension | Poorly crystalline |
| 2-9 | TBME | Free flowing suspension | — | Suspension | Amorphous |
| 2-10 | Toluene | Solid - not free flowing | Free flowing suspension | Suspension | Amorphous |
| 2-11 | Heptane | Free flowing suspension | — | Suspension | Amorphous |

The seven samples (Samples 2-2, 2-3, 2-4, 2-5, 2-6, 2-7 and 2-8) were analyzed by DSC, TGA, $^1$H-NMR and IC (Table 10, FIG. 8A, FIG. 8B, FIG. 9A, FIG. 91B, FIG. 10A, FIG. 10B, FIG. 11A, and FIG. 11B) as well as by XRPD following 6 days storage at 25° C./6000 relative humidity (RH) (all samples remained crystalline/poorly crystalline following stability). All samples retained roughly half an equivalent of sulfate, but contained a relatively large amount of residual solvent. An overlay of the X-ray diffractograms of amorphous samples 2-9, 2-10, and 2-11 is shown in FIG. 7B.

TABLE 10

| Characterization of crystalline Compound 1-A samples | | | | | |
|---|---|---|---|---|---|
| Sample ID | Solvent | DSC | TGA | $^1$HNMR | IC (corrected for TGA) |
| 2-2 | Isobutanol | Endo 113.8° C. | 8.3% ambient-140° C. | 1.1 eq isobutanol | 0.45 eq |
| 2-3 | Acetone | Endo 30-95° C. Endo 100-145° C. | 7.6% ambient - 140° C. | 0.5 eq acetone | 0.46 eq |
| 2-4 | MEK | Broad complex endo 30-115° C. Endo 115-145° C. | 8.5% ambient - 140° C. | 0.8 eq MEK | 0.45 eq |
| 2-5 | MIBK | Broad endo 30-105° C. Endo 114.7° C. | 5.2% ambient - 110° C. | 0.2 eq MIBK | 0.46 eq |

TABLE 10-continued

| Characterization of crystalline Compound 1-A samples | | | | | |
|---|---|---|---|---|---|
| Sample ID | Solvent | DSC | TGA | $^1$HNMR | IC (corrected for TGA) |
| 2-6 | EtOAc | Sharp endo 113.6° C. | 2.0% ambient-100° C. | 0.9 eq EtOAc | 0.46 eq |
| 2-7 | iPrOAc | Endo 30-90° C. | 1.6% ambient-90° C. | 0.8 eq iPrOAc | 0.45 eq |
| 2-8 | THF | Endo 30-100° C. Sharper endo 115.6° C. | 4.2% ambient-130° C. | 0.7 eq THF | 0.45 eq |

$^1$HNMR spectrum were taken for all samples and listed below.

Sample 2-2:

$^1$HNMR (400 MHz, DMSO-$d_6$) δ ppm 0.83 (d, J=6.69 Hz, 7H), 0.99-1.26 (m, 14H), 1.61 (dt, J=13.26, 6.63 Hz, 1H), 3.73-3.87 (m, 2H), 4.03-4.18 (m, 1H), 4.18-4.51 (m, 4H), 4.66-4.92 (m, 1H), 4.70-4.90 (m, 1H), 4.72-4.88 (m, 1H), 5.81 (br s, 1H), 5.93-6.11 (m, 2H), 7.10-7.26 (m, 3H), 7.14-7.26 (m, 1H), 7.30-7.41 (m, 2H), 7.94 (br s, 1H)

Sample 2-3:

$^1$H NMR (400 MHz, DMSO-$d_6$) δ ppm 1.00-1.26 (m, 13H), 2.09 (s, 3H), 3.74-3.87 (m, 2H), 4.10 (br d, J=7.70 Hz, 1H), 4.22-4.50 (m, 3H), 4.81 (quin, J=6.28 Hz, 1H), 5.71-5.90 (m, 1H), 5.96-6.15 (m, 2H), 7.12-7.26 (m, 3H), 7.31-7.41 (m, 2H), 7.79-8.07 (m, 1H)

Sample 2-4:

$^1$H NMR (400 MHz, DMSO-$d_6$) δ ppm 0.91 (t, J=7.33 Hz, 3H), 1.01-1.28 (m, 13H), 2.08 (s, 2H), 3.72-3.89 (m, 2H), 4.10 (br d, J=8.08 Hz, 1H), 4.23-4.47 (m, 3H), 4.81 (quin, J=6.25 Hz, 1H), 5.69-5.89 (m, 1H), 5.94-6.13 (m, 2H), 7.14-7.25 (m, 3H), 7.32-7.41 (m, 2H), 7.79-8.11 (m, 1H)

Sample 2-5:

$^1$H NMR (400 MHz, DMSO-$d_6$) δ ppm 0.86 (d, J=6.69 Hz, 1H), 0.98-1.33 (m, 13H), 2.02-2.09 (m, 1H), 4.03-4.17 (m, 1H), 4.22-4.50 (m, 3H), 4.81 (quin, J=6.25 Hz, 1H), 5.81 (br s, 1H), 5.93-6.15 (m, 2H), 7.11-7.27 (m, 3H), 7.31-7.41 (m, 2H), 7.77-8.21 (m, 1H)

Sample 2-6:

$^1$H NMR (400 MHz, DMSO-$d_6$) δ ppm 0.98-1.28 (m, 15H), 2.00 (s, 3H), 3.99-4.14 (m, 3H), 4.21-4.49 (m, 3H), 4.81 (quin, J=6.22 Hz, 1H), 5.82 (br s, 1H), 5.93-6.14 (m, 2H), 7.11-7.26 (m, 3H), 7.29-7.42 (m, 2H), 7.79-8.17 (m, 1H)

Sample 2-7:

$^1$H NMR (400 MHz, DMSO-$d_6$) δ ppm 0.92-1.28 (m, 17H), 1.97 (s, 2H), 4.04-4.16 (m, 1H), 4.20-4.51 (m, 3H), 4.71-4.93 (m, 2H), 5.82 (br s, 1H), 5.95-6.14 (m, 2H), 7.11-7.28 (m, 3H), 7.31-7.43 (m, 2H), 7.75-8.21 (m, 1H)

Sample 2-8:

$^1$H NMR (400 MHz, DMSO-$d_6$) δ ppm 0.81-1.11 (m, 13H), 1.19 (s, 1H), 1.53-1.66 (m, 1H), 3.87-4.01 (m, 1H), 4.06-4.32 (m, 3H), 4.64 (quin, J=6.25 Hz, 1H), 5.55-5.75 (m, 1H), 5.77-5.97 (m, 2H), 6.94-7.10 (m, 3H), 7.13-7.26 (m, 2H), 7.66-7.96 (m, 1H)

Example 7. Failure to Crystallize Amorphous Malonate Salt (Compound 1-B)

As shown in Example 3, a crystalline oxalate salt was identified when determining appropriate salts for Compound 1, but oxalate salt Compound 1-B could not be carried forward in clinical trials due to its potential for causing kidney stones. Therefore, crystallization of the chemically related malonate salt (Compound 1-E) was attempted using the same 11 solvents as for the hemi-sulfate salt. Compound 1 (12×50 mg, samples 3-1, 3-2, 3-3, 3-4, 3-5, 3-6, 3-7, 3-8, 3-9, 3-10, 3-11, and 3-12) was dissolved in t-butanol (20 vol) and the solutions were then treated with 1 equivalence of a malonic acid stock solution (1 M in THF). The samples were then frozen with the solvent removed by lyophilisation. To samples 3-1, 3-2, 3-3, 3-4, 3-5, 3-6, 3-7, 3-8, 3-9, 3-10, and 3-11, relevant solvent (5 volumes) was added at room temperature. Any resulting solutions were allowed to evaporate under ambient conditions, while gums or solids were matured at 25-50° C. (1° C./min between temperatures and 4 hour at each temperature) for 5 days. The solids were analyzed by XRPD (FIG. 12B), but all samples were found to either form a gum or were amorphous (FIG. 12B). Results are shown in Table 11. The one solid (amorphous) sample (3-12) was analyzed by $^1$H-NMR and HPLC, and was found to contain around 1 equivalents of malonic acid (peaks overlap) as well as 0.6 eq. t-BuOH. The compound was 99.2% pure (FIG. 13A). FIG. 12A is an XRDP of sample 3-12 and FIG. 13A is the HPLC chromatograph of sample 3-12.

Sample 3-12:

$^1$H NMR (400 MHz, DMSO-$d_6$) δ ppm 0.81-1.11 (m, 13H), 1.19 (s, 1H), 1.53-1.66 (m, 1H), 3.87-4.01 (m, 1H), 4.06-4.32 (m, 3H), 4.64 (quin, J=6.25 Hz, 1H), 5.55-5.75 (m, 1H), 5.77-5.97 (m, 2H), 6.94-7.10 (m, 3H), 7.13-7.26 (m, 2H), 7.66-7.96 (m, 1H)

TABLE 11

Crystallization Conditions of Amorphous Malonate Salt Compound 1-E

| Sample ID | Solvent | Observation after 5 volumes | Observation after 5 days maturation/ evaporation | XRPD |
|---|---|---|---|---|
| 3-1 | IPA | Clear solution* | Clear gum | — |
| 3-2 | Isobutanol | Clear solution* | Clear gum | — |
| 3-3 | Acetone | Clear solution* | Clear gum | — |
| 3-4 | MEK | Clear solution* | Clear gum | — |
| 3-5 | MIBK | Solution & some gum | Clear gum | — |
| 3-6 | EtOAc | Clear solution* | Clear gum & crystal-like appearance | Amorphous |
| 3-7 | iPrOAc | Gum | Clear gum | — |
| 3-8 | THF | Clear solution* | Clear gum | — |
| 3-9 | TBME | Thick suspension | Clear gum | — |
| 3-10 | Toluene | White gum/ solid | White gum | Amorphous |
| 3-11 | Heptane | White solid (static) | White gum | Amorphous |
| 3-12 | — | (White solid - no solvent) | (Sticky white solid - ambient conditions) | Amorphous |

*Evaporated at room temperature

Example 8. Failure of Adequate Salt Formation Using Liquid Assisted Grinding (LAG)

A liquid assisted grinding (LAG) study to determine appropriate salts other than hemi-sulfate was performed using the 14 acidic counter ions in Table 12.

TABLE 12

Counter-ion stock solutions used in LAG Crystallization

| Counter-ion | Solvent (1M) |
|---|---|
| Pamoic | DMSO |
| Malonic | THF |
| D-Glucuronic | Water |
| DL-Mandelic | THF |
| D-Gluconic | THF |
| Glycolic | THF |
| L-Lactic | THF |
| Oleic | THF |
| L-Ascorbic | Water |
| Adipic | THF (heat) |
| Caproic | THF |
| Stearic | THF |
| Palmitic | THF |
| Methanesulfonic | THF |

Compound 1 (30 mg) was placed in PLC vials with two 3 mm ball bearings. The materials were wetted with solvent (15 μl ethanol, sample 4-1, 4-2, 4-3, 4-4, 4-5, 4-6, 4-7, 4-8, 4-9, 4-10, 4-11, 4-12, 4-13, and 4-14) and 1 equivalence of the acid counter-ion was added. The samples were then ground for 2 hours at 650 rpm using a Fritsch milling system with an Automaxion adapter. Most of the samples after grinding were found to be clear gums and were not analyzed further (Table 13). Those that were observed to contain solid were analyzed by XRPD and, in all cases, the patterns obtained were found to match those of the crystalline acid counter ion with no additional peaks (FIG. 13B).

TABLE 13

Observations and XRPD Results from LAG of Compounds 1

| Sample ID | Acid | Observation after grinding | XRPD |
|---|---|---|---|
| 4-1 | Pamoic | Yellow gum/solid | Pamoic acid & amorphous halo |
| 4-2 | Malonic | Clear gum | — |
| 4-3 | D-Glucuronic | White gum/solid | D-Glucuronic acid & amorphous halo |
| 4-4 | DL-Mandelic | Clear gum | — |
| 4-5 | D-Gluconic | Clear gum | — |
| 4-6 | Glycolic | Clear gum | |
| 4-7 | L-Lactic | Clear gum | — |
| 4-8 | Oleic | Clear gum | — |
| 4-9 | L-Ascorbic | White gum/solid | L-Ascorbic acid & amorphous halo |
| 4-10 | Adipic | Clear gum | — |
| 4-11 | Caproic | Clear gum | — |
| 4-12 | Stearic | White gum/solid | Stearic acid & amorphous halo |
| 4-13 | Palmitic | White gum/solid | Palmitic acid & amorphous halo |
| 4-4 | Methanesulfonic | Clear gum | — |

Example 9. Failure to Obtain Adequate Salt Formation Using Methyl Ethyl Ketone (MEK)

Methyl ethyl ketone (MEK) was next utilized as a solvent to study appropriate salts other than the hemi-sulfate salt. Using the 14 acidic counter ions in Table 12, the study was performed by dissolving Compound 1 (50 mg) in MEK (20 vol) at room temperature. The solutions were treated with 1 equivalence of the selected counter-ions (Table 12). The samples were then cooled down to 5° C. at 0.1° C./min and stirred at this temperature overnight. All samples were allowed to evaporate under ambient conditions and any solids observed were analyzed by XRPD. This evaporation mainly produced gums, with the exception of the samples with steric acid (sample 4-12) and palmitic acid (sample 5-13), which afforded glassy solvents. These solids were amorphous by XRPD, but no crystalline forms of the salt were obtained. Results are shown in Table 14.

TABLE 14

Results from dissolving Compound 1 in MEK (20 volumes)

| Sample ID | Acid | Solvent for acid at 1M | Observation upon acid addition | Observation upon cooling | Observation upon evaporation |
|---|---|---|---|---|---|
| 5-1 | Pamoic | DMSO | Yellow solution | Yellow solution | Yellow gum |
| 5-2 | Malonic | THF | Solution | Solution | Clear gum |
| 5-3 | D-Glucuronic | Water | Solution | Solution | Clear gum |
| 5-4 | DL-Mandelic | THF | Solution | Solution | Clear gum |
| 5-5 | D-Gluconic | THF | White precipitate | Turbid solution | Clear gum |
| 5-6 | Glycolic | THF | Solution | Solution | Clear gum |
| 5-7 | L-Lactic | THF | Solution | Solution | Clear gum |
| 5-8 | Oleic | THF | Solution | Solution | Clear gum |
| 5-9 | L-Ascorbic | Water | Solution | Solution | Yellow gum |
| 5-10 | Adipic | THF (heat) | Solution | Solution | Clear gum |
| 5-11 | Caproic | THF | Solution | Solution | Clear gum |
| 5-12 | Stearic | THF | Solution | Turbid solution | Clear glassy solid* |
| 5-13 | Palmitic | THF | Solution | Solution | Clear glassy solid* |
| 5-14 | Methanesulfonic | THF | Solution | Solution | Clear gum |

Stock solution prepared prior to acid addition

*Samples were analyzed by XRPD and gave amorphous patterns plus peaks from the acid counter ion Since all samples were amorphous, all samples were redissolved in MEK (5 vol) and cyclohexane was added (20 vol antisolvent) at room temperature followed by 1 hour of stirring at 25° C. The samples were then matured between 50-5° C. (1° C./min between temperatures, 4 hours at each temperature) for 2 days before the cycle was changed to 50-25° C. for a further 4 days. The samples were observed by eye following maturation. Results are shown in Table 15. Following the maturation, all samples except 5-1 (with pamoic acid) were found to be gums. Sample 5-1, a yellow solid, was analyzed by XRPD, and the pattern was found to match the known form of pamoic acid (FIG. 14B), and therefore no crystalline forms of the salt were obtained.

TABLE 15

Results from redissolving Compound 1 in MEK (5 volumes) and antisolvent

| Sample ID | Immediate Observation | Observation after 10 minutes | Observation after 60 minutes | Observation after Maturation |
|---|---|---|---|---|
| 5-1 | Precipitate | Gum | Gum | Yellow suspension** |
| 5-2 | Precipitate | Gum | Gum | Gum |
| 5-3 | Precipitate/gum | Gum | Gum | Gum |
| 5-4 | Precipitate | Gum | Gum | Gum |
| 5-5 | Precipitate/gum | Gum | Gum | Gum |
| 5-6 | Precipitate | Gum | Gum | Gum |
| 5-7 | Precipitate | Gum | Gum | Gum |
| 5-8 | Precipitate | Light suspension | Gum | Gum |
| 5-9 | Precipitate | Gum | Gum | Gum |
| 5-10 | Precipitate | Gum | Gum | Gum |
| 5-11 | Precipitate | Light suspension | Gum | Gum |
| 5-12 | Precipitate | Light suspension | Gum | Gum |
| 5-13 | Precipitate | Light suspension | Gum | Gum |
| 5-14 | Precipitate | Gum | Gum | Gum |

**Sample analyzed by XRPD with pattern matching known form of pamoic acid (no additional peaks

Example 10. Failure to Obtain Adequate Salt Formation Using Ethyl Acetate

Ethyl acetate was next utilized to study appropriate salts other than hemi-sulfate salt. Utilizing the 14 acidic counter ions in Table 12, the study was performed by dissolving Compound 1 (50 mg) in ethyl acetate (20 vol) at 50° C. The solutions were treated with 1 equivalent of the selected counter-ions (Table 12). The samples were then cooled down to 5° C. at 0.1 DC/min and stirred at this temperature for 4 days. The solutions were allowed to evaporate under ambient conditions while any solids were analyzed by XRPD. The results from the crystallizations using ethyl acetate are in Table 16. In contrast to Example 8 where MEK was the solvent, the majority of samples were observed to be suspensions following cooling of the acid:compound mixture (those that were solutions were allowed to evaporate under ambient conditions). However, the XRPD diffractograms were generally found to match crystalline Compound 1. Samples 6-2, 6-4, and 6-5 have some slight differences (FIG. 14A and FIG. 15A). No crystalline forms of the salt were obtained.

TABLE 16

Results from dissolving Compound 1 in EtOAc (20 volumes)

| Sample ID | Acid | Solvent for acid at 1M | Observation upon acid addition | Observation upon Cooling | XRPD | Observation upon Evaporation |
|---|---|---|---|---|---|---|
| 6-1 | Pamoic | DMSO | Yellow solution | Yellow solution* | — | Gum |
| 6-2 | Malonic | THF | Solution | White suspension | Slight differences to freebase | — |
| 6-3 | D-Glucuronic | Water | Solution | Solution* | — | Gum |
| 6-4 | DL-Mandelic | THF | Solution | White suspension | Slight differences to freebase | — |
| 6-5 | D-Gluconic | THF | White precipitate | Possible white gum | Slight differences to freebase | — |

TABLE 16-continued

| Results from dissolving Compound 1 in EtOAc (20 volumes) | | | | | | |
|---|---|---|---|---|---|---|
| Sample ID | Acid | Solvent for acid at 1M | Observation upon acid addition | Observation upon Cooling | XRPD | Observation upon Evaporation |
| 6-6 | Glycolic | THF | Solution | White suspension | Freebase | — |
| 6-7 | L-Lactic | THF | Solution | White suspension | Freebase | — |
| 6-8 | Oleic | THF | Solution | White suspension | Freebase | — |
| 6-9 | L-Ascorbic | Water | Solution | Solution* | — | White solid on side/ yellow gum - amorphous |
| 6-10 | Adipic | THF (heat) | Solution | White suspension | Freebase | — |
| 6-11 | Caproic | THF | Solution | White suspension | Freebase | — |
| 6-12 | Stearic | THF | Solution | White suspension | Freebase | — |
| 6-13 | Palmitic | THF | Solution | White suspension | Freebase | — |
| 6-14 | Methanesulfonic | THF | White precipitate | Solution/ clear gum* | — | Clear gum |

Example 11. Chemical Purity Determination by HPLC

Purity analysis in Example 2 and Example 4 was performed on an Agilent IP 100 series system equipped with a diode array detector and using ChemStation software vB.04.03 using the method shown in Table 17.

TABLE 17

| HPLC method for chemical purity determinations | | | |
|---|---|---|---|
| Parameter | Value | | |
| Type of method | Reverse phase with gradient elution | | |
| Sample Preparation | 0.5 mg/ml in acetonitrile:water 1:1 | | |
| Column | Supelco Ascentis Express C18, 100 × 4.6 mm, 2.7 μm | | |
| Column Temperature (° C.) | 25 | | |
| Injection (□l) | 5 | | |
| Wavelength, Bandwidth (nm) | 255, 90 | | |
| Flow Rate (ml/min) | 2 | | |
| Phase A | 0.1% TFA in water | | |
| Phase B | 0.085% TFA in acetonitrile | | |
| | Time (min) | % Phase A | % Phase B |
| Timetable | 0 | 95 | 5 |
| | 6 | 5 | 95 |
| | 6.2 | 95 | 5 |
| | 8 | 95 | 5 |

Example 12. X-Ray Powder Diffraction (XRPD) Techniques

The XRPD patterns in Examples 2, 3, 4, 5, 6, 7, 8, and 9 were collected on a PANalytical Empyrean diffractometer using Cu Kα radiation (45 kV, 40 mA) in transmission geometry. A 0.50 slit, 4 mm mask and 0.4 rad Soller slits with a focusing mirror were used on the incident beam. A PIXcel$^{3D}$ detector, placed on the diffracted beam, was fitted with a receiving slit and 0.04 rad Soller slits. The instrument is performance checked using silicon powder on a weekly basis. The software used for data collection was X'Pert Data Collector v. 5.3 and the data were analyzed and presented using Diffrac Plus EVA v. 15.0.0.0 or Highscore Plus v. 4.5. Samples were prepared and analyzed in either a metal or Millipore 96 well-plate in transmission mode. X-ray transparent film was used between the metal sheets on the metal well-plate and powders (approximately 1-2 mg) were used as received. The Millipore plate was used to isolate and analyze solids from suspensions by adding a small amount of suspension directly to the plate before filtration under a light vacuum.

The scan mode for the metal plate used the gonio scan axis, whereas a 2θ scan was utilized for the Millipore plate. A performance check was carried out using silicon powder (metal well-plate). The details of the data collection were an angular range of 2.5 to 32.0° 2θ, a step size of 0.0130° 2θ, and a total collection time of 2.07 minutes.

Samples were also collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was DiffracPlus XRD Commander v2.6.1 and the data were analyzed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection were an angular range of 2 to 42° 2θ, a step size of 0.05° 2θ, and collection time of 0.5 s/step.

Example 13. Synthesis of Amorphous Compound 1-A

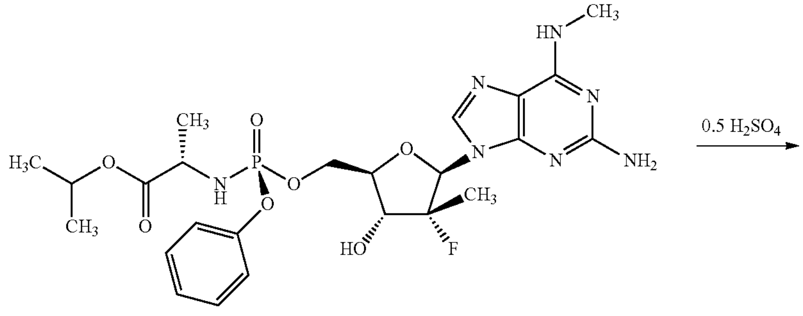

Compound 1

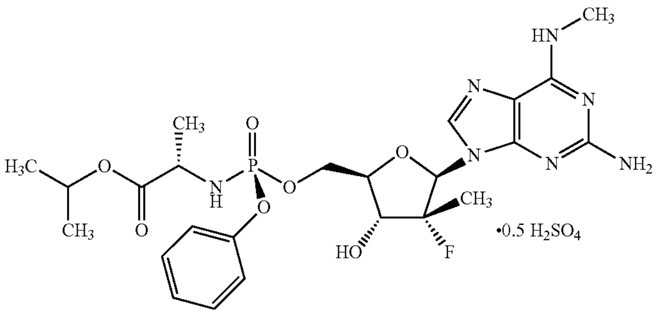

Compound 1-A

A 250 mL flask was charged with MeOH (151 mL) and the solution was cooled to 0-5° C. A concentrated solution of $H_2SO_4$ was added dropwise over 10 minutes. A separate flask was charged with Compound 1 (151 g) and acetone (910 mL), and the $H_2SO_4$/MeOH solution was added dropwise at 25-30° C. over 2.5 hours. A large amount of solid was precipitated. After the solution was stirred for 12-15 hours at 25-30° C., the mixture was filtered, washed with MeOH/acetone (25 mL/150 mL), and dried at 55-60° C. in vacuum to afford Compound 1-A (121 g, 74%). $^1$HNMR: (400 MHz, DMSO-$d_6$): δ 8.41 (br, 1H), 7.97 (s, 1H), 7.36 (t, J=8.0 Hz, 2H), 7.22 (d, J=8.0 Hz, 2H), 7.17 (t, J=8.0 Hz, 1H), 6.73 (s, 2H), 6.07 (d, J=8.0 Hz, 1H), 6.00 (dd, J=12.0, 8.0 Hz, 1H), 5.81 (br, 1H), 4.84-4.73 (m, 1H), 4.44-4.28 (m, 3H), 4.10 (t, J=8.0 Hz, 2H), 3.85-3.74 (m, 1H), 2.95 (s, 3H), 1.21 (s, J=4.0 Hz, 3H), 1.15-1.10 (m, 9H).

Analytic Method for Compound 1-A: The purity of Compound 1-A was obtained using an Agilent 1100 HPLC system with a Waters XTerra Phenyl 5 μm 4.6*250 mm column with the following conditions: 1 mL/min flow rate, read at 254 nm, 30° C. column temperature, 10 μL injection volume, and a 30 minute run time. The sample was dissolved in ACN:water (90:10, v/v). The Gradient method for separation is shown below. $R_t$(min) of Compound 1-A was approximately 12.0 minutes.

| Time (min) | 0.1% $H_3PO_4$ in Water (A)% | Acetonitrile (B)% |
|---|---|---|
| 0 | 90 | 10 |
| 20 | 20 | 80 |
| 20.1 | 90 | 10 |
| 30 | 90 | 10 |

Example 14. Characterization of Compound 1-A

Compound 1-A was further characterized by eye, $^1$HNMR, $^{13}$CNMR, $^{19}$FNMR, MS, HPLC, and XRPD (FIG. 15B). Residual solvent was measured by GC. Water content was measured by Karl Fischer Titration, and the water content was only 0.70%. Data is summarized in Table 18.

TABLE 18

Summary of Additional Characterization Data of Compound 1-A

| Test | Result |
|---|---|
| Appearance | White Solid |
| NMR | $^1$HNMR peaks are listed in Example 4 |

TABLE 18-continued

| Summary of Additional Characterization Data of Compound 1-A | |
|---|---|
| Test | Result |
| MS | MS(ESI + ve) $[M + H]^+$ = 582.3 - conforms to structure |
| HPLC | 99.8% by AUC at 254 nm (average of two preparations) |
| Residual Solvent by GC | Methanol - 57 ppm<br>Acetone - 752 ppm<br>Dichloromethane - 50 ppm<br>Ethyl Acetate - 176 ppm |
| Water Content | 0.70% |

Example 15. Solubility of Compound 1 and Compound 1-A

Compound 1 and Compound 1-A were both tested for solubility in biorelevant test medias, including simulated gastric fluid (SGF), fasted-state simulated gastric fluid (FaSSIF), and fed-state gastric fluid (FeSSIF). Results for Compound 1 are shown in Table 19 and results for Compound 1-A are shown in Table 20. Samples were stirred at room temperature (20-25° C.). Compound 1-A was more than 40-fold more soluble than Compound 1 in water at 2 hours and more than 25-fold more soluble at 24 hours. In SGF conditions, Compound 1-A had a solubility of 84.2 mg/mL at 24 hours compared to the solubility of 15.6 mg/mL of Compound 1 at the same time point. Compound 1-A was also more soluble at 2 hours in the SGF conditions than Compound 1, and soluble enough to allow for testing even after 48 hours while testing at 48 hours was not done with Compound 1.

TABLE 19

Compound 1 solubility testing results

| Test | Solubility (in mg/mL) | | | Descriptive |
|---|---|---|---|---|
| Media | 2 hours | 24 hours | Appearance | term |
| Water | 1.5 | 2.5 | Clear Solution | Slightly Soluble |
| SGF | 13.8 | 15.6 | Clear Solution with gum at the bottom | Sparingly Soluble |
| FaSSIF | 1.7 | 1.7 | Turbid | Slightly Soluble |
| FeSSIF | 2.8 | 2.9 | Turbid | Slightly Soluble |

*Sample appeared to be clear, yet a solubility of only 1.5 mg/mL was achieved. Upon further investigation, it was noted that a gummy film formed on the stir bar. The compound 1 active pharmaceutical ingredient formed a gummy ball in diluent (90% water/10% acetonitrile) during standard preparation which required a long sonication time to dissolve completely.

TABLE 20

Compound 1-A solubility testing results

| Test | Solubility (in mg/mL salt base) | | | | Descriptive |
|---|---|---|---|---|---|
| Media | 2 hours | 24 hours | 48 hours | Appearance | term |
| Water | 65.3 | 68.0 | N/A | Turbid | Soluble |
| SGF | 89.0 | 84.2 | 81.3 | Turbid | Soluble |
| FaSSIF | 1.9 | 2.0 | N/A | Turbid | Slightly Soluble |
| FeSSIF | 3.3 | 3.4 | N/A | Turbid | Slightly Soluble |

Example 16. Chemical Stability of Compound 1-A

Compound 1-A was tested for chemical stability at 25 and 40° C. over a 6 month time period by monitoring organic purity, water content, $^1$HNMR, DSC, and Raman IR. The container closure system for the study was a combination medicinal valve bag with a pharmaceutical laminated film over the pouch and desiccant silica gel between the two layers. Compound 1-A (1 g) was measured into each container. Bags were then stored at 25° C./60% RH (relative humidity) and 40° C./75% RH (relative humidity). Organic purity, water content, $^1$HNMR, DSC and Raman were measured at Time 0, Month 1, Month 2, Month 3 and Month 6.

The purity of Compound 1-A was obtained using a Shimadzu LC-20AD system with a Waters XTerra Phenyl, 5 μm, 4.6×250 mm column with the following conditions: 1 mL/min flow rate, read at 254 nm, 35° C. column temperature, and 10 μL injection volume. The sample was dissolved in acetonitrile-water (90:10) (v/v). The gradient method is shown below.

| Time (min) | A % (ACN) | B % (water) |
|---|---|---|
| 0 | 90 | 10 |
| 20 | 20 | 80 |
| 20.1 | 90 | 10 |
| 30 | 90 | 10 |

The water content of Compound 1-A (250 mg) was determined by a water titration apparatus using the Karl Fischer titration method.

Results are shown in Table 21 and Table 22. When Compound 1-A was stored for 6 months at 25 and 40° C., the rate of degradation was minimal. At 3 months, Compound 1-A was 99.75% percent pure at the 25° C. conditions and 99.58% pure at the 40° C. conditions. At 6 months, Compound 1-A was still 99.74% pure at the 25° C. conditions and 99.30% pure at the 40° C. conditions. At 25° C., the percent of degradation product increased from 0.03% at Day 0 to 0.08% after 6 months. At 40° C., the percent of degradation product increased from 0.03% to 0.39%. Over the course of 6 months, the percent of water increased approximately 0.6% at 25° C. and increased approximately 0.7% at 40° C.

Characterization by $^1$HNMR, Raman, and DSC of Compound 1-A at 1, 2, 3, and 6 months was the same as the characterization of Compound 1-A on day 0 at both temperature conditions (Table 22), highlighting the long-term stability of Compound 1-A.

TABLE 21

Compound 1-A rate of degradation over 6 months at 25 and 40° C.

| | Time Tested | Percent Water | Percent Purity | Percent of Degradation Product | Maximum Impurity Percent |
|---|---|---|---|---|---|
| 25° C. | Day 0 | 1.2 | 99.82 | 0.03 | 0.12 |
| | Month 1 | 1.9 | 99.77 | 0.04 | 0.12 |
| | Month 2 | 1.8 | 99.75 | 0.06 | 0.12 |
| | Month 3 | 1.8 | 99.75 | 0.06 | 0.12 |
| | Month 6 | 1.8 | 99.74 | 0.08 | 0.13 |
| 40° C. | Day 0 | 1.2 | 99.82 | 0.03 | 0.12 |
| | Month 1 | 2.0 | 99.71 | 0.09 | 0.12 |
| | Month 2 | 1.9 | 99.63 | 0.15 | 0.12 |
| | Month 3 | 1.9 | 99.58 | 0.20 | 0.12 |
| | Month 6 | 1.9 | 99.30 | 0.39 | 0.14 |

TABLE 22

Characterization of Compound 1-A during degradation study

| | Time Tested | ¹HNMR | Raman | DSC |
|---|---|---|---|---|
| 25° C. | Day 0 | Initial Test | Initial Test | Initial Test |
| | Month 1 | The same as Day 0 | The same as Day 0 | The same as Day 0 |
| | Month 2 | The same as Day 0 | The same as Day 0 | The same as Day 0 |
| | Month 3 | The same as Day 0 | The same as Day 0 | The same as Day 0 |
| | Month 6 | The same as Day 0 | The same as Day 0 | The same as Day 0 |
| 40° C. | Day 0 | Initial Test | Initial Test | Initial Test |
| | Month 1 | The same as Day 0 | The same as Day 0 | The same as Day 0 |
| | Month 2 | The same as Day 0 | The same as Day 0 | The same as Day 0 |
| | Month 3 | The same as Day 0 | The same as Day 0 | The same as Day 0 |
| | Month 6 | The same as Day 0 | The same as Day 0 | The same as Day 0 |

Additional chemical stability studies of Compound 1-A were measured to determine the impurity and water levels. Three conditions were tested: accelerated stability (40±2° C./75±500 RH) over a 6-month time period, ambient stability (25±2° C./60±50% RH) over a 9-month period, and stability under refrigerator conditions (5±3° C.) over a 9-month time period. The results for accelerated stability, ambient stability, and refrigerator conditions are shown in Table 23, Table 24, and Table 25, respectively. Based on the results of these studies, Compound 1-A is very chemically stable.

In the accelerated stability study (Table 23), at each time point ($1^{st}$ month, $3^{rd}$ month, and $6^{th}$ month) where Compound 1-A was measured, the appearance of Compound 1-A was always a white solid and the JR matched the reference standard. After six months, the total related substance 1 impurities was only 0.080 and there was no detection of related substance 2 and isomers.

TABLE 23

Accelerated Stability (40 ± 2° C./75 ± 5% RH) of Compound 1-A

| | | Items | | | | |
|---|---|---|---|---|---|---|
| | | | Testing time point | | | |
| | | Specification | 0 month | $1^{st}$ month | $3^{rd}$ month | $6^{th}$ month |
| | | Appearance | | | | |
| | | White or off-white solid | White solid | White solid | White solid | White solid |
| | | IR | | | | |
| | | correspond with reference standard | correspond with reference standard | / | correspond with reference standard | correspond with reference standard |
| | Water | ≤2.0% | 0.45% | 0.21% | 0.36% | 0.41% |
| Related Substance 1 | Impurity A | ≤0.15% | N.D. | N.D. | N.D. | N.D. |
| | Impurity B | ≤0.15% | N.D. | N.D. | N.D. | N.D. |
| | Impurity F | ≤0.15% | N.D. | N.D. | N.D. | 0.01% |
| | Impurity H | ≤0.15% | N.D. | N.D. | N.D. | N.D. |
| | Any other single impurity | ≤0.10% | 0.01% | 0.02% | 0.01% | 0.05% |
| | Total Impurities | ≤0.2% | 0.01% | 0.02% | 0.02% | 0.08% |
| Related Substance 2 | Impurity G | ≤0.15% | N.D. | N.D. | N.D. | N.D. |
| Isomer | Impurity C | ≤0.15% | N.D. | / | N.D. | N.D. |
| | Impurity D | ≤0.15% | N.D. | / | N.D. | N.D. |
| | Impurity E | ≤0.15% | N.D. | / | N.D. | N.D. |
| | Assay | 98.0%~102.0% | 98.8% | 101.5% | 99.6% | 99.5% |
| Microbial Testing | TAMC | ≤1000 cfu/g | <1 cfu/g | / | / | / |
| | Mold and Yeast | ≤100 cfu/g | <1 cfu/g | / | / | / |
| | *E. Coli* | Not Detected | N.D. | / | / | / |

N.D.: Not Detected

In the ambient stability study where the appearance, IR, water and impurity levels were measured for nine months, the appearance of Compound 1-A was always a white solid and the IR always corresponded with the reference sample. The results (Table 24) highlight how chemically stable Compound 1-A is. After 9 months, the percentage of water in the sample was only 0.2000 and the total related substance 1 impurities was only 0.02%. Similarly to the accelerated stability studies, related substance 2 and any isomers of Compound 1-A were not detected.

The results of measuring the stability under refrigerator conditions are shown in Table 25. The only impurities detected even after 9 months were those from related substance 1 and water. The water content after 9 months was 0.3200 and the total impurities of related substance 1 were only 0.0100 of the sample. Compound 1-A is very chemically stable under refrigerator conditions.

TABLE 24

Ambient stability (25 ± 2° C./60 ± 5% RH) of Compound 1-A

| | | Item | | | | | |
|---|---|---|---|---|---|---|---|
| | | | Testing time point | | | | |
| | | Specification | 0 month | $1^{st}$ month | $3^{rd}$ month | $6^{th}$ month | $9^{th}$ month |
| | | Appearance | | | | | |
| | | White or off-white solid | White solid | White solid | White solid | White solid | Off-white solid |
| | | IR | | | | | |
| | | correspond with reference standard | correspond with reference standard | / | correspond with reference standard | correspond with reference standard | correspond with reference standard |
| Water | | ≤2.0% | 0.45% | 0.19% | 0.29% | 0.46% | 0.20% |
| Related Substance 1 | Impurity A | ≤0.15% | N.D. | N.D. | N.D. | N.D. | N.D. |
| | Impurity B | ≤0.15% | N.D. | N.D. | 0.03% | N.D. | N.D. |
| | Impurity F | ≤0.15% | N.D. | N.D. | 0.02% | 0.01% | N.D. |
| | Impurity H | ≤0.15% | N.D. | N.D. | N.D. | N.D. | N.D. |
| | Any other single impurity | ≤0.10% | 0.01% | 0.01% | 0.03% | 0.02% | 0.02% |
| | Total Impurities | ≤0.2% | 0.01% | 0.02% | 0.11% | 0.05% | 0.02% |
| Related Substance 2 | Impurity G | ≤0.15% | N.D. | N.D. | N.D. | N.D. | N.D. |
| Isomer | Impurity C | ≤0.15% | N.D. | / | N.D. | N.D. | N.D. |
| | Impurity D | ≤0.15% | N.D. | / | N.D. | N.D. | N.D. |
| | Impurity E | ≤0.15% | N.D. | / | N.D. | N.D. | N.D. |
| Assay | | 98.0%~102.0% | 98.8% | 101.1% | 99.6% | 99.7% | 100.9% |
| Microbial Testing | TAMC | ≤1000 cfu/g | <1 cfu/g | / | / | / | / |
| | Mold and Yeast | ≤100 cfu/g | <1 cfu/g | / | / | / | / |
| | *E. Coli* | Not Detected | N.D. | / | / | / | / |

N.D.: Not Detected

TABLE 25

Stability under refrigerator conditions (5 ± 3° C.) of Compound 1-A time

| Item | | Specification | Testing time point: 0 month | 1st month | $3^{rd}$ month | $6^{th}$ month | $9^{th}$ month |
|---|---|---|---|---|---|---|---|
| Appearance | | White or off-white solid | White solid | White solid | White solid | White solid | Off-white solid |
| IR | | correspond with reference standard | correspond with reference standard | | correspond with reference standard | correspond with reference standard | correspond with reference standard |
| Water | | ≤2.0% | 0.45% | 0.19% | 0.32% | 0.42% | 0.32% |
| Related Substance 1 | Impurity A | ≤0.15% | N.D. | N.D. | N.D. | N.D. | N.D. |
| | Impurity B | ≤0.15% | N.D. | N.D. | 0.01% | N.D. | N.D. |
| | Impurity F | ≤0.15% | N.D. | N.D. | N.D. | N.D. | N.D. |
| | Impurity H | ≤0.15% | N.D. | N.D. | N.D. | N.D. | N.D. |
| | Any other single impurity | ≤0.10% | 0.01% | 0.01% | 0.01% | 0.01% | 0.01% |
| | Total Impurities | ≤0.2% | 0.01% | 0.01% | 0.03% | 0.03% | 0.01% |
| Related Substance 2 | Impurity G | ≤0.15% | N.D. | N.D. | N.D. | N.D. | N.D. |
| Isomer | Impurity C | ≤0.15% | N.D. | / | N.D. | N.D. | N.D. |
| | Impurity D | ≤0.15% | N.D. | / | N.D. | N.D. | N.D. |
| | Impurity E | ≤0.15% | N.D. | / | N.D. | N.D. | N.D. |
| Assay | | 98.0%~102.0% | 98.8% | 101.1% | 100.2% | 98.6% | 101.4% |
| Microbial Testing | TAMC | ≤1000 cfu/g | <1 cfu/g | / | / | / | / |
| | Mold and Yeast | ≤100 cfu/g | <1 cfu/g | / | / | / | / |
| | *E. Coli* | Not Detected | N.D. | / | / | / | / |

N.D.: Not Detected

Example 17. Plasma Levels of Metabolites Following Single Oral Doses of Compound 1-A A single oral dose of Compound 1-A was administered to rats, dogs, and monkeys, and the plasma levels of certain metabolites shown in Scheme 1 were measured.

The conversion of Compound 1-A to Compound 1 and metabolite 1-7 are shown in Table 26 and the results for metabolite 1-8 and metabolite 1-2 are shown in Table 27. In rats, low levels of Compound 1 exposure were observed, but high levels of metabolite 1-7, the nucleoside metabolite of the active triphosphate (metabolite 1-6), were observed. In monkeys, roughly dose-proportional exposures of Compound 1 were measured. In dogs, supra-proportional Compound 1 exposures, indicative of first-pass metabolic clearance in the liver, were measured. Throughout the study, significantly more vomiting in dogs (5/5 in high dose group) than in monkeys (⅕ in high dose group) was observed.

TABLE 26

Plasma levels of Compound 1 and metabolite 1-7 after single oral doses of Compound 1-A

| | | Compound 1 | | | Metabolite 1-7 | |
|---|---|---|---|---|---|---|
| Species | Dose* (mg/kg) | $C_{max}$ (ng/mL) | $T_{max}$ (hr) | $AUC_{0\text{-}last}$ (hr*ng/mL) | $C_{max}$ (ng/mL) | $AUC_{0\text{-}last}$ (hr*ng/mL) |
| Rat[a] | 500 | 70.5 | 0.25 | 60.9 | 748 | 12000 |
| Dog[b] | 30 | 1530 | 0.25-1 | 1300 | 783 | 9270 |
| | 100 | 8120 | 0.5-1 | 10200 | 2030 | 24200 |
| | 300 | 21300 | 204 | 44300 | 4260 | 60800 |
| Monkey[b] | 30 | 63.5 | 0.5-2 | 176 | 42.5 | 1620 |
| | 100 | 783 | 1-2 | 1100 | 131 | 3030 |
| | 300 | 501 | 204 | 1600 | 93.6 | 3660 |

3 males per dose per species;
*dose formulations: 20.5% CMC, 0.5% Tween 80 in water;
[b]powder in capsules

TABLE 27

Plasma levels of metabolites 1-8 and 1-2 after single oral dose of Compound 1-A

| | | Metabolite 1-8 | | Metabolite 1-2 | |
|---|---|---|---|---|---|
| Species | Dose* (mg/kg) | $C_{max}$ (ng/mL) | $AUC_{0\text{-}last}$ (hr*ng/mL) | $C_{max}$ (ng/mL) | $AUC_{0\text{-}last}$ (hr*ng/mL) |
| Rat[a] | 500 | 5060 | 35100 | 9650 | 20300 |
| Dog[b] | 30 | 291 | 905 | 196 | 610 |
| | 100 | 1230 | 4370 | 886 | 2830 |
| | 300 | 5380 | 35300 | 2380 | 8710 |
| Monkey[b] | 30 | 209 | 5690 | 300 | 1730 |
| | 100 | 406 | 12300 | 1350 | 8160 |
| | 300 | 518 | 16800 | 1420 | 11400 |

3 males per dose per species;
*dose formulations:
[a]0.5% CMC, 0.5% Tween 80 in water;
[b]powder in capsules

Example 18. Tissue Exposure of Active Triphosphate Following Compound 1-A Oral Dose Heart and liver tissue levels of the active triphosphate (TP) of Compound 1-A (metabolite 1-6) were measured 4 hours after oral doses of Compound 1-A. Samples of liver and heart were obtained at 4 hours after a single dose of Compound 1-A, flash-frozen, homogenized and analyzed by LC-MS/MS for intracellular levels of the active TP. Tissue levels were measured in rats, dogs, and monkeys as shown in FIG. 16A. High levels of the active TP were measured in the liver of all species tested. Relatively low levels of the active TP were measured in the hearts of dogs due to saturation of first-pass hepatic metabolism, and unquantifiable levels of TP were measured in rat and monkey hearts, indicative of liver-specific formation of the active TP. While not shown, compared to Compound 1 dosing, Compound 1-A dosing improved TP distribution.

Example 19. Pharmacological Comparison of Compound 1 and Compound 1-A in Dogs A head-to-head comparison of dogs dosed with Compound 1 and Compound 1-A was conducted. The study measured plasma levels of Compound 1 and metabolite 1-7 (from Scheme 1) out to 4 hours after dosing with Compound 1 (25 mg/kg) and Compound 1-A (30 mg/kg) (Table 28), and the $AUC_{(0\text{-}4\ hr)}$ of metabolite 1-7 was twice as great with Compound 1-A compared to Compound 1. Dose-normalized exposures to Compound 1 and metabolite 1-7 are shown in Table 28. Values for $AUC_{(0\text{-}4\ hr)}$ for Compound 1, metabolite 1-7, and the sum of Compound 1+metabolite 1-7 were greater after dosing with Compound 1-A.

TABLE 28

Comparison of Plasma Levels following dosing with Compound 1 and Compound 1-A

| | Mean Dose-normalized $AUC_{(0\text{-}4hr)}$[a] (μM*hr) for: | | |
|---|---|---|---|
| Dosed Compound | Compound 1 | Metabolite 1-7 | Compound 1 + Metabolite 1-7 |
| Compound 1 (25 mg/kg) | 0.2 | 1.9 | 2.1 |
| Compound 1-A (30 mg/kg) | 1.0 | 4.1 | 5.1 |

[a]$AUC_{(0\text{-}4hr)}$ values normalized to a dose of 25 mg/kg

Liver/heart ratio triphosphate concentrations indicate that dosing with Compound 1-A, as compared to Compound 1, increases the selective delivery of the triphosphate to the liver, as shown in Table 29. The $AUC_{(0\text{-}4\ hr)}$ of the active guanine metabolite (1-6) after administration of Compound 1 measured in the heart was 17 μM*hr, while the $AUC_{(0\text{-}4\ hr)}$ of the active guanine metabolite (1-6) after administration of Compound 1-A measured in the heart was 28 μM*hr. The liver/heart ratio for Compound 1-A was 20 compared to a liver/heart ratio of 3.1 for Compound 1.

TABLE 29

Comparison of Liver and Heart Exposure following dosing with Compound 1 and Compound 1-A

| Dosed | Mean Dose-normalized $AUC_{(0\text{-}4hr)}$[a] (μM*hr) for: | | |
|---|---|---|---|
| Compound | Liver | Heart | Liver/Heart |
| Compound 1-A | 565 | 28[b] | 20 |
| Compound 1 | 537 | 174 | 3.1 |

[a]Active TP concentrations (1-6; Scheme 1) normalized to a dose of 25 mg/kg
[b]Extrapolated below the lower limit of quantitation of the calibration curve The effect of increased selectivity for the liver over the heart when Compound 1-A was administered compared to Compound 1 is also shown in FIG. 16B. The heart and liver tissue levels of the active triphosphate following a dosage of Compound 1-A (30 mg/kg) were compared to the tissue levels of the active triphosphate following a dosage of Compound 1 (25 mg/kg). The concentration of the active TP was higher in the liver than the heart for both Compound 1 and Compound 1-A, but the active TP was more selective for the liver over the heart when Compound 1-A was dosed compared to Compound 1.

Example 20. Plasma Profiles of Compound 1-A Metabolites in Rats and Monkeys

Male Sprague-Dawley rats and cynomolgus monkeys (3 animals per dose group) were given single oral doses of Compound 1-A. Aliquots of plasma prepared from blood samples treated with Dichlorvos were analyzed by LC-MS/MS for concentrations of Compound 1 and metabolite 1-7 (the nucleoside metabolite of the active triphosphate of Compound 1-A shown in Scheme 1), and pharmacokinetic parameters were determined using WinNonlin. The results for a single 500 mg/kg dose in rats is shown in FIG. 17 and the results for a single 30, 100, or 300 mg/kg dose in monkeys is shown in FIG. 18. The results are also summarized in Table 30.

High plasma levels of metabolite 1-7, the nucleoside metabolite of the active triphosphate (TP) of Compound 1-A, are indicative of formation of high levels of the TP, even in rats where very low plasma levels of parent nucleotide prodrug are observed due to the short half-life of Compound 1 in rat blood (<2 min). Persistent plasma levels of metabolite 1-7 reflect the long half-life of the TP.

In monkeys, plasma exposures (AUC) of Compound 1 were roughly dose-proportional, while metabolite 1-7 exposures were somewhat less than dose-proportional, although AUC values for both parent drug and the nucleoside metabolite of the active TP continue to increase up to the highest dose tested (300 mg/kg).

Oral administration of Compound 1-A in rats and monkeys produced high and dose-dependent plasma exposures to metabolite 1-7 (the nucleoside metabolite of the intracellular active triphosphate of Compound 1-A); metabolite 1-7 exposures continued to increase up to the highest dose tested, reflecting substantial formation of the active TP in these species.

TABLE 30

Plasma levels of Compounds 1 and 1-7 after single oral dose of Compound 1-A

| | | Species | | | |
|---|---|---|---|---|---|
| | | Rat[a] | Monkey[b] | | |
| | | Dose (mg/kg) | | | |
| | | 500 | 30 | 100 | 300 |
| Compound 1 | $C_{max}$ (ng/mL) | 60.8 | 63.5 | 783 | 501 |
| | $T_{max}$ (hr) | 0.25 | 0.5-2 | 1-2 | 204 |
| | $AUC_{0\text{-}last}$ (hr*ng/mL) | 78.2 | 176 | 1100 | 1600 |
| Metabolite 1-7 | $C_{max}$ (ng/mL) | 541 | 42.5 | 131 | 93.6 |
| | $AUC_{0\text{-}last}$ (hr*ng/mL) | 9640 | 1620 | 3030 | 3660 |
| | $T_{max}$ (hr) | 6-8 | 12-24 | 4 | 4-24 |
| | $T_{1/2}$ (hr) | 15.3 | 11.5 | 15.0 | 18.8 |

dose formulations:
[a]0.5% CMC, 0.5% Tween 80 in water;
[b]powder in capsules

Example 21. The Effect of the Active Triphosphate of Compound 1 and Compound 1-A on Mitochondrial Integrity The relative efficiency of incorporation of the active triphosphate (TP) of Compound 1 and Compound 1-A, metabolite 1-6 (Scheme 1), by human mitochondrial RNA polymerase was compared to the relative efficiency of the active TP of sofosbuvir and the active TP of INN-189. Compound 1 and Compound 1-A are not likely to affect mitochondrial integrity since their active triphosphate is poorly incorporated by human mitochondrial RNA polymerase with an efficiency similar to that of the triphosphate of sofosbuvir; the relative efficiency of incorporation of the triphosphate of INX-189 was up to 55-fold greater. Results are shown in Table 31. The incorporation of these analogs by human mitochondrial RNA-dependent RNA polymerase (POLRMT) were determined according to Arnold et al. (Sensitivity of Mitochondrial Transcription and Resistance of RNA Polymerase II Dependent Nuclear Transcription to Antiviral Ribonucleotides. *PLoS Pathog.,* 2012, 8, e1003030).

TABLE 31

Kinetic Parameters for Nucleotide Analogs Evaluated with Human Mitochondrial RNA Polymerase

| Nucleotide Analog | $K_{pol}$ ($s^{-1}$) | $K_{d,app}$ (μM) | $K_{pol}/K_{d,app}$ ($\mu M^{-1}s^{-1}$) | Relative Efficiency* |
|---|---|---|---|---|
| 2'-deoxy-2'-F-2'-C-methyl UTP (active TP of sofosbuvir) | 0.00034 ± 0.00005 | 590 ± 250 | $5.8 \times 10^{-7}$ ± $2.6 \times 10^{-7}$ | $1.0 \times 10^{-6}$ |
| 2'-C-methyl GTP (active TP of INX-189) | 0.051 ± 0.002 | 240 ± 26 | $2.1 \times 10^{-4}$ ± $0.2 \times 10^{-4}$ | $5.5 \times 10^{-5}$ |
| Active TP of Compound 1 and Compound 1-A (metabolite 1-6) | 0.0017 ± 0.0002 | 204 ± 94 | $8.3 \times 10^{-6}$ ± $4.0 \times 10^{-6}$ | $2.2 \times 10^{-6}$ |

*Relative efficiency = $(K_{pol}/K_{d,app})_{analog\ nucleotide}/(K_{pol}/K_{d,app})_{natural\ nucleotide}$ Example 22. Activity of Compound 1 Against Replicons Containing the NS5B Sequence A panel of replicons containing the NS5B sequences from various HCV genotypes derived from 6 laboratory reference strains (GT1a, 1b, 2a, 3a, 4a and 5a) (FIG. 19) and from 8 HCV patient plasma samples (GT1a, 1b, 2a, 2b, 3a-1, 3a-2, 4a and 4d) (FIG. 20) were used to determine the potency of Compound 1 and sofosbuvir.

Compound 1 was more potent than sofosbuvir against clinical and laboratory strains of HCV. Compound 1 showed potent pan-genotypic antiviral activity in vitro against wild-type clinical isolates with $EC_{95}$<80 nM, which is 4- to 14-fold more potent than sofosbuvir. As shown in FIG. 20, $EC_{95}$ values for Compound 1 were 7-33 times lower than sofosbuvir against clinical isolates of all HCV genotypes tested. $EC_{50}$ values for Compound 1 were 6-11 times lower than sofosbuvir against laboratory strains of HCV Genotypes 1-5 (FIG. 19).

Example 23. Single Ascending Dose (SAD) Study of Compound 1-A in Healthy Volunteers (Part A) and GT1-HCV Infected Patients (Part B)

Compound 1-A was tested in a single ascending dose (SAD) study to measure its safety, tolerability, and pharmacokinetic in healthy subjects (Part A). Part A was a randomized, double-blind, placebo-controlled SAD study. Healthy subjects in Part A received a single dose of Compound 1-A or placebo in the fasting state. Subjects were confined to the clinic from Day −1 to Day 6.

Dosing in each cohort was staggered such that 2 subjects (1 active:1 placebo) were evaluated for 48 hours after dosing before the remainder of the cohort was dosed. Each cohort received Compound 1-A in ascending order. Dosing of sequential cohorts occurred based on review of available safety data (through Day 5) and plasma pharmacokinetic data (through 24 h) of the prior cohort.

Dose escalation proceeded following satisfactory review of these data. As pharmacokinetic and safety data emerged from prior cohorts, doses evaluated in Cohorts 3a-4a were adjusted by increments no more than 100 mg. The total maximum dose evaluated in Part A did not exceed 800 mg. The dosing regimen for Part A is shown in Table 32.

TABLE 32

Dosing Regimen for Compound 1-A Administration Part A of Study

| Cohort | Population | N (active:placebo) | Compound 1-A (Compound 1)* |
|---|---|---|---|
| 1a | Healthy | 6:2 | 50 (45) mg × 1 day |
| 2a | Healthy | 6:2 | 100 (90) mg × 1 day |
| 3a | Healthy | 6:2 | 200 (180) mg × 1 day |
| 4a | Healthy | 6:2 | 400 (360) mg × 1 day |

*Clinical doses are expressed in terms of Compound 1-A, with the approximate Compound 1 base equivalent in parenthesis Healthy volunteers in the Part A portion of the study were male and female subjects between the ages of 18 and 65. Active and placebo recipients were pooled within each Part A cohort to preserve the study blind.

Compound 1-A was also tested in a single ascending dose (SAD) study to measure its safety, tolerability, pharmacokinetic, and antiviral activity in GT1-HCV infected patients (Part B). Subjects in Part B received a single dose of Compound 1-A in the fasting state. Patients were confined to the clinic from Day −1 to Day 6.

Part B was initiated after the safety (through Day 5) and plasma pharmacokinetic (through 24 h) data review from Cohort 3a in Part A. Available safety data (through Day 5) and pharmacokinetic data (through 24 h) was reviewed for the first cohort in Part B (Cohort 1b) before enrolling subsequent Part B cohorts. Subsequent Part B cohorts were only dosed following review of available safety and pharmacokinetic data from the respective doses in Part A as well as available safety (through Day 5) from the prior Part B cohorts.

Dose escalation up to 600 mg in HCV-infected patients proceeded following satisfactory review of these data. The dosing regimen for Part B is shown in Table 33.

TABLE 33

Dosing Regimen for Compound 1-A in Part B of Study

| Cohort | Population | N (active) | Compound 1-A (Compound 1)* |
|---|---|---|---|
| 1b | GT1 HCV-Infected | 3 | 100 (90) mg × 1 day |
| 2b | GT1 HCV-Infected | 3 | 300 (270) mg × 1 day |
| 3b | GT1 HCV-Infected | 3 | 400 (360) mg × 1 day |
| 4b | GT1 HCV-Infected | 3 | 600 (540) mg × 1 day |

*Clinical doses are expressed in terms of Compound 1-A, with the approximate Compound 1 base equivalent in parenthesis.

Patients infected with HCV were treatment-naïve, non-cirrhotic GT1-infected subjects with a viral load of ≥5 $log_{10}$ IU/mL.

No serious adverse events were recorded and no premature discontinuations were required in either Part A or Part B. All adverse effects were mild to moderate in intensity and no dose-related patterns, including laboratory parameters, vital signs, and ECGs were evident.

Example 24. Results of the Single Ascending Dose (SAD) Study of Compound 1-A

Pharmacokinetic of Compound 1 and nucleoside metabolite 1-7 were measured following the single dose of Compound 1-A. The $C_{24}$ trough plasma concentrations ($C_{24\ h}$) of metabolite 1-7 in HCV-infected patients following a 600 mg dose of Compound 1-A was 25.8 ng/mL, which is more than double the plasma concentration dose following a 300 mg dose of Compound 1-A. Metabolite 1-7 (shown in Scheme 1) can only be generated via dephosphorylation of the intracellular phosphate metabolite 1-4, metabolite 1-5, and metabolite 1-6, which is the active species. Therefore, metabolite 1-7 can be considered a surrogate of the active species. The pharmacokinetic data for all cohorts is shown in Table 34 and Table 35. Values are reported as mean±SD, except tor $T_{max}$ where median (range) is reported. Pharmacokinetic parameters were comparable in healthy and HCV-infected patients.

TABLE 34

Human Pharmacokinetic of Compound 1 and Metabolite 1-7 after Administration of a single dose of Compound 1-A in Healthy Volunteers max

| | Dose (mg) | $C_{max}$ (ng/mL) | $T_{max}$ (h) | $AUC_{tot}$ (ng*h/mL) | $T_{1/2}$ (h) | $C_{24h}$ (ng/mL) |
|---|---|---|---|---|---|---|
| Part A, Healthy Subjects | | | | | | |
| Compd 1 | 50 | 46.4 ± 17.6 | 0.5 (0.5-0.5) | 36.4 ± 12.3 | 0.32 ± 0.02 | — |
| | 100 | 156 ± 96.3 | 0.5 (0.5-1.0) | 167 ± 110 | 0.53 ± 0.24 | — |
| | 200 | 818 ± 443 | 0.5 (0.5-3.0) | 656 ± 255 | 0.71 ± 0.16 | — |
| | 400 | 1194 ± 401 | 0.5 (0.5-1.0) | 1108 ± 326 | 0.86 ± 0.15 | — |
| Metabolite 1-7 | 50 | 27.9 ± 5.62 | 3.5 (3.0-4.0) | 285 ± 69.4 | 7.07 ± 4.59 | 2.28 ± 0.95 |
| | 100 | 56.6 ± 14.0 | 4.0 (3.0-6.0) | 663 ± 242 | 17.7 ± 14.7 | 4.45 ± 1.87 |
| | 200 | 111 ± 38.8 | 5.0 (3.0-6.0) | 1524 ± 497 | 15.9 ± 7.95 | 13.7 ± 5.09 |
| | 400 | 153 ± 49.4 | 6.0 (4.0-8.0) | 2342 ± 598 | 15.6 ± 6.37 | 23.5 ± 6.31 |

*Based on 24-hr profile.

TABLE 35

| | Human Pharmacokinetic of Compound 1 and Metabolite 1-7 after Administration of Compound 1-A in GT1-HCV Infected Patients | | | | | |
|---|---|---|---|---|---|---|
| | Dose (mg) | $C_{max}$ (ng/mL) | $T_{max}$ (h) | $AUC_{tot}$ (ng*h/mL) | $T_{1/2}$ (h) | $C_{24h}$ (ng/mL) |
| Compd 1 | 100 | 212 ± 32.0 | 0.5 (0.5-1.0) | 179 ± 54.4 | 0.54 ± 0.12 | — |
| | 300 | 871 ± 590 | 0.5 (0.5-1.0) | 818 ± 475 | 0.64 ± 0.20 | — |
| | 300 | 2277 ± 893 | 0.5 (0.5-1.0) | 1856 ± 1025 | 0.84 ± 0.18 | — |
| | 400 | 2675 ± 2114 | 1.0 (1.0-2.0) | 2408 ± 1013 | 0.86 ± 0.18 | — |
| | 600 | 3543 ± 1649 | 1.0 (0.5-1.0) | 4132 ± 1127 | 0.70 ± 0.13 | — |
| Metabolite | 100 | 50.2 ± 15.4 | 6.0 (4.0-6.0) | 538 ± 103* | 8.4 ± 4.3* | 3.60 ± 0.40 |
| 1-7 | 300 | 96.9 ± 38.9 | 6.0 (3.0-6.0) | 1131 ± 273* | 8.1 ± 2.4* | 10.9 ± 3.51 |
| | 300 | 123 ± 16.6 | 4.0 (3.0-6.0) | 1420 ± 221 | — | 18.0 ± 8.83 |
| | 400 | 160 ± 36.7 | 4.0 (4.0-4.0) | 2132 ± 120 | 11.6 ± 1.21 | 22.5 ± 3.29 |
| | 600 | 198 ± 19.3 | 4.0 (4.0-6.0) | 2176 ± 116 | — | 25.8 ± 4.08 |

*Based on 24-hr profile.

The mean plasma concentration-time profiles of Compound 1 and metabolite 1-7 were also calculated for all cohorts of Part A and Part B of the study. FIG. 21 is the mean plasma-concentration of Compound 1 following a single dose of Compound 1-A and FIG. 22 is the mean plasma-concentration of metabolite 1-7 following a single dose of Compound 1-A. As shown in FIG. 21, Compound 1 was quickly absorbed and rapidly/extensively metabolized in all cohorts from Part B. As shown in FIG. 22, metabolite 1-7 was a major metabolite and exhibited sustained plasma concentrations. Plasma exposure of Compound 1 was dose-related while exposure of metabolite 1-7 was dose-proportional.

For the HCV-infected subjects of Part B, measurements of HCV RNA quantitation were performed before, during, and after administration of Compound 1-A. Plasma HCV RNA determinations were performed through the use of a validated commercial assay. Baseline was defined as the mean of Day −1 and Day 1 (pre-dose). A single 300 mg dose of Compound 1-A (equivalent to 270 mg of Compound 1) resulted in significant antiviral activity in GT1b-HCV infected subjects. The mean maximum HCV RNA reduction 24 hours post-dose following a single 300 mg dose was 1.7 $\log_{10}$ IU/mL and this compares to a −2 log 10 IU/mL reduction after 1 day of 400 mg of sofosbuvir monotherapy in GT1a HCV-infected subjects. The mean maximum HCV RNA reduction 24 hours post-dose following a single 100 mg dose was 0.8 $\log_{10}$ IU/mL. The mean maximum HCV RNA reduction was 2.2 $\log_{10}$ IU/mL following a single 400 mg dose. Individual pharmacokinetic/pharmacodynamic analyses for the individual subjects from Part B of the study are shown in FIGS. 23A-23F. Metabolite 1-7 concentration is plotted against HCV RNA reduction concentration, and as shown in FIGS. 23A-23F, plasma HCV RNA reduction correlates with plasma metabolite 1-7 exposure. Viral response is sustained with metabolite 1-7 plasma concentrations that are greater than the $EC_{95}$ value against GT1b. The correlation between plasma concentration and HCV RNA reduction levels indicates that a more profound response will be achievable with higher doses of Compound 1-A.

Example 25. Predicted Steady-State Trough Levels of Metabolite 1-7 Exceed Compound 1 $EC_{95}$ Values Against Clinical Isolates of HCV GT 1-4

As shown in FIG. 24, the steady-state trough plasma levels ($C_{24,ss}$) of metabolite 1-7 following Compound 1-A dosing in humans (600 mg QD (550 mg free base equivalent) and 450 mg QD (400 mg free base equivalent)) was predicted and compared to the $EC_{95}$ of Compound 1 in vitro across all tested clinical isolates to determine if the steady state plasma concentration is consistently higher than the $EC_{95}$, which would result in high efficacy against any or all tested clinical isolates in vivo. The $EC_{95}$ for Compound 1 is the same as the $EC_{95}$ of Compound 1-A. For Compound 1-A to be effective, the steady-state trough plasma level of metabolite 1-7 should exceed the $EC_{95}$.

As shown in FIG. 24, the $EC_{95}$ of Compound 1-A against all tested clinical isolates ranged from approximately 18 to 24 nM.

As shown in FIG. 24, Compound 1-A at a dose of 450 mg QD (400 mg free base equivalent) in humans of provides a steady state trough plasma concentration ($C_{24,ss}$) of approximately 40 ng/mL. Compound 1-A at a dose of 600 mg QD (550 mg free base equivalent) in humans of provides a steady state trough plasma concentration ($C_{24,ss}$) of approximately 50 ng/mL.

Therefore, the steady state plasma concentration of surrogate metabolite 1-7 is almost double the $EC_{95}$ against all tested clinical isolates (even the hard to treat GT3a), which indicates superior performance.

In contrast, the $EC_{95}$ of the standard of care nucleotide sofosbuvir ranges from 50 to 265 nM across all tested HCV clinical isolates, with an $EC_{95}$ less than the predicted steady state concentration at the commercial dosage of 400 mg for only two isolates, GT2a and GT2b. The $EC_{95}$ for the commercial dosage of 400 mg of sofosbuvir is greater than the predicted steady state concentration for other clinical isolates, GT1a, GT1b, GT3a, GT4a, and GT4d.

The Compound 1-A 450 mg steady state trough plasma concentration ($C_{24,ss}$) was predicted using the 300 mg steady state trough plasma concentration ($C_{24,ss}$). The mean steady state trough plasma concentration ($C_{24,ss}$) at 300 mg was 26.4 ng/mL, and therefore the calculation was 26.4*450/300=39.6 ng/mL.

The 600 mg steady state trough plasma concentration ($C_{24,ss}$) was predicted using three approaches: 1) the 600 mg Day 1 $C_{24}$ mean was 25.8 ng/mL and a 60% increase was assumed for reaching steady state. Therefore the calculation was 25.8*1.6=41.3 ng/mL; 2) the 400 mg day 1 $C_{24}$ mean was 22.5 ng/mL and a 60% increase was assumed for reaching steady state. Taking dose proportional PK into account, the calculation was 22.5*1.6*600/400=54 ng/mL; and 3) the 300 mg steady state trough plasma concentration ($C_{24,ss}$) was 26.4 ng/mL and a proportional PK was assumed. Therefore the calculation was 26.4*2=52.8 ng/mL. The 600 mg steady state trough plasma concentration ($C_{24,ss}$) is the average of the 3 data points ((41.3+54+52.8)/3=49.3 ng/mL). There is generally about a 60% increase in $C_{24}$ at steady state compared to $C_{24}$ following a single dose.

The data comparing the efficacy and pharmacokinetic steady state parameters in FIG. 24 clearly demonstrates the unexpected therapeutic importance of Compound 1-A for the treatment of hepatitis C. In fact, the predicted steady-state plasma level after administration of Compound 1-A is predicted to be at least 2-fold higher than the $EC_{95}$ for all genotypes tested, and is 3- to 5-fold more potent against GT2. This data indicates that Compound 1-A has potent pan-genotypic antiviral activity in humans. As shown in FIG. 24, the $EC_{95}$ of sofosbuvir at GT1, GT3, and GT4 is greater than 100 ng/mL. Thus surprisingly, Compound 1-A is active against HCV at a dosage form that delivers a lower steady-state trough concentration (40-50 ng/mL) than the steady-state trough concentration (approximately 100 ng/mL) achieved by a similar dosage form of sofosbuvir.

Example 26. Three-Part Study to Evaluate Safety/Tolerability, Pharmacokinetics (PK), and Anti-Viral Activity of Compound 1-A A three-part study was conducted with Compound 1-A to evaluate safety/tolerability, pharmacokinetics (PK), and anti-viral activity. The three parts included: 1) the administration of multiple doses of up to 600 mg of Compound 1-A (equivalent to 550 mg of Compound 1) once daily (QD) for 7 days in NC (non-cirrhotic) GT1 HCV-infected patients (Part C); 2) the administration of 600 mg of Compound 1-A (equivalent to 550 mg of Compound 1) QD for 7 days in NC GT3 HCV-infected patients (Part D); and, 3) the administration of 600 mg of Compound 1-A (equivalent to 550 mg of Compound 1) QD for 7 days in a cohort of Child-Pugh A (CPA) cirrhotic patients with either GT1, GT2, or GT3 HCV infections (Part E). Doses were administered as the Compound 1-A salt base. The free base Compound 1 equivalent is often given in parenthesis.

Part C was a randomized, double-blind, placebo-controlled MAD study divided into three cohorts. Subjects were given 150 mg, 300 mg, or 600 mg of Compound 1-A or placebo for 7 days in the fasting state. The dose escalation only proceeded following satisfactory review of the data. Part D and Part E were open-labeled studies where patients received a dose of 600 mg of Compound 1-A (equivalent to 550 mg of Compound 1) for 7 days in the fasting state.

HCV-infected patients were treatment-naïve with HCV RNA ≥5 log 10 IU/mL. HCV RNA was quantified using COBAS® AmpliPrep TaqMAN® v2.0 with LLQ of 15 IU/mL. Plasma drug levels were measured using LC-MS/MS. Baseline HCV RNA averaged >6 logs in all cohorts of patients administered 500 mg of Compound 1-A. Cirrhosis was confirmed by prior liver biopsy or Fibroscan >12.5 kPa. The mean baseline Fibroscan was 6.3, 6.8, and 17.6 kPa in patients administered 600 mg equivalent of Compound 1-A in Part C, Part D, and Part E, respectively. Mean ages of enrolled subjects were 44, 39, and 56 years in the non-cirrhotic GT1b 600 mg dose cohort, non-cirrhotic GT3 cohort, and the cirrhotic cohort, respectively.

Part A and Part B were previously conducted and described in WO 2018/144640. Part A and Part B were single ascending dose (SAD) studies. In Part A, healthy subjects were given up to 400 mg of Compound 1-A (equivalent to 367 mg of Compound 1) and in Part B, GT1 NC HCV-infected subjects were given single doses of up to 600 mg of Compound 1-A (equivalent to 550 mg of Compound 1).

Example 27. Results of Study of Compound 1-A

No serious adverse events (AEs), dose-limiting toxicities, or premature discontinuations were reported. Compound 1-A was well tolerated up to the highest doses tested (600 mg salt form) for seven days. The only pattern observed was a higher incidence of mostly low-grade lipid abnormalities (cholesterol and triglyceride increase) in subjects receiving Compound 1-A compared to placebo. However, this observation is consistent with previously published data showing rapid increase in lipids with HCV clearance upon initiation of DAA therapy in HCV-infected subjects. In addition, there were no findings suggestive of liver injury. ALT/AST values decreased over time during the treatment period in subjects receiving Compound 1-A. Finally, there were no other clinically relevant, dose-related patterns upon analysis of AEs, laboratory parameters, ECGs and vital signs.

In part B, a single dose of the Compound 1-A equivalent of 92 mg, 275 mg, 368 mg, or 550 mg of Compound 1 was administered to non-cirrhotic GT1b HCV-infected subjects separated into dosing cohorts (n=3 for each cohort) to determine the mean maximum reduction of HCV RNA, the results of which are shown in FIG. 25 and Table 36. A single dose of 600 mg of Compound 1-A (equivalent to 550 mg of Compound 1) administered to non-cirrhotic GT1b HCV-infected subjects (n=3) resulted in a mean maximum HCV RNA reduction of 2.3 $\log_{10}$ IU/mL, with individual maximum HCV RNA reductions of 2.1, 2.3, and 2.6 $\log_{10}$ IU/mL in this cohort.

TABLE 36

HCV RNA Change from Baseline in GT1b HCV Patients after a Single Dose of Compound 1-A

| Dosing Cohort (Compound 1-A Equivalent of Compound 1) | Mean (Individual) Max Reduction ($\log_{10}$ IU/ml) |
|---|---|
| 92 mg | 0.8 (0.6, 0.8, 0.9) |
| 275 mg | 1.7 (1.1, 1.8, 2.2) |
| 368 mg | 2.2 (1.8, 2.2, 2.6) |
| 550 mg | 2.3 (2.1, 2.3, 2.6) |

In Part C, dose-related antiviral activity was observed 7 days after dosing with a mean maximum HCV RNA reduction up to 4.4 $\log_{10}$ IU/mL in non-cirrhotic GT1b HCV-infected subjects (n=6). 50% of subjects achieved HCV RNA <LOQ. FIG. 26 is a graph of the mean HCV RNA change from baseline in subjects given placebo, 150 mg, 300 mg, or 600 mg of Compound 2 once daily (QD). The mean maximum reduction was observed following 7 days of dosing in the three cohorts given 150 mg, 300 mg, or 600 mg of Compound 1-A once daily (QD).

In Part D, potent antiviral activity was observed in non-cirrhotic GT3 HCV-infected subjects (n=6) with a mean maximum HCV RNA reduction of 4.5 $\log_{10}$ IU/mL. The mean HCV RNA reduction was 2.4 $\log_{10}$ IU/mL after the first dose of 600 mg of Compound 1-A (equivalent to 550 mg of Compound 1) and one subject achieved HCV RNA <LOQ within four days after the first dose.

Antiviral activity in the CPA cirrhotic HCV-infected subjects of Part E was similar to non-cirrhotic GT1b and GT3 cohorts. In Part E, the mean maximum HCV RNA reduction of cirrhotic HCV infected patients was 4.6 $\log_{10}$ IU/mL.

Mean HCV RNA changes from baseline in these populations are presented in FIG. 27. For comparison, the curves for the ascending dose cohorts (Part C, non-cirrhotic GT1b HCV-infected patients) are shown in FIG. 26 and the curves for all 600 mg QD cohorts (Parts C/D/E) are included in FIG. 27. Metabolite 1-7 antiviral activity observed in each cohort is summarized in Table 39A, Table 39B, and Table 39C.

The mean maximum HCV RNA change for Part C, Part D, and Part E is shown in Table 37. FIGS. 28A-28C are graphs comparing the mean maximum reduction of non-cirrhotic subjects with GT1 HCV infection from Part C, non-cirrhotic subjects with GT3 HCV infection from Part D, and cirrhotic subjects with GT1/GT2/GT3 HCV from Part E. The mean maximum reduction following 7 days of dosing was similar for subjects, regardless of whether the subject was infected with GT1 or GT3 HCV and regardless of whether the subject was cirrhotic or non-cirrhotic. A summary of the antiviral activity among all of these cohorts is shown in Table 37 and Table 38. A profound early viral response in cirrhotic subjects was observed, leading to a 2.4 and 2.2 $\log_{10}$ HCV RNA reduction for GT1 and GT3 HCV subjects, respectively, within the first 24 hours. Five subjects receiving the 600 mg QD dose of metabolite 1-7 (3 subjects in Part C (50%) and 1 subject each in Parts D and E (17%)) achieved HCV RNA levels below the lower limit of quantitation in the study.

TABLE 37

Maximum HCV RNA Change in Part B, Part C, Part D, and Part E

| | Part C | | | | Part D | Part E |
|---|---|---|---|---|---|---|
| Endpoint, $\log_{10}$ IU/mL | Placebo N = 6 | 150 mg/day Compd 2 N = 6 | 300 mg/day Compd 2 N = 6 | 600 mg/day Compd 2 N = 6 | 600 mg/day Compd 2 N = 6 | 600 mg/day Compd 2 N = 6 |
| Mean ± SD HCV RNA change from baseline to 24 h | 0.0 ± 0.2 | 1.2 ± 0.3 | 1.9 ± 0.2 | 2.1 ± 0.2 | 2.3 ± 0.3 | 2.4 ± 0.2 |
| Mean ± SD HCV RNA maximum change from baseline | 0.4 ± 0.1 (0.2-0.5)* | 2.6 ± 1.1 (1.5-3.7)* | 4.0 ± 0.4 (3.5-4.4)* | 4.4 ± 0.7 (3.7-5.1)* | 4.5 ± 0.3 (4.1-5.0)* | 4.6 ± 0.5 |
| Individual HCV RNA maximum change from baseline | 0.3, 0.3, 0.4, 0.4, 0.5, 0.6 | 1.7, 1.8, 1.8, 2.7, 3.0, 4.5 | 3.4, 3.7, 3.9, 4.2, 4.2, 4.5 | 3.5, 4.0, 4.1, 4.3, 5.2, 5.3 | 4.2, 4.4, 4.4, 4.5, 4.5, 5.0 | GT1b: 4.0, 4.0, 4.5 GT2: 4.8 GT3: 5.0, 5.2 |

*95% C.I.

TABLE 38

Summary of Antiviral Activity of Compound 1-A in Part C, Part D, and Part E for 600 mg of Compound 1-A

| Dosing Cohort | Mean Reduction After 24 hours ($\log_{10}$ IU/mL) | Mean (Individual) Max Reduction ($\log_{10}$ IU/mL) | HCV RNA < LOQ (15 IU/mL) |
|---|---|---|---|
| GT1, non-cirrhotic (n = 6) | 2.1 | 4.4 (3.5, 4.0. 4.1, 4.3, 5.2, 5.3) | 3/6 |
| GT3, non-cirrhotic (n = 6) | 2.4 | 4.5 (4.2, 4.4, 4.5, 4.5, 5.0) | 1/6 |
| GT1, Child-Pugh A (n = 3) | 2.4 | 4.2 (4.0, 4.1, 4.5) | 1/3 |
| GT3, Child-Pugh A (n = 1) | 2.2 | 4.8 (n = 1) | 0/1 |

Compound 1, the free base of Compound 1-A, was rapidly and well-absorbed with estimated fraction absorbed approximating 50% based on urine recovery. After repeated QD administrations for seven days in a fasted state, Compound 1 was quickly absorbed followed by rapid metabolic activation.

Following daily dosing for 7 days in Part C, Compound 1 exhibited a short half-life and did not accumulate over time. Plasma exposure of Compound 1 was slightly more than dose proportional from 150 mg to 300 mg and mostly dose proportional thereafter. While plasma peak and total exposure of metabolite 1-7 was dose proportional from 150 to 300 mg and less than dose proportional from 300 mg to 600 mg, trough levels of metabolite 1-7 were mostly dose proportional in the studied dose range. Based on metabolite 1-7 trough levels, steady state PK was essentially reached after the third or fourth dose. The formation of metabolite 1-7 peaked at approximately 6 hours after dosing and metabolite 1-7 exhibited a long half-life (-13-30 h) which supports once a day (QD) dosing. The long half-life resulted in the desired higher metabolite 1-7 trough (50%-60%) upon reaching steady state. (Active triphosphate 1-6 is not measurable in plasma since it does not leave the cell, and therefore 1-7, which is measurable is plasma, acts as a surrogate for triphosphate 1-6 and reflects intracellular active triphosphate).

Steady state of metabolite 1-7 concentrations was reached by day 3 or 4 in NC subjects and by day 5 in the subjects with cirrhosis. Overall, mild hepatic impairment did not significantly impact the PK of Compound 1-A based on plasma exposures. No food effect on total and trough exposure of metabolite 1-7 was observed.

FIG. 29 is a graph of the mean plasma concentration-time profile of metabolite 1-7 at steady-state comparing non-cirrhotic subjects with GT1 HCV infection given the Compound 1-A equivalent of 138 mg/d QD of Compound 1, non-cirrhotic subjects with GT 1 HCV infection given the Compound 1-A equivalent of 275 mg/d QD of Compound 1, non-cirrhotic subjects with GT3 HCV infection given 600 mg of Compound 1-A (equivalent to 550 mg of Compound 1), and cirrhotic subjects with GT1 or GT3 HCV infections given 600 mg of Compound 1-A (equivalent to 550 mg of Compound 1). Plasma levels of metabolite 1-7 were measured using LC-MS/MS.

Tables 39A, 39B, and 39C shows the mean PK results of subjects enrolled in the study. As shown in Tables 39A-39C and FIG. 29, the PK of metabolite 1-7 is similar in non-cirrhotic and cirrhotic subjects.

TABLE 39A $C_{max}$ and $T_{max}$ for Compound 1 and Metabolite 1-7 at Day 1 and Steady State (SS)

| Analyte | Part | Dose (n) (mg/d) | $C_{max}$ (ng/mL) Day 1 | $C_{max}$ (ng/mL) SS | $T_{max}$ (h) Day 1 | $T_{max}$ (h) SS |
|---|---|---|---|---|---|---|
| Compd 1 | C | 150 (6) | 573 ± 280 | 462 ± 409 | 0.5 (0.5-1.0) | 1.0 (0.5-1.0) |
| | | 300 (6) | 2277 ± 893 | 1834 ± 1313 | 0.5 (0.5-0.9) | 0.5 (0.4-1.0) |
| | | 600 (6) | 4211 ± 2302 | 3604 ± 1742 | 0.5 (0.5-0.5) | 0.5 (0.5-1.0) |
| | D | 600 (6) | 3971 ± 1943 | 4144 ± 2280 | 0.5 (0.5-0.5) | 0.5 (0.5-1.0) |
| | E | 600 (6) | 3412 ± 2175 | 3192 ± 2085 | 0.5 (0.5-1.0) | 0.5 (0.5-1.0) |
| Metabolite 1-7 | C | 150 (6) | 75.6 ± 15.4 | 81.1 ± 33.9 | 4.0 (4.0-6.0) | 4.0 (4.0-8.0) |
| | | 300 (6) | 123 ± 16.6 | 220 ± 203 | 4.0 (2.9-6.0) | 4.0 (2.0-5.9) |
| | | 600 (6) | 197 ± 57.1 | 233 ± 42.9 | 5.0 (4.0-6.0) | 4.0 (4.0-6.0) |
| | D | 600 (6) | 195 ± 42.9 | 263 ± 104 | 5.0 (3.0-6.0) | 4.0 (4.0-6.0) |
| | E | 600 (6) | 201 ± 68.1 | 255 ± 95.4 | 5.0 (3.0-6.0) | 6.0 (4.0-6.0) |

TABLE 39B

AUC and $T_{1/2}$ for Compound 1 and Metabolite 1-7 at Day 1 and Steady State (SS)

| Analyte | Part | Dose (n) (mg/d) | AUC# (ng/mLxh) Day 1 | AUC# (ng/mLxh) SS | $T_{1/2}$ (h) Day 1 | $T_{1/2}$ (h) SS |
|---|---|---|---|---|---|---|
| Compd 1 | C | 150 (6) | 492 ± 141 | 475 ± 301 | 0.62 ± 0.11 | 0.64 ± 0.20 |
| | | 300 (6) | 1947 ± 1120 | 1510 ± 976 | 0.80 ± 0.18 | 0.73 ± 0.15 |
| | | 600 (6) | 3335 ± 1502 | 4036 ± 2093 | 0.86 ± 0.11 | 0.85 ± 0.12 |
| | D | 600 (6) | 3333 ± 1241 | 3754 ± 2275 | 0.73 ± 0.12 | 0.83 ± 0.06 |
| | E | 600 (6) | 3323 ± 1467 | 3527 ± 1605 | 0.86 ± 0.18 | 0.81 ± 0.12 |
| Metabolite 1-7 | C | 150 (6) | 800 ± 213 | 962 ± 409 | | 12.5 ± 6.33 |
| | | 300 (6) | 1414± 220 | 1828 ± 453 | | 24.5 ± 15.3 |
| | | 600 (6) | 2204 ± 486 | 2839 ± 572 | | 28.9 ± 14.4 |
| | D | 600 (6) | 2253 ± 595 | 3117 ± 1048 | | 27.9 ± 18.3 |
| | E | 600 (6) | 2625 ± 873 | 3569 ± 1214 | | 24.4 ± 9.81 |

#$AUC_{inf}$ for Compound 1 and AUC, for Metabolite 1-7

TABLE 39C $C_{24\,h}$ for Compound 1 and Metabolite 1-7 at Day 1 and Steady State (SS)

| Analyte | Part | Dose (n) (mg/d) | $C_{24h}$* (ng/mL) Day 1 | $C_{24h}$* (ng/mL) SS* |
|---|---|---|---|---|
| Compd 1 | C | 150 (6) | | |
| | | 300 (6) | | |
| | | 600 (6) | | |
| | D | 600 (6) | | |
| | E | 600 (6) | | |
| Metabolite 1-7 | C | 150 (6) | 8.08 ± 3.48 | 12.8 ± 4.45 |
| | | 300 (6) | 18.0 ± 8.83 | 26.1 ± 7.56 |
| | | 600 (6) | 27.5 ± 5.21 | 46.9 ± 15.5 |
| | D | 600 (6) | 30.1 ± 10.9 | 37.8 ± 11.4 |
| | E | 600 (6) | 41.6 ± 12.9 | 69.9 ± 18.5 |

*$C_{24}$ only reported for Metabolite 1-7; $C_{24}$ at steady state was the mean of $C_{24}$ at 72, 96, 120, 144 and 168 h.

FIGS. 30A-30D are PK/PD analysis of non-cirrhotic subjects with GT1 HCV infection (FIG. 30A), non-cirrhotic subjects with GT3 HCV infection (FIG. 30B), the cirrhotic subject with GT1 HCV infection (FIG. 30C), and the cirrhotic subject with GT3 HCV infection (FIG. 30D). The left y-axis is the mean metabolite 1-7 concentration and the right y-axis is the mean HCV RNA reduction. The dashed horizontal line (-----) represents the $EC_{95}$ value of Compound 1 and the dots represent $C_{\tau}$, the steady-state plasma trough level of metabolite 1-7 following 600 mg of Compound 1-A (equivalent to 550 mg of Compound 1). As shown in FIGS. 30A-30D, the steady state plasma trough level of metabolite 1-7 consistently exceeds the $EC_{95}$ of Compound 1 in inhibiting HCV GT1 and GT3 in non-cirrhotic and cirrhotic subjects. The steady state plasma trough level of metabolite 1-7 in cirrhotic patients is 45.7 ng/mL, and the $EC_{95}$ of Compound 1 in HCV GT1, GT2, and GT3 is approximately 21.7 ng/mL, 11.6 ng/mL, and 17.5 ng/mL equivalents of metabolite 1-7, respectively. FIGS. 30A-30D also demonstrate that antiviral activity correlated with plasma exposure.

An $E_{max}$ model, generated by plotting the AUC of metabolite 1-7 against the HCV RNA reduction, was used to predict that metabolite 1-7 exposures of ≥2000 ng/mL×h will result in a maximal viral load reduction of at least 4 log units after 7 days of QD dosing with Compound 1-A (FIG. 31). A 600 mg dose of Compound 1-A (equivalent to 550 mg of Compound 1) consistently reaches this threshold in non-cirrhotic and cirrhotic subjects, demonstrating that 550 mg QD of Compound 1 (equivalent to 600 mg of Compound 1-A) will result in maximum viral-load reduction.

Example 28. Formulation Description and Manufacturing of Compound 1-A

A representative non-limiting batch formula for Compound 1-A tablets (50 mg and 100 mg) is presented in Table 40. The tablets were produced from a common blend using a direct compression process as shown in FIG. 32.

TABLE 40

Formulation of 50 mg and 100 mg Compound 1-A Tablets

| Raw Material | % w/w | g/batch | Mg/unit 50 mg Tablet | Mg/unit 100 mg Tablet |
|---|---|---|---|---|
| Compound 1-A | 50.0 | 180.0 | 50.0 | 100.0 |
| Microcrystalline Cellulose, USP/NF, EP | 20.0 | 72.0 | 20.0 | 40.0 |
| Lactose Monohydrate, USP/NF, BP, EP, JP | 24.0 | 86.4 | 24.0 | 48.0 |
| Croscarmellose Sodium, USP/NF, EP | 5.0 | 18.0 | 5.0 | 10.0 |
| Magnesium Stearate, USP/NF, BP, EP JP | 1.0 | 3.6 | 1.0 | 2.0 |
| Total | | | 100.0 | 200.0 |

Compound 1-A was adjusted based on the as-is assay, with the adjustment made in the percentage of microcrystalline cellulose. Compound 1-A and excipients (microcrystalline cellulose, lactose monohydrate, and croscarmellose sodium) were screened, placed into a V-blender (PK Blendmaster, 0.5 L bowl) and mixed for 5 minutes at 25 rpm. Magnesium stearate was then screened, added and the blend was mixed for an additional 2 minutes. The common blend was divided for use in producing 50 mg and 100 mg tablets. The lubricated blend was then compressed at a speed of 10 tablets/minutes using a single punch research tablet press (Korsch XP1) and a gravity powder feeder. The 50 mg tablets were produced using round standard concave 6 mm tooling and 3.5 kN forces. The 100 mg tablets were produced using 8 mm round standard concave tooling and 3.9-4.2 kN forces. The specifications of the 50 mg and 100 mg tablets are shown in Table 41.

TABLE 41

Specifications of 50 mg and 100 mg Tablets of Compound 1-A

| | 50 mg Tablets | 100 mg Tablets |
|---|---|---|
| Average Weight (n = 10) | 100 ± 5 mg | 200 ± 10 mg |
| Individual Weight | 100 ± 10 mg | 200 ± 20 mg |
| Hardness | 5.3 kp | 8.3 kp |
| Disintegration | <15 minutes | <15 minutes |
| Friability | NMT 0.5% | NMT 0.5% |

The 50 mg and 100 mg tablets produced as described above were subjected to 6 month stability studies under three conditions: 5° C. (refrigeration), 25° C./60% RH (ambient), and 40° C./75% RH (accelerated). Both the 50 mg and 100 mg tablets were chemically stable under all three conditions tested.

Under refrigeration conditions (5° C.), both the 50 mg and 100 mg tablets remained white solids that did not change in appearance from T=0 to T=6 months. Throughout the 6-month study, no impurities were reported that were greater than 0.05% for either the 50 mg tablets or the 100 mg tablets. The water content after 6 months was also less than 3.0% w/w for both tablets. Similar results were reported when the tablets were subjected to ambient conditions (25° C./60% RH); no impurities that were greater than 0.05% were reported throughout the 6 months for both tablets and the water content did not exceed 3.0% w/w at the 6-month mark. When the tablets were subjected to accelerated conditions (40° C./75% RH), the appearance of the 50 mg and 100 mg tablets did not change from a white, round tablet. One impurity was reported after 3 months, but the impurity was only 0.09%. A second impurity was reported after 6 months, but the total impurity percentage was only 0.21% for both the 50 mg and 100 mg tablets. Water content was 3.4% w/w at 6 months for the 50 mg tablets and 3.2% w/w for the 100 mg tablets.

In a separate study, the stability of 50 mg and 100 mg tablets of Compound 1-A at ambient conditions (25° C./60% RH) was measured over 9 months. The appearance of the 50 mg and 100 mg tablet did not change from a white round tablet over the course of 9 months. Impurities in the 50 mg tablet were less than 0.10% after 9 months and impurities in the 100 mg tablet were less than 0.05%. The water content of the 50 mg tablet and the 100 mg tablet after 9 months was only 2.7% w/w and 2.6% w/w, respectively.

Example 29: Synthesis of Compound 2

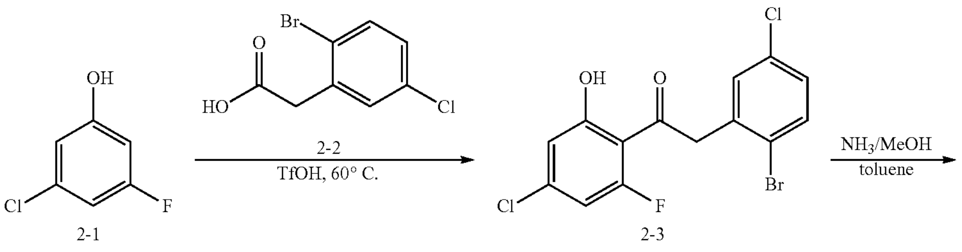

-continued
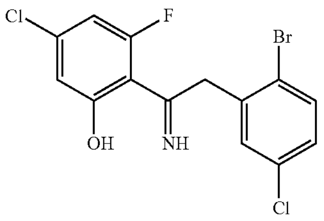
2-4
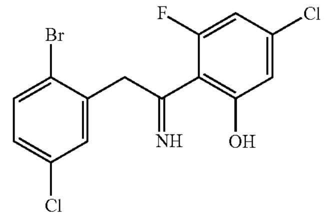
2-4
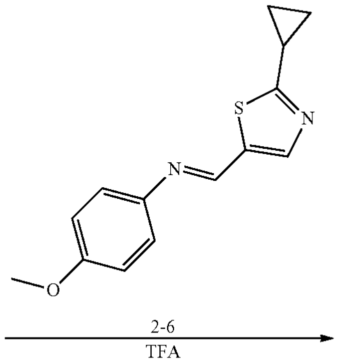
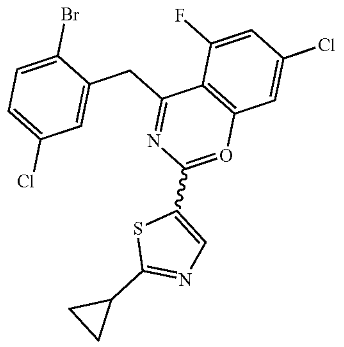
2-7
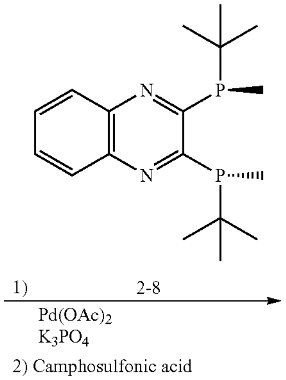
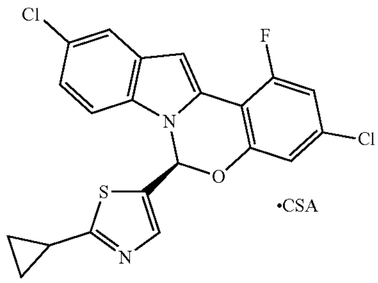
2-9
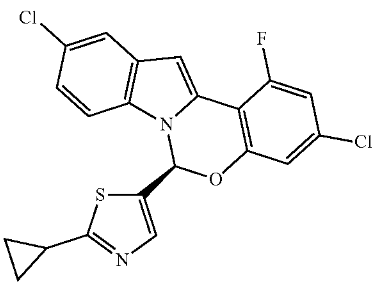
2-9
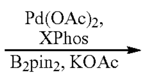

-continued
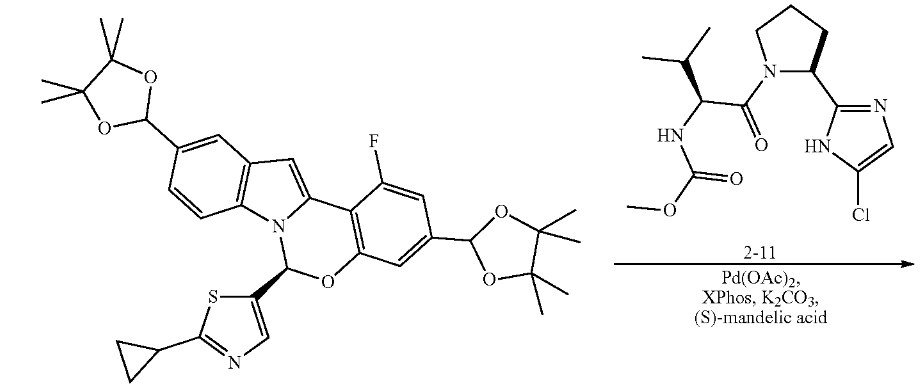
2-10
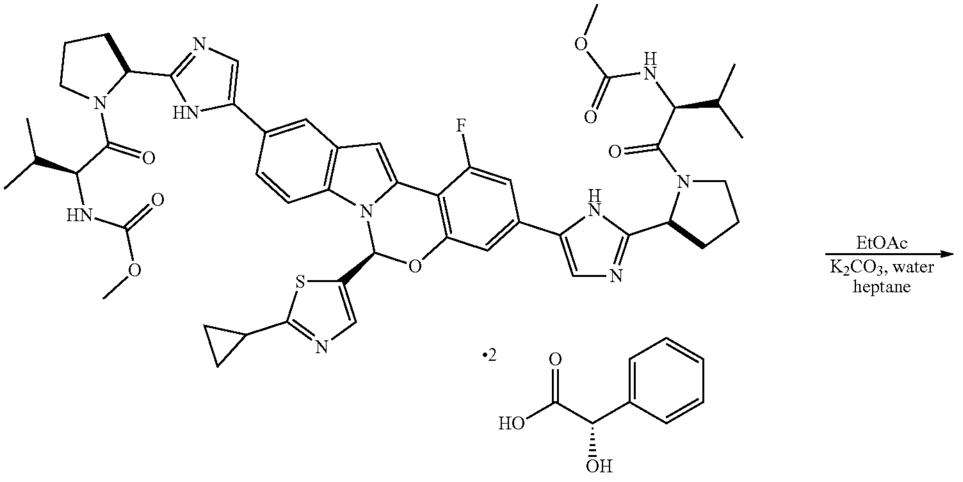
2-12
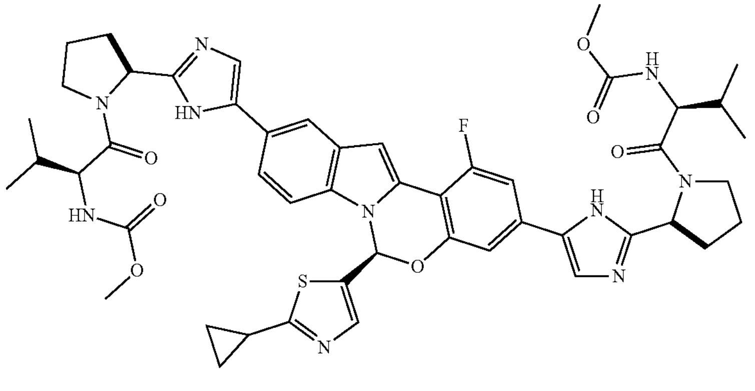
Compound 2
Synthesis of Compound 2-9
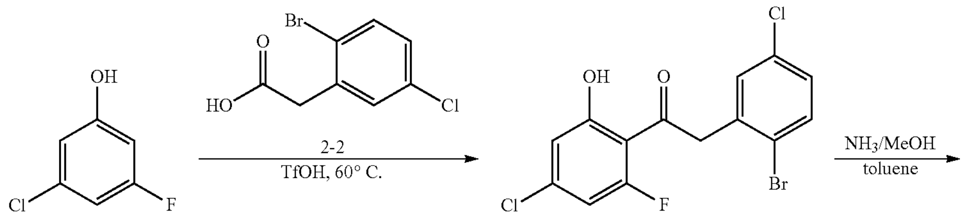
2-1
2-3

-continued

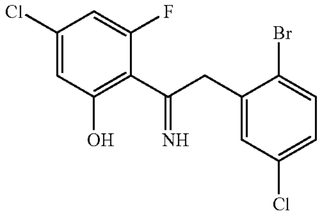

2-3

To a 250 mL round bottom flask was added 3-chloro-5-fluorophenol (Compound 2-1) and 2-(2-bromo-5-chlorophenyl)acetic acid (Compound 2-2 20.02 g, 80.0 mmol) were mixed with TfOH (91 mL) and heated to 60° C. under an nitrogen atmosphere. After stirring at this temperature for 16 hours, the mixture was cooled to room temperature and poured over a 20 minute period into isopropanol (500 mL) that had been cooled in an ice/water bath. The resulting slurry was diluted with water (125 mL), which was added over 10 minutes. After aging for 30 minutes in the ice/water bath, the mixture was filtered, and the collected solid washed with 4:1 isopropanol/water (50 mL). The solid was dried in vacuo to provide Compound 2-3 (20.14 g, 53.3 mmol, 80% yield).

Compound 2-3 (2.03 g, 5.37 mmol) was taken up in 2-methyltetrahydrofuran (20.3 mL, 10 volumes), and to this solution was added ammonia in methanol (11.51 mL of 7N, 81 mmol, 15 eq.). The resulting solution was aged at room temperature for 16 hours, then concentrated by the removal of 25 mL of solvent and the slurry treated with toluene (70 mL). The resulting solution was then redistilled to remove a further 35 mL of solvent and achieve a final solution of the Compound 2-5 in 20 volumes of toluene. This solution was used without further purification.

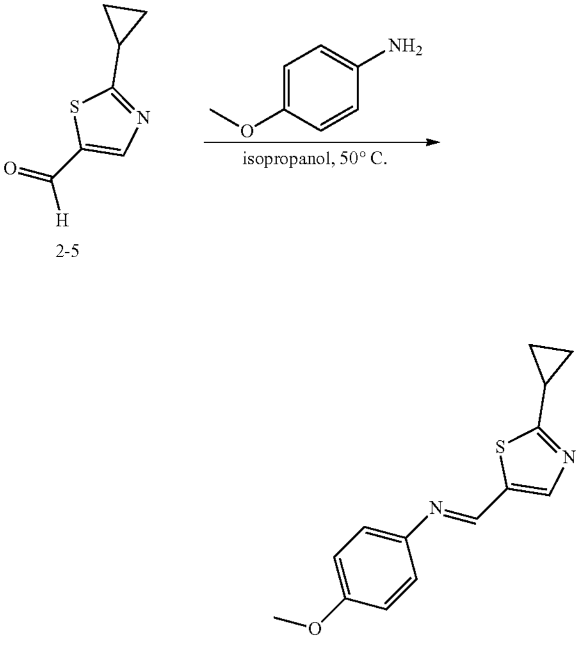

-continued

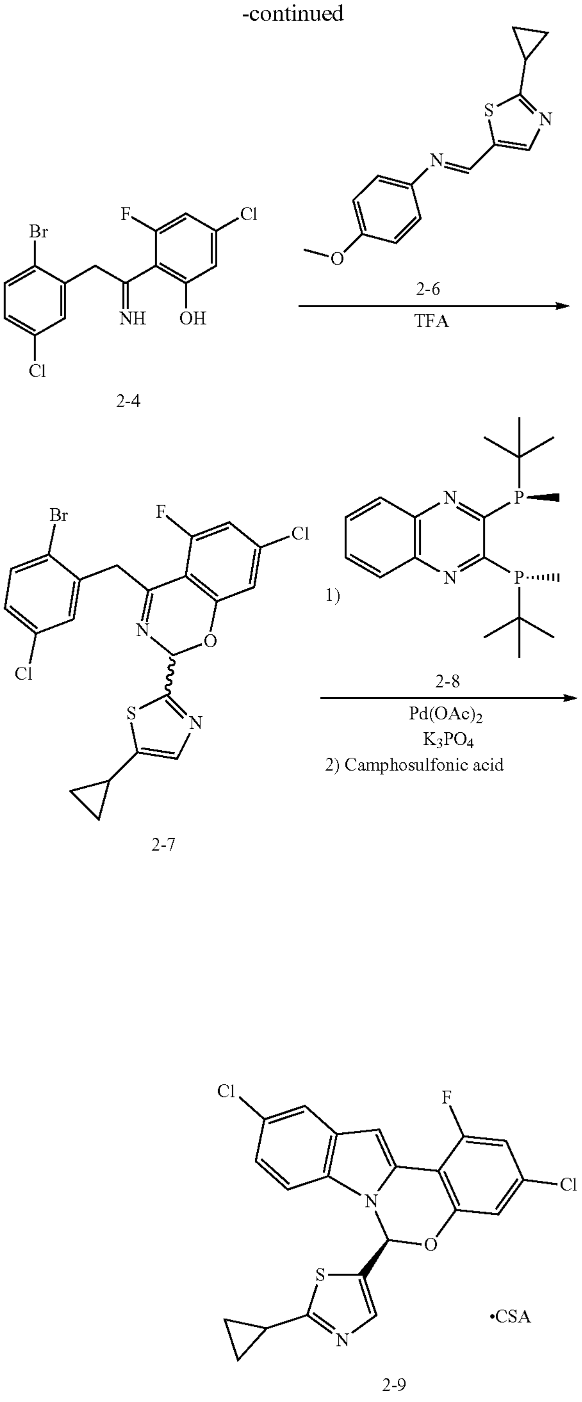

A 1 L round-bottom flask equipped with an air condenser was charged with Compound 2-5 (25 g, 163 mmol), 4-methoxyaniline (22.1 g, 180 mmol), and isopropanol (250 mL). The resulting slurry was warmed to 50° C. and stirred for 3.5 hours, during which time a precipitate formed. The resulting slurry was cooled to 0° C., aged for 1 hour, and filtered. The flask and pad were rinsed twice with 0° C. isopropanol (84 mL), and the solid dried to a constant weight in a vacuum oven at 50° C. to provide Compound 2-6. (39.0 g, 93% yield). $^1$H NMR (DMSO-$d_6$, 400 MHz): δ 8.77 (s, 1H), 8.06 (s, 1H), 7.26 (d, J=8.8 Hz, 2H), 6.96 (d, J=8.8 Hz, 2H), 3.77 (s, 3H), 2.45 (m, 1H), 1.19 (m, 2H), 1.05 (m, 2H)-imine geometry not determined, drawn as (E) for convenience.

A 3-neck roundbottom flask equipped with a magnetic stirbar, a temperature probe, and a nitrogen inlet was charged with Compound 2-6 (7.54 g, 29.2 mmol) and a solution of Compound 2-4 in toluene (5.72 wt %, 174.8 g, 26.5 mmol) was added. The resulting suspension was allowed to stir at room temperature until the solid dissolved, and the resulting solution was cooled using an ice/water bath. TFA (2.45 mL, 31.8 mmol) was added while the internal temperature was maintained below 5° C. The resulting solution was allowed to stir in the ice/water bath for 16 hours as it warmed to room temperature. The resulting slurry was filtered, the flask and pad were washed with toluene (27 mL), and the organic solution washed with aqueous $NaHCO_3$ (4 wt %, 54 mL) and water (54 mL). The organic layer was concentrated in vacuo to ~25 mL, diluted with isopropanol (110 mL), and concentrated in vacuo to ~50 mL total volume The resulting slurry was warmed to 40° C., diluted with water (10 mL, added over 30 minutes), aged at 0° C. for 1 hour, and filtered. The flask and pad were washed with 4:1 isopropanol/water (25 mL), and the solid dried to a constant weight in a vacuum oven at 50° C. to provide Compound 2-7. (10.1 g, 74% yield)

To a solution of $Pd(OAc)_2$ (219 mg, 0.98 mmol) and (R)-QuinoxP* (Compound 2-8) (343 mg, 1.03 mmol) in a 100 ml, round bottom flask was added degassed toluene (45 mL). The solution was subjected to three cycles of evacuation with vacuum and backfill with nitrogen and then purged with nitrogen above surface for 5 minutes. The catalyst solution was then allowed to age at 20° C. for 2 hours. A 1 L, 3-neck round bottom flask fitted with an overhead stirrer was then charged with Compound 2-7 (25 g, 48.8 mmol) and $K_3PO_4$ (41.4 g, 195 mmol) and toluene (700 mL). The mixture was subjected to three cycles of vacuum evacuation and nitrogen backfill and then purged with nitrogen above surface for 5 minutes. Degassed water (0.88 mL, 48.8 mmol) was then added dropwise, after which the premade catalyst solution was added and the resulting reaction heated to 50-55° C. and stirred at this temperature for 11 hours. During the first 6 hours of the reaction time, additional water (5.28 mL, 293 mmol) was added in six equal portions, each hour. After a total of 11 hours at 50-55° C., the reaction mixture was cooled to 20° C. and charged with 75 mL, of water and 5 mL. 50% w/v KOH (~9N). The aqueous layer was cut away and the organic layer washed with 100 mL of water. The organic layer was then filtered and concentrated in vacuo and the resulting residue was purified using flash column chromatography to provide Compound 2-9.

The ee was determined using SFC under the following conditions:

Column: ChiralCel OJ-3; 4.6 mm×150 mm; 3 μm particle size

Temperature: 40° C.

Pressure: 200 bar

Modifier: IPA with 25 mM isobutyl amine added

Flowrate: 3.0 mL·min

Conditions: 1% modifier/99% $CO_2$ to 40% modifier/60% $CO_2$ over 5 minutes with 1 minute hold at 40% modifier For purified Compound 2-9: (23 mg, 90% yield, in 91% ee). $^1$H NMR (CDCl3, 500 MHz): δ 7.663 (d, J=2.0 Hz, 1H), 7.407 (d, J=0.4 Hz, 11H), 7.200 (dd, J=2.0, 8.8 Hz, 1H), 7.092 (d, J=0.4 8.4 Hz. 1H), 7.048-7.039 (m, 2H), 6.958-6.910 (m, 21H), 2.194-2.153 (m, 1H), 1.275-1.075 (m, 2H), 1.018-0.991 (n, 2H).

The crude product Compound 2-9 was dissolved in about 50 mL of toluene and 128 mL of iPAC at 15° C. (S)-Camphorsulfonic acid (10.8 g, 46.4 mmol) was added over 2.5 hours in three portions at 45° C. It was cooled to room temperature and additional (S)-camphorsulfonic acid (0.57 g, 2.4 mmol) was added. The mixture was aged at room temperature for 16 hrs, then filtered. The solid was washed with 50 ml 1/2.5 toluene/isopropyl acetate and then 50 ml isopropyl acetate, and dried with vacuum to afford 27.1 g of Compound 2-9 as the camphorsulfonic acid salt in 96 to >99% ee.

Synthesis of Compound 2

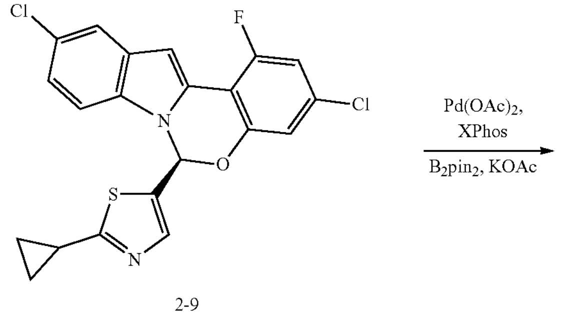

2-9

-continued

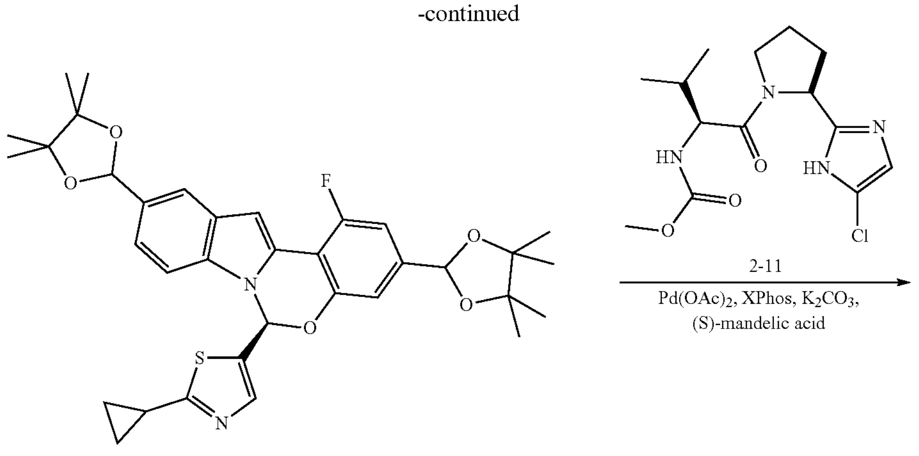

2-10

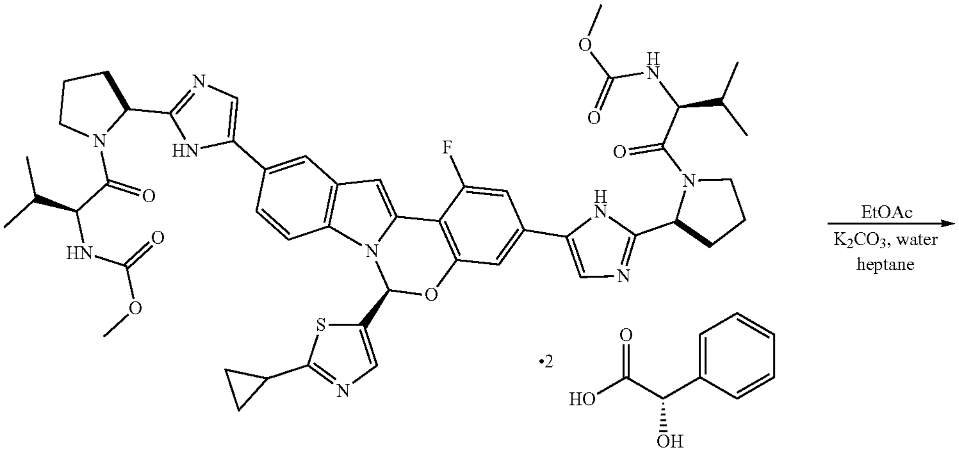

2-12

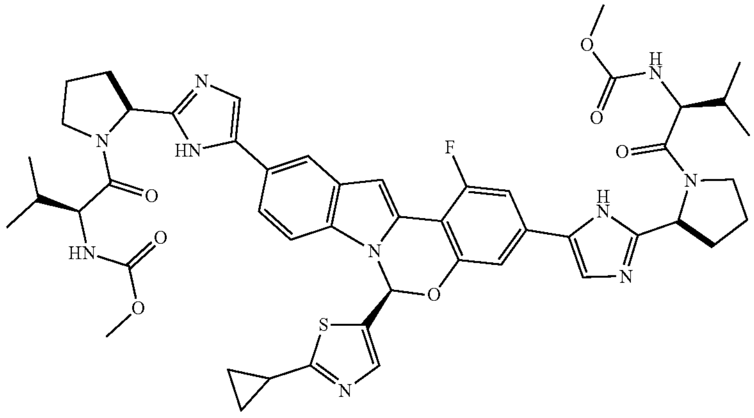

Compound 2

A 500 mL 3-necked round-bottomed flask with an overhead stirrer was charged with Compound 2-9 ((S)-CSA salt, 10.0 g, or equivalent amount of the free base), bis(pinacolato)diboron (8.50 g), potassium acetate (8.78 g), and 5-chloroindole (0.46 g) under nitrogen. Degassed 2-Me-TIF (130 mL) and water (0.54 mL) were added. A separate vessel was charged with palladium acetate (0.067 g) and Xphos (2-dicyclohexylphosphino-2',4',6'-triisopropylbiphenyl) (0.293 g) and degassed 2-Me-THF (20 mL) under nitrogen, and the mixture was allowed to stir for 30 minutes then added to the flask Compound 2-9. The mixture was then heated to 75° C. and allowed to age at this temperature for 1 hour or until complete conversion, then allowed to cool to room temperature. Water (30 mL) was added to the mixture, and the layers separated The organic layer was washed with 10% brine (30 mL), then treated with Cuno-3-carbon (1.0 g) for about 15 hours. The mixture was filtered through a Celite-pad to remove carbon. The solution was concentrated in vacuo to about approximately 35 mL mixture. Seed crystals were added to initiate the crystallization. The mixture was allowed to age at room temperature for 10 minutes before acetonitrile (105 mL) was added slowly. The resultant slurry was filtered and the collected solid washed with a mixture of acetonitrile/2-Me-THF (3:7, 30 mL), then dried in a nitrogen stream to provide Compound 2-10. 1H NMR (CDCl3, 500 MHz), 8.23 (s, 1H), 7.70 (d, J=8.3 Hz, 1H), 7.50 (s, 1H), 7.31 (d, J=9.6 Hz, 1H), 7.29 (d, J=7.1 Hz, 1H), 7.23 (d, J=8.3 Hz, 1H), 7.18 (d, J=3.3 Hz, 1H), 7.10 (s, 1H), 2.15-2.10 (m, 1H), 1.39 (s, 6H), 1.37 (s, 3H), 1.37 (s, 3H), 1.06-1.02 (m, 4H), 1.01-0.95 (m, 4H).

To a high-pressure vessel was charged with compound 2-10 (10.0 g, 16.28 mmol, 1.0 eq), compound 2-11 (11.5 g, 2.15 eq.), 2-Me-THF (90 mL) and $K_2CO_3$ (98 mL, 1 M, 6 eq.). The vessel was degassed. A second reaction vessel was charged with $Pd(OAc)_2$ (0.11 g, 3%) and Xphos (0.58 g, 7.5%), then degassed followed by addition of degassed 2-Me-THF (20 mL). The resulting catalyst/ligand slurry was allowed to age for 2 hours at room temperature under nitrogen atmosphere. It was then transferred to the reaction vessel containing Compound 2-11 and rinsed with degassed 2-Me-THF (10 mL). The resulting reaction mixture was degassed again, and the reaction vessel sealed and heated to 85 to 90° C. for about 8 hours until >99.5% conversion was reached. The reaction was cooled down to room temperature, and the organic layer was sequentially washed with 10% NaCl solution (18 mL) and 3% NaCl solution (18 mL). The organic layer was then concentrated in vacuo and azeotropically dried via distillation to provide crude product (14.66 g)

The crude product (14.66 g) in 2-Me-THF (135 mL) was added to a solution of tri-n-butylphosphine (2.32 mL) in MeOH (19.4 mL). The mixture was heated to 70° C. followed by addition of a solution of (S)-mandelic acid (0.94 g) dissolved in 2-Me-THF (3.87 mL). After aging at 70° C. for several hours, the reaction mixture was cooled to 60° C. and another portion of (S)-mandelic acid (3.06 g) in 2-Me-THF (12.58 mL) was added. The batch was seeded with the mandelate salt Compound 2-12. A final portion of S-mandelic acid (35.41 g) in 2-Me-THF (222.5 mL) was charged over 4 hours at 60° C. The reaction mixture was gradually cooled to 20° C. over 8 hours and aged at 20° C. for 1 hour. The slurry was filtered, and rinsed with 2-Me-THF (containing 2% wt (S)-mandelic acid). The collected solid was dried at 60° C. to provide the bis-mandelate salt Compound 2-12 as a solid (18.74 g)

The bis-mandelate salt Compound 2-12 (6 g) was mixed with ethyl acetate (48 mL) and water (25.7 mL). To the biphasic mixture was added 2M potassium carbonate solution (6 mL, 2.5 equivalents) over 10 minutes, during which a biphasic solution results. The lower aqueous layer was removed, and the organic layer washed sequentially with 8% brine solution (30 mL) and water (2×30 mL). The organic layer was azeotropically dried via distillation (final solution volume=30 mL). Heptane (66 mL) was charged to an inerted flask. The ethyl acetate stream containing product was added to the heptane over a period of 2 hours. After aging for another 2 hours, the product slurry was filtered, and the wet filter cake washed with a mixture of heptane (10.8 mL) and EtOAc (2 mL). The solid was dried in vacuo for about 15 hours at 60° C. to provide Compound 2 as the free base. (4.40 g, MS: M+H 947.4047). 1H NMR (d6-DMSO, 500 MHz) δ (ppm) 8.30 (s, 1H), 8.22 (br s, 1H), 8.10 (br s, 11-H), 8.00 (s, 1H), 7.78 (d, J=8.7 Hz, 1H), 7.67-7.65 (m, 2H), 7.52 (hr s, 1H), 7.38 (s, 1H), 7.31-7.28 (m, 2H), 7.19 (d, J=3.2 Hz, 1H), 5.16 (t, J=7.4 Hz, 1H), 5.14 (t, J=7.4 Hz, 1H), 4.15-4.11 (m, 2H), 3.91-3.81 (m, 4H), 3.55 (s, 6H), 2.45-2.36 (m, 2H), 2.26 (m, 1H), 2.20-2.13 (m, 2H), 2.13-2.06 (m, 2H), 2.06-2.00 (m, 4H), 0.99 (m, 2H), 0.85-0.77 (m, 14H). 13C NMR (d6-DMSO, 126 MHz) δ (ppm) 175.20, 171.21, 171.15, 158.61 (d, J=251.0 Hz), 156.95, 156.94, 150.05, 149.54 (d, J==7.3 Hz), 148.88, 141.37, 133.88, 133.00, 131,11, 130.68, 129.14, 128.78, 125.35, 121.40, 120.38, 118.15, 117.01, 114.18, 111.04, 110.75, 107.30 (d, J=23.4 Hz), 106.67 (d, J=18.2 Hz), 102.94 (d, J=8.6 Hz), 78.46, 57.95, 57.93, 53.06, 52.91, 51.51, 47.16, 47.11, 31.02, 30.95, 29.08, 24.80, 24.75, 19.35, 19.32, 17.74, 13.88, 11.17, 11.05.

Example 30: Synergistic Anti-HCV Activity of Compound 1 and Compound 2

Cell Culture—The reporter cell line Huh-luc/neo-ET harbors the persistently replicating 13sgluc-ubi-neo/NS3-3'/ET replicon containing the firefly luciferase gene-ubiquitin-neomycin phosphotransferase fusion protein and EMCV IRES driven NS3-5B HCV coding sequences containing the ET tissue culture adaptive mutations (E1202G, T1208I, and K1846T). A stock culture of the Huh-luc/neo-ET was expanded by culture in DMEM supplemented with 10% FCS, 2 mM glutamine, penicillin (100 IU/ml)/streptomycin (100 μg/ml) and 1× nonessential amino acids plus 1 mg/ml G418. The cells were split 1:4 and cultured for two passages in the same media plus 250 μg/ml G418. The cells were treated with trypsin and enumerated by staining with trypan blue and seeded into 96-well tissue culture plates at a cell culture density 7.5×103 cells per well and incubated at 37 C 5% $CO_2$ for 24 hours.

Compound Addition—Following the 24 hour incubation, medium was removed and replaced with the same medium minus the G418 plus the diluted test compounds in triplicate. Six wells in each plate received medium alone as a no-treatment control. The cells were incubated an additional 72 hours at 37° C. 5% $CO_2$ then anti-HCV activity was measured by luciferase endpoint. Duplicate plates were treated and incubated in parallel for assessment of cellular toxicity by XTT staining.

Cellular Viability—The cell culture monolayers from treated cells were stained with the tetrazolium dye XTT (2,3-bis(2-methoxy-4-nitro-5-sulfophenyl)-5-[(phenylamino)carbonyl]-2H-tetrazolium hydroxide) following 72 hours incubation to evaluate the cellular viability of the Huh-luc/neo-ET reporter cell line in the presence of the compounds. The cells were stained with the tetrazolium dye XTT. XTT-tetrazolium was metabolized by the mitochondrial enzymes of metabolically active cells to a soluble formazan product, allowing rapid quantitative analysis of the inhibition of virus-induced cell killing by antiviral test substances. XTT solution was prepared daily as a stock of 1 mg/ml in RPMI1640. Phenazine methosulfate (PMS) solution was prepared at 0.15 mg/ml in PBS and stored in the dark at −20° C. XTT/PMS stock was prepared immediately before use by adding 40 μl of PMS per ml of XTT solution. Fifty microliters of XTT/PMS was added to each well of the plate and the plate was reincubated for 4 hours at 37° C. Plates were sealed with adhesive plate sealers and shaken gently or inverted several times to mix the soluble formazan product and the plate was read spectrophotometrically at 450/650 nm with a Molecular Devices Vmax plate reader.

Measurement of Virus Replication—HCV replication from the replicon assay system was measured by luciferase activity following 72 hours incubation using the britelite plus luminescence reporter gene kit according to the manufacturer's instructions (Perkin Elmer, Shelton, CT). Briefly, one vial of britelite plus lyophilized substrate was solubilized in 10 ml of britelite reconstitution buffer and mixed gently by inversion. After a 5 minute incubation at room temperature, the britelite plus reagent was added to the 96 well plates at 100 μL per well. The plates were sealed with adhesive film and incubated at room temperature for approximately 10 minutes to lyse the cells. The well contents were transferred to a white 96-well plate and luminescence was measured within 15 minutes using the Wallac 1450 Microbeta Trilux liquid scintillation counter. The data were imported into a customized Microsoft Excel 2010 spreadsheet for determination of the 50% virus inhibition concentration ($EC_{50}$) for single concentration evaluations.

Combination Therapy Assays

Compound 2 was evaluated using a high-test concentration of 0.008 nM and four serial twofold dilutions in combination with nine concentrations of Compound 1 in the anti-HCV assay described above. Fifty microliters of each compound at 4 times (4×) the desired concentration was added to the 96 well microtiter plate containing cells in the antiviral assays. Fifty microliters of assay media were added to wells where test compound was being evaluated for antiviral activity as a single compound.

Data Analysis—The raw data was collected from Softmax Pro and imported into the Prichard and Shipman MacSynergy II software template (Prichard et al. 1993. Antiviral Research 14: 181-206). Effects of the drug combination are calculated based on the activity of the two compounds when tested alone. The expected additive antiviral protection was subtracted from the experimentally determined antiviral activity at each combination concentration resulting in a positive value (synergy, or potentiation), a negative value (antagonism), or zero (additivity). The results of the combination assays are presented three dimensionally at each combination concentration, yielding a surface of activity extending above (synergy) or below (antagonism) the plane of additivity. The volume of the surface was calculated and expressed as a synergy volume ($\mu M^2\%$) calculated at the 95% confidence interval.

For these studies, synergy was defined as drug combinations yielding synergy volumes greater than 50 $\mu M^2\%$ at the 95% confidence interval. Slightly synergistic activity and highly synergistic activity have been defined as yielding synergy volumes of 50 to 100 $\mu M^2\%$ and >100 $\mu M^2\%$, respectively. Synergy volumes between −50 and 50 $\mu M^2\%$ are considered additive and synergy volumes less than −50 $\mu M^2\%$ are considered antagonistic.

Anti-HCV Combination Therapy Evaluations: Compound 2 was evaluated in combination with Compound 1 for the inhibition of HCV replication in Huh-luc/neo-ET replicon cells. The percent of virus replication inhibition above expected at each concentration for each two-drug combination was calculated at the 95%, 99% and 99.9% confidence interval. The data obtained at the 95% confidence value were plotted three dimensionally and synergy volumes calculated. The synergy volume for the combination at the 95% confidence is summarized in the Table 42 below.

TABLE 42

Combination Anti-HCV Activity Evaluation

| | HCV 1b Replicon | |
|---|---|---|
| Compound | Synergy/Antagonism Volume (μM2/%) | Definition of interaction |
| 20 nM Compound 1<br>0.004 nM Compound 2 | 103/−6.01 | Highly synergistic |
| 40 nM Compound 1<br>0.008 nM Compound 2 | 255/−25.1 | Highly synergistic |

Results of the HCV replicon assays demonstrate that within the concentration ranges employed in the combination antiviral assays, Compound 1 at 20 and 40 nM yielded a synergistic interaction with Compound 2 at concentrations of 0.004 and 0.008 nM. Antagonistic or synergistic toxicity interactions were not observed at the concentrations evaluated.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

What is claimed is:

1. A method of treating HCV in a non-cirrhotic human in need thereof, comprising administering an effective amount of Compound 1, or a pharmaceutically acceptable salt thereof, Compound 1

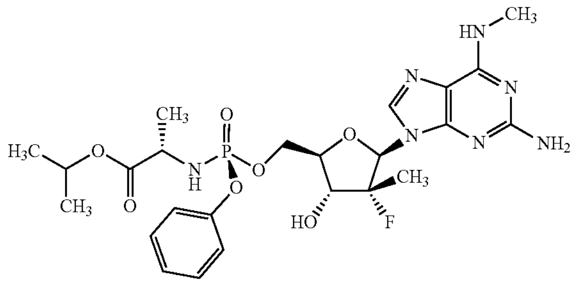

in a dosage form in combination with an effective amount of Compound 2, or a pharmaceutically acceptable salt thereof, Compound 2

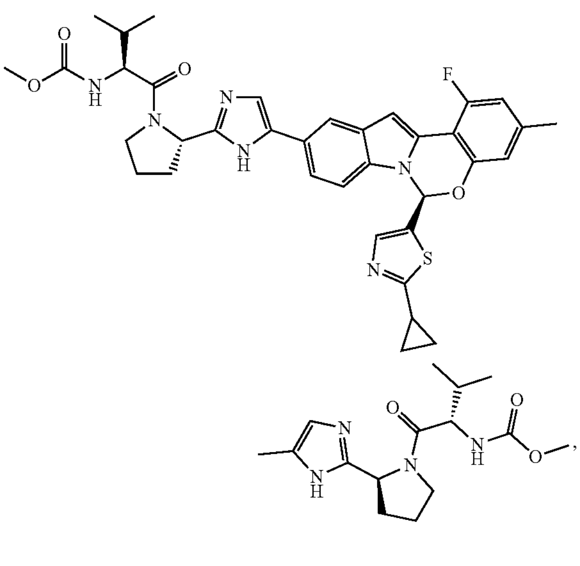

, in a dosage form.

2. The method of claim 1, wherein Compound 1 is Compound 1-A

Compound 1-A

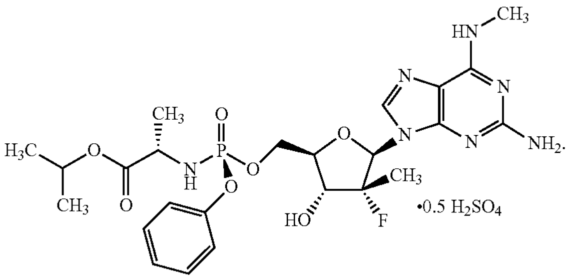

3. The method of claim 1, wherein Compound 1 or a pharmaceutically acceptable salt thereof and Compound 2 or a pharmaceutically acceptable salt thereof are in the same dosage form.

4. The method of claim 1, wherein Compound 1 or a pharmaceutically acceptable salt thereof and Compound 2 or a pharmaceutically acceptable salt thereof are in different dosage forms.

5. The method of claim 1, wherein the combination is administered orally.

6. The method of claim 1, wherein the combination is administered parenterally.

7. The method of claim 1, wherein from about 100 mg to about 800 mg of Compound 1, or an equivalent amount of a pharmaceutically acceptable salt thereof, is administered.

8. The method of claim 7, wherein about 550 mg of Compound 1, or an equivalent amount of a pharmaceutically acceptable salt thereof, is administered.

9. The method of claim 2, wherein about 600 mg of Compound 1-A, is administered.

10. The method of claim 1, wherein from about 90 to about 360 mg of Compound 2 or a pharmaceutically acceptable salt thereof is administered.

11. The method of claim 10, wherein about 180 mg of Compound 2 or a pharmaceutically acceptable salt is administered.

12. The method of claim 1, wherein Compound 1 or a pharmaceutically acceptable salt thereof and Compound 2 or a pharmaceutically acceptable salt thereof are in two dosage forms.

13. The method of claim 2, wherein about 300 mg of Compound 1-A is administered, wherein Compound 1-A and Compound 2 or a pharmaceutically acceptable salt thereof are in two dosage forms.

14. The method of claim 12, wherein about 90 mg of Compound 2 or a pharmaceutically acceptable salt is administered.

15. The method of claim 1, wherein the combination is administered once per day.

16. The method of claim 1, wherein the combination is administered twice per day.

17. The method of claim 1, wherein the combination is administered for up to 12 weeks.

18. The method of claim 1, wherein the combination is administered for up to 8 weeks.

19. The method of claim 2, wherein about 600 mg of Compound 1-A and about 180 mg of Compound 2 is administered.

20. The method of claim 2, wherein about 600 mg of Compound 1-A and about 180 mg of Compound 2 is administered in two dosage forms.

* * * * *